(12) United States Patent
Wessells et al.

(10) Patent No.: US 11,939,607 B2
(45) Date of Patent: *Mar. 26, 2024

(54) GENE EDITING SYSTEMS COMPRISING AN RNA GUIDE TARGETING LACTATE DEHYDROGENASE A (LDHA) AND USES THEREOF

(71) Applicant: Arbor Biotechnologies, Inc., Cambridge, MA (US)

(72) Inventors: Quinton Norman Wessells, Cambridge, MA (US); Jeffrey Raymond Haswell, Needham, MA (US); Tia Marie Ditommaso, Newton, MA (US); Noah Michael Jakimo, San Francisco, CA (US); Sejuti Sengupta, Ashland, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,791

(22) Filed: Nov. 4, 2022

(65) Prior Publication Data

US 2023/0212540 A1 Jul. 6, 2023

Related U.S. Application Data

(63) Continuation of application No. 17/832,114, filed on Jun. 3, 2022.

(60) Provisional application No. 63/300,743, filed on Jan. 19, 2022, provisional application No. 63/292,912, filed on Dec. 22, 2021, provisional application No. 63/225,214, filed on Jul. 23, 2021, provisional application No. 63/197,067, filed on Jun. 4, 2021.

(51) Int. Cl.
| | |
|---|---|
| *C12N 9/22* | (2006.01) |
| *A61K 31/7105* | (2006.01) |
| *A61K 38/46* | (2006.01) |
| *A61K 47/54* | (2017.01) |
| *A61P 13/12* | (2006.01) |
| *C12N 9/04* | (2006.01) |
| *C12N 15/10* | (2006.01) |
| *C12N 15/11* | (2006.01) |
| *C12N 15/86* | (2006.01) |
| *C12N 15/90* | (2006.01) |

(52) U.S. Cl.
CPC ............ *C12N 9/22* (2013.01); *A61K 31/7105* (2013.01); *A61K 38/465* (2013.01); *A61K 47/549* (2017.08); *A61P 13/12* (2018.01); *C12N 9/0006* (2013.01); *C12N 15/102* (2013.01); *C12N 15/11* (2013.01); *C12N 15/86* (2013.01); *C12N 15/907* (2013.01); *C12Y 101/01027* (2013.01); *C12N 2310/20* (2017.05); *C12N 2320/30* (2013.01); *C12N 2750/14143* (2013.01); *C12N 2800/80* (2013.01)

(58) Field of Classification Search
CPC ...... C12N 9/22; C12N 9/0006; C12N 15/102; C12N 15/11; C12N 15/86; C12N 15/907; C12N 2310/20; C12N 2320/30; C12N 2750/14143; C12N 2800/80; C12N 2320/34; C12N 15/1137; A61K 31/7105; A61K 38/465; A61K 47/549; A61P 13/12; C12Y 101/01027
See application file for complete search history.

(56) References Cited

U.S. PATENT DOCUMENTS

| | | |
|---|---|---|
| 2021/0060179 A1 | 3/2021 | Conway et al. |
| 2021/0163943 A1 | 6/2021 | Dymek et al. |

FOREIGN PATENT DOCUMENTS

| | | |
|---|---|---|
| WO | WO 2016/057932 A1 | 4/2016 |
| WO | WO 2019/178427 A1 | 9/2019 |
| WO | WO 2020/069296 A1 | 4/2020 |
| WO | WO 2020/132659 A1 | 6/2020 |
| WO | WO-2021202800 A1 * | 10/2021 |

OTHER PUBLICATIONS

Slaymaker et al. Rationally Engineered Cas9 Nucleases With Improved Specificity. Science, 2016. 351(6268): pp. 84-88, with Supplement (Year: 2016).*
Gao et al., Engineered Cpf1 Variants with Altered PAM Specificities. Nature Biotechnology, 2016. 35(8): pp. 789-793, with Supplement (Year: 2016).*
Strecker et al., Engineering of CRISPR-12b for Human Genome Editing. Nature Communications, 2019. 10 (212): 8 pages, with Supplement. https://doi.org/10.1038/s41467-018-08224-4 (Year: 2019).*
Huang et al., Structural Basis for Two Metal-Ion Catalysis of DNA Cleavage by Cas12i2. Nature Communications, 2020. 11 (5241): 14 pages, with Supplement. https://doi.org/10.1038/s41467-020-19072-6 (Year: 2020).*
U.S. Appl. No. 17/832,114, filed Jun. 3, 2022, Wessells et al.

(Continued)

*Primary Examiner* — Neil P Hammell
*Assistant Examiner* — Kyle Thomas Rega
(74) *Attorney, Agent, or Firm* — Mintz, Levin, Cohn, Ferris, Glovsky and Popeo, P.C.

(57) ABSTRACT

Provided herein are gene editing systems and/or compositions comprising RNA guides targeting LDHA for use in genetic editing of the LDHA gene. Also provide herein are methods of using the gene editing system for introducing edits to the LDHA gene and/or for treatment of primary hyperoxaluria (PH), and processes for characterizing the gene editing system.

21 Claims, 10 Drawing Sheets

Specification includes a Sequence Listing.

(56) References Cited

OTHER PUBLICATIONS

Hubner, CRISPR/Cas9-Mediated Gene Knockout to Address Primary Hyperoxaluria. Intellia Therapeutics. May 2, 2019;14 pages.
Lee et al., Site-specific integration in CHO cells mediated by CRISPR/Cas9 and homology-directed DNA repair pathway. Sci Rep. Feb. 25, 2015;5:8572.
Li et al., Cas121 nickase variant Cas12i2-6.1, SEQ ID 18. Geneseq Accession No. BIV42112. Mar. 4, 2021. 1 page.

* cited by examiner

SEQUENCE LISTING

```
Sequence total quantity: 1273
SEQ ID NO: 1                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 1
gttgcaaaac ccaagaaatc cgtctttcat tgacgg                                   36

SEQ ID NO: 2                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 2
aatagcggcc ctaagaaatc cgtctttcat tgacgg                                   36

SEQ ID NO: 3                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 3
attggaactg gcgagaaatc cgtctttcat tgacgg                                   36

SEQ ID NO: 4                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 4
ccagcaaacac ctaagaaatc cgtctttcat tgacgg                                  36

SEQ ID NO: 5                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 5
cggcgctcga ataggaaatc cgtctttcat tgacgg                                   36

SEQ ID NO: 6                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 6
gtggcaacac ctaagaaatc cgtctttcat tgacgg                                   36

SEQ ID NO: 7                    moltype = RNA   length = 36
FEATURE                         Location/Qualifiers
misc_feature                    1..36
                                note = Synthetic
source                          1..36
                                mol_type = other RNA
                                organism = synthetic construct
SEQUENCE: 7
gttgcaacac ctaagaaatc cgtctttcat tgacgg                                   36

SEQ ID NO: 8                    moltype = RNA   length = 36
FEATURE                         Location/Qualifiers
misc_feature                    1..36
                                note = Synthetic
source                          1..36
                                mol_type = other RNA
                                organism = synthetic construct
```

```
SEQUENCE: 8
gttgcaatgc ctaagaaatc cgtctttcat tgacgg                              36

SEQ ID NO: 9            moltype = RNA   length = 34
FEATURE                 Location/Qualifiers
misc_feature            1..34
                        note = Synthetic
source                  1..34
                        mol_type = other RNA
                        organism = synthetic construct
SEQUENCE: 9
gcaacaccta agaaatccgt ctttcattga cggg                                34

SEQ ID NO: 10           moltype = RNA   length = 23
FEATURE                 Location/Qualifiers
misc_feature            1..23
                        note = Synthetic
source                  1..23
                        mol_type = other RNA
                        organism = synthetic construct
SEQUENCE: 10
agaaatccgt ctttcattga cgg                                            23

SEQ ID NO: 11           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 11
cggatctcat tgccacgcgc ccccgacgac                                     30

SEQ ID NO: 12           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 12
ccacgcgccc ccgacgaccg cccgacgtgc                                     30

SEQ ID NO: 13           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 13
ccggtacggt agggccctgc gcgcacggcg                                     30

SEQ ID NO: 14           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 14
ctgtaggagc cggagtagct cagagtgatc                                     30

SEQ ID NO: 15           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 15
cacccaaacg tcgatattcc ttttccacgc                                     30

SEQ ID NO: 16           moltype = DNA   length = 30
FEATURE                 Location/Qualifiers
misc_feature            1..30
                        note = Synthetic
source                  1..30
                        mol_type = other DNA
```

```
                           organism = synthetic construct
SEQUENCE: 16
ataaaccgcg atgggtgaac cctcaggagg                                    30

SEQ ID NO: 17              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 17
gggttaataa accgcgatgg gtgaaccctc                                    30

SEQ ID NO: 18              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 18
cttgagaagc ctggctgtgt ccttgctgta                                    30

SEQ ID NO: 19              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 19
acttgagaag cctggctgtg tccttgctgt                                    30

SEQ ID NO: 20              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 20
tgcacgtatc tctggtgttt acttgagaag                                    30

SEQ ID NO: 21              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 21
ctgcacgtat ctctggtgtt tacttgagaa                                    30

SEQ ID NO: 22              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 22
atggcttttc tgcacgtatc tctggtgttt                                    30

SEQ ID NO: 23              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 23
cttttccacg ctaaggtatg ggccttcact                                    30

SEQ ID NO: 24              moltype = DNA   length = 30
FEATURE                    Location/Qualifiers
misc_feature               1..30
                           note = Synthetic
source                     1..30
```

```
                        mol_type = other DNA
                        organism = synthetic construct
SEQUENCE: 24
tggcagttaa tggctttcct gcacgtatct                              30

SEQ ID NO: 25           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 25
gtggcagtta atggctttc tgcacgtatc                               30

SEQ ID NO: 26           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 26
agctttgtgg cagttaatgg ctttctgca                               30

SEQ ID NO: 27           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 27
ggcttgagct ttgtggcagt taatggcttt                              30

SEQ ID NO: 28           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 28
cgagcgggaa ggagagccac aaagcgcgca                              30

SEQ ID NO: 29           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 29
agaagcctgg ctgtgtcctt gctgtaggag                              30

SEQ ID NO: 30           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 30
tctgcacgta tctctggtgt ttacttgaga                              30

SEQ ID NO: 31           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 31
tctgaggaaa ggccagcccc acttgggtt                               30

SEQ ID NO: 32           moltype = DNA  length = 30
FEATURE                 Location/Qualifiers
misc_feature            1..30
                        note = Synthetic
```

```
source                          1..30
                                mol_type = other DNA
                                organism = synthetic construct
SEQUENCE: 32
ccacgctaag gtatgggcct tcactcttca                                           30

SEQ ID NO: 33              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 33
cgcccacctt tccgagcggg aaggagagcc                                           30

SEQ ID NO: 34              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 34
ccgctcggaa aggtgggcgg aaatcagact                                           30

SEQ ID NO: 35              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 35
tggctctcct tcccgctcgg aaaggtgggc                                           30

SEQ ID NO: 36              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 36
gtggctctcc ttcccgctcg gaaaggtggg                                           30

SEQ ID NO: 37              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 37
actgccacaa agctcaagcc caaggcacag                                           30

SEQ ID NO: 38              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 38
tcaagtaaac accagagata cgtgcagaaa                                           30

SEQ ID NO: 39              moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 39
ctcagacaag atcactctga gctactccgg                                           30

SEQ ID NO: 40              moltype = DNA   length = 30
FEATURE                    Location/Qualifiers
misc_feature               1..30
```

```
                          note = Synthetic
source                    1..30
                          mol_type = other DNA
                          organism = synthetic construct
SEQUENCE: 40
cctcagacaa gatcactctg agctactccg                                    30

SEQ ID NO: 41             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 41
accccaagtg gggctggcct ttcctcagac                                    30

SEQ ID NO: 42             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 42
ttaaccccaa gtggggctgg cctttcctca                                    30

SEQ ID NO: 43             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 43
attaacccca agtggggctg gcctttcctc                                    30

SEQ ID NO: 44             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 44
acccatcgcg gtttattaac cccaagtggg                                    30

SEQ ID NO: 45             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 45
ggtgtaagta tagcctcctg agggttcacc                                    30

SEQ ID NO: 46             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 46
gggtgtaagt atagcctcct gagggttcac                                    30

SEQ ID NO: 47             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 47
gcgtggaaaa ggaatatcga cgtttgggtg                                    30

SEQ ID NO: 48             moltype = DNA  length = 30
FEATURE                   Location/Qualifiers
```

```
                         -continued misc_feature         1..30
                     note = Synthetic
source               1..30
                     mol_type = other DNA
                     organism = synthetic construct
SEQUENCE: 48
cacgctaagg tatgggcctt cactcttcac                                    30

SEQ ID NO: 49        moltype = DNA  length = 30
FEATURE              Location/Qualifiers
misc_feature         1..30
                     note = Synthetic
source               1..30
                     mol_type = other DNA
                     organism = synthetic construct
SEQUENCE: 49
tccacgctaa ggtatgggcc ttcactcttc                                    30

SEQ ID NO: 50        moltype = DNA  length = 30
FEATURE              Location/Qualifiers
misc_feature         1..30
                     note = Synthetic
source               1..30
                     mol_type = other DNA
                     organism = synthetic construct
SEQUENCE: 50
ccgcccacct ttccgagcgg gaaggagagc                                    30

SEQ ID NO: 51        moltype = DNA  length = 30
FEATURE              Location/Qualifiers
misc_feature         1..30
                     note = Synthetic
source               1..30
                     mol_type = other DNA
                     organism = synthetic construct
SEQUENCE: 51
ccgagcggga aggagagcca caaagcgcgc                                    30

SEQ ID NO: 52        moltype = DNA  length = 30
FEATURE              Location/Qualifiers
misc_feature         1..30
                     note = Synthetic
source               1..30
                     mol_type = other DNA
                     organism = synthetic construct
SEQUENCE: 52
gtctgatttc cgcccacctt tccgagcggg                                    30

SEQ ID NO: 53        moltype = DNA  length = 21
FEATURE              Location/Qualifiers
misc_feature         1..21
                     note = Synthetic
source               1..21
                     mol_type = other DNA
                     organism = synthetic construct
SEQUENCE: 53
acagaccctg tcattaggcc t                                             21

SEQ ID NO: 54        moltype = DNA  length = 28
FEATURE              Location/Qualifiers
misc_feature         1..28
                     note = Synthetic
source               1..28
                     mol_type = other DNA
                     organism = synthetic construct
SEQUENCE: 54
actcttcaca gaccctgtca ttaggcct                                      28

SEQ ID NO: 55        moltype = DNA  length = 30
FEATURE              Location/Qualifiers
misc_feature         1..30
                     note = Synthetic
source               1..30
                     mol_type = other DNA
                     organism = synthetic construct
SEQUENCE: 55
agtgtcacta cagcttcttt aatgtttatt                                    30

SEQ ID NO: 56        moltype = DNA  length = 30
```

```
FEATURE                 Location/Qualifiers
misc_feature            1..30
                        note = Synthetic
source                  1..30
                        mol_type = other DNA
                        organism = synthetic construct
SEQUENCE: 56
ttggggttgg tgctgttggc atggcctgtg                                              30

SEQ ID NO: 57           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 57
taaaggaaga acagaccccc cagaataaga                                              30

SEQ ID NO: 58           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 58
taatcttcta aaggaagaac agacccccca                                              30

SEQ ID NO: 59           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 59
ataatcttct aaggaagaa cagacccccc                                               30

SEQ ID NO: 60           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 60
caagtccaat atgcaactc taaaggatca                                               30

SEQ ID NO: 61           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 61
gttccaagtc caatatggca actctaaagg                                              30

SEQ ID NO: 62           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 62
ggttccaagt ccaatatggc aactctaaag                                              30

SEQ ID NO: 63           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 63
tggttccaag tccaatatgg caactctaaa                                              30
```

-continued

```
SEQ ID NO: 64            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 64
cttttggttc caagtccaat atggcaactc                                      30

SEQ ID NO: 65            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 65
ctcctataga ttcctttttgg ttccaagtcc                                     30

SEQ ID NO: 66            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 66
cctcctatag attcctttttg gttccaagtc                                     30

SEQ ID NO: 67            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 67
tcctcctata gattcctttt ggttccaagt                                      30

SEQ ID NO: 68            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 68
ttcctcctat agattccttt tggttccaag                                      30

SEQ ID NO: 69            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 69
aagaagctgt agtgacacta aatgttttc                                       30

SEQ ID NO: 70            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 70
gggttggtgc tgttggcatg gcctgtgcca                                      30

SEQ ID NO: 71            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 71
gtgctgttgg catggcctgt gccatcagta                                      30
```

```
SEQ ID NO: 72            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 72
cagttgttgg ggttggtgct gttggcatgg                                              30

SEQ ID NO: 73            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 73
atgaaggtaa gtgagagtct accacactgg                                              30

SEQ ID NO: 74            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 74
gaaccaaaag gaatctatag gaggaaaaac                                              30

SEQ ID NO: 75            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 75
gacttggaac caaaaggaat ctataggagg                                              30

SEQ ID NO: 76            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 76
ccatattgga cttggaacca aaaggaatct                                              30

SEQ ID NO: 77            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 77
gcatggcctg tgccatcagt atcttaatga                                              30

SEQ ID NO: 78            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 78
agagttgcca tattggactt ggaaccaaaa                                              30

SEQ ID NO: 79            moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 79
```

```
taaatcagct gatcctttag agttgccata                                    30

SEQ ID NO: 80           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 80
gaagattata aatcagctga tcctttagag                                    30

SEQ ID NO: 81           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 81
agaagattat aaatcagctg atcctttaga                                    30

SEQ ID NO: 82           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 82
gagttgccat attggacttg gaaccaaaag                                    30

SEQ ID NO: 83           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 83
ttcctttaga agattataaa tcagctgatc                                    30

SEQ ID NO: 84           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 84
tgggggtct gttcttcctt tagaagatta                                     30

SEQ ID NO: 85           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 85
ttctgggggg tctgttcttc ctttagaaga                                    30

SEQ ID NO: 86           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 86
agatactgat ggcacaggcc atgccaacag                                    30

SEQ ID NO: 87           moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 87
attaagatac tgatggcaca ggccatgcca                                              30

SEQ ID NO: 88           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 88
ccttcattaa gatactgatg gcacaggcca                                              30

SEQ ID NO: 89           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 89
cagtgtggta gactctcact taccttcatt                                              30

SEQ ID NO: 90           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 90
ctttagaaga ttataaatca gctgatcctt                                              30

SEQ ID NO: 91           moltype = DNA  length = 29
FEATURE                 Location/Qualifiers
misc_feature            1..29
                        note = Synthetic
source                  1..29
                        mol_type = other DNA
                        organism = synthetic construct
SEQUENCE: 91
gtgtcactac agcttcttta atgtttatt                                               29

SEQ ID NO: 92           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 92
taaggaaaag gctgccatgt tggagatcca                                              30

SEQ ID NO: 93           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 93
gagatccatc atctctccct tcaatttgtc                                              30

SEQ ID NO: 94           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 94
aatttgtctt cgatgacatc aacaagagca                                              30

SEQ ID NO: 95           moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 95
atctgccaag tcctaaaaga catcaaatct                                              30

SEQ ID NO: 96           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 96
tcttcgatga catcaacaag agcaagttca                                              30

SEQ ID NO: 97           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 97
gatgacatca acaagagcaa gttcatctgc                                              30

SEQ ID NO: 98           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 98
agttaaatgg aaaattgcca cttctagatt                                              30

SEQ ID NO: 99           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 99
gtcttcgatg acatcaacaa gagcaagttc                                              30

SEQ ID NO: 100          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 100
ggtgttctaa ggaaaaggct gccatgttgg                                              30

SEQ ID NO: 101          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 101
gtgttctaag gaaaaggctg ccatgttgga                                              30

SEQ ID NO: 102          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 102
gccagagaca atctttggtg ttctaaggaa                                              30

SEQ ID NO: 103          moltype = DNA   length = 30
FEATURE                 Location/Qualifiers
misc_feature            1..30
                        note = Synthetic
source                  1..30
```

```
                        mol_type = other DNA
                        organism = synthetic construct
SEQUENCE: 103
tccatttaac taaagatttg atgtctttta                                      30

SEQ ID NO: 104          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 104
ccatttaact aaagatttga tgtcttttag                                      30

SEQ ID NO: 105          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 105
catttaacta aagatttgat gtcttttagg                                      30

SEQ ID NO: 106          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 106
aactaaagat tgatgtctt ttaggacttg                                       30

SEQ ID NO: 107          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 107
gatgtctttt aggacttggc agatgaactt                                      30

SEQ ID NO: 108          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 108
atgtctttta ggacttggca gatgaacttg                                      30

SEQ ID NO: 109          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 109
taggacttgg cagatgaact tgctcttgtt                                      30

SEQ ID NO: 110          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 110
aggacttggc agatgaactt gctcttgttg                                      30

SEQ ID NO: 111          moltype = DNA   length = 30
FEATURE                 Location/Qualifiers
misc_feature            1..30
                        note = Synthetic
```

```
source                          1..30
                                mol_type = other DNA
                                organism = synthetic construct
SEQUENCE: 111
ggacttggca gatgaacttg ctcttgttga                                          30

SEQ ID NO: 112                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 112
gcagatgaac ttgctcttgt tgatgtcatc                                          30

SEQ ID NO: 113                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 113
ctcttgttga tgtcatcgaa gacaaattga                                          30

SEQ ID NO: 114                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 114
ttgatgtcat cgaagacaaa ttgaagggag                                          30

SEQ ID NO: 115                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 115
atgtcatcga agacaaattg aagggagaga                                          30

SEQ ID NO: 116                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 116
aagggagaga tgatggatct ccaacatggc                                          30

SEQ ID NO: 117                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 117
tccttagaac accaaagatt gtctctggca                                          30

SEQ ID NO: 118                  moltype = DNA  length = 30
FEATURE                         Location/Qualifiers
misc_feature                    1..30
                                note = Synthetic
source                          1..30
                                mol_type = other DNA
                                organism = synthetic construct
SEQUENCE: 118
ccttagaaca ccaaagattg tctctggcaa                                          30

SEQ ID NO: 119                  moltype = DNA  length = 30
FEATURE                         Location/Qualifiers
misc_feature                    1..30
```

```
                        note = Synthetic
source                  1..30
                        mol_type = other DNA
                        organism = synthetic construct
SEQUENCE: 119
cttagaacac caaagattgt ctctggcaaa                                        30

SEQ ID NO: 120          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 120
gaacaccaaa gattgtctct ggcaaaggtt                                        30

SEQ ID NO: 121          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 121
tctctggcaa aggttgattt caacaagttt                                        30

SEQ ID NO: 122          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 122
atttcaacaa gtttatatta taatccatgc                                        30

SEQ ID NO: 123          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 123
caacaagttt atattataat ccatgcttga                                        30

SEQ ID NO: 124          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 124
aacaagttta tattataatc catgcttgac                                        30

SEQ ID NO: 125          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 125
atattataat ccatgcttga cttaaattct                                        30

SEQ ID NO: 126          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 126
tattataatc catgcttgac ttaaattctt                                        30

SEQ ID NO: 127          moltype = DNA  length = 30
FEATURE                 Location/Qualifiers
```

```
misc_feature            1..30
                        note = Synthetic
source                  1..30
                        mol_type = other DNA
                        organism = synthetic construct
SEQUENCE: 127
aagtcaagca tggattataa tataaacttg                                          30

SEQ ID NO: 128          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 128
agtcaagcat ggattataat ataaacttgt                                          30

SEQ ID NO: 129          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 129
taatataaac ttgttgaaat caacctttgc                                          30

SEQ ID NO: 130          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 130
ttgaaatcaa cctttgccag agacaatctt                                          30

SEQ ID NO: 131          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 131
aaatcaacct tgccagaga caatctttgg                                           30

SEQ ID NO: 132          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 132
ccagagacaa tctttggtgt tctaaggaaa                                          30

SEQ ID NO: 133          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 133
actaaagatt tgatgtcttt taggacttgg                                          30

SEQ ID NO: 134          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 134
taatccatgc ttgacttaaa ttcttt                                              26

SEQ ID NO: 135          moltype = DNA   length = 29
```

```
FEATURE              Location/Qualifiers
misc_feature         1..29
                     note = Synthetic
source               1..29
                     mol_type = other DNA
                     organism = synthetic construct
SEQUENCE: 135
gttaaatgga aaattgccac ttctagatt                                    29

SEQ ID NO: 136       moltype = DNA  length = 25
FEATURE              Location/Qualifiers
misc_feature         1..25
                     note = Synthetic
source               1..25
                     mol_type = other DNA
                     organism = synthetic construct
SEQUENCE: 136
aatggaaaat tgccacttct agatt                                        25

SEQ ID NO: 137       moltype = DNA  length = 30
FEATURE              Location/Qualifiers
misc_feature         1..30
                     note = Synthetic
source               1..30
                     mol_type = other DNA
                     organism = synthetic construct
SEQUENCE: 137
attctaaagg ccttaatctg gtcattattc                                   30

SEQ ID NO: 138       moltype = DNA  length = 30
FEATURE              Location/Qualifiers
misc_feature         1..30
                     note = Synthetic
source               1..30
                     mol_type = other DNA
                     organism = synthetic construct
SEQUENCE: 138
tagtctagag aaaagggaa taatgaccag                                    30

SEQ ID NO: 139       moltype = DNA  length = 30
FEATURE              Location/Qualifiers
misc_feature         1..30
                     note = Synthetic
source               1..30
                     mol_type = other DNA
                     organism = synthetic construct
SEQUENCE: 139
gactgcataa aaattgacaa gctatagtaa                                   30

SEQ ID NO: 140       moltype = DNA  length = 30
FEATURE              Location/Qualifiers
misc_feature         1..30
                     note = Synthetic
source               1..30
                     mol_type = other DNA
                     organism = synthetic construct
SEQUENCE: 140
tgactgcata aaaattgaca agctatagta                                   30

SEQ ID NO: 141       moltype = DNA  length = 30
FEATURE              Location/Qualifiers
misc_feature         1..30
                     note = Synthetic
source               1..30
                     mol_type = other DNA
                     organism = synthetic construct
SEQUENCE: 141
aaatccaggt gaggcttttg actgcataaa                                   30

SEQ ID NO: 142       moltype = DNA  length = 30
FEATURE              Location/Qualifiers
misc_feature         1..30
                     note = Synthetic
source               1..30
                     mol_type = other DNA
                     organism = synthetic construct
SEQUENCE: 142
caaatccagg tgaggctttt gactgcataa                                   30
```

```
SEQ ID NO: 143          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 143
tttcaaatcc aggtgaggct tttgactgca                                           30

SEQ ID NO: 144          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 144
ttgtttcaaa tccaggtgag gcttttgact                                           30

SEQ ID NO: 145          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 145
cttattgttt caaatccagg tgaggctttt                                           30

SEQ ID NO: 146          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 146
taaaatacag cccgaactgc aagttgctta                                           30

SEQ ID NO: 147          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 147
ctaatgttgt aaaatacagc ccgaactgca                                           30

SEQ ID NO: 148          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 148
atcattccta atgttgtaaa atacagcccg                                           30

SEQ ID NO: 149          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 149
aattcatcat tcctaatgtt gtaaaataca                                           30

SEQ ID NO: 150          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 150
actgcataaa aattgacaag ctatagtaaa                                           30
```

```
SEQ ID NO: 151            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 151
aaattcatca ttcctaatgt tgtaaaatac                                              30

SEQ ID NO: 152            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 152
ggtccagcgt aacgtgaaca tctttaaatt                                              30

SEQ ID NO: 153            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 153
atttggtcca gcgtaacgtg aacatcttta                                              30

SEQ ID NO: 154            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 154
tcacggctgg ggcacgtcag caagagggag                                              30

SEQ ID NO: 155            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 155
tctagactat aatgtaactg caaactccaa                                              30

SEQ ID NO: 156            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 156
ctctagacta taatgtaact gcaaactcca                                              30

SEQ ID NO: 157            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 157
tctctagact ataatgtaac tgcaaactcc                                              30

SEQ ID NO: 158            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 158
```

```
cccttttctc tagactataa tgtaactgca                                              30

SEQ ID NO: 159          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 159
ttcccctttt ctctagacta taatgtaact                                              30

SEQ ID NO: 160          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 160
atctggtcat tattcccctt ttctctagac                                              30

SEQ ID NO: 161          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 161
taaaggcctt aatctggtca ttattcccct                                              30

SEQ ID NO: 162          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 162
ttctaaaggc cttaatctgg tcattattcc                                              30

SEQ ID NO: 163          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 163
gtccagcgta acgtgaacat ctttaaattc                                              30

SEQ ID NO: 164          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 164
actatagctt gtcaattttt atgcagtcaa                                              30

SEQ ID NO: 165          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 165
tactatagct tgtcaatttt tatgcagtca                                              30

SEQ ID NO: 166          moltype = DNA  length = 30
FEATURE                 Location/Qualifiers
misc_feature            1..30
                        note = Synthetic
source                  1..30
                        mol_type = other DNA
                        organism = synthetic construct
```

```
SEQUENCE: 166
aaagatgttc acgttacgct ggaccaaatt                                             30

SEQ ID NO: 167          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 167
gcagttacat tatagtctag agaaaagggg                                             30

SEQ ID NO: 168          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 168
gagtttgcag ttacattata gtctagagaa                                             30

SEQ ID NO: 169          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 169
ctgacgtgcc ccagccgtga taatgaccag                                             30

SEQ ID NO: 170          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 170
tccctcttgc tgacgtgccc cagccgtgat                                             30

SEQ ID NO: 171          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 171
ctccctcttg ctgacgtgcc ccagccgtga                                             30

SEQ ID NO: 172          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 172
agacggcttt ctccctcttg ctgacgtgcc                                             30

SEQ ID NO: 173          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 173
cgctggacca aattaagacg gctttctccc                                             30

SEQ ID NO: 174          moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 174
acgttacgct ggaccaaatt aagacggctt                                              30

SEQ ID NO: 175          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 175
aagatgttca cgttacgctg gaccaaatta                                              30

SEQ ID NO: 176          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 176
ctatagcttg tcaattttta tgcagtcaaa                                              30

SEQ ID NO: 177          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 177
ggaatgatga atttaaagat gttcacgtta                                              30

SEQ ID NO: 178          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 178
caacattagg aatgatgaat ttaaagatgt                                              30

SEQ ID NO: 179          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 179
acaacattag gaatgatgaa tttaaagatg                                              30

SEQ ID NO: 180          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 180
tacaacatta ggaatgatga atttaaagat                                              30

SEQ ID NO: 181          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 181
gggctgtatt ttacaacatt aggaatgatg                                              30

SEQ ID NO: 182          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 182
cagttcgggc tgtattttac aacattagga                                        30

SEQ ID NO: 183          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 183
aaacaataag caacttgcag ttcgggctgt                                        30

SEQ ID NO: 184          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 184
gaaacaataa gcaacttgca gttcgggctg                                        30

SEQ ID NO: 185          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 185
tgcagtcaaa agcctcacct ggatttgaaa                                        30

SEQ ID NO: 186          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 186
atgcagtcaa aagcctcacc tggatttgaa                                        30

SEQ ID NO: 187          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 187
tatgcagtca aaagcctcac ctggatttga                                        30

SEQ ID NO: 188          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 188
ttatgcagtc aaaagcctca cctggatttg                                        30

SEQ ID NO: 189          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 189
tcaattttta tgcagtcaaa agcctcacct                                        30

SEQ ID NO: 190          moltype = DNA  length = 30
FEATURE                 Location/Qualifiers
misc_feature            1..30
                        note = Synthetic
```

```
source                      1..30
                            mol_type = other DNA
                            organism = synthetic construct
SEQUENCE: 190
cagttacatt atagtctaga gaaaagggga                                              30

SEQ ID NO: 191              moltype = DNA  length = 30
FEATURE                     Location/Qualifiers
misc_feature                1..30
                            note = Synthetic
source                      1..30
                            mol_type = other DNA
                            organism = synthetic construct
SEQUENCE: 191
cattatagtc tagagaaaag gggaataatg                                              30

SEQ ID NO: 192              moltype = DNA  length = 23
FEATURE                     Location/Qualifiers
misc_feature                1..23
                            note = Synthetic
source                      1..23
                            mol_type = other DNA
                            organism = synthetic construct
SEQUENCE: 192
acaagctata gtaaaactga tag                                                     23

SEQ ID NO: 193              moltype = DNA  length = 20
FEATURE                     Location/Qualifiers
misc_feature                1..20
                            note = Synthetic
source                      1..20
                            mol_type = other DNA
                            organism = synthetic construct
SEQUENCE: 193
aggcctttag aataaatttt                                                         20

SEQ ID NO: 194              moltype = DNA  length = 30
FEATURE                     Location/Qualifiers
misc_feature                1..30
                            note = Synthetic
source                      1..30
                            mol_type = other DNA
                            organism = synthetic construct
SEQUENCE: 194
tcttccaagc cacgtaggtc aagatatcca                                              30

SEQ ID NO: 195              moltype = DNA  length = 30
FEATURE                     Location/Qualifiers
misc_feature                1..30
                            note = Synthetic
source                      1..30
                            mol_type = other DNA
                            organism = synthetic construct
SEQUENCE: 195
caagccacgt aggtcaagat atccactatg                                              30

SEQ ID NO: 196              moltype = DNA  length = 30
FEATURE                     Location/Qualifiers
misc_feature                1..30
                            note = Synthetic
source                      1..30
                            mol_type = other DNA
                            organism = synthetic construct
SEQUENCE: 196
ggaaaaccac ttatcttcca agccacgtag                                              30

SEQ ID NO: 197              moltype = DNA  length = 30
FEATURE                     Location/Qualifiers
misc_feature                1..30
                            note = Synthetic
source                      1..30
                            mol_type = other DNA
                            organism = synthetic construct
SEQUENCE: 197
acctacgtgg cttggaagat aagtggtttt                                              30

SEQ ID NO: 198              moltype = DNA  length = 30
FEATURE                     Location/Qualifiers
misc_feature                1..30
```

```
                    note = Synthetic
source              1..30
                    mol_type = other DNA
                    organism = synthetic construct
SEQUENCE: 198
tgggaaaacc acttatcttc caagccacgt                                           30

SEQ ID NO: 199      moltype = DNA  length = 30
FEATURE             Location/Qualifiers
misc_feature        1..30
                    note = Synthetic
source              1..30
                    mol_type = other DNA
                    organism = synthetic construct
SEQUENCE: 199
cctaatgggg gaaaggctgg gagttcaccc                                           30

SEQ ID NO: 200      moltype = DNA  length = 30
FEATURE             Location/Qualifiers
misc_feature        1..30
                    note = Synthetic
source              1..30
                    mol_type = other DNA
                    organism = synthetic construct
SEQUENCE: 200
cgttacctaa tgggggaaag gctgggagtt                                           30

SEQ ID NO: 201      moltype = DNA  length = 30
FEATURE             Location/Qualifiers
misc_feature        1..30
                    note = Synthetic
source              1..30
                    mol_type = other DNA
                    organism = synthetic construct
SEQUENCE: 201
agcccgattc cgttacctaa tgggggaaag                                           30

SEQ ID NO: 202      moltype = DNA  length = 30
FEATURE             Location/Qualifiers
misc_feature        1..30
                    note = Synthetic
source              1..30
                    mol_type = other DNA
                    organism = synthetic construct
SEQUENCE: 202
caatctggat tcagcccgat tccgttacct                                           30

SEQ ID NO: 203      moltype = DNA  length = 30
FEATURE             Location/Qualifiers
misc_feature        1..30
                    note = Synthetic
source              1..30
                    mol_type = other DNA
                    organism = synthetic construct
SEQUENCE: 203
gaagcggttg caatctggat tcagcccgat                                           30

SEQ ID NO: 204      moltype = DNA  length = 30
FEATURE             Location/Qualifiers
misc_feature        1..30
                    note = Synthetic
source              1..30
                    mol_type = other DNA
                    organism = synthetic construct
SEQUENCE: 204
ccaaaaaccg tgttattgga agcggttgca                                           30

SEQ ID NO: 205      moltype = DNA  length = 30
FEATURE             Location/Qualifiers
misc_feature        1..30
                    note = Synthetic
source              1..30
                    mol_type = other DNA
                    organism = synthetic construct
SEQUENCE: 205
cccaaaaacc gtgttattgg aagcggttgc                                           30

SEQ ID NO: 206      moltype = DNA  length = 30
FEATURE             Location/Qualifiers
```

```
                        misc_feature      1..30
                                          note = Synthetic
                        source            1..30
                                          mol_type = other DNA
                                          organism = synthetic construct
SEQUENCE: 206
tcccaaaaac cgtgttattg gaagcggttg                                                30

SEQ ID NO: 207          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 207
gaagataagt ggttttccca aaaccgtgt                                                 30

SEQ ID NO: 208          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 208
atagtggata tcttgaccta cgtggcttgg                                                30

SEQ ID NO: 209          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 209
catagtggat atcttgacct acgtggcttg                                                30

SEQ ID NO: 210          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 210
tcatagtgga tatcttgacc tacgtggctt                                                30

SEQ ID NO: 211          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 211
ttcatagtgg atatcttgac ctacgtggct                                                30

SEQ ID NO: 212          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 212
tcctttttca tagtggatat cttgacctac                                                30

SEQ ID NO: 213          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 213
ctcctttttc atagtggata tcttgaccta                                                30

SEQ ID NO: 214          moltype = DNA  length = 30
```

```
FEATURE                 Location/Qualifiers
misc_feature            1..30
                        note = Synthetic
source                  1..30
                        mol_type = other DNA
                        organism = synthetic construct
SEQUENCE: 214
tctcctttt catagtggat atcttgacct                                 30

SEQ ID NO: 215          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 215
ttttctcctt tttcatagtg gatatcttga                                30

SEQ ID NO: 216          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 216
attttctcct tttcatagt ggatatcttg                                 30

SEQ ID NO: 217          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 217
tattttctcc tttttcatag tggatatctt                                30

SEQ ID NO: 218          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 218
ttattttctc ctttttcata gtggatatct                                30

SEQ ID NO: 219          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 219
gggaaaacca cttatcttcc aagccacgta                                30

SEQ ID NO: 220          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 220
acccattaag ctgtcatggg tgggtccttg                                30

SEQ ID NO: 221          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 221
agctgtcatg ggtgggtcct tggggaacat                                30
```

```
SEQ ID NO: 222          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 222
ttggaagcgg ttgcaatctg gattcagccc                                     30

SEQ ID NO: 223          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 223
cagtggtaag cataagttat tttcttttttg                                    30

SEQ ID NO: 224          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 224
ttgggaaaac cacttatctt ccaagccacg                                     30

SEQ ID NO: 225          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 225
caataacacg gttttttggga aaaccactta                                    30

SEQ ID NO: 226          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 226
caaccgcttc caataacacg gttttttggga                                    30

SEQ ID NO: 227          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 227
ggtaacggaa tcgggctgaa tccagattgc                                     30

SEQ ID NO: 228          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 228
gggaacatgg agattccagt ggtaagcata                                     30

SEQ ID NO: 229          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 229
cccccattag gtaacggaat cgggctgaat                                     30
```

```
SEQ ID NO: 230          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 230
atgggtgaac tcccagcctt tcccccatta                                        30

SEQ ID NO: 231          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 231
cccaaggacc cacccatgac agcttaatgg                                        30

SEQ ID NO: 232          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 232
ccactggaat ctccatgttc cccaaggacc                                        30

SEQ ID NO: 233          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 233
tgcttaccac tggaatctcc atgttcccca                                        30

SEQ ID NO: 234          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 234
aaaaacaaaa agaaaataac ttatgcttac                                        30

SEQ ID NO: 235          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 235
ccccattagg taacggaatc gggctgaatc                                        30

SEQ ID NO: 236          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 236
cttttttgttt ttgaaaagat tatataaaaa                                       30

SEQ ID NO: 237          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 237
```

```
tcaaaaacaa aaagaaaata acttatgctt                                            30

SEQ ID NO: 238          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 238
tataatcttt tcaaaaacaa aaagaaaata                                            30

SEQ ID NO: 239          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 239
atataatctt ttcaaaaaca aaagaaaat                                             30

SEQ ID NO: 240          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 240
tatataatct tttcaaaaac aaaaagaaaa                                            30

SEQ ID NO: 241          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 241
ttatataatc ttttcaaaaa caaaaagaaa                                            30

SEQ ID NO: 242          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 242
tttttgtttt tgaaaagatt atataaaaag                                            30

SEQ ID NO: 243          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 243
ttttcttttt gttttgaaa agattatata                                             30

SEQ ID NO: 244          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 244
tcttttgtt tttgaaaaga ttatataaaa                                             30

SEQ ID NO: 245          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 245
caaaaacaaa aagaaaataa cttatgctta                                      30

SEQ ID NO: 246          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 246
gaaaagatta tataaaaagt                                                 20

SEQ ID NO: 247          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 247
tgaaaagatt atataaaaag t                                               21

SEQ ID NO: 248          moltype = DNA  length = 22
FEATURE                 Location/Qualifiers
misc_feature            1..22
                        note = Synthetic
source                  1..22
                        mol_type = other DNA
                        organism = synthetic construct
SEQUENCE: 248
ttgaaaagat tatataaaaa gt                                              22

SEQ ID NO: 249          moltype = DNA  length = 26
FEATURE                 Location/Qualifiers
misc_feature            1..26
                        note = Synthetic
source                  1..26
                        mol_type = other DNA
                        organism = synthetic construct
SEQUENCE: 249
gtttttgaaa agattatata aaaagt                                          26

SEQ ID NO: 250          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 250
tgtttttgaa aagattatat aaaaagt                                         27

SEQ ID NO: 251          moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 251
ttgtttttga aaagattata taaaaagt                                        28

SEQ ID NO: 252          moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 252
tttttgaaaa gattatataa aaagt                                           25

SEQ ID NO: 253          moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 253
agaggtaata aatctttcaa tttggcaaca                                       30

SEQ ID NO: 254          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 254
gtacatgaaa ataaatgtag tctgtactat                                       30

SEQ ID NO: 255          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 255
aatttggcaa cacagaatat taacatttac                                       30

SEQ ID NO: 256          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 256
acaagcaggt ggttgagagg taataaatct                                       30

SEQ ID NO: 257          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 257
ggcaacacag aatattaaca tttactattt                                       30

SEQ ID NO: 258          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 258
caatttggca acacagaata ttaacattta                                       30

SEQ ID NO: 259          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 259
gggactgata aagataagga acagtggaaa                                       30

SEQ ID NO: 260          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 260
tagtgcctgt atggagtgga atgaatgttg                                       30

SEQ ID NO: 261          moltype = DNA   length = 30
FEATURE                 Location/Qualifiers
misc_feature            1..30
                        note = Synthetic
source                  1..30
```

-continued

```
                        mol_type = other DNA
                        organism = synthetic construct
SEQUENCE: 261
ctggtgtctc tctgaagact ctgcacccag                                    30

SEQ ID NO: 262          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 262
gtgcctgtat ggagtggaat gaatgttgct                                    30

SEQ ID NO: 263          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 263
agtgcctgta tggagtggaa tgaatgttgc                                    30

SEQ ID NO: 264          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 264
ttttagtgcc tgtatggagt ggaatgaatg                                    30

SEQ ID NO: 265          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 265
cttttagtgc ctgtatggag tggaatgaat                                    30

SEQ ID NO: 266          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 266
gcaacacaga atattaacat ttactatttt                                    30

SEQ ID NO: 267          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 267
agggactgat aaagataagg aacagtggaa                                    30

SEQ ID NO: 268          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 268
atattctgtg ttgccaaatt gaaagattta                                    30

SEQ ID NO: 269          moltype = DNA   length = 30
FEATURE                 Location/Qualifiers
misc_feature            1..30
                        note = Synthetic
```

```
source                     1..30
                           mol_type = other DNA
                           organism = synthetic construct
SEQUENCE: 269
tcagtcccta aatctgggtg cagagtcttc                                      30

SEQ ID NO: 270             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 270
ccaaattgaa agatttatta cctctcaacc                                      30

SEQ ID NO: 271             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 271
tgtgttgcca aattgaaaga tttattacct                                      30

SEQ ID NO: 272             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 272
cactccatac aggcactaaa agaaatagta                                      30

SEQ ID NO: 273             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 273
agagagacac cagcaacatt cattccactc                                      30

SEQ ID NO: 274             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 274
atcagtccct aaatctgggt gcagagtctt                                      30

SEQ ID NO: 275             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 275
tctttatcag tccctaaatc tgggtgcaga                                      30

SEQ ID NO: 276             moltype = DNA   length = 30
FEATURE                    Location/Qualifiers
misc_feature               1..30
                           note = Synthetic
source                     1..30
                           mol_type = other DNA
                           organism = synthetic construct
SEQUENCE: 276
cttatcttta tcagtcccta aatctgggtg                                      30

SEQ ID NO: 277             moltype = DNA   length = 30
FEATURE                    Location/Qualifiers
misc_feature               1..30
```

```
                        note = Synthetic
source                  1..30
                        mol_type = other DNA
                        organism = synthetic construct
SEQUENCE: 277
attccactcc atacaggcac taaaagaaat                                      30

SEQ ID NO: 278          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 278
ccactgttcc ttatctttat cagtccctaa                                      30

SEQ ID NO: 279          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 279
tgaacctctt tccactgttc cttatcttta                                      30

SEQ ID NO: 280          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 280
cctctcaacc acctgcttgt gaacctcttt                                      30

SEQ ID NO: 281          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 281
ttacctctca accacctgct tgtgaacctc                                      30

SEQ ID NO: 282          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 282
attacctctc aaccacctgc ttgtgaacct                                      30

SEQ ID NO: 283          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 283
cactgttcct tatctttatc agtccctaaa                                      30

SEQ ID NO: 284          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 284
aaagatttat tacctctcaa ccacctgctt                                      30

SEQ ID NO: 285          moltype = DNA  length = 22
FEATURE                 Location/Qualifiers
```

```
                        -continued misc_feature            1..22
                        note = Synthetic
source                  1..22
                        mol_type = other DNA
                        organism = synthetic construct
SEQUENCE: 285
ttttcatgta ccaacagatt ag                                          22

SEQ ID NO: 286          moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 286
attttcatgt accaacagat tag                                         23

SEQ ID NO: 287          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 287
gactctctgt agcagatttg gcagagagta                                  30

SEQ ID NO: 288          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 288
tgaggtgatc aaactcaaag gctacacatc                                  30

SEQ ID NO: 289          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 289
ctatcataca gtgcttatga ggtgatcaaa                                  30

SEQ ID NO: 290          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 290
cctatcatac agtgcttatg aggtgatcaa                                  30

SEQ ID NO: 291          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 291
acctatggtt tcctatcata cagtgcttat                                  30

SEQ ID NO: 292          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 292
tgcctttacc tatggtttcc tatcatacag                                  30

SEQ ID NO: 293          moltype = DNA  length = 30
```

```
FEATURE                 Location/Qualifiers
misc_feature            1..30
                        note = Synthetic
source                  1..30
                        mol_type = other DNA
                        organism = synthetic construct
SEQUENCE: 293
ctgcctttac ctatggtttc ctatcataca                                           30

SEQ ID NO: 294          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 294
ggcagagagt ataatgaaga atcttaggcg                                           30

SEQ ID NO: 295          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 295
cctatggttt cctatcatac agtgcttatg                                           30

SEQ ID NO: 296          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 296
gcagagagta taatgaagaa tcttaggcgg                                           30

SEQ ID NO: 297          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 297
attatactct ctgccaaatc tgctacagag                                           30

SEQ ID NO: 298          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 298
ccaccatgat taaggtaggt ctatgtagtg                                           30

SEQ ID NO: 299          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 299
caccatgatt aaggtaggtc tatgtagtga                                           30

SEQ ID NO: 300          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 300
aggtaggtct atgtagtgat acgctgcatt                                           30
```

```
SEQ ID NO: 301           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 301
aaatgcagcg tatcactaca tagacctacc                                    30

SEQ ID NO: 302           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 302
atcatggtgg aaactgggtg cacccgccta                                    30

SEQ ID NO: 303           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 303
ttcattatac tctctgccaa atctgctaca                                    30

SEQ ID NO: 304           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 304
tactctctgc caaatctgct acagagagtc                                    30

SEQ ID NO: 305           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 305
gagtttgatc acctcataag cactgtatga                                    30

SEQ ID NO: 306           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 306
agtttgatca cctcataagc actgtatgat                                    30

SEQ ID NO: 307           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 307
tctgccttta cctatggttt cctatcatac                                    30

SEQ ID NO: 308           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 308
ggcgggtgca cccagtttcc accatgatta                                    30
```

```
SEQ ID NO: 309          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 309
ttctgccttt acctatggtt tcctatcata                                          30

SEQ ID NO: 310          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 310
atcacctcat aagcactgta tgataggaaa                                          30

SEQ ID NO: 311          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 311
gatcacctca taagcactgt atgataggaa                                          30

SEQ ID NO: 312          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 312
gaatgctttt tgctggcttt t                                                   21

SEQ ID NO: 313          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 313
aatgcttttt gctggctttt                                                     20

SEQ ID NO: 314          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 314
tgaggaagag gcccgtttga agaagagtgc                                          30

SEQ ID NO: 315          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 315
caaattaata taataactag cagctttatg                                          30

SEQ ID NO: 316          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 316
```

```
atataataac tagcagctttt atgactttat                                               30

SEQ ID NO: 317          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 317
atgactttat atcttaatat aatgaattaa                                                30

SEQ ID NO: 318          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 318
tgactttata tcttaatata atgaattaac                                                30

SEQ ID NO: 319          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 319
atatcttaat ataatgaatt aaccaaagta                                                30

SEQ ID NO: 320          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 320
tatcttaata taatgaatta accaaagtag                                                30

SEQ ID NO: 321          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 321
atataatgaa ttaaccaaag tagtcactgt                                                30

SEQ ID NO: 322          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 322
accaaagtag tcactgttca aggtttattg                                                30

SEQ ID NO: 323          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 323
aaggtttatt gggggtttta gttggtataa                                                30

SEQ ID NO: 324          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 324
attggggtt ttagttggta taacacttgg                                              30

SEQ ID NO: 325          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 325
ttggggttt tagttggtat aacacttgga                                              30

SEQ ID NO: 326          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 326
ggggttttag ttggtataac acttggatag                                             30

SEQ ID NO: 327          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 327
tagttggtat aacacttgga tagttggttg                                             30

SEQ ID NO: 328          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 328
ccaaattaat ataataacta gcagctttat                                             30

SEQ ID NO: 329          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 329
agttggtata acacttggat agttggttgc                                             30

SEQ ID NO: 330          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 330
gtataacact tggatagttg gttgcattgt                                             30

SEQ ID NO: 331          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 331
gatagttggt tgcattgttt gtatgtagat                                             30

SEQ ID NO: 332          moltype = DNA  length = 30
FEATURE                 Location/Qualifiers
misc_feature            1..30
                        note = Synthetic
source                  1..30
                        mol_type = other DNA
```

```
                            organism = synthetic construct
SEQUENCE: 332
gttgcattgt ttgtatgtag atctttttac                                  30

SEQ ID NO: 333          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 333
cattgtttgt atgtagatct ttttacatta                                  30

SEQ ID NO: 334          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 334
tttgtatgta gatcttttta cattatatgg                                  30

SEQ ID NO: 335          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 335
gtatgtagat cttttacat tatatggtaa                                   30

SEQ ID NO: 336          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 336
tatgtagatc ttttacatt atatggtaat                                   30

SEQ ID NO: 337          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 337
ttacattata tggtaatgta cactactgat                                  30

SEQ ID NO: 338          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 338
tacattatat ggtaatgtac actactgata                                  30

SEQ ID NO: 339          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 339
acattatatg gtaatgtaca ctactgatat                                  30

SEQ ID NO: 340          moltype = DNA  length = 30
FEATURE                 Location/Qualifiers
misc_feature            1..30
                        note = Synthetic
source                  1..30
```

```
                      mol_type = other DNA
                      organism = synthetic construct
SEQUENCE: 340
cattatatgg taatgtacac tactgatata                                    30

SEQ ID NO: 341        moltype = DNA  length = 30
FEATURE               Location/Qualifiers
misc_feature          1..30
                      note = Synthetic
source                1..30
                      mol_type = other DNA
                      organism = synthetic construct
SEQUENCE: 341
tatggtaatg tacactactg atatagttca                                    30

SEQ ID NO: 342        moltype = DNA  length = 30
FEATURE               Location/Qualifiers
misc_feature          1..30
                      note = Synthetic
source                1..30
                      mol_type = other DNA
                      organism = synthetic construct
SEQUENCE: 342
acaaaataag atcctttgga agaattatgc                                    30

SEQ ID NO: 343        moltype = DNA  length = 30
FEATURE               Location/Qualifiers
misc_feature          1..30
                      note = Synthetic
source                1..30
                      mol_type = other DNA
                      organism = synthetic construct
SEQUENCE: 343
ggaagaatta tgcacaagac atgatattgg                                    30

SEQ ID NO: 344        moltype = DNA  length = 30
FEATURE               Location/Qualifiers
misc_feature          1..30
                      note = Synthetic
source                1..30
                      mol_type = other DNA
                      organism = synthetic construct
SEQUENCE: 344
gttggtataa cacttggata gttggttgca                                    30

SEQ ID NO: 345        moltype = DNA  length = 30
FEATURE               Location/Qualifiers
misc_feature          1..30
                      note = Synthetic
source                1..30
                      mol_type = other DNA
                      organism = synthetic construct
SEQUENCE: 345
cccaagaata gcctaatatt tccaaattaa                                    30

SEQ ID NO: 346        moltype = DNA  length = 30
FEATURE               Location/Qualifiers
misc_feature          1..30
                      note = Synthetic
source                1..30
                      mol_type = other DNA
                      organism = synthetic construct
SEQUENCE: 346
cagggttgcc caagaatagc ctaatatttc                                    30

SEQ ID NO: 347        moltype = DNA  length = 30
FEATURE               Location/Qualifiers
misc_feature          1..30
                      note = Synthetic
source                1..30
                      mol_type = other DNA
                      organism = synthetic construct
SEQUENCE: 347
gaaaaaatcg ttgcagggtt gcccaagaat                                    30

SEQ ID NO: 348        moltype = DNA  length = 30
FEATURE               Location/Qualifiers
misc_feature          1..30
                      note = Synthetic
```

```
source                  1..30
                        mol_type = other DNA
                        organism = synthetic construct
SEQUENCE: 348
tttttaattg ttaccagctt ccagaggaca                                30

SEQ ID NO: 349          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 349
ttaattgtta ccagcttcca gaggacaaga                                30

SEQ ID NO: 350          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 350
taattgttac cagcttccag aggacaagat                                30

SEQ ID NO: 351          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 351
aattgttacc agcttccaga ggacaagatc                                30

SEQ ID NO: 352          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 352
attgttacca gcttccagag gacaagatct                                30

SEQ ID NO: 353          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 353
ttaccagctt ccagaggaca agatctcaaa                                30

SEQ ID NO: 354          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 354
ccagcttcca gaggacaaga tctcaaaaat                                30

SEQ ID NO: 355          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 355
cagaggacaa gatctcaaaa atctgtgttc                                30

SEQ ID NO: 356          moltype = DNA  length = 30
FEATURE                 Location/Qualifiers
misc_feature            1..30
```

```
                        note = Synthetic
source                  1..30
                        mol_type = other DNA
                        organism = synthetic construct
SEQUENCE: 356
cctatagtga cacactatca ttgcctatat                                             30

SEQ ID NO: 357          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 357
cctatattca gttggcaaat aaattttaca                                             30

SEQ ID NO: 358          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 358
agttggcaaa taaattttac atttacatat                                             30

SEQ ID NO: 359          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 359
gcaaataaat tttacattta catatagaat                                             30

SEQ ID NO: 360          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 360
tacatttaca tatagaatgt tactttccaa                                             30

SEQ ID NO: 361          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 361
acatttacat atagaatgtt actttccaat                                             30

SEQ ID NO: 362          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 362
gaagaattat gcacaagaca tgatattgga                                             30

SEQ ID NO: 363          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 363
catttacata tagaatgtta ctttccaatt                                             30

SEQ ID NO: 364          moltype = DNA  length = 30
FEATURE                 Location/Qualifiers
```

```
                        misc_feature         1..30
                                             note = Synthetic
                        source               1..30
                                             mol_type = other DNA
                                             organism = synthetic construct
                        SEQUENCE: 364
                        catatagaat gttactttcc aattatgatt                              30

SEQ ID NO: 365       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 365
                        ctttccaatt atgattagca ttattatcaa                              30

SEQ ID NO: 366       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 366
                        ccaattatga ttagcattat tatcaaatat                              30

SEQ ID NO: 367       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 367
                        caattatgat tagcattatt atcaaatata                              30

SEQ ID NO: 368       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 368
                        tgattagcat tattatcaaa tatataatac                              30

SEQ ID NO: 369       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 369
                        gcattattat caaatatata atactttggg                              30

SEQ ID NO: 370       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 370
                        ttatcaaata tataatactt tgggacttac                              30

SEQ ID NO: 371       moltype = DNA   length = 30
                        FEATURE              Location/Qualifiers
                        misc_feature         1..30
                                             note = Synthetic
                        source               1..30
                                             mol_type = other DNA
                                             organism = synthetic construct
                        SEQUENCE: 371
                        tcaaatatat aatactttgg gacttacaat                              30

SEQ ID NO: 372       moltype = DNA   length = 30
```

```
FEATURE                 Location/Qualifiers
misc_feature            1..30
                        note = Synthetic
source                  1..30
                        mol_type = other DNA
                        organism = synthetic construct
SEQUENCE: 372
gggacttaca atggaagtgg taccaataca                                    30

SEQ ID NO: 373          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 373
ggacttacaa tggaagtggt accaatacaa                                    30

SEQ ID NO: 374          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 374
caatggaagt ggtaccaata caactcagtt                                    30

SEQ ID NO: 375          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 375
actattacat cctctgctat tagtcaataa                                    30

SEQ ID NO: 376          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 376
catcctctgc tattagtcaa taatatccct                                    30

SEQ ID NO: 377          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 377
gtcaataata tccctgttag aaaaaatcgt                                    30

SEQ ID NO: 378          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 378
acatatagaa tgttactttc caattatgat                                    30

SEQ ID NO: 379          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 379
tgcacaagac atgatattgg atttatacac                                    30
```

```
SEQ ID NO: 380            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 380
gatttataca ctggatccca ggatgtgact                                          30

SEQ ID NO: 381            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 381
atacactgga tcccaggatg tgactcactg                                          30

SEQ ID NO: 382            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 382
aaacgggcct cttcctcaga agtcagagtc                                          30

SEQ ID NO: 383            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 383
ctcagaagtc agagtcacct tcacaaggtc                                          30

SEQ ID NO: 384            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 384
acaaggtctg agattccatt ctgtcccaaa                                          30

SEQ ID NO: 385            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 385
cattctgtcc caaaatgcaa ggaacactaa                                          30

SEQ ID NO: 386            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 386
tgtcccaaaa tgcaaggaac actaaggaag                                          30

SEQ ID NO: 387            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 387
attccgtaaa gaccctgaag atgaaatgaa                                          30
```

```
SEQ ID NO: 388          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 388
ttccgtaaag accctgaaga tgaaatgaaa                                          30

SEQ ID NO: 389          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 389
cgtaaagacc ctgaagatga aatgaaaaaa                                          30

SEQ ID NO: 390          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 390
ggacagaatg gaatctcaga ccttgtgaag                                          30

SEQ ID NO: 391          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 391
gggacagaat ggaatctcag accttgtgaa                                          30

SEQ ID NO: 392          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 392
tgggacagaa tggaatctca gaccttgtga                                          30

SEQ ID NO: 393          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 393
cattttggga cagaatggaa tctcagacct                                          30

SEQ ID NO: 394          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 394
cttgcatttt gggacagaat ggaatctcag                                          30

SEQ ID NO: 395          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 395
```

```
cttagtgttc cttgcatttt gggacagaat                                              30

SEQ ID NO: 396          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 396
ttcaaacggg cctcttcctc agaagtcaga                                              30

SEQ ID NO: 397          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 397
cggaataaag gatgatgtct tccttagtgt                                              30

SEQ ID NO: 398          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 398
agggtcttta cggaataaag gatgatgtct                                              30

SEQ ID NO: 399          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 399
atcttcaggg tctttacgga ataaggatg                                               30

SEQ ID NO: 400          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 400
catcttcagg gtctttacgg aataaggat                                               30

SEQ ID NO: 401          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 401
atttcatctt cagggtcttt acggaataaa                                              30

SEQ ID NO: 402          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 402
catttcatct tcagggtctt tacggaataa                                              30

SEQ ID NO: 403          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 403
tcatttcatc ttcagggtct ttacggaata                                    30

SEQ ID NO: 404           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 404
ttcatttcat cttcagggtc tttacggaat                                    30

SEQ ID NO: 405           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 405
tttcatttca tcttcagggt ctttacggaa                                    30

SEQ ID NO: 406           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 406
ttttcatttc atcttcaggg tctttacgga                                    30

SEQ ID NO: 407           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 407
tttttcattt catcttcagg gtctttacgg                                    30

SEQ ID NO: 408           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 408
ttttttcatt tcatcttcag ggtctttacg                                    30

SEQ ID NO: 409           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 409
tttttttcat ttcatcttca gggtctttac                                    30

SEQ ID NO: 410           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 410
ttttttttca tttcatcttc agggtcttta                                    30

SEQ ID NO: 411           moltype = DNA  length = 30
FEATURE                  Location/Qualifiers
misc_feature             1..30
                         note = Synthetic
source                   1..30
                         mol_type = other DNA
```

```
                         organism = synthetic construct
SEQUENCE: 411
ttttttttttc atttcatctt cagggtcttt                                   30

SEQ ID NO: 412           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 412
acggaataaa ggatgatgtc ttccttagtg                                    30

SEQ ID NO: 413           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 413
agattgtttt taattgttac cagcttccag                                    30

SEQ ID NO: 414           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 414
gatcccccaa agtgtatctg cactcttctt                                    30

SEQ ID NO: 415           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 415
tggatccccc aaagtgtatc tgcactcttc                                    30

SEQ ID NO: 416           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 416
tacactggat cccaggatgt gactcactgg                                    30

SEQ ID NO: 417           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 417
gactaggcat gttcagtgaa ggagccagga                                    30

SEQ ID NO: 418           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 418
agtgaaggag ccaggaagtt atataacaca                                    30

SEQ ID NO: 419           moltype = DNA  length = 30
FEATURE                  Location/Qualifiers
misc_feature             1..30
                         note = Synthetic
source                   1..30
```

```
                        mol_type = other DNA
                        organism = synthetic construct
SEQUENCE: 419
tataacacac ggtaaacatc cacctggctc                                      30

SEQ ID NO: 420          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 420
gcagtggtgc gtcagaggtg gcagaactat                                      30

SEQ ID NO: 421          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 421
cacactaacc agttgaagac tacacaagat                                      30

SEQ ID NO: 422          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 422
acactaacca gttgaagact acacaagatt                                      30

SEQ ID NO: 423          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 423
aagactacac aagattaata ccatccagca                                      30

SEQ ID NO: 424          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 424
ataccatcca gcatcaggat atagctgtgg                                      30

SEQ ID NO: 425          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 425
tacaaaccat tcttatttct aacttcagga                                      30

SEQ ID NO: 426          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 426
acaaaccatt cttatttcta acttcaggag                                      30

SEQ ID NO: 427          moltype = DNA  length = 30
FEATURE                 Location/Qualifiers
misc_feature            1..30
                        note = Synthetic
```

```
source                    1..30
                          mol_type = other DNA
                          organism = synthetic construct
SEQUENCE: 427
caaaccattc ttatttctaa cttcaggagt                                          30

SEQ ID NO: 428            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 428
ttatttctaa cttcaggagt tgatgttttt                                          30

SEQ ID NO: 429            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 429
tttctaactt caggagttga tgttttccc                                           30

SEQ ID NO: 430            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 430
ggatcccca aagtgtatct gcactcttct                                           30

SEQ ID NO: 431            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 431
ctaacttcag gagttgatgt ttttcccagt                                          30

SEQ ID NO: 432            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 432
aggagttgat gttttcccca gtccatctta                                          30

SEQ ID NO: 433            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 433
atgttttcc cagtccatct taaaatatta                                           30

SEQ ID NO: 434            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 434
ttcccagtcc atcttaaaat attactgctt                                          30

SEQ ID NO: 435            moltype = DNA   length = 30
FEATURE                   Location/Qualifiers
misc_feature              1..30
```

```
                        note = Synthetic
source                  1..30
                        mol_type = other DNA
                        organism = synthetic construct
SEQUENCE: 435
tcccagtcca tcttaaaata ttactgcttt                                     30

SEQ ID NO: 436          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 436
cccagtccat cttaaaatat tactgcttta                                     30

SEQ ID NO: 437          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 437
ccagtccatc ttaaatatt actgctttaa                                      30

SEQ ID NO: 438          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 438
aaatattact gctttaatca cagatcagat                                     30

SEQ ID NO: 439          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 439
ctgctttaat cacagatcag ataaaaagga                                     30

SEQ ID NO: 440          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 440
aatcacagat cagataaaaa ggacaacatg                                     30

SEQ ID NO: 441          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 441
atcacagatc agataaaaag gacaacatgc                                     30

SEQ ID NO: 442          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 442
tagcctagac agtgaaatga tatgacatca                                     30

SEQ ID NO: 443          moltype = DNA   length = 30
FEATURE                 Location/Qualifiers
```

```
misc_feature            1..30
                        note = Synthetic
source                  1..30
                        mol_type = other DNA
                        organism = synthetic construct
SEQUENCE: 443
aaaattgcag ctcctttttgg atcccccaaa                                             30

SEQ ID NO: 444          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 444
aaattgcagc tccttttgga tcccccaaag                                              30

SEQ ID NO: 445          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 445
cagctccttt tggatccccc aaagtgtatc                                              30

SEQ ID NO: 446          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 446
taacttcagg agttgatgtt tttcccagtc                                              30

SEQ ID NO: 447          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 447
tgaaggtgac tctgacttct gaggaagagg                                              30

SEQ ID NO: 448          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 448
taggcatgag ccactgcacc ctgccttaag                                              30

SEQ ID NO: 449          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 449
ctggcctcca gtgatcagcc cacctgggct                                              30

SEQ ID NO: 450          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 450
tataacttcc tggctccttc actgaacatg                                              30

SEQ ID NO: 451          moltype = DNA  length = 30
```

```
                          -continued

FEATURE                 Location/Qualifiers
misc_feature            1..30
                        note = Synthetic
source                  1..30
                        mol_type = other DNA
                        organism = synthetic construct
SEQUENCE: 451
ctggctcctt cactgaacat gcctagtcca                                    30

SEQ ID NO: 452          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 452
actgaacatg cctagtccaa catttttcc                                     30

SEQ ID NO: 453          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 453
tttcccagtg agtcacatcc tgggatccag                                    30

SEQ ID NO: 454          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 454
ttcccagtga gtcacatcct gggatccagt                                    30

SEQ ID NO: 455          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 455
tcccagtgag tcacatcctg ggatccagtg                                    30

SEQ ID NO: 456          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 456
cccagtgagt cacatcctgg gatccagtgt                                    30

SEQ ID NO: 457          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 457
ccagtgagtc acatcctggg atccagtgta                                    30

SEQ ID NO: 458          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 458
tgcataattc ttccaaagga tcttattttg                                    30
```

```
SEQ ID NO: 459          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 459
ttccaaagga tcttatttg tgaactatat                                              30

SEQ ID NO: 460          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 460
caaaggatct tattttgtga actatatcag                                             30

SEQ ID NO: 461          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 461
ttttgtgaac tatatcagta gtgtacatta                                             30

SEQ ID NO: 462          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 462
tgtgaactat atcagtagtg tacattacca                                             30

SEQ ID NO: 463          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 463
gtgaactata tcagtagtgt acattaccat                                             30

SEQ ID NO: 464          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 464
ccgtgtgtta tataacttcc tggctccttc                                             30

SEQ ID NO: 465          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 465
tgaactatat cagtagtgta cattaccata                                             30

SEQ ID NO: 466          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 466
taccaactaa aaccccaat aaaccttgaa                                              30
```

```
SEQ ID NO: 467         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 467
aacagtgact actttggtta attcattata                                        30

SEQ ID NO: 468         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 468
ggttaattca ttatattaag atataaagtc                                        30

SEQ ID NO: 469         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 469
gttaattcat tatattaaga tataaagtca                                        30

SEQ ID NO: 470         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 470
attcattata ttaagatata aagtcataaa                                        30

SEQ ID NO: 471         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 471
attatattaa gatataaagt cataaagctg                                        30

SEQ ID NO: 472         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 472
tattaagata taaagtcata aagctgctag                                        30

SEQ ID NO: 473         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 473
agatataaag tcataaagct gctagttatt                                        30

SEQ ID NO: 474         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 474
```

```
ttatattaat ttggaaatat taggctattc                                    30

SEQ ID NO: 475          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 475
tattaatttg gaaatattag gctattcttg                                    30

SEQ ID NO: 476          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 476
atttggaaat attaggctat tcttgggcaa                                    30

SEQ ID NO: 477          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 477
ggaaatatta ggctattctt gggcaaccct                                    30

SEQ ID NO: 478          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 478
gaaatattag gctattcttg ggcaaccctg                                    30

SEQ ID NO: 479          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 479
ggctattctt gggcaaccct gcaacgattt                                    30

SEQ ID NO: 480          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 480
ccatataatg taaaaagatc tacatacaaa                                    30

SEQ ID NO: 481          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 481
ttgggcaacc ctgcaacgat tttttctaac                                    30

SEQ ID NO: 482          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 482
accgtgtgtt atataacttc ctggctcctt                               30

SEQ ID NO: 483          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 483
cccccttgagc caggtggatg tttaccgtgt                              30

SEQ ID NO: 484          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 484
gaagaagagt gcagatacac tttgggggat                               30

SEQ ID NO: 485          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 485
aagaagagtg cagatacact ttgggggatc                               30

SEQ ID NO: 486          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 486
gggggatcca aaaggagctg caattttaaa                               30

SEQ ID NO: 487          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 487
ggggatccaa aaggagctgc aattttaaag                               30

SEQ ID NO: 488          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 488
taaagtcttc tgatgtcata tcatttcact                               30

SEQ ID NO: 489          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 489
aaagtcttct gatgtcatat catttcactg                               30

SEQ ID NO: 490          moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 490
aagtcttctg atgtcatatc atttcactgt                                              30

SEQ ID NO: 491          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 491
tgatgtcata tcatttcact gtctaggcta                                              30

SEQ ID NO: 492          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 492
cactgtctag gctacaacag gattctaggt                                              30

SEQ ID NO: 493          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 493
actgtctagg ctacaacagg attctaggtg                                              30

SEQ ID NO: 494          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 494
taggtggagg ttgtgcatgt tgtccttttt                                              30

SEQ ID NO: 495          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 495
tgcatgttgt ccttttttatc tgatctgtga                                             30

SEQ ID NO: 496          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 496
tcctttttat ctgatctgtg attaaagcag                                              30

SEQ ID NO: 497          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 497
ttatctgatc tgtgattaaa gcagtaatat                                              30

SEQ ID NO: 498          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 498
agccaggtgg atgtttaccg tgtgttatat                                          30

SEQ ID NO: 499          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 499
tatctgatct gtgattaaag cagtaatatt                                          30

SEQ ID NO: 500          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 500
tctgatctgt gattaaagca gtaatatttt                                          30

SEQ ID NO: 501          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 501
aagcagtaat attttaagat ggactgggaa                                          30

SEQ ID NO: 502          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 502
taagatggac tgggaaaaac atcaactcct                                          30

SEQ ID NO: 503          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 503
aagatggact gggaaaaaca tcaactcctg                                          30

SEQ ID NO: 504          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 504
agatggactg ggaaaaacat caactcctga                                          30

SEQ ID NO: 505          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 505
gaaataagaa tggtttgtaa aatccacagc                                          30

SEQ ID NO: 506          moltype = DNA  length = 30
FEATURE                 Location/Qualifiers
misc_feature            1..30
                        note = Synthetic
```

```
source                    1..30
                          mol_type = other DNA
                          organism = synthetic construct
SEQUENCE: 506
gtaaaatcca cagctatatc ctgatgctgg                                    30

SEQ ID NO: 507            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 507
taaaatccac agctatatcc tgatgctgga                                    30

SEQ ID NO: 508            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 508
atcttgtgta gtcttcaact ggttagtgtg                                    30

SEQ ID NO: 509            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 509
tgtagtcttc aactggttag tgtgaaatag                                    30

SEQ ID NO: 510            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 510
aactggttag tgtgaaatag ttctgccacc                                    30

SEQ ID NO: 511            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 511
gtgtgaaata gttctgccac ctctgacgca                                    30

SEQ ID NO: 512            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 512
tgccacctct gacgcaccac tgccaatgct                                    30

SEQ ID NO: 513            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 513
gccccttgag ccaggtggat gtttaccgtg                                    30

SEQ ID NO: 514            moltype = DNA  length = 30
FEATURE                   Location/Qualifiers
misc_feature              1..30
```

```
                    note = Synthetic
source              1..30
                    mol_type = other DNA
                    organism = synthetic construct
SEQUENCE: 514
atctgatctg tgattaaagc agtaatattt                                     30

SEQ ID NO: 515      moltype = DNA  length = 30
FEATURE             Location/Qualifiers
misc_feature        1..30
                    note = Synthetic
source              1..30
                    mol_type = other DNA
                    organism = synthetic construct
SEQUENCE: 515
ccaaagtgct gggattatag gcatgagcca                                     30

SEQ ID NO: 516      moltype = DNA  length = 30
FEATURE             Location/Qualifiers
misc_feature        1..30
                    note = Synthetic
source              1..30
                    mol_type = other DNA
                    organism = synthetic construct
SEQUENCE: 516
ggcaaccctg caacgatttt ttctaacagg                                     30

SEQ ID NO: 517      moltype = DNA  length = 30
FEATURE             Location/Qualifiers
misc_feature        1..30
                    note = Synthetic
source              1..30
                    mol_type = other DNA
                    organism = synthetic construct
SEQUENCE: 517
ttctaacagg gatattattg actaatagca                                     30

SEQ ID NO: 518      moltype = DNA  length = 30
FEATURE             Location/Qualifiers
misc_feature        1..30
                    note = Synthetic
source              1..30
                    mol_type = other DNA
                    organism = synthetic construct
SEQUENCE: 518
tcagaaaaat gtgcagaaaa cttgagtaga                                     30

SEQ ID NO: 519      moltype = DNA  length = 30
FEATURE             Location/Qualifiers
misc_feature        1..30
                    note = Synthetic
source              1..30
                    mol_type = other DNA
                    organism = synthetic construct
SEQUENCE: 519
cagaaaatg tgcagaaaac ttgagtagac                                      30

SEQ ID NO: 520      moltype = DNA  length = 30
FEATURE             Location/Qualifiers
misc_feature        1..30
                    note = Synthetic
source              1..30
                    mol_type = other DNA
                    organism = synthetic construct
SEQUENCE: 520
agaaaaatgt gcagaaaact tgagtagaca                                     30

SEQ ID NO: 521      moltype = DNA  length = 30
FEATURE             Location/Qualifiers
misc_feature        1..30
                    note = Synthetic
source              1..30
                    mol_type = other DNA
                    organism = synthetic construct
SEQUENCE: 521
agtagacatc caccaaggtt acttgttttt                                     30

SEQ ID NO: 522      moltype = DNA  length = 30
FEATURE             Location/Qualifiers
```

```
                        misc_feature     1..30
                                         note = Synthetic
                        source           1..30
                                         mol_type = other DNA
                                         organism = synthetic construct
SEQUENCE: 522
cttgtttttt ttggttttgt tttgtttttt                                          30

SEQ ID NO: 523          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 523
tttttttggg ttttgttttg ttttttttaac                                         30

SEQ ID NO: 524          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 524
tttttggttt tgttttgttt ttttaacaga                                          30

SEQ ID NO: 525          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 525
ttttggtttt gttttgtttt tttaacagat                                          30

SEQ ID NO: 526          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 526
tttggttttg tttttgttttt ttaacagatg                                         30

SEQ ID NO: 527          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 527
ttggttttgt tttgtttttt taacagatgg                                          30

SEQ ID NO: 528          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 528
tggttttgtt ttgtttttttt aacagatggg                                         30

SEQ ID NO: 529          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 529
ggttttgttt tgtttttta acagatgggg                                           30

SEQ ID NO: 530          moltype = DNA   length = 30
```

```
                               -continued

FEATURE                 Location/Qualifiers
misc_feature            1..30
                        note = Synthetic
source                  1..30
                        mol_type = other DNA
                        organism = synthetic construct
SEQUENCE: 530
gttttgtttt gttttttttaa cagatggggt                                          30

SEQ ID NO: 531          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 531
tgttttgttt ttttaacaga tggggttttg                                           30

SEQ ID NO: 532          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 532
tattttcaga aaaatgtgca gaaaacttga                                           30

SEQ ID NO: 533          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 533
gttttgtttt tttaacagat ggggttttgt                                           30

SEQ ID NO: 534          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 534
tgttttttta acagatgggg ttttgttgtg                                           30

SEQ ID NO: 535          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 535
gttttttttaa cagatggggt tttgttgtgt                                          30

SEQ ID NO: 536          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 536
ttttttttaac agatggggtt ttgttgtgtt                                          30

SEQ ID NO: 537          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 537
ttttaacaga tggggttttg ttgtgttggc                                           30
```

```
SEQ ID NO: 538            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 538
tttaacagat ggggttttgt tgtgttggcc                                    30

SEQ ID NO: 539            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 539
ttaacagatg ggttttgtt gtgttggcca                                     30

SEQ ID NO: 540            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 540
taacagatgg ggttttgttg tgttggccag                                    30

SEQ ID NO: 541            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 541
aacagatggg gttttgttgt gttggccagg                                    30

SEQ ID NO: 542            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 542
acagatgggg ttttgttgtg ttggccaggc                                    30

SEQ ID NO: 543            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 543
tgttgtgttg gccaggctgg tccccaattc                                    30

SEQ ID NO: 544            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 544
gttgtgttgg ccaggctggt ccccaattcc                                    30

SEQ ID NO: 545            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 545
ttgtgttggc caggctggtc cccaattcct                                    30
```

```
SEQ ID NO: 546         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 546
tgttggccag gctggtcccc aattcctggc                                            30

SEQ ID NO: 547         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 547
gccaggctgg tccccaattc ctggcctcca                                            30

SEQ ID NO: 548         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 548
ttttgttttt ttaacagatg gggttttgtt                                            30

SEQ ID NO: 549         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 549
tttctaacag ggatattatt gactaatagc                                            30

SEQ ID NO: 550         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 550
tgcacatttt tctgaaaata caactgtgac                                            30

SEQ ID NO: 551         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 551
tctgcacatt tttctgaaaa tacaactgtg                                            30

SEQ ID NO: 552         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 552
tctaacaggg atattattga ctaatagcag                                            30

SEQ ID NO: 553         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 553
```

```
ctaacaggga tattattgac taatagcaga                                       30

SEQ ID NO: 554          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 554
taacagggat attattgact aatagcagag                                       30

SEQ ID NO: 555          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 555
ttgactaata gcagaggatg taatagtcaa                                       30

SEQ ID NO: 556          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 556
actaatagca gaggatgtaa tagtcaactg                                       30

SEQ ID NO: 557          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 557
tattggtacc acttccattg taagtcccaa                                       30

SEQ ID NO: 558          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 558
gtaccacttc cattgtaagt cccaaagtat                                       30

SEQ ID NO: 559          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 559
cattgtaagt cccaaagtat tatatatttg                                       30

SEQ ID NO: 560          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 560
taagtcccaa agtattatat atttgataat                                       30

SEQ ID NO: 561          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 561
tatatttgat aataatgcta atcataattg                                             30

SEQ ID NO: 562          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 562
gataataatg ctaatcataa ttggaaagta                                             30

SEQ ID NO: 563          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 563
ataatatgc taatcataat tggaaagtaa                                              30

SEQ ID NO: 564          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 564
gaaagtaaca ttctatatgt aaatgtaaaa                                             30

SEQ ID NO: 565          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 565
tatatgtaaa tgtaaaattt atttgccaac                                             30

SEQ ID NO: 566          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 566
ctgcacattt ttctgaaaat acaactgtga                                             30

SEQ ID NO: 567          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 567
atttgccaac tgaatatagg caatgatagt                                             30

SEQ ID NO: 568          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 568
gccaactgaa tataggcaat gatagtgtgt                                             30

SEQ ID NO: 569          moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 569
ccaactgaat ataggcaatg atagtgtgtc                                               30

SEQ ID NO: 570          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 570
ttgagatctt gtcctctgga agctggtaac                                               30

SEQ ID NO: 571          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 571
tgagatcttg tcctctggaa gctggtaaca                                               30

SEQ ID NO: 572          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 572
gagatcttgt cctctggaag ctggtaacaa                                               30

SEQ ID NO: 573          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 573
agatcttgtc ctctggaagc tggtaacaat                                               30

SEQ ID NO: 574          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 574
tcctctggaa gctggtaaca attaaaaaca                                               30

SEQ ID NO: 575          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 575
aaaacaatct taaggcaggg tgcagtggct                                               30

SEQ ID NO: 576          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 576
aggcagggtg cagtggctca tgcctataat                                               30

SEQ ID NO: 577          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 577
gggaagccca ggtgggctga tcactggagg                                        30

SEQ ID NO: 578          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 578
ggaagcccag gtgggctgat cactggaggc                                        30

SEQ ID NO: 579          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 579
gggaccagcc tggccaacac aacaaaaccc                                        30

SEQ ID NO: 580          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 580
aaaaaacaaa acaaaaccaa aaaaaacaag                                        30

SEQ ID NO: 581          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 581
gtggatgtct actcaagttt tctgcacatt                                        30

SEQ ID NO: 582          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 582
tttgccaact gaatataggc aatgatagtg                                        30

SEQ ID NO: 583          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 583
gtgttccttg cattttggga cagaatggaa                                        30

SEQ ID NO: 584          moltype = DNA  length = 26
FEATURE                 Location/Qualifiers
misc_feature            1..26
                        note = Synthetic
source                  1..26
                        mol_type = other DNA
                        organism = synthetic construct
SEQUENCE: 584
ttctgaaaat acaactgtga ccctta                                            26

SEQ ID NO: 585          moltype = DNA  length = 25
FEATURE                 Location/Qualifiers
misc_feature            1..25
                        note = Synthetic
```

```
source                   1..25
                         mol_type = other DNA
                         organism = synthetic construct
SEQUENCE: 585
tctgaaaata caactgtgac cctta                                          25

SEQ ID NO: 586           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 586
ctgaaaatac aactgtgacc ctta                                           24

SEQ ID NO: 587           moltype = DNA  length = 23
FEATURE                  Location/Qualifiers
misc_feature             1..23
                         note = Synthetic
source                   1..23
                         mol_type = other DNA
                         organism = synthetic construct
SEQUENCE: 587
tgaaaataca actgtgaccc tta                                            23

SEQ ID NO: 588           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 588
cggatctcat tgccacgcgc ccccgacgac                                     30

SEQ ID NO: 589           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 589
ccacgcgccc ccgacgaccg cccgacgtgc                                     30

SEQ ID NO: 590           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 590
ccggtacggt agggccctgc gcgcacggcg                                     30

SEQ ID NO: 591           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 591
ctgtaggagc cggagtagct cagagtgatc                                     30

SEQ ID NO: 592           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 592
cacccaaacg tcgatattcc ttttccacgc                                     30

SEQ ID NO: 593           moltype = RNA  length = 30
FEATURE                  Location/Qualifiers
misc_feature             1..30
```

```
                            note = Synthetic
source                      1..30
                            mol_type = other RNA
                            organism = synthetic construct
SEQUENCE: 593
ataaaccgcg atgggtgaac cctcaggagg                                      30

SEQ ID NO: 594              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 594
gggttaataa accgcgatgg gtgaaccctc                                      30

SEQ ID NO: 595              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 595
cttgagaagc ctggctgtgt ccttgctgta                                      30

SEQ ID NO: 596              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 596
acttgagaag cctggctgtg tccttgctgt                                      30

SEQ ID NO: 597              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 597
tgcacgtatc tctggtgttt acttgagaag                                      30

SEQ ID NO: 598              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 598
ctgcacgtat ctctggtgtt tacttgagaa                                      30

SEQ ID NO: 599              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 599
atggcttttc tgcacgtatc tctggtgttt                                      30

SEQ ID NO: 600              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 600
cttttccacg ctaaggtatg ggccttcact                                      30

SEQ ID NO: 601              moltype = RNA   length = 30
FEATURE                     Location/Qualifiers
```

```
                           misc_feature        1..30
                                               note = Synthetic
                           source              1..30
                                               mol_type = other RNA
                                               organism = synthetic construct
SEQUENCE: 601
tggcagttaa tggctttcct gcacgtatct                                               30

SEQ ID NO: 602             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 602
gtggcagtta atggctttc tgcacgtatc                                                30

SEQ ID NO: 603             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 603
agctttgtgg cagttaatgg cttttctgca                                               30

SEQ ID NO: 604             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 604
ggcttgagct ttgtggcagt taatggcttt                                               30

SEQ ID NO: 605             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 605
cgagcgggaa ggagagccac aaagcgcgca                                               30

SEQ ID NO: 606             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 606
agaagcctgg ctgtgtcctt gctgtaggag                                               30

SEQ ID NO: 607             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 607
tctgcacgta tctctggtgt ttacttgaga                                               30

SEQ ID NO: 608             moltype = RNA   length = 30
FEATURE                    Location/Qualifiers
misc_feature               1..30
                           note = Synthetic
source                     1..30
                           mol_type = other RNA
                           organism = synthetic construct
SEQUENCE: 608
tctgaggaaa ggccagcccc acttggggtt                                               30

SEQ ID NO: 609             moltype = RNA   length = 30
```

```
FEATURE                 Location/Qualifiers
misc_feature            1..30
                        note = Synthetic
source                  1..30
                        mol_type = other RNA
                        organism = synthetic construct
SEQUENCE: 609
ccacgctaag gtatgggcct tcactcttca                                           30

SEQ ID NO: 610          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 610
cgcccacctt tccgagcggg aaggagagcc                                           30

SEQ ID NO: 611          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 611
ccgctcggaa aggtgggcgg aaatcagact                                           30

SEQ ID NO: 612          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 612
tggctctcct tcccgctcgg aaaggtgggc                                           30

SEQ ID NO: 613          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 613
gtggctctcc ttcccgctcg gaaaggtggg                                           30

SEQ ID NO: 614          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 614
actgccacaa agctcaagcc caaggcacag                                           30

SEQ ID NO: 615          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 615
tcaagtaaac accagagata cgtgcagaaa                                           30

SEQ ID NO: 616          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 616
ctcagacaag atcactctga gctactccgg                                           30
```

```
SEQ ID NO: 617        moltype = RNA   length = 30
FEATURE               Location/Qualifiers
misc_feature          1..30
                      note = Synthetic
source                1..30
                      mol_type = other RNA
                      organism = synthetic construct
SEQUENCE: 617
cctcagacaa gatcactctg agctactccg                                          30

SEQ ID NO: 618        moltype = RNA   length = 30
FEATURE               Location/Qualifiers
misc_feature          1..30
                      note = Synthetic
source                1..30
                      mol_type = other RNA
                      organism = synthetic construct
SEQUENCE: 618
accccaagtg gggctggcct ttcctcagac                                          30

SEQ ID NO: 619        moltype = RNA   length = 30
FEATURE               Location/Qualifiers
misc_feature          1..30
                      note = Synthetic
source                1..30
                      mol_type = other RNA
                      organism = synthetic construct
SEQUENCE: 619
ttaaccccaa gtggggctgg cctttcctca                                          30

SEQ ID NO: 620        moltype = RNA   length = 30
FEATURE               Location/Qualifiers
misc_feature          1..30
                      note = Synthetic
source                1..30
                      mol_type = other RNA
                      organism = synthetic construct
SEQUENCE: 620
attaacccca agtggggctg gcctttcctc                                          30

SEQ ID NO: 621        moltype = RNA   length = 30
FEATURE               Location/Qualifiers
misc_feature          1..30
                      note = Synthetic
source                1..30
                      mol_type = other RNA
                      organism = synthetic construct
SEQUENCE: 621
acccatcgcg gtttattaac cccaagtggg                                          30

SEQ ID NO: 622        moltype = RNA   length = 30
FEATURE               Location/Qualifiers
misc_feature          1..30
                      note = Synthetic
source                1..30
                      mol_type = other RNA
                      organism = synthetic construct
SEQUENCE: 622
ggtgtaagta tagcctcctg agggttcacc                                          30

SEQ ID NO: 623        moltype = RNA   length = 30
FEATURE               Location/Qualifiers
misc_feature          1..30
                      note = Synthetic
source                1..30
                      mol_type = other RNA
                      organism = synthetic construct
SEQUENCE: 623
gggtgtaagt atagcctcct gagggttcac                                          30

SEQ ID NO: 624        moltype = RNA   length = 30
FEATURE               Location/Qualifiers
misc_feature          1..30
                      note = Synthetic
source                1..30
                      mol_type = other RNA
                      organism = synthetic construct
SEQUENCE: 624
gcgtggaaaa ggaatatcga cgtttgggtg                                          30
```

```
SEQ ID NO: 625          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 625
cacgctaagg tatgggcctt cactcttcac                                           30

SEQ ID NO: 626          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 626
tccacgctaa ggtatgggcc ttcactcttc                                           30

SEQ ID NO: 627          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 627
ccgcccacct ttccgagcgg gaaggagagc                                           30

SEQ ID NO: 628          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 628
ccgagcggga aggagagcca caaagcgcgc                                           30

SEQ ID NO: 629          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 629
gtctgatttc cgcccacctt tccgagcggg                                           30

SEQ ID NO: 630          moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 630
acagaccctg tcattaggcc t                                                    21

SEQ ID NO: 631          moltype = RNA   length = 28
FEATURE                 Location/Qualifiers
misc_feature            1..28
                        note = Synthetic
source                  1..28
                        mol_type = other RNA
                        organism = synthetic construct
SEQUENCE: 631
actcttcaca gaccctgtca ttaggcct                                             28

SEQ ID NO: 632          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 632
```
agtgtcacta cagcttcttt aatgtttatt                                              30

```
SEQ ID NO: 633          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 633
```
ttggggttgg tgctgttggc atggcctgtg                                              30

```
SEQ ID NO: 634          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 634
```
taaaggaaga acagaccccc cagaataaga                                              30

```
SEQ ID NO: 635          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 635
```
taatcttcta aaggaagaac agaccccca                                               30

```
SEQ ID NO: 636          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 636
```
ataatcttct aaaggaagaa cagaccccc                                               30

```
SEQ ID NO: 637          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 637
```
caagtccaat atggcaactc taaaggatca                                              30

```
SEQ ID NO: 638          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 638
```
gttccaagtc caatatggca actctaaagg                                              30

```
SEQ ID NO: 639          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 639
```
ggttccaagt ccaatatggc aactctaaag                                              30

```
SEQ ID NO: 640          moltype = RNA   length = 30
FEATURE                 Location/Qualifiers
misc_feature            1..30
                        note = Synthetic
source                  1..30
                        mol_type = other RNA
                        organism = synthetic construct
```

```
SEQUENCE: 640
tggttccaag tccaatatgg caactctaaa                                          30

SEQ ID NO: 641         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 641
cttttggttc caagtccaat atggcaactc                                          30

SEQ ID NO: 642         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 642
ctcctataga ttccttttgg ttccaagtcc                                          30

SEQ ID NO: 643         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 643
cctcctatag attcctttg gttccaagtc                                           30

SEQ ID NO: 644         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 644
tcctcctata gattcctttt ggttccaagt                                          30

SEQ ID NO: 645         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 645
ttcctcctat agattccttt tggttccaag                                          30

SEQ ID NO: 646         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 646
aagaagctgt agtgacacta aatgttttc                                           30

SEQ ID NO: 647         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 647
gggttggtgc tgttggcatg gcctgtgcca                                          30

SEQ ID NO: 648         moltype = RNA  length = 30
FEATURE                Location/Qualifiers
misc_feature           1..30
                       note = Synthetic
source                 1..30
                       mol_type = other RNA
```

```
                         organism = synthetic construct
SEQUENCE: 648
gtgctgttgg catggcctgt gccatcagta                                          30

SEQ ID NO: 649          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 649
cagttgttgg ggttggtgct gttggcatgg                                          30

SEQ ID NO: 650          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 650
atgaaggtaa gtgagagtct accacactgg                                          30

SEQ ID NO: 651          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 651
gaaccaaaag gaatctatag gaggaaaaac                                          30

SEQ ID NO: 652          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 652
gacttggaac caaaaggaat ctataggagg                                          30

SEQ ID NO: 653          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 653
ccatattgga cttggaacca aaaggaatct                                          30

SEQ ID NO: 654          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 654
gcatggcctg tgccatcagt atcttaatga                                          30

SEQ ID NO: 655          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 655
agagttgcca tattggactt ggaaccaaaa                                          30

SEQ ID NO: 656          moltype = RNA   length = 30
FEATURE                 Location/Qualifiers
misc_feature            1..30
                        note = Synthetic
source                  1..30
```

```
                        mol_type = other RNA
                        organism = synthetic construct
SEQUENCE: 656
taaatcagct gatcctttag agttgccata                                              30

SEQ ID NO: 657          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 657
gaagattata aatcagctga tcctttagag                                              30

SEQ ID NO: 658          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 658
agaagattat aaatcagctg atcctttaga                                              30

SEQ ID NO: 659          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 659
gagttgccat attggacttg gaaccaaaag                                              30

SEQ ID NO: 660          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 660
ttcctttaga agattataaa tcagctgatc                                              30

SEQ ID NO: 661          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 661
tgggggtct gttcttcctt tagaagatta                                               30

SEQ ID NO: 662          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 662
ttctgggggg tctgttcttc ctttagaaga                                              30

SEQ ID NO: 663          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 663
agatactgat ggcacaggcc atgccaacag                                              30

SEQ ID NO: 664          moltype = RNA  length = 30
FEATURE                 Location/Qualifiers
misc_feature            1..30
                        note = Synthetic
```

```
source                   1..30
                         mol_type = other RNA
                         organism = synthetic construct
SEQUENCE: 664
attaagatac tgatggcaca ggccatgcca                                      30

SEQ ID NO: 665           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 665
ccttcattaa gatactgatg gcacaggcca                                      30

SEQ ID NO: 666           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 666
cagtgtggta gactctcact taccttcatt                                      30

SEQ ID NO: 667           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 667
ctttagaaga ttataaatca gctgatcctt                                      30

SEQ ID NO: 668           moltype = RNA   length = 29
FEATURE                  Location/Qualifiers
misc_feature             1..29
                         note = Synthetic
source                   1..29
                         mol_type = other RNA
                         organism = synthetic construct
SEQUENCE: 668
gtgtcactac agcttcttta atgtttatt                                       29

SEQ ID NO: 669           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 669
taaggaaaag gctgccatgt tggagatcca                                      30

SEQ ID NO: 670           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 670
gagatccatc atctctccct tcaatttgtc                                      30

SEQ ID NO: 671           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 671
aatttgtctt cgatgacatc aacaagagca                                      30

SEQ ID NO: 672           moltype = RNA   length = 30
FEATURE                  Location/Qualifiers
misc_feature             1..30
```

```
                            note = Synthetic
source                      1..30
                            mol_type = other RNA
                            organism = synthetic construct
SEQUENCE: 672
atctgccaag tcctaaaaga catcaaatct                                              30

SEQ ID NO: 673              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 673
tcttcgatga catcaacaag agcaagttca                                              30

SEQ ID NO: 674              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 674
gatgacatca acaagagcaa gttcatctgc                                              30

SEQ ID NO: 675              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 675
agttaaatgg aaaattgcca cttctagatt                                              30

SEQ ID NO: 676              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 676
gtcttcgatg acatcaacaa gagcaagttc                                              30

SEQ ID NO: 677              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 677
ggtgttctaa ggaaaaggct gccatgttgg                                              30

SEQ ID NO: 678              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 678
gtgttctaag gaaaaggctg ccatgttgga                                              30

SEQ ID NO: 679              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 679
gccagagaca atctttggtg ttctaaggaa                                              30

SEQ ID NO: 680              moltype = RNA   length = 30
FEATURE                     Location/Qualifiers
```

```
misc_feature            1..30
                        note = Synthetic
source                  1..30
                        mol_type = other RNA
                        organism = synthetic construct
SEQUENCE: 680
tccatttaac taaagatttg atgtctttta                                          30

SEQ ID NO: 681          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 681
ccatttaact aaagatttga tgtcttttag                                          30

SEQ ID NO: 682          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 682
catttaacta aagatttgat gtcttttagg                                          30

SEQ ID NO: 683          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 683
aactaaagat tgatgtctt ttaggacttg                                           30

SEQ ID NO: 684          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 684
gatgtctttt aggacttggc agatgaactt                                          30

SEQ ID NO: 685          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 685
atgtctttta ggacttggca gatgaacttg                                          30

SEQ ID NO: 686          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 686
taggacttgg cagatgaact tgctcttgtt                                          30

SEQ ID NO: 687          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 687
aggacttggc agatgaactt gctcttgttg                                          30

SEQ ID NO: 688          moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 688
ggacttggca gatgaacttg ctcttgttga                                    30

SEQ ID NO: 689          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 689
gcagatgaac ttgctcttgt tgatgtcatc                                    30

SEQ ID NO: 690          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 690
ctcttgttga tgtcatcgaa gacaaattga                                    30

SEQ ID NO: 691          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 691
ttgatgtcat cgaagacaaa ttgaagggag                                    30

SEQ ID NO: 692          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 692
atgtcatcga agacaaattg aagggagaga                                    30

SEQ ID NO: 693          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 693
aagggagaga tgatggatct ccaacatggc                                    30

SEQ ID NO: 694          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 694
tccttagaac accaaagatt gtctctggca                                    30

SEQ ID NO: 695          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 695
ccttagaaca ccaaagattg tctctggcaa                                    30
```

```
SEQ ID NO: 696              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 696
cttagaacac caaagattgt ctctggcaaa                                      30

SEQ ID NO: 697              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 697
gaacaccaaa gattgtctct ggcaaaggtt                                      30

SEQ ID NO: 698              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 698
tctctggcaa aggttgattt caacaagttt                                      30

SEQ ID NO: 699              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 699
atttcaacaa gtttatatta taatccatgc                                      30

SEQ ID NO: 700              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 700
caacaagttt atattataat ccatgcttga                                      30

SEQ ID NO: 701              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 701
aacaagttta tattaatc catgcttgac                                        30

SEQ ID NO: 702              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 702
atattataat ccatgcttga cttaaattct                                      30

SEQ ID NO: 703              moltype = RNA   length = 30
FEATURE                     Location/Qualifiers
misc_feature                1..30
                            note = Synthetic
source                      1..30
                            mol_type = other RNA
                            organism = synthetic construct
SEQUENCE: 703
tattataatc catgcttgac ttaaattctt                                      30
```

```
SEQ ID NO: 704          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 704
aagtcaagca tggattataa tataaacttg                                         30

SEQ ID NO: 705          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 705
agtcaagcat ggattataat ataaacttgt                                         30

SEQ ID NO: 706          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 706
taatataaac ttgttgaaat caacctttgc                                         30

SEQ ID NO: 707          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 707
ttgaaatcaa cctttgccag agacaatctt                                         30

SEQ ID NO: 708          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 708
aaatcaacct tgccagaga caatctttgg                                          30

SEQ ID NO: 709          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 709
ccagagacaa tctttggtgt tctaaggaaa                                         30

SEQ ID NO: 710          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 710
actaaagatt tgatgtcttt taggacttgg                                         30

SEQ ID NO: 711          moltype = RNA   length = 26
FEATURE                 Location/Qualifiers
misc_feature            1..26
                        note = Synthetic
source                  1..26
                        mol_type = other RNA
                        organism = synthetic construct
SEQUENCE: 711
```

```
taatccatgc ttgacttaaa ttcttt                                            26

SEQ ID NO: 712         moltype = RNA   length = 29
FEATURE                Location/Qualifiers
misc_feature           1..29
                       note = Synthetic
source                 1..29
                       mol_type = other RNA
                       organism = synthetic construct
SEQUENCE: 712
gttaaatgga aaattgccac ttctagatt                                         29

SEQ ID NO: 713         moltype = RNA   length = 25
FEATURE                Location/Qualifiers
misc_feature           1..25
                       note = Synthetic
source                 1..25
                       mol_type = other RNA
                       organism = synthetic construct
SEQUENCE: 713
aatgaaaaat tgccacttct agatt                                             25

SEQ ID NO: 714         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 714
attctaaagg ccttaatctg gtcattattc                                        30

SEQ ID NO: 715         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 715
tagtctagag aaaagggaa taatgaccag                                         30

SEQ ID NO: 716         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 716
gactgcataa aaattgacaa gctatagtaa                                        30

SEQ ID NO: 717         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 717
tgactgcata aaaattgaca agctatagta                                        30

SEQ ID NO: 718         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 718
aaatccaggt gaggcttttg actgcataaa                                        30

SEQ ID NO: 719         moltype = RNA   length = 30
FEATURE                Location/Qualifiers
misc_feature           1..30
                       note = Synthetic
source                 1..30
                       mol_type = other RNA
                       organism = synthetic construct
```

```
SEQUENCE: 719
caaatccagg tgaggctttt gactgcataa                                    30

SEQ ID NO: 720          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 720
tttcaaatcc aggtgaggct tttgactgca                                    30

SEQ ID NO: 721          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 721
ttgtttcaaa tccaggtgag gcttttgact                                    30

SEQ ID NO: 722          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 722
cttattgttt caaatccagg tgaggctttt                                    30

SEQ ID NO: 723          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 723
taaaatacag cccgaactgc aagttgctta                                    30

SEQ ID NO: 724          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 724
ctaatgttgt aaaatacagc ccgaactgca                                    30

SEQ ID NO: 725          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 725
atcattccta atgttgtaaa atacagcccg                                    30

SEQ ID NO: 726          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 726
aattcatcat tcctaatgtt gtaaaataca                                    30

SEQ ID NO: 727          moltype = RNA  length = 30
FEATURE                 Location/Qualifiers
misc_feature            1..30
                        note = Synthetic
source                  1..30
                        mol_type = other RNA
```

```
                             -continued organism = synthetic construct
SEQUENCE: 727
actgcataaa aattgacaag ctatagtaaa                               30

SEQ ID NO: 728        moltype = RNA  length = 30
FEATURE               Location/Qualifiers
misc_feature          1..30
                      note = Synthetic
source                1..30
                      mol_type = other RNA
                      organism = synthetic construct
SEQUENCE: 728
aaattcatca ttcctaatgt tgtaaaatac                               30

SEQ ID NO: 729        moltype = RNA  length = 30
FEATURE               Location/Qualifiers
misc_feature          1..30
                      note = Synthetic
source                1..30
                      mol_type = other RNA
                      organism = synthetic construct
SEQUENCE: 729
ggtccagcgt aacgtgaaca tctttaaatt                               30

SEQ ID NO: 730        moltype = RNA  length = 30
FEATURE               Location/Qualifiers
misc_feature          1..30
                      note = Synthetic
source                1..30
                      mol_type = other RNA
                      organism = synthetic construct
SEQUENCE: 730
atttggtcca gcgtaacgtg aacatcttta                               30

SEQ ID NO: 731        moltype = RNA  length = 30
FEATURE               Location/Qualifiers
misc_feature          1..30
                      note = Synthetic
source                1..30
                      mol_type = other RNA
                      organism = synthetic construct
SEQUENCE: 731
tcacggctgg ggcacgtcag caagagggag                               30

SEQ ID NO: 732        moltype = RNA  length = 30
FEATURE               Location/Qualifiers
misc_feature          1..30
                      note = Synthetic
source                1..30
                      mol_type = other RNA
                      organism = synthetic construct
SEQUENCE: 732
tctagactat aatgtaactg caaactccaa                               30

SEQ ID NO: 733        moltype = RNA  length = 30
FEATURE               Location/Qualifiers
misc_feature          1..30
                      note = Synthetic
source                1..30
                      mol_type = other RNA
                      organism = synthetic construct
SEQUENCE: 733
ctctagacta taatgtaact gcaaactcca                               30

SEQ ID NO: 734        moltype = RNA  length = 30
FEATURE               Location/Qualifiers
misc_feature          1..30
                      note = Synthetic
source                1..30
                      mol_type = other RNA
                      organism = synthetic construct
SEQUENCE: 734
tctctagact ataatgtaac tgcaaactcc                               30

SEQ ID NO: 735        moltype = RNA  length = 30
FEATURE               Location/Qualifiers
misc_feature          1..30
                      note = Synthetic
source                1..30
```

```
                        mol_type = other RNA
                        organism = synthetic construct
SEQUENCE: 735
ccctttctc tagactataa tgtaactgca                                       30

SEQ ID NO: 736          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 736
ttcccctttt ctctagacta taatgtaact                                      30

SEQ ID NO: 737          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 737
atctggtcat tattcccctt ttctctagac                                      30

SEQ ID NO: 738          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 738
taaaggcctt aatctggtca ttattcccct                                      30

SEQ ID NO: 739          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 739
ttctaaaggc cttaatctgg tcattattcc                                      30

SEQ ID NO: 740          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 740
gtccagcgta acgtgaacat ctttaaattc                                      30

SEQ ID NO: 741          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 741
actatagctt gtcaattttt atgcagtcaa                                      30

SEQ ID NO: 742          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 742
tactatagct tgtcaatttt tatgcagtca                                      30

SEQ ID NO: 743          moltype = RNA   length = 30
FEATURE                 Location/Qualifiers
misc_feature            1..30
                        note = Synthetic
```

```
source                  1..30
                        mol_type = other RNA
                        organism = synthetic construct
SEQUENCE: 743
aaagatgttc acgttacgct ggaccaaatt                                              30

SEQ ID NO: 744          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 744
gcagttacat tatagtctag agaaaagggg                                              30

SEQ ID NO: 745          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 745
gagtttgcag ttacattata gtctagagaa                                              30

SEQ ID NO: 746          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 746
ctgacgtgcc ccagccgtga taatgaccag                                              30

SEQ ID NO: 747          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 747
tccctcttgc tgacgtgccc cagccgtgat                                              30

SEQ ID NO: 748          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 748
ctccctcttg ctgacgtgcc ccagccgtga                                              30

SEQ ID NO: 749          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 749
agacggcttt ctccctcttg ctgacgtgcc                                              30

SEQ ID NO: 750          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 750
cgctggacca aattaagacg gctttctccc                                              30

SEQ ID NO: 751          moltype = RNA   length = 30
FEATURE                 Location/Qualifiers
misc_feature            1..30
```

```
                    note      = Synthetic
source              1..30
                    mol_type  = other RNA
                    organism  = synthetic construct
SEQUENCE: 751
acgttacgct ggaccaaatt aagacggctt                                              30

SEQ ID NO: 752          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 752
aagatgttca cgttacgctg gaccaaatta                                              30

SEQ ID NO: 753          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 753
ctatagcttg tcaatttta tgcagtcaaa                                               30

SEQ ID NO: 754          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 754
ggaatgatga atttaaagat gttcacgtta                                              30

SEQ ID NO: 755          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 755
caacattagg aatgatgaat ttaaagatgt                                              30

SEQ ID NO: 756          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 756
acaacattag gaatgatgaa tttaaagatg                                              30

SEQ ID NO: 757          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 757
tacaacatta ggaatgatga atttaaagat                                              30

SEQ ID NO: 758          moltype = RNA   length = 30
FEATURE                 Location/Qualifiers
misc_feature            1..30
                        note      = Synthetic
source                  1..30
                        mol_type  = other RNA
                        organism  = synthetic construct
SEQUENCE: 758
gggctgtatt ttacaacatt aggaatgatg                                              30

SEQ ID NO: 759          moltype = RNA   length = 30
FEATURE                 Location/Qualifiers
```

```
misc_feature            1..30
                        note = Synthetic
source                  1..30
                        mol_type = other RNA
                        organism = synthetic construct
SEQUENCE: 759
cagttcgggc tgtatttttac aacattagga                                           30

SEQ ID NO: 760          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 760
aaacaataag caacttgcag ttcgggctgt                                            30

SEQ ID NO: 761          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 761
gaaacaataa gcaacttgca gttcgggctg                                            30

SEQ ID NO: 762          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 762
tgcagtcaaa agcctcacct ggatttgaaa                                            30

SEQ ID NO: 763          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 763
atgcagtcaa aagcctcacc tggatttgaa                                            30

SEQ ID NO: 764          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 764
tatgcagtca aaagcctcac ctggatttga                                            30

SEQ ID NO: 765          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 765
ttatgcagtc aaaagcctca cctggatttg                                            30

SEQ ID NO: 766          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 766
tcaattttta tgcagtcaaa agcctcacct                                            30

SEQ ID NO: 767          moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 767
cagttacatt atagtctaga gaaaagggga                                          30

SEQ ID NO: 768          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 768
cattatagtc tagagaaaag gggaataatg                                          30

SEQ ID NO: 769          moltype = RNA  length = 23
FEATURE                 Location/Qualifiers
misc_feature            1..23
                        note = Synthetic
source                  1..23
                        mol_type = other RNA
                        organism = synthetic construct
SEQUENCE: 769
acaagctata gtaaaactga tag                                                 23

SEQ ID NO: 770          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 770
aggcctttag aataaatttt                                                     20

SEQ ID NO: 771          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 771
tcttccaagc cacgtaggtc aagatatcca                                          30

SEQ ID NO: 772          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 772
caagccacgt aggtcaagat atccactatg                                          30

SEQ ID NO: 773          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 773
ggaaaaccac ttatcttcca agccacgtag                                          30

SEQ ID NO: 774          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 774
acctacgtgg cttggaagat aagtggtttt                                          30
```

```
SEQ ID NO: 775          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 775
tgggaaaacc acttatcttc caagccacgt                                          30

SEQ ID NO: 776          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 776
cctaatgggg gaaaggctgg gagttcaccc                                          30

SEQ ID NO: 777          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 777
cgttacctaa tgggggaaag gctgggagtt                                          30

SEQ ID NO: 778          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 778
agcccgattc cgttacctaa tgggggaaag                                          30

SEQ ID NO: 779          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 779
caatctggat tcagcccgat tccgttacct                                          30

SEQ ID NO: 780          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 780
gaagcggttg caatctggat tcagcccgat                                          30

SEQ ID NO: 781          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 781
ccaaaaaccg tgttattgga agcggttgca                                          30

SEQ ID NO: 782          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 782
cccaaaaacc gtgttattgg aagcggttgc                                          30
```

```
SEQ ID NO: 783          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 783
tcccaaaaac cgtgttattg gaagcggttg                                           30

SEQ ID NO: 784          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 784
gaagataagt ggttttccca aaaaccgtgt                                           30

SEQ ID NO: 785          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 785
atagtggata tcttgaccta cgtggcttgg                                           30

SEQ ID NO: 786          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 786
catagtggat atcttgacct acgtggcttg                                           30

SEQ ID NO: 787          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 787
tcatagtgga tatcttgacc tacgtggctt                                           30

SEQ ID NO: 788          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 788
ttcatagtgg atatcttgac ctacgtggct                                           30

SEQ ID NO: 789          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 789
tcctttttca tagtggatat cttgacctac                                           30

SEQ ID NO: 790          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 790
```
ctcctttttc atagtggata tcttgaccta                                30

SEQ ID NO: 791         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 791
tctccttttt catagtggat atcttgacct                                30

SEQ ID NO: 792         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 792
ttttctcctt tttcatagtg gatatcttga                                30

SEQ ID NO: 793         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 793
attttctcct tttcatagt ggatatcttg                                 30

SEQ ID NO: 794         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 794
tattttctcc tttttcatag tggatatctt                                30

SEQ ID NO: 795         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 795
ttattttctc cttttcata gtggatatct                                 30

SEQ ID NO: 796         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 796
gggaaaacca cttatcttcc aagccacgta                                30

SEQ ID NO: 797         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 797
acccattaag ctgtcatggg tgggtccttg                                30

SEQ ID NO: 798         moltype = RNA   length = 30
FEATURE                Location/Qualifiers
misc_feature           1..30
                       note = Synthetic
source                 1..30
                       mol_type = other RNA
                       organism = synthetic construct

```
SEQUENCE: 798
agctgtcatg ggtgggtcct tggggaacat                                              30

SEQ ID NO: 799             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 799
ttggaagcgg ttgcaatctg gattcagccc                                              30

SEQ ID NO: 800             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 800
cagtggtaag cataagttat tttcttttg                                               30

SEQ ID NO: 801             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 801
ttgggaaaac cacttatctt ccaagccacg                                              30

SEQ ID NO: 802             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 802
caataacacg gttttgggga aaaccactta                                              30

SEQ ID NO: 803             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 803
caaccgcttc caataacacg gttttggga                                               30

SEQ ID NO: 804             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 804
ggtaacggaa tcgggctgaa tccagattgc                                              30

SEQ ID NO: 805             moltype = RNA  length = 30
FEATURE                    Location/Qualifiers
misc_feature               1..30
                           note = Synthetic
source                     1..30
                           mol_type = other RNA
                           organism = synthetic construct
SEQUENCE: 805
gggaacatgg agattccagt ggtaagcata                                              30

SEQ ID NO: 806             moltype = RNA  length = 30
FEATURE                    Location/Qualifiers
misc_feature               1..30
                           note = Synthetic
source                     1..30
                           mol_type = other RNA
```

```
                          organism = synthetic construct
SEQUENCE: 806
cccccattag gtaacggaat cgggctgaat                                          30

SEQ ID NO: 807          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 807
atgggtgaac tcccagcctt tcccccatta                                          30

SEQ ID NO: 808          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 808
cccaaggacc cacccatgac agcttaatgg                                          30

SEQ ID NO: 809          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 809
ccactggaat ctccatgttc cccaaggacc                                          30

SEQ ID NO: 810          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 810
tgcttaccac tggaatctcc atgttcccca                                          30

SEQ ID NO: 811          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 811
aaaaacaaaa agaaaataac ttatgcttac                                          30

SEQ ID NO: 812          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 812
ccccattagg taacggaatc gggctgaatc                                          30

SEQ ID NO: 813          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 813
cttttttgttt ttgaaaagat tatataaaaa                                         30

SEQ ID NO: 814          moltype = RNA   length = 30
FEATURE                 Location/Qualifiers
misc_feature            1..30
                        note = Synthetic
source                  1..30
```

```
                        mol_type = other RNA
                        organism = synthetic construct
SEQUENCE: 814
tcaaaaacaa aaagaaaata acttatgctt                                        30

SEQ ID NO: 815          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 815
tataatcttt tcaaaaacaa aaagaaaata                                        30

SEQ ID NO: 816          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 816
atataatctt ttcaaaaaca aaaagaaaat                                        30

SEQ ID NO: 817          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 817
tatataatct tttcaaaaac aaaaagaaaa                                        30

SEQ ID NO: 818          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 818
ttatataatc ttttcaaaaa caaaaagaaa                                        30

SEQ ID NO: 819          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 819
tttttgtttt tgaaaagatt atataaaaag                                        30

SEQ ID NO: 820          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 820
ttttcttttt gtttttgaaa agattatata                                        30

SEQ ID NO: 821          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 821
tctttttgtt tttgaaaaga ttatataaaa                                        30

SEQ ID NO: 822          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 822
caaaaacaaa aagaaaataa cttatgctta                                              30

SEQ ID NO: 823          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 823
gaaaagatta tataaaaagt                                                         20

SEQ ID NO: 824          moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 824
tgaaaagatt atataaaaag t                                                       21

SEQ ID NO: 825          moltype = RNA   length = 22
FEATURE                 Location/Qualifiers
misc_feature            1..22
                        note = Synthetic
source                  1..22
                        mol_type = other RNA
                        organism = synthetic construct
SEQUENCE: 825
ttgaaaagat tatataaaaa gt                                                      22

SEQ ID NO: 826          moltype = RNA   length = 26
FEATURE                 Location/Qualifiers
misc_feature            1..26
                        note = Synthetic
source                  1..26
                        mol_type = other RNA
                        organism = synthetic construct
SEQUENCE: 826
gtttttgaaa agattatata aaaagt                                                  26

SEQ ID NO: 827          moltype = RNA   length = 27
FEATURE                 Location/Qualifiers
misc_feature            1..27
                        note = Synthetic
source                  1..27
                        mol_type = other RNA
                        organism = synthetic construct
SEQUENCE: 827
tgttttgaa aagattatat aaaaagt                                                  27

SEQ ID NO: 828          moltype = RNA   length = 28
FEATURE                 Location/Qualifiers
misc_feature            1..28
                        note = Synthetic
source                  1..28
                        mol_type = other RNA
                        organism = synthetic construct
SEQUENCE: 828
ttgttttga aagattata taaaagt                                                   28

SEQ ID NO: 829          moltype = RNA   length = 25
FEATURE                 Location/Qualifiers
misc_feature            1..25
                        note = Synthetic
source                  1..25
                        mol_type = other RNA
                        organism = synthetic construct
SEQUENCE: 829
tttttgaaaa gattatataa aaagt                                                   25

SEQ ID NO: 830          moltype = RNA   length = 30
FEATURE                 Location/Qualifiers
misc_feature            1..30
```

```
                        note = Synthetic
source                  1..30
                        mol_type = other RNA
                        organism = synthetic construct
SEQUENCE: 830
agaggtaata aatctttcaa tttggcaaca                                               30

SEQ ID NO: 831          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 831
gtacatgaaa ataaatgtag tctgtactat                                               30

SEQ ID NO: 832          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 832
aatttggcaa cacagaatat taacatttac                                               30

SEQ ID NO: 833          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 833
acaagcaggt ggttgagagg taataaatct                                               30

SEQ ID NO: 834          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 834
ggcaacacag aatattaaca tttactattt                                               30

SEQ ID NO: 835          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 835
caatttggca acacagaata ttaacattta                                               30

SEQ ID NO: 836          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 836
gggactgata aagataagga acagtggaaa                                               30

SEQ ID NO: 837          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 837
tagtgcctgt atggagtgga atgaatgttg                                               30

SEQ ID NO: 838          moltype = RNA  length = 30
FEATURE                 Location/Qualifiers
```

```
misc_feature            1..30
                        note = Synthetic
source                  1..30
                        mol_type = other RNA
                        organism = synthetic construct
SEQUENCE: 838
ctggtgtctc tctgaagact ctgcacccag                                      30

SEQ ID NO: 839          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 839
gtgcctgtat ggagtggaat gaatgttgct                                      30

SEQ ID NO: 840          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 840
agtgcctgta tggagtggaa tgaatgttgc                                      30

SEQ ID NO: 841          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 841
ttttagtgcc tgtatggagt ggaatgaatg                                      30

SEQ ID NO: 842          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 842
cttttagtgc ctgtatggag tggaatgaat                                      30

SEQ ID NO: 843          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 843
gcaacacaga atattaacat ttactatttt                                      30

SEQ ID NO: 844          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 844
agggactgat aaagataagg aacagtggaa                                      30

SEQ ID NO: 845          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 845
atattctgtg ttgccaaatt gaaagattta                                      30

SEQ ID NO: 846          moltype = RNA  length = 30
```

```
                        -continued

FEATURE                 Location/Qualifiers
misc_feature            1..30
                        note = Synthetic
source                  1..30
                        mol_type = other RNA
                        organism = synthetic construct
SEQUENCE: 846
tcagtcccta aatctgggtg cagagtcttc                                    30

SEQ ID NO: 847          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 847
ccaaattgaa agatttatta cctctcaacc                                    30

SEQ ID NO: 848          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 848
tgtgttgcca aattgaaaga tttattacct                                    30

SEQ ID NO: 849          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 849
cactccatac aggcactaaa agaaatagta                                    30

SEQ ID NO: 850          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 850
agagagacac cagcaacatt cattccactc                                    30

SEQ ID NO: 851          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 851
atcagtccct aaatctgggt gcagagtctt                                    30

SEQ ID NO: 852          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 852
tctttatcag tccctaaatc tgggtgcaga                                    30

SEQ ID NO: 853          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 853
cttatcttta tcagtcccta aatctgggtg                                    30
```

```
SEQ ID NO: 854          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 854
attccactcc atacaggcac taaaagaaat                                            30

SEQ ID NO: 855          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 855
ccactgttcc ttatctttat cagtccctaa                                            30

SEQ ID NO: 856          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 856
tgaacctctt tccactgttc cttatcttta                                            30

SEQ ID NO: 857          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 857
cctctcaacc acctgcttgt gaacctcttt                                            30

SEQ ID NO: 858          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 858
ttacctctca accacctgct tgtgaacctc                                            30

SEQ ID NO: 859          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 859
attacctctc aaccacctgc ttgtgaacct                                            30

SEQ ID NO: 860          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 860
cactgttcct tatctttatc agtccctaaa                                            30

SEQ ID NO: 861          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 861
aaagattat taccctctcaa ccacctgctt                                            30
```

| | | |
|---|---|---|
| SEQ ID NO: 862 | moltype = RNA length = 22 | |
| FEATURE | Location/Qualifiers | |
| misc_feature | 1..22 | |
| | note = Synthetic | |
| source | 1..22 | |
| | mol_type = other RNA | |
| | organism = synthetic construct | |
| SEQUENCE: 862 | | |
| ttttcatgta ccaacagatt ag | | 22 |
| | | |
| SEQ ID NO: 863 | moltype = RNA length = 23 | |
| FEATURE | Location/Qualifiers | |
| misc_feature | 1..23 | |
| | note = Synthetic | |
| source | 1..23 | |
| | mol_type = other RNA | |
| | organism = synthetic construct | |
| SEQUENCE: 863 | | |
| attttcatgt accaacagat tag | | 23 |
| | | |
| SEQ ID NO: 864 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 864 | | |
| gactctctgt agcagatttg gcagagagta | | 30 |
| | | |
| SEQ ID NO: 865 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 865 | | |
| tgaggtgatc aaactcaaag gctacacatc | | 30 |
| | | |
| SEQ ID NO: 866 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 866 | | |
| ctatcataca gtgcttatga ggtgatcaaa | | 30 |
| | | |
| SEQ ID NO: 867 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 867 | | |
| cctatcatac agtgcttatg aggtgatcaa | | 30 |
| | | |
| SEQ ID NO: 868 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 868 | | |
| acctatggtt tcctatcata cagtgcttat | | 30 |
| | | |
| SEQ ID NO: 869 | moltype = RNA length = 30 | |
| FEATURE | Location/Qualifiers | |
| misc_feature | 1..30 | |
| | note = Synthetic | |
| source | 1..30 | |
| | mol_type = other RNA | |
| | organism = synthetic construct | |
| SEQUENCE: 869 | | | tgcctttacc tatggtttcc tatcatacag                                            30

SEQ ID NO: 870         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 870
ctgcctttac ctatggtttc ctatcataca                                            30

SEQ ID NO: 871         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 871
ggcagagagt ataatgaaga atcttaggcg                                            30

SEQ ID NO: 872         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 872
cctatggttt cctatcatac agtgcttatg                                            30

SEQ ID NO: 873         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 873
gcagagagta taatgaagaa tcttaggcgg                                            30

SEQ ID NO: 874         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 874
attatactct ctgccaaatc tgctacagag                                            30

SEQ ID NO: 875         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 875
ccaccatgat taaggtaggt ctatgtagtg                                            30

SEQ ID NO: 876         moltype = RNA   length = 30
FEATURE                Location/Qualifiers
misc_feature           1..30
                       note = Synthetic
source                 1..30
                       mol_type = other RNA
                       organism = synthetic construct
SEQUENCE: 876
caccatgatt aaggtaggtc tatgtagtga                                            30

SEQ ID NO: 877         moltype = RNA   length = 30
FEATURE                Location/Qualifiers
misc_feature           1..30
                       note = Synthetic
source                 1..30
                       mol_type = other RNA
                       organism = synthetic construct

```
SEQUENCE: 877
aggtaggtct atgtagtgat acgctgcatt                                              30

SEQ ID NO: 878          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 878
aaatgcagcg tatcactaca tagacctacc                                              30

SEQ ID NO: 879          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 879
atcatggtgg aaactgggtg cacccgccta                                              30

SEQ ID NO: 880          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 880
ttcattatac tctctgccaa atctgctaca                                              30

SEQ ID NO: 881          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 881
tactctctgc caaatctgct acagagagtc                                              30

SEQ ID NO: 882          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 882
gagtttgatc acctcataag cactgtatga                                              30

SEQ ID NO: 883          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 883
agtttgatca cctcataagc actgtatgat                                              30

SEQ ID NO: 884          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 884
tctgccttta cctatggttt cctatcatac                                              30

SEQ ID NO: 885          moltype = RNA   length = 30
FEATURE                 Location/Qualifiers
misc_feature            1..30
                        note = Synthetic
source                  1..30
                        mol_type = other RNA
```

```
                        organism = synthetic construct
SEQUENCE: 885
ggcgggtgca cccagtttcc accatgatta                                              30

SEQ ID NO: 886          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 886
ttctgccttt acctatggtt tcctatcata                                              30

SEQ ID NO: 887          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 887
atcacctcat aagcactgta tgataggaaa                                              30

SEQ ID NO: 888          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 888
gatcacctca taagcactgt atgataggaa                                              30

SEQ ID NO: 889          moltype = RNA  length = 21
FEATURE                 Location/Qualifiers
misc_feature            1..21
                        note = Synthetic
source                  1..21
                        mol_type = other RNA
                        organism = synthetic construct
SEQUENCE: 889
gaatgctttt tgctggcttt t                                                       21

SEQ ID NO: 890          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 890
aatgcttttt gctggctttt                                                         20

SEQ ID NO: 891          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 891
tgaggaagag gcccgtttga agaagagtgc                                              30

SEQ ID NO: 892          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 892
caaattaata taataactag cagctttatg                                              30

SEQ ID NO: 893          moltype = RNA  length = 30
FEATURE                 Location/Qualifiers
misc_feature            1..30
                        note = Synthetic
source                  1..30
```

```
                              mol_type = other RNA
                              organism = synthetic construct
SEQUENCE: 893
atataataac tagcagcttt atgactttat                                      30

SEQ ID NO: 894            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 894
atgactttat atcttaatat aatgaattaa                                      30

SEQ ID NO: 895            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 895
tgactttata tcttaatata atgaattaac                                      30

SEQ ID NO: 896            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 896
atatcttaat ataatgaatt aaccaaagta                                      30

SEQ ID NO: 897            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 897
tatcttaata taatgaatta accaaagtag                                      30

SEQ ID NO: 898            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 898
atataatgaa ttaaccaaag tagtcactgt                                      30

SEQ ID NO: 899            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 899
accaaagtag tcactgttca aggtttattg                                      30

SEQ ID NO: 900            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 900
aaggtttatt ggggtttta gttggtataa                                       30

SEQ ID NO: 901            moltype = RNA  length = 30
FEATURE                   Location/Qualifiers
misc_feature              1..30
                          note = Synthetic
```

```
source                  1..30
                        mol_type = other RNA
                        organism = synthetic construct
SEQUENCE: 901
attggggtt ttagttggta taacacttgg                                            30

SEQ ID NO: 902          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 902
ttggggttt tagttggtat aacacttgga                                            30

SEQ ID NO: 903          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 903
ggggttttag ttggtataac acttggatag                                           30

SEQ ID NO: 904          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 904
tagttggtat aacacttgga tagttggttg                                           30

SEQ ID NO: 905          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 905
ccaaattaat ataataacta gcagctttat                                           30

SEQ ID NO: 906          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 906
agttggtata acacttggat agttggttgc                                           30

SEQ ID NO: 907          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 907
gtataacact tggatagttg gttgcattgt                                           30

SEQ ID NO: 908          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 908
gatagttggt tgcattgttt gtatgtagat                                           30

SEQ ID NO: 909          moltype = RNA   length = 30
FEATURE                 Location/Qualifiers
misc_feature            1..30
```

```
                    note = Synthetic
source              1..30
                    mol_type = other RNA
                    organism = synthetic construct
SEQUENCE: 909
gttgcattgt ttgtatgtag atcttttac                                      30

SEQ ID NO: 910      moltype = RNA  length = 30
FEATURE             Location/Qualifiers
misc_feature        1..30
                    note = Synthetic
source              1..30
                    mol_type = other RNA
                    organism = synthetic construct
SEQUENCE: 910
cattgtttgt atgtagatct tttacatta                                      30

SEQ ID NO: 911      moltype = RNA  length = 30
FEATURE             Location/Qualifiers
misc_feature        1..30
                    note = Synthetic
source              1..30
                    mol_type = other RNA
                    organism = synthetic construct
SEQUENCE: 911
tttgtatgta gatctttta cattatatgg                                      30

SEQ ID NO: 912      moltype = RNA  length = 30
FEATURE             Location/Qualifiers
misc_feature        1..30
                    note = Synthetic
source              1..30
                    mol_type = other RNA
                    organism = synthetic construct
SEQUENCE: 912
gtatgtagat cttttacat tatatggtaa                                      30

SEQ ID NO: 913      moltype = RNA  length = 30
FEATURE             Location/Qualifiers
misc_feature        1..30
                    note = Synthetic
source              1..30
                    mol_type = other RNA
                    organism = synthetic construct
SEQUENCE: 913
tatgtagatc ttttacatt atatggtaat                                      30

SEQ ID NO: 914      moltype = RNA  length = 30
FEATURE             Location/Qualifiers
misc_feature        1..30
                    note = Synthetic
source              1..30
                    mol_type = other RNA
                    organism = synthetic construct
SEQUENCE: 914
ttacattata tggtaatgta cactactgat                                     30

SEQ ID NO: 915      moltype = RNA  length = 30
FEATURE             Location/Qualifiers
misc_feature        1..30
                    note = Synthetic
source              1..30
                    mol_type = other RNA
                    organism = synthetic construct
SEQUENCE: 915
tacattatat ggtaatgtac actactgata                                     30

SEQ ID NO: 916      moltype = RNA  length = 30
FEATURE             Location/Qualifiers
misc_feature        1..30
                    note = Synthetic
source              1..30
                    mol_type = other RNA
                    organism = synthetic construct
SEQUENCE: 916
acattatatg gtaatgtaca ctactgatat                                     30

SEQ ID NO: 917      moltype = RNA  length = 30
FEATURE             Location/Qualifiers
```

```
misc_feature              1..30
                          note = Synthetic
source                    1..30
                          mol_type = other RNA
                          organism = synthetic construct
SEQUENCE: 917
cattatatgg taatgtacac tactgatata                                    30

SEQ ID NO: 918            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 918
tatggtaatg tacactactg atatagttca                                    30

SEQ ID NO: 919            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 919
acaaaataag atcctttgga agaattatgc                                    30

SEQ ID NO: 920            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 920
ggaagaatta tgcacaagac atgatattgg                                    30

SEQ ID NO: 921            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 921
gttggtataa cacttggata gttggttgca                                    30

SEQ ID NO: 922            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 922
cccaagaata gcctaatatt tccaaattaa                                    30

SEQ ID NO: 923            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 923
cagggttgcc caagaatagc ctaatatttc                                    30

SEQ ID NO: 924            moltype = RNA  length = 30
FEATURE                   Location/Qualifiers
misc_feature              1..30
                          note = Synthetic
source                    1..30
                          mol_type = other RNA
                          organism = synthetic construct
SEQUENCE: 924
gaaaaaatcg ttgcagggtt gcccaagaat                                    30

SEQ ID NO: 925            moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 925
tttttaattg ttaccagctt ccagaggaca                                        30

SEQ ID NO: 926          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 926
ttaattgtta ccagcttcca gaggacaaga                                        30

SEQ ID NO: 927          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 927
taattgttac cagcttccag aggacaagat                                        30

SEQ ID NO: 928          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 928
aattgttacc agcttccaga ggacaagatc                                        30

SEQ ID NO: 929          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 929
attgttacca gcttccagag gacaagatct                                        30

SEQ ID NO: 930          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 930
ttaccagctt ccagaggaca agatctcaaa                                        30

SEQ ID NO: 931          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 931
ccagcttcca gaggacaaga tctcaaaaat                                        30

SEQ ID NO: 932          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 932
cagaggacaa gatctcaaaa atctgtgttc                                        30
```

```
SEQ ID NO: 933            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 933
cctatagtga cacactatca ttgcctatat                                    30

SEQ ID NO: 934            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 934
cctatattca gttggcaaat aaattttaca                                    30

SEQ ID NO: 935            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 935
agttggcaaa taaattttac atttacatat                                    30

SEQ ID NO: 936            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 936
gcaaataaat tttacattta catatagaat                                    30

SEQ ID NO: 937            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 937
tacatttaca tatagaatgt tactttccaa                                    30

SEQ ID NO: 938            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 938
acatttacat atagaatgtt actttccaat                                    30

SEQ ID NO: 939            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 939
gaagaattat gcacaagaca tgatattgga                                    30

SEQ ID NO: 940            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 940
catttacata tagaatgtta ctttccaatt                                    30
```

```
SEQ ID NO: 941            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 941
catatagaat gttactttcc aattatgatt                                          30

SEQ ID NO: 942            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 942
ctttccaatt atgattagca ttattatcaa                                          30

SEQ ID NO: 943            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 943
ccaattatga ttagcattat tatcaaatat                                          30

SEQ ID NO: 944            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 944
caattatgat tagcattatt atcaaatata                                          30

SEQ ID NO: 945            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 945
tgattagcat tattatcaaa tatataatac                                          30

SEQ ID NO: 946            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 946
gcattattat caaatatata atactttggg                                          30

SEQ ID NO: 947            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 947
ttatcaaata tataatactt tgggacttac                                          30

SEQ ID NO: 948            moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 948
```
tcaaatatat aatactttgg gacttacaat                                              30

SEQ ID NO: 949         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 949
gggacttaca atggaagtgg taccaataca                                              30

SEQ ID NO: 950         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 950
ggacttacaa tggaagtggt accaatacaa                                              30

SEQ ID NO: 951         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 951
caatggaagt ggtaccaata caactcagtt                                              30

SEQ ID NO: 952         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 952
actattacat cctctgctat tagtcaataa                                              30

SEQ ID NO: 953         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 953
catcctctgc tattagtcaa taatatccct                                              30

SEQ ID NO: 954         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 954
gtcaataata tccctgttag aaaaaatcgt                                              30

SEQ ID NO: 955         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 955
acatatagaa tgttactttc caattatgat                                              30

SEQ ID NO: 956         moltype = RNA  length = 30
FEATURE                Location/Qualifiers
misc_feature           1..30
                       note = Synthetic
source                 1..30
                       mol_type = other RNA
                       organism = synthetic construct

```
SEQUENCE: 956
tgcacaagac atgatattgg atttatacac                              30

SEQ ID NO: 957          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 957
gatttataca ctggatccca ggatgtgact                              30

SEQ ID NO: 958          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 958
atacactgga tcccaggatg tgactcactg                              30

SEQ ID NO: 959          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 959
aaacgggcct cttcctcaga agtcagagtc                              30

SEQ ID NO: 960          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 960
ctcagaagtc agagtcacct tcacaaggtc                              30

SEQ ID NO: 961          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 961
acaaggtctg agattccatt ctgtcccaaa                              30

SEQ ID NO: 962          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 962
cattctgtcc caaatgcaa ggaacactaa                               30

SEQ ID NO: 963          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 963
tgtcccaaaa tgcaaggaac actaaggaag                              30

SEQ ID NO: 964          moltype = RNA   length = 30
FEATURE                 Location/Qualifiers
misc_feature            1..30
                        note = Synthetic
source                  1..30
                        mol_type = other RNA
```

```
                       organism = synthetic construct
SEQUENCE: 964
attccgtaaa gaccctgaag atgaaatgaa                                              30

SEQ ID NO: 965          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 965
ttccgtaaag accctgaaga tgaaatgaaa                                              30

SEQ ID NO: 966          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 966
cgtaaagacc ctgaagatga aatgaaaaaa                                              30

SEQ ID NO: 967          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 967
ggacagaatg gaatctcaga ccttgtgaag                                              30

SEQ ID NO: 968          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 968
gggacagaat ggaatctcag accttgtgaa                                              30

SEQ ID NO: 969          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 969
tgggacagaa tggaatctca gaccttgtga                                              30

SEQ ID NO: 970          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 970
cattttggga cagaatggaa tctcagacct                                              30

SEQ ID NO: 971          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 971
cttgcatttt gggacagaat ggaatctcag                                              30

SEQ ID NO: 972          moltype = RNA   length = 30
FEATURE                 Location/Qualifiers
misc_feature            1..30
                        note = Synthetic
source                  1..30
```

```
                        mol_type = other RNA
                        organism = synthetic construct
SEQUENCE: 972
cttagtgttc cttgcatttt gggacagaat                                30

SEQ ID NO: 973          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 973
ttcaaacggg cctcttcctc agaagtcaga                                30

SEQ ID NO: 974          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 974
cggaataaag gatgatgtct tccttagtgt                                30

SEQ ID NO: 975          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 975
agggtcttta cggaataaag gatgatgtct                                30

SEQ ID NO: 976          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 976
atcttcaggg tctttacgga ataaaggatg                                30

SEQ ID NO: 977          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 977
catcttcagg gtctttacgg aataaaggat                                30

SEQ ID NO: 978          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 978
atttcatctt cagggtcttt acggaataaa                                30

SEQ ID NO: 979          moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 979
catttcatct tcagggtctt tacggaataa                                30

SEQ ID NO: 980          moltype = RNA   length = 30
FEATURE                 Location/Qualifiers
misc_feature            1..30
                        note = Synthetic
```

```
source                   1..30
                         mol_type = other RNA
                         organism = synthetic construct
SEQUENCE: 980
tcatttcatc ttcagggtct ttacggaata                                          30

SEQ ID NO: 981           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 981
ttcatttcat cttcagggtc tttacggaat                                          30

SEQ ID NO: 982           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 982
tttcatttca tcttcagggt ctttacggaa                                          30

SEQ ID NO: 983           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 983
ttttcatttc atcttcaggg tctttacgga                                          30

SEQ ID NO: 984           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 984
tttttcattt catcttcagg gtctttacgg                                          30

SEQ ID NO: 985           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 985
ttttttcatt tcatcttcag ggtctttacg                                          30

SEQ ID NO: 986           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 986
tttttttcat ttcatcttca gggtctttac                                          30

SEQ ID NO: 987           moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 987
tttttttt ca tttcatcttc agggtcttta                                         30

SEQ ID NO: 988           moltype = RNA   length = 30
FEATURE                  Location/Qualifiers
misc_feature             1..30
```

-continued

```
                    note = Synthetic
source              1..30
                    mol_type = other RNA
                    organism = synthetic construct
SEQUENCE: 988
ttttttttc atttcatctt cagggtcttt                                      30

SEQ ID NO: 989      moltype = RNA   length = 30
FEATURE             Location/Qualifiers
misc_feature        1..30
                    note = Synthetic
source              1..30
                    mol_type = other RNA
                    organism = synthetic construct
SEQUENCE: 989
acggaataaa ggatgatgtc ttccttagtg                                     30

SEQ ID NO: 990      moltype = RNA   length = 30
FEATURE             Location/Qualifiers
misc_feature        1..30
                    note = Synthetic
source              1..30
                    mol_type = other RNA
                    organism = synthetic construct
SEQUENCE: 990
agattgtttt taattgttac cagcttccag                                     30

SEQ ID NO: 991      moltype = RNA   length = 30
FEATURE             Location/Qualifiers
misc_feature        1..30
                    note = Synthetic
source              1..30
                    mol_type = other RNA
                    organism = synthetic construct
SEQUENCE: 991
gatccccaa agtgtatctg cactcttctt                                      30

SEQ ID NO: 992      moltype = RNA   length = 30
FEATURE             Location/Qualifiers
misc_feature        1..30
                    note = Synthetic
source              1..30
                    mol_type = other RNA
                    organism = synthetic construct
SEQUENCE: 992
tggatccccc aaagtgtatc tgcactcttc                                     30

SEQ ID NO: 993      moltype = RNA   length = 30
FEATURE             Location/Qualifiers
misc_feature        1..30
                    note = Synthetic
source              1..30
                    mol_type = other RNA
                    organism = synthetic construct
SEQUENCE: 993
tacactggat cccaggatgt gactcactgg                                     30

SEQ ID NO: 994      moltype = RNA   length = 30
FEATURE             Location/Qualifiers
misc_feature        1..30
                    note = Synthetic
source              1..30
                    mol_type = other RNA
                    organism = synthetic construct
SEQUENCE: 994
gactaggcat gttcagtgaa ggagccagga                                     30

SEQ ID NO: 995      moltype = RNA   length = 30
FEATURE             Location/Qualifiers
misc_feature        1..30
                    note = Synthetic
source              1..30
                    mol_type = other RNA
                    organism = synthetic construct
SEQUENCE: 995
agtgaaggag ccaggaagtt atataacaca                                     30

SEQ ID NO: 996      moltype = RNA   length = 30
FEATURE             Location/Qualifiers
```

```
misc_feature            1..30
                        note = Synthetic
source                  1..30
                        mol_type = other RNA
                        organism = synthetic construct
SEQUENCE: 996
tataacacac ggtaaacatc cacctggctc                                    30

SEQ ID NO: 997          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 997
gcagtggtgc gtcagaggtg gcagaactat                                    30

SEQ ID NO: 998          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 998
cacactaacc agttgaagac tacacaagat                                    30

SEQ ID NO: 999          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 999
acactaacca gttgaagact acacaagatt                                    30

SEQ ID NO: 1000         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1000
aagactacac aagattaata ccatccagca                                    30

SEQ ID NO: 1001         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1001
ataccatcca gcatcaggat atagctgtgg                                    30

SEQ ID NO: 1002         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1002
tacaaaccat tcttatttct aacttcagga                                    30

SEQ ID NO: 1003         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1003
acaaaccatt cttatttcta acttcaggag                                    30

SEQ ID NO: 1004         moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 1004
caaaccattc ttatttctaa cttcaggagt                                              30

SEQ ID NO: 1005         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1005
ttatttctaa cttcaggagt tgatgttttt                                              30

SEQ ID NO: 1006         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1006
tttctaactt caggagttga tgttttccc                                               30

SEQ ID NO: 1007         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1007
ggatccccca aagtgtatct gcactcttct                                              30

SEQ ID NO: 1008         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1008
ctaacttcag gagttgatgt ttttcccagt                                              30

SEQ ID NO: 1009         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1009
aggagttgat gttttcccca gtccatctta                                              30

SEQ ID NO: 1010         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1010
atgttttcc cagtccatct taaaatatta                                               30

SEQ ID NO: 1011         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1011
ttcccagtcc atcttaaaat attactgctt                                              30
```

```
SEQ ID NO: 1012         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1012
tcccagtcca tcttaaaata ttactgcttt                                   30

SEQ ID NO: 1013         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1013
cccagtccat cttaaaatat tactgcttta                                   30

SEQ ID NO: 1014         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1014
ccagtccatc ttaaaatatt actgctttaa                                   30

SEQ ID NO: 1015         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1015
aaatattact gctttaatca cagatcagat                                   30

SEQ ID NO: 1016         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1016
ctgctttaat cacagatcag ataaaaagga                                   30

SEQ ID NO: 1017         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1017
aatcacagat cagataaaaa ggacaacatg                                   30

SEQ ID NO: 1018         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1018
atcacagatc agataaaaag gacaacatgc                                   30

SEQ ID NO: 1019         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1019
tagcctagac agtgaaatga tatgacatca                                   30
```

```
SEQ ID NO: 1020          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1020
aaaattgcag ctccttttgg atcccccaaa                                          30

SEQ ID NO: 1021          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1021
aaattgcagc tccttttgga tcccccaaag                                          30

SEQ ID NO: 1022          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1022
cagctccttt tggatccccc aaagtgtatc                                          30

SEQ ID NO: 1023          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1023
taacttcagg agttgatgtt tttcccagtc                                          30

SEQ ID NO: 1024          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1024
tgaaggtgac tctgacttct gaggaagagg                                          30

SEQ ID NO: 1025          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1025
taggcatgag ccactgcacc ctgccttaag                                          30

SEQ ID NO: 1026          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1026
ctggcctcca gtgatcagcc cacctgggct                                          30

SEQ ID NO: 1027          moltype = RNA   length = 30
FEATURE                  Location/Qualifiers
misc_feature             1..30
                         note = Synthetic
source                   1..30
                         mol_type = other RNA
                         organism = synthetic construct
SEQUENCE: 1027
```

```
tataacttcc tggctccttc actgaacatg                                        30

SEQ ID NO: 1028         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1028
ctggctcctt cactgaacat gcctagtcca                                        30

SEQ ID NO: 1029         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1029
actgaacatg cctagtccaa catttttcc                                         30

SEQ ID NO: 1030         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1030
tttcccagtg agtcacatcc tgggatccag                                        30

SEQ ID NO: 1031         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1031
ttcccagtga gtcacatcct gggatccagt                                        30

SEQ ID NO: 1032         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1032
tcccagtgag tcacatcctg ggatccagtg                                        30

SEQ ID NO: 1033         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1033
cccagtgagt cacatcctgg gatccagtgt                                        30

SEQ ID NO: 1034         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1034
ccagtgagtc acatcctggg atccagtgta                                        30

SEQ ID NO: 1035         moltype = RNA   length = 30
FEATURE                 Location/Qualifiers
misc_feature            1..30
                        note = Synthetic
source                  1..30
                        mol_type = other RNA
                        organism = synthetic construct
```

```
SEQUENCE: 1035
tgcataattc ttccaaagga tcttattttg                                        30

SEQ ID NO: 1036         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1036
ttccaaagga tcttattttg tgaactatat                                        30

SEQ ID NO: 1037         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1037
caaaggatct tattttgtga actatatcag                                        30

SEQ ID NO: 1038         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1038
ttttgtgaac tatatcagta gtgtacatta                                        30

SEQ ID NO: 1039         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1039
tgtgaactat atcagtagtg tacattacca                                        30

SEQ ID NO: 1040         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1040
gtgaactata tcagtagtgt acattaccat                                        30

SEQ ID NO: 1041         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1041
ccgtgtgtta tataacttcc tggctccttc                                        30

SEQ ID NO: 1042         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1042
tgaactatat cagtagtgta cattaccata                                        30

SEQ ID NO: 1043         moltype = RNA   length = 30
FEATURE                 Location/Qualifiers
misc_feature            1..30
                        note = Synthetic
source                  1..30
                        mol_type = other RNA
```

```
                        organism = synthetic construct
SEQUENCE: 1043
taccaactaa aacccccaat aaaccttgaa                                30

SEQ ID NO: 1044         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1044
aacagtgact actttggtta attcattata                                30

SEQ ID NO: 1045         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1045
ggttaattca ttatattaag atataaagtc                                30

SEQ ID NO: 1046         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1046
gttaattcat tatattaaga tataaagtca                                30

SEQ ID NO: 1047         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1047
attcattata ttaagatata aagtcataaa                                30

SEQ ID NO: 1048         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1048
attatattaa gatataaagt cataaagctg                                30

SEQ ID NO: 1049         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1049
tattaagata taaagtcata aagctgctag                                30

SEQ ID NO: 1050         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1050
agatataaag tcataaagct gctagttatt                                30

SEQ ID NO: 1051         moltype = RNA  length = 30
FEATURE                 Location/Qualifiers
misc_feature            1..30
                        note = Synthetic
source                  1..30
```

```
                            mol_type = other RNA
                            organism = synthetic construct
SEQUENCE: 1051
ttatattaat ttggaaatat taggctattc                                              30

SEQ ID NO: 1052         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1052
tattaatttg gaaatattag gctattcttg                                              30

SEQ ID NO: 1053         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1053
atttggaaat attaggctat tcttgggcaa                                              30

SEQ ID NO: 1054         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1054
ggaaatatta ggctattctt gggcaaccct                                              30

SEQ ID NO: 1055         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1055
gaaatattag gctattcttg ggcaaccctg                                              30

SEQ ID NO: 1056         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1056
ggctattctt gggcaaccct gcaacgattt                                              30

SEQ ID NO: 1057         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1057
ccatataatg taaaaagatc tacatacaaa                                              30

SEQ ID NO: 1058         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1058
ttgggcaacc ctgcaacgat tttttctaac                                              30

SEQ ID NO: 1059         moltype = RNA   length = 30
FEATURE                 Location/Qualifiers
misc_feature            1..30
                        note = Synthetic
```

-continued

```
                        source          1..30
                                        mol_type = other RNA
                                        organism = synthetic construct
SEQUENCE: 1059
accgtgtgtt atataacttc ctggctcctt                                          30

SEQ ID NO: 1060         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1060
cccccttgagc caggtggatg tttaccgtgt                                         30

SEQ ID NO: 1061         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1061
gaagaagagt gcagatacac tttgggggat                                          30

SEQ ID NO: 1062         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1062
aagaagagtg cagatacact ttgggggatc                                          30

SEQ ID NO: 1063         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1063
gggggatcca aaaggagctg caattttaaa                                          30

SEQ ID NO: 1064         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1064
ggggatccaa aaggagctgc aattttaaag                                          30

SEQ ID NO: 1065         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1065
taaagtcttc tgatgtcata tcatttcact                                          30

SEQ ID NO: 1066         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1066
aaagtcttct gatgtcatat catttcactg                                          30

SEQ ID NO: 1067         moltype = RNA   length = 30
FEATURE                 Location/Qualifiers
misc_feature            1..30
```

```
                        note = Synthetic
source                  1..30
                        mol_type = other RNA
                        organism = synthetic construct
SEQUENCE: 1067
aagtcttctg atgtcatatc atttcactgt                                    30

SEQ ID NO: 1068         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1068
tgatgtcata tcatttcact gtctaggcta                                    30

SEQ ID NO: 1069         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1069
cactgtctag gctacaacag gattctaggt                                    30

SEQ ID NO: 1070         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1070
actgtctagg ctacaacagg attctaggtg                                    30

SEQ ID NO: 1071         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1071
taggtggagg ttgtgcatgt tgtccttttt                                    30

SEQ ID NO: 1072         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1072
tgcatgttgt ccttttatc tgatctgtga                                     30

SEQ ID NO: 1073         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1073
tccttttat ctgatctgtg attaaagcag                                     30

SEQ ID NO: 1074         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1074
ttatctgatc tgtgattaaa gcagtaatat                                    30

SEQ ID NO: 1075         moltype = RNA   length = 30
FEATURE                 Location/Qualifiers
```

```
misc_feature              1..30
                          note = Synthetic
source                    1..30
                          mol_type = other RNA
                          organism = synthetic construct
SEQUENCE: 1075
agccaggtgg atgtttaccg tgtgttatat                                    30

SEQ ID NO: 1076           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1076
tatctgatct gtgattaaag cagtaatatt                                    30

SEQ ID NO: 1077           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1077
tctgatctgt gattaaagca gtaatatttt                                    30

SEQ ID NO: 1078           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1078
aagcagtaat attttaagat ggactgggaa                                    30

SEQ ID NO: 1079           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1079
taagatggac tgggaaaaac atcaactcct                                    30

SEQ ID NO: 1080           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1080
aagatggact gggaaaaaca tcaactcctg                                    30

SEQ ID NO: 1081           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1081
agatggactg ggaaaaacat caactcctga                                    30

SEQ ID NO: 1082           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1082
gaaataagaa tggtttgtaa aatccacagc                                    30

SEQ ID NO: 1083           moltype = RNA   length = 30
```

-continued

```
FEATURE                 Location/Qualifiers
misc_feature            1..30
                        note = Synthetic
source                  1..30
                        mol_type = other RNA
                        organism = synthetic construct
SEQUENCE: 1083
gtaaatccca cagctatatc ctgatgctgg                                          30

SEQ ID NO: 1084         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1084
taaaatccac agctatatcc tgatgctgga                                          30

SEQ ID NO: 1085         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1085
atcttgtgta gtcttcaact ggttagtgtg                                          30

SEQ ID NO: 1086         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1086
tgtagtcttc aactggttag tgtgaaatag                                          30

SEQ ID NO: 1087         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1087
aactggttag tgtgaaatag ttctgccacc                                          30

SEQ ID NO: 1088         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1088
gtgtgaaata gttctgccac ctctgacgca                                          30

SEQ ID NO: 1089         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1089
tgccacctct gacgcaccac tgccaatgct                                          30

SEQ ID NO: 1090         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1090
gccccttgag ccaggtggat gtttaccgtg                                          30
```

```
SEQ ID NO: 1091           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1091
atctgatctg tgattaaagc agtaatattt                                    30

SEQ ID NO: 1092           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1092
ccaaagtgct gggattatag gcatgagcca                                    30

SEQ ID NO: 1093           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1093
ggcaaccctg caacgatttt ttctaacagg                                    30

SEQ ID NO: 1094           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1094
ttctaacagg gatattattg actaatagca                                    30

SEQ ID NO: 1095           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1095
tcagaaaaat gtgcagaaaa cttgagtaga                                    30

SEQ ID NO: 1096           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1096
cagaaaaatg tgcagaaaac ttgagtagac                                    30

SEQ ID NO: 1097           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1097
agaaaaatgt gcagaaaact tgagtagaca                                    30

SEQ ID NO: 1098           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1098
agtagacatc caccaaggtt acttgttttt                                    30
```

```
SEQ ID NO: 1099           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1099
cttgtttttt ttggttttgt tttgttttt                                    30

SEQ ID NO: 1100           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1100
ttttttttgg ttttgttttg ttttttaac                                    30

SEQ ID NO: 1101           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1101
tttttggttt tgttttgttt ttttaacaga                                   30

SEQ ID NO: 1102           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1102
ttttggtttt gttttgtttt tttaacagat                                   30

SEQ ID NO: 1103           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1103
tttggttttg ttttgttttt ttaacagatg                                   30

SEQ ID NO: 1104           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1104
ttggttttgt ttgtttttt taacagatgg                                    30

SEQ ID NO: 1105           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1105
tggttttgtt ttgttttttt aacagatggg                                   30

SEQ ID NO: 1106           moltype = RNA   length = 30
FEATURE                   Location/Qualifiers
misc_feature              1..30
                          note = Synthetic
source                    1..30
                          mol_type = other RNA
                          organism = synthetic construct
SEQUENCE: 1106
```

```
ggttttgttt tgttttttta acagatgggg                                    30

SEQ ID NO: 1107         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1107
gttttgtttt gtttttttaa cagatggggt                                    30

SEQ ID NO: 1108         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1108
tgttttgttt ttttaacaga tggggttttg                                    30

SEQ ID NO: 1109         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1109
tattttcaga aaaatgtgca gaaaacttga                                    30

SEQ ID NO: 1110         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1110
gttttgtttt tttaacagat ggggttttgt                                    30

SEQ ID NO: 1111         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1111
tgtttttta acagatgggg ttttgttgtg                                     30

SEQ ID NO: 1112         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1112
gttttttaa cagatgggt tttgttgtgt                                      30

SEQ ID NO: 1113         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1113
ttttttaac agatggggtt ttgttgtgtt                                     30

SEQ ID NO: 1114         moltype = RNA   length = 30
FEATURE                 Location/Qualifiers
misc_feature            1..30
                        note = Synthetic
source                  1..30
                        mol_type = other RNA
                        organism = synthetic construct
```

```
SEQUENCE: 1114
ttttaacaga tggggttttg ttgtgttggc                                            30

SEQ ID NO: 1115         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1115
tttaacagat ggggttttgt tgtgttggcc                                            30

SEQ ID NO: 1116         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1116
ttaacagatg ggttttgtt gtgttggcca                                             30

SEQ ID NO: 1117         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1117
taacagatgg ggttttgttg tgttggccag                                            30

SEQ ID NO: 1118         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1118
aacagatggg gttttgttgt gttggccagg                                            30

SEQ ID NO: 1119         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1119
acagatgggg ttttgttgtg ttggccaggc                                            30

SEQ ID NO: 1120         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1120
tgttgtgttg gccaggctgg tccccaattc                                            30

SEQ ID NO: 1121         moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 1121
gttgtgttgg ccaggctggt ccccaattcc                                            30

SEQ ID NO: 1122         moltype = RNA  length = 30
FEATURE                 Location/Qualifiers
misc_feature            1..30
                        note = Synthetic
source                  1..30
                        mol_type = other RNA
```

```
                        organism = synthetic construct
SEQUENCE: 1122
ttgtgttggc caggctggtc cccaattcct                                        30

SEQ ID NO: 1123         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1123
tgttggccag gctggtcccc aattcctggc                                        30

SEQ ID NO: 1124         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1124
gccaggctgg tccccaattc ctggcctcca                                        30

SEQ ID NO: 1125         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1125
ttttgttttt ttaacagatg gggttttgtt                                        30

SEQ ID NO: 1126         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1126
tttctaacag ggatattatt gactaatagc                                        30

SEQ ID NO: 1127         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1127
tgcacatttt tctgaaaata caactgtgac                                        30

SEQ ID NO: 1128         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1128
tctgcacatt tttctgaaaa tacaactgtg                                        30

SEQ ID NO: 1129         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1129
tctaacaggg atattattga ctaatagcag                                        30

SEQ ID NO: 1130         moltype = RNA   length = 30
FEATURE                 Location/Qualifiers
misc_feature            1..30
                        note = Synthetic
source                  1..30
```

```
                        mol_type = other RNA
                        organism = synthetic construct
SEQUENCE: 1130
ctaacaggga tattattgac taatagcaga                                      30

SEQ ID NO: 1131         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1131
taacagggat attattgact aatagcagag                                      30

SEQ ID NO: 1132         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1132
ttgactaata gcagaggatg taatagtcaa                                      30

SEQ ID NO: 1133         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1133
actaatagca gaggatgtaa tagtcaactg                                      30

SEQ ID NO: 1134         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1134
tattggtacc acttccattg taagtcccaa                                      30

SEQ ID NO: 1135         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1135
gtaccacttc cattgtaagt cccaaagtat                                      30

SEQ ID NO: 1136         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1136
cattgtaagt cccaaagtat tatatatttg                                      30

SEQ ID NO: 1137         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1137
taagtcccaa agtattatat atttgataat                                      30

SEQ ID NO: 1138         moltype = RNA   length = 30
FEATURE                 Location/Qualifiers
misc_feature            1..30
                        note = Synthetic
```

```
source                   1..30
                         mol_type = other RNA
                         organism = synthetic construct
SEQUENCE: 1138
tatatttgat aataatgcta atcataattg                                30

SEQ ID NO: 1139          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1139
gataataatg ctaatcataa ttggaaagta                                30

SEQ ID NO: 1140          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1140
ataataatgc taatcataat tggaaagtaa                                30

SEQ ID NO: 1141          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1141
gaaagtaaca ttctatatgt aaatgtaaaa                                30

SEQ ID NO: 1142          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1142
tatatgtaaa tgtaaaattt atttgccaac                                30

SEQ ID NO: 1143          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1143
ctgcacattt ttctgaaaat acaactgtga                                30

SEQ ID NO: 1144          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1144
atttgccaac tgaatatagg caatgatagt                                30

SEQ ID NO: 1145          moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 1145
gccaactgaa tataggcaat gatagtgtgt                                30

SEQ ID NO: 1146          moltype = RNA  length = 30
FEATURE                  Location/Qualifiers
misc_feature             1..30
```

-continued

```
                        note        = Synthetic
source                  1..30
                        mol_type    = other RNA
                        organism    = synthetic construct
SEQUENCE: 1146
ccaactgaat ataggcaatg atagtgtgtc                                           30

SEQ ID NO: 1147         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1147
ttgagatctt gtcctctgga agctggtaac                                           30

SEQ ID NO: 1148         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1148
tgagatcttg tcctctggaa gctggtaaca                                           30

SEQ ID NO: 1149         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1149
gagatcttgt cctctggaag ctggtaacaa                                           30

SEQ ID NO: 1150         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1150
agatcttgtc ctctggaagc tggtaacaat                                           30

SEQ ID NO: 1151         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1151
tcctctggaa gctggtaaca attaaaaaca                                           30

SEQ ID NO: 1152         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1152
aaaacaatct taaggcaggg tgcagtggct                                           30

SEQ ID NO: 1153         moltype = RNA   length = 30
FEATURE                 Location/Qualifiers
misc_feature            1..30
                        note        = Synthetic
source                  1..30
                        mol_type    = other RNA
                        organism    = synthetic construct
SEQUENCE: 1153
aggcagggtg cagtggctca tgcctataat                                           30

SEQ ID NO: 1154         moltype = RNA   length = 30
FEATURE                 Location/Qualifiers
```

```
misc_feature            1..30
                        note = Synthetic
source                  1..30
                        mol_type = other RNA
                        organism = synthetic construct
SEQUENCE: 1154
gggaagccca ggtgggctga tcactggagg                                    30

SEQ ID NO: 1155         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1155
ggaagcccag gtgggctgat cactggaggc                                    30

SEQ ID NO: 1156         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1156
gggaccagcc tggccaacac aacaaaaccc                                    30

SEQ ID NO: 1157         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1157
aaaaaacaaa acaaaaccaa aaaaaacaag                                    30

SEQ ID NO: 1158         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1158
gtggatgtct actcaagttt tctgcacatt                                    30

SEQ ID NO: 1159         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1159
tttgccaact gaatataggc aatgatagtg                                    30

SEQ ID NO: 1160         moltype = RNA   length = 30
FEATURE                 Location/Qualifiers
misc_feature            1..30
                        note = Synthetic
source                  1..30
                        mol_type = other RNA
                        organism = synthetic construct
SEQUENCE: 1160
gtgttccttg cattttggga cagaatggaa                                    30

SEQ ID NO: 1161         moltype = RNA   length = 26
FEATURE                 Location/Qualifiers
misc_feature            1..26
                        note = Synthetic
source                  1..26
                        mol_type = other RNA
                        organism = synthetic construct
SEQUENCE: 1161
ttctgaaaat acaactgtga ccctta                                        26

SEQ ID NO: 1162         moltype = RNA   length = 25
```

```
FEATURE                 Location/Qualifiers
misc_feature            1..25
                        note = Synthetic
source                  1..25
                        mol_type = other RNA
                        organism = synthetic construct
SEQUENCE: 1162
tctgaaaata caactgtgac cctta                                            25

SEQ ID NO: 1163         moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 1163
ctgaaaatac aactgtgacc ctta                                             24

SEQ ID NO: 1164         moltype = RNA  length = 23
FEATURE                 Location/Qualifiers
misc_feature            1..23
                        note = Synthetic
source                  1..23
                        mol_type = other RNA
                        organism = synthetic construct
SEQUENCE: 1164
tgaaaataca actgtgaccc tta                                              23

SEQ ID NO: 1165         moltype = DNA  length = 3162
FEATURE                 Location/Qualifiers
misc_feature            1..3162
                        note = Synthetic
source                  1..3162
                        mol_type = other DNA
                        organism = synthetic construct
SEQUENCE: 1165
atgagcagcg cgatcaaaag ctacaagagc gttctgcgtc cgaacgagcg taagaaccaa        60
ctgctgaaaa gcaccattca gtgcctgaaa gacggtagcg cgttctttttt caagatgctg       120
caaggcctgt ttggtggcat caccccggag attgttcgtt tcagcaccga acaggagaaa       180
cagcaacagg atatcgcgct gtggtgcgcg gttaactggt tccgtccggt gagccaagac       240
agcctgaccc acaccattgc gagcgataac ctggtggaga gtttgaggaa atactatggt       300
ggcaccgcga gcgacgcgat caaacagtac ttcagcgcga gcattggcga aagctactac       360
tggaacgact gccgtcaaca gtactatgat ctgtgccgtg agctgggtgt tgaggtgagc       420
gacctgaccc atgatctgga gatcctgtgc cgtgaaaagt gcctggcggt tgcgaccgag       480
agcaaccaga caacagcat cattagcgtt ctgtttggca ccggcgaaaa agaggaccgt        540
agcgtgaaac tgcgtatcac caagaaaatt ctggaggcga tcagcaacct gaaagaaatc       600
ccgaagaacg ttgcgccgat tcaagagatc attctgaacg tggcgaaagc gaccaaggaa       660
accttccgtc aggtgtatgc gggtaacctg ggtcgcgccga gcaccctgga gaaatttatc       720
gcgaaggacg gccaaaaaga gttcgatctg aagaaactgc agaccgacct gaagaaagtt       780
attcgtggta aaagcaagga gcgtgattgg tgctgccaag aagagctgcg tagctacgtg       840
gagcaaaaaca ccatccagta tgacctgtgg gcgtggggcg aaatgttcaa caaagcgcac       900
accgcgctga aaatcaagag cacccgtaac tacaactttg cgaagcaacg tctgaacag        960
ttcaaagaga ttcagagcct gaacaacctg ctggttgtga agaagctgaa cgactttttc      1020
gatagcgaat ttttcagcgg cgaggaaacc tacaccatct gcgttcacca tctgggtggt      1080
aaggacctga gcaaactgta taggcgtggg gaggatgatc cggcggaccc ggaaaacgcg      1140
attgtggttc tgtgcgacga tctgaaaaac aactttaaga aagagccgat ccgtaacatt      1200
ctgcgttaca tcttcaccat tcgtcaagaa tgcagcgcgc aggacatcct ggcggcggcg      1260
aagtacaacc aacagctgga tcgttataaa agccaaaagg cgaaacccga cgttctgggt      1320
aaccagggct ttacctggac caacgcggtg atcctgccgg agaaggcga gcgtaacgac      1380
cgtccgaaca gcctggatct gcgtatttgg ctgtacctga aactgcgtca cccggacggt      1440
cgttggaaga acaccatat cccgttctac gataccgtt tcttccaaga atttatgcg        1500
gcgggcaaca gcccggttga cacctgccag tttcgtaccc gcgtttcgg ttatcacctg      1560
ccgaaactga ccgatcagac cgcgatccgt gttaacaaga aacatgtgaa agcggcgaag      1620
accgaggcgc gtattcgtct ggcgatccaa cagggcaccc tgccggtgag caacctgaag      1680
atcaccgaaa ttagcgcgac catcaacagc aaaggtcaag tgcgtattcc ggttaagttt      1740
gacgtgggtc gtcaaaaagg caccctgcag atcggtgacc gttctgcgg ctacgatcaa       1800
aaccagaccg cgagccacgc gtatagcctg tgggaagtgg ttaaagaggg tcaataccat      1860
aaagctgg gctgctttgt tcgtttcatc agcagcggtg acatcgtgag cattaccgtg       1920
aaccgtggca accaatttga tcagctgagc tatgaaggtc tggcgtaccc gcaatatgcg      1980
gactggcgta agaaagcgag caagttcgtg agcctgtggc agatcaccaa gaaaacaag       2040
aaaaaggaaa tcgtgaccgt tgaagcgaaa gagaagtttg acgcgatctg caagtaccag      2100
ccgcgtctgt ataaattcaa caaggagtac gcgtatctgc tgcgtgatat tgttcgtggc      2160
aaaaagctgg tggaactgca acagattcgt caagagatct ttcgtttcat tgaacaggac      2220
tgcggtgtta cccgtctggg cagcctgagc ctgagcaccc tggaaaccgt gaaagcggtt      2280
aagggtatca tttacagcta tttttagcacc gcgctgaacg cgagcaagaa caacccgatc      2340
agcgacgaac agcgtaaaga gtttgatccg gaactgttcg cgctgctgga aaagctggaa      2400
ctgattcgta cccgtaaaaa gaaacaaaaa gtggaacgta tcgcgaacag cctgattcag      2460
acctgcctgg agaacaacat caagttcatt cgtggtgaag cgacctgag caccaccaac      2520
```

| | | | | | |
|---|---|---|---|---|---|
| aacgcgacca | agaaaaaggc | gaacagccgt | agcatggatt | ggttggcgcg | tggtgttttt | 2580 |
| aacaaaatcc | gtcaactggc | gccgatgcac | aacattaccc | tgttcggttg | cggcagcctg | 2640 |
| tacaccagcc | accaggaccc | gctggtgcat | cgtaacccgg | ataaagcgat | gaagtgccgt | 2700 |
| tgggcggcga | tcccggttaa | ggacattggc | gattgggtgc | tgcgtaagct | gagccaaaac | 2760 |
| ctgcgtgcga | aaaacatcgg | caccgcgagc | tactatcacc | aaggtgttaa | agagttcctg | 2820 |
| agccattatg | aactgcagga | cctggaggaa | gagctgctga | gtggcgtag | cgatcgtaaa | 2880 |
| agcaacattc | cgtgctgggt | gctgcagaac | cgtctggcgg | agaagctggg | caacaaagaa | 2940 |
| gcggtggttt | acatcccggt | tcgtggtggc | cgtatttatt | ttgcgaccca | aaggtggcg | 3000 |
| accggtgcgg | tgagcatcgt | tttcgaccaa | aaacaagtgt | gggtttgcaa | cgcggatcat | 3060 |
| gttgcgcggg | cgaacatcgc | gctgaccgtg | aagggtattg | gcgaacaaag | cagcgacgaa | 3120 |
| gagaacccgg | atggtagccg | tatcaaactg | cagctgacca | gc | | 3162 |

```
SEQ ID NO: 1166          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1166
MSSAIKSYKS VLRPNERKNQ LLKSTIQCLE DGSAFFFKML QGLFGGITPE IVRFSTEQEK   60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF DVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNIGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH 1020
VAAANIALTV KGIGEQSSDE ENPDGSRIKL QLTS                             1054

SEQ ID NO: 1167          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1167
MSSAIKSYKS VLRPNERKNQ LLKSTIQCLE DGSAFFFKML QGLFGGITPE IVRFSTEQEK   60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG RWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH 1020
VAAANIALTG KGIGEQSSDE ENPDGSRIKL QLTS                             1054

SEQ ID NO: 1168          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1168
MSSAIKSYKS VLRPNERKNQ LLKSTIQCLE DGSAFFFKML QGLFGGITPE IVRFSTEQEK   60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
```

```
TALKIKSTRN YNFAKQRLEQ FKEIQSLNNL LVVKKLNDFF DSEFFSGEET YTICVHHLGG    360
KDLSKLYKAW EDDPADPENA IVVLCDDLKN NFKKEPIRNI LRYIFTIRQE CSAQDILAAA    420
KYNQQLDRYK SQKANPSVLG NQGFTWTNAV ILPEKAQRND RPNSLDLRIW LYLKLRHPDG    480
RWKKHHIPFY DTRFFQEIYA AGNSPVDTCQ FRTPRFGYHL PKLTDQTAIR VNKKHVKAAK    540
TEARIRLAIQ QGTLPVSNLK ITEISATINS KGQVRIPVKF RVGRQKGTLQ IGDRFCGYDQ    600
NQTASHAYSL WEVVKEGQYH KELGCFVRFI SSGDIVSITE NRGNQFDQLS YEGLAYPQYA    660
DWRKKASKFV SLWQITKKNK KKEIVTVEAK EKFDAICKYQ PRLYKFNKEY AYLLRDIVRG    720
KSLVELQQIR QEIFRFIEQD CGVTRLGSLS LSTLETVKAV KGIIYSYFST ALNASKNNPI    780
SDEQRKEFDP ELFALLEKLE LIRTRKKKQK VERIANSLIQ TCLENNIKFI RGEGDLSTTN    840
NATKKKANSR SMDWLARGVF NKIRQLAPMH NITLFGCGSL YTSHQDPLVH RNPDKAMKCR    900
WAAIPVKDIG DWVLRKLSQN LRAKNRGTGE YYHQGVKEFL SHYELQDLEE ELLKWRSDRK    960
SNIPCWVLQN RLAEKLGNKE AVVYIPVRGG RIYFATHKVA TGAVSIVFDQ KQVWVCNADH   1020
VAAANIALTG KGIGEQSSDE ENPDGSRIKL QLTS                              1054

SEQ ID NO: 1169          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1169
MSSAIKSYKS VLRPNERKNQ LLKSTIQCLE DGSAFFFKML QGLFGGITPE IVRFSTEQEK     60
QQQDIALWCA VNWFRPVSQD SLTHTIASDN LVEKFEEYYG GTASDAIKQY FSASIGESYY    120
WNDCRQQYYD LCRELGVEVS DLTHDLEILC REKCLAVATE SNQNNSIISV LFGTGEKEDR    180
SVKLRITKKI LEAISNLKEI PKNVAPIQEI ILNVAKATKE TFRQVYAGNL GAPSTLEKFI    240
AKDGQKEFDL KKLQTDLKKV IRGKSKERDW CCQEELRSYV EQNTIQYDLW AWGEMFNKAH    300
TALKIKSTRN YNFAKQRLEQ FKEIQSLNNL LVVKKLNDFF DSEFFSGEET YTICVHHLGG    360
KDLSKLYKAW EDDPADPENA IVVLCDDLKN NFKKEPIRNI LRYIFTIRQE CSAQDILAAA    420
KYNQQLDRYK SQKANPSVLG NQGFTWTNAV ILPEKAQRND RPNSLDLRIW LYLKLRHPDG    480
RWKKHHIPFY DTRFFQEIYA AGNSPVDTCQ FRTPRFGYHL PKLTDQTAIR VNKKHVKAAK    540
TEARIRLAIQ QGTLPVSNLK ITEISATINS KGQVRIPVKF RVGRQKGTLQ IGDRFCGYDQ    600
NQTASHAYSL WEVVKEGQYH KELGCFVRFI SSGDIVSITE NRGNQFDQLS YEGLAYPQYA    660
DWRKKASKFV SLWQITKKNK KKEIVTVEAK EKFDAICKYQ PRLYKFNKEY AYLLRDIVRG    720
KSLVELQQIR QEIFRFIEQD CGVTRLGSLS LSTLETVKAV KGIIYSYFST ALNASKNNPI    780
SDEQRKEFDP ELFALLEKLE LIRTRKKKQK VERIANSLIQ TCLENNIKFI RGEGDLSTTN    840
NATKKKANSR SMDWLARGVF NKIRQLAPMH NITLFGCGSL YTSHQDPLVH RNPDKAMKCR    900
WAAIPVKDIG DWVLRKLSQN LRAKNRGTGE YYHQGVKEFL SHYELQDLEE ELLKWRSDRK    960
SNIPCWVLQN RLAEKLGNKE AVVYIPVRGG RIYFATHKVA TGAVSIVFDQ KQVWVCNADH   1020
VAAANIALTG KGIGEQSSDE ENPDGGRIKL QLTS                              1054

SEQ ID NO: 1170          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1170
MSSAIKSYKS VLRPNERKNQ LLKSTIQCLE DGSAFFFKML QGLFGGITPE IVRFSTEQEK     60
QQQDIALWCA VNWFRPVSQD SLTHTIASDN LVEKFEEYYG GTASDAIKQY FSASIGESYY    120
WNDCRQQYYD LCRELGVEVS DLTHDLEILC REKCLAVATE SNQNNSIISV LFGTGEKEDR    180
SVKLRITKKI LEAISNLKEI PKNVAPIQEI ILNVAKATKE TFRQVYAGNL GAPSTLEKFI    240
AKDGQKEFDL KKLQTDLKKV IRGKSKERDW CCQEELRSYV EQNTIQYDLW AWGEMFNKAH    300
TALKIKSTRN YNFAKQRLEQ FKEIQSLNNL LVVKKLNDFF DSEFFSGEET YTICVHHLGG    360
KDLSKLYKAW EDDPADPENA IVVLCDDLKN NFKKEPIRNI LRYIFTIRQE CSAQDILAAA    420
KYNQQLDRYK SQKANPSVLG NQGFTWTNAV ILPEKAQRND RPNSLDLRIW LYLKLRHPDG    480
RWKKHHIPFY DTRFFQEIYA AGNSPVDTCQ FRTPRFGYHL PKLTDQTAIR VNKKHVKAAK    540
TEARIRLAIQ QGTLPVSNLK ITEISATINS KGQVRIPVKF RVGRQKGTLQ IGDRFCGYDQ    600
NQTASHAYSL WEVVKEGQYH KELRCRVRFI SSGDIVSITE NRGNQFDQLS YEGLAYPQYA    660
DWRKKASKFV SLWQITKKNK KKEIVTVEAK EKFDAICKYQ PRLYKFNKEY AYLLRDIVRG    720
KSLVELQQIR QEIFRFIEQD CGVTRLGSLS LSTLETVKAV KGIIYSYFST ALNASKNNPI    780
SDEQRKEFDP ELFALLEKLE LIRTRKKKQK VERIANSLIQ TCLENNIKFI RGEGDLSTTN    840
NATKKKANSR SMDWLARGVF NKIRQLAPMH NITLFGCGSL YTSHQDPLVH RNPDKAMKCR    900
WAAIPVKDIG DWVLRKLSQN LRAKNRGTGE YYHQGVKEFL SHYELQDLEE ELLKWRSDRK    960
SNIPCWVLQN RLAEKLGNKE AVVYIPVRGG RIYFATHKVA TGAVSIVFDQ KQVWVCNADH   1020
VAAANIALTG KGIGRQSSDE ENPDGGRIKL QLTS                              1054

SEQ ID NO: 1171          moltype = AA  length = 1054
FEATURE                  Location/Qualifiers
REGION                   1..1054
                         note = Synthetic
source                   1..1054
                         mol_type = protein
                         organism = synthetic construct
SEQUENCE: 1171
MSSAIKSYKS VLRPNERKNQ LLKSTIQCLE DGSAFFFKML QGLFGGITPE IVRFSTEQEK     60
QQQDIALWCA VNWFRPVSQD SLTHTIASDN LVEKFEEYYG GTASDAIKQY FSASIGESYY    120
WNDCRQQYYD LCRELGVEVS DLTHDLEILC REKCLAVATE SNQNNSIISV LFGTGEKEDR    180
```

```
SVKLRITKKI LEAISNLKEI PKNVAPIQEI ILNVAKATKE TFRQVYAGNL GAPSTLEKFI    240
AKDGQKEFDL KKLQTDLKKV IRGKSKERDW CCQEELRSYV EQNTIQYDLW AWGEMFNKAH    300
TALKIKSTRN YNFAKQRLEQ FKEIQSLNNL LVVKKLNDFF DSEFFSGEET YTICVHHLGG    360
KDLSKLYKAW EDDPADPENA IVVLCDDLKN NFKKEPIRNI LRYIFTIRQE CSAQDILAAA    420
KYNQQLDRYK SQKANPSVLG NQGFTWTNAV ILPEKAQRND RPNSLDLRIW LYLKLRHPDG    480
RWKKHHIPFY DTRFFQEIYA AGNSPVDTCQ FRTPRFGYHL PKLTDQTAIR VNKKHVKAAK    540
TEARIRLAIQ QGTLPVSNLK ITEISATINS KGQVRIPVKF RVGRQKGTLQ IGDRFCGYDQ    600
NQTASHAYSL WEVVKEGQYH KELRCRVRFI SSGDIVSITE NRGNQFDQLS YEGLAYPQYA    660
DWRKKASKFV SLWQITKKNK KKEIVTVEAK EKFDAICKYQ PRLYKFNKEY AYLLRDIVRG    720
KSLVELQQIR QEIFRFIEQD CGVTRLGSLS LSTLETVKAV KGIIYSYFST ALNASKNNPI    780
SDEQRKEFDP ELFALLEKLE LIRTRKKKQK VERIANSLIQ TCLENNIKFI RGEGDLSTTN    840
NATKKKANSR SMDWLARGVF NKIRQLATMH NITLFGCGSL YTSHQDPLVH RNPDKAMKCR    900
WAAIPVKDIG DWVLRKLSQN LRAKNRGTGE YYHQGVKEFL SHYELQDLEE ELLKWRSDRK    960
SNIPCWVLQN RLAEKLGNKE AVVYIPVRGG RIYFATHKVA TGAVSIVFDQ KQVWVCNADH   1020
VAAANIALTG KGIGRQSSDE ENPDGGRIKL QLTS                               1054

SEQ ID NO: 1172         moltype = DNA  length = 13863
FEATURE                 Location/Qualifiers
misc_feature            1..13863
                        note = Synthetic
source                  1..13863
                        mol_type = other DNA
                        organism = synthetic construct
SEQUENCE: 1172
gtgctgcagc cgctgccgcc gattccggat ctcattgcca cgcgccccg acgaccgccc      60
gacgtgcatt cccggtacgg tagggccctg cgcgcacggc gccagaggga tgggcgggta    120
gagccaactg cctctggttc tgctggcctc cgctgctcgc gaagggattc ctgctcccgg    180
gaggtgtagg agccgctttc cagaagcaca gcccagagac gtctgggcgg cggcccacac    240
aacgcatgtg ttcggagctc gccgcgctct gcttttgctc taagcgggaa ccatggcttc    300
tggccacgct ggggaaccga ggaggtggcc gcacccaggc gcacccaggc agcccgggtg    360
gatgcggaac aaggatatga taggccttaa gggtgggga tacctctggg ctcgaaatcg    420
gcgggcggtg caaaactcga ggtccagttc tcggagccca tagagccaaa aaagcctcag    480
cttgtccggg gcgggttctt gaaagacgga aagcggctga gtaccacgcg gcttgcattt    540
ttctcttggg acgctcgaga ggtgggctcc gtgagggcag ctgctgcctg cagattatag    600
ggagccctt gcgcatttat taagaagcta ctggtgtatc tcgggctgcg ctaggcacgg    660
cgcatgcaaa gatgaagcag gcagcatccc agcccttccg cacctcagac ggtcagttga    720
gtaggatccg ccggtaccaa ctcctccttt taacaaatag ggagaccgaa agctaggaga    780
cagtcaggga tctctaagtt cccagtgagt aggaggcaga ggtgaggtgt agaactcgtt    840
tttgcatgtc tctcgcctct agacgcaccc ttccctcatc ccatgccctc ccacctccgg    900
ccctacatta aaggtagcat tggatcccgg ggccgttcag tgaagctagc aggtgtccgc    960
aggaactccc ttcccctgc caggctagaa accttacaag gctgtctaga aatagcagtg   1020
atttgtaagg agagacccgg ctccagcttg gtgactctgg gctgactgcc tgcctagagg   1080
tcctctcgga ttttttgccct ttggagtggt gtcaaaacta gacgtgatac tttggggatg   1140
cagcctgtga tatttcctcc agcgaatgca gtgcagggtt ggattaacaa ggtggaaaga   1200
attcgagggt tccaccaagt agctattaac tctagggctg caggcctcag gccttctgca   1260
gctatttcta cactccctgt actgaaacta tttcttcata ctgggcctga caggcctttg   1320
caacaaggat cacggccgaa gccacaccgt gcgcctccct ccggttggt taacaggccc   1380
tggtttctag tattgcgatt taaagtctgg cgctggctgc gcgccagacc tgggaggctg   1440
ccagctaggc ttcacgttgc tggcgtctgc ttcggggcat tcattaggtc tgaagtctga   1500
atcccagctc cctccctctc acccactgag ctgcatagct ccagattgcc tctgcttacg   1560
ggcggggctt ctcagcttc tgccttctgg cccgatgccc gcttcccaac ggccggaggc   1620
cgctagacta atcggcttcg ccctgcgcgc tgtaatgcgc atgcgcacgc gcacaagttc   1680
ctgggcccgc ccatcttccg gacttgggcg gggcgtaaaa gccgggcgtt cggaggaccc   1740
agcaattagt ctgatttccg cccacctttc cgagcgggaa ggagagccac aaagcgcgca   1800
tgcgcgcgga tcaccgcagg ctcctgtgcc ttgggcttga gctttgtggc agttaatggc   1860
ttttctgcac gtatctctgg tgtttacttg agaagcctgg ctgtgtcctt gctgtaggag   1920
ccggagtagc tcagagtgat cttgtctgag gaaaggccag cccacttgg ggttaataaa    1980
ccgcgatggg tgaaccctca ggaggctata cttacaccca aacgtcgata ttccttttcc   2040
acgctaaggt atgggccttc actcttcaca gaccctgtca ttaggccttt caactctctt   2100
ttggcaacca ttaggttttt tcccctcct tttagtcat ctctagtgat ttatagtggc     2160
aaatacccc aaaggaagta aaatagctta aaaaaatctc ttggttaata aacattaaag    2220
aagctgtagt gacactaaat gttttcctc ctatagattc cttttggttc caagtccaat    2280
atggcaactc taaaggatca gctgatttat aatcttctaa aggaagaaca gaccccccag   2340
aataagatta cagttgttgg ggttggtgct gttggcattgg cctgtgccat cagtatctta   2400
atgaaggtaa gtgagagtct accacactgg aagcccatac cttgacccca tcctctaccc   2460
ccactcctac cctagaact gtattattac atttcatgta acagtatta gatttatgca     2520
ctcattcgga taactttctg tgaaacaaac ttttgaaata tgataataca ccaaaagtgt   2580
atctgaaatt aaaaagaatc aaaggttgtc aggctggaga ccccgttcct aaaattcatt   2640
attctgtatt aacatgcatg gattgactac caatgaaaag gaagggtcca tgattttaaa   2700
tgagccaaaa ttcttttaaa gtgatttttg aattgaaaat gacaattcaa aaattgtcat   2760
ttattggtaa aattatatgg gaaatcataa gttctcccac tcaaatctca ttgccctgt    2820
gccttgata gcaattttgt tatcaattat ggagctaaaa tttaattaga aaaagaaat     2880
tgtgagtaaa gcactcctta ttcacactatt gaaagctgat ttatatttaa agaaattga   2940
ggcagcttac aacattaaaa tgtctgaggc ggggcacagt ggctcatgcc tgtaatgcca   3000
gcactttagg aggctgaggt gggtggatca cgaggtcagg agatgagac catcctggct   3060
aacacgatga aaccccatct ttactagaaa tacaaaaaat tagccgggcg tggtggcata   3120
cgcctatagt cccagctact tgggaggctg aggcaggaga attgcttgaa cccaggaggt   3180
ggaggttgca gtgacccgag atagcaccac tccactccaa cctgggcgac agtgagactc   3240
catctcaaaa aaaaaaatct gaagttaaga tgtggagtgt ctaataaaag taaaatgatg   3300
```

```
aattctgggt tctaaataga aatggattca agtgagaagg gactaaagac agaaatgagc  3360
tatgaaaagg cctcgtaaca acacaggtga ctctacatat gttcttagga aaggccacat  3420
aatacaccaa cttttattcc ttacccacta gatgagaaat tgatgctgtt ttccccacac  3480
ctacaaaccg cctatgtttt ttctctgtga tggcctctgg ctcaggtgtg ggtaagaaga  3540
gtaactgaca ctcattatat tgtggatgat ttagggataq atctgcagct tgaataactt  3600
ttggtaacga tagaccacat ccagttgtat taaagctgtt attggtgctc ctggcctgaa  3660
atggacctat gaactttgag ttgcaactat aaggatattt tttgccagta ttatacactg  3720
cacaaaccta tttatccata actgttagta ttggttcata tatggaatca accagggaat  3780
agttcagatt ccatctctga aagatgggcg gaaatcagac ttttttaactt tttaagtttt  3840
tttttttga gacggaatct cgctttgttg ccctggctgg agtgcagtgg cacgatcttg  3900
gctcacttga cctcctgggt tcaagtgatt ctcctgcctc agcctcccga gtagctggga  3960
ctacaggcac ccaccgccac gcctggctga ttttgtatt tttagtagag acaggccttc  4020
accatattgg ccaggctggt ctttttttt tttttttttt ttttttttctg agaaggagtc  4080
tcgccgtgtc gcccaggcta gagtgcagtg gcgtgaactc cgctcactgc tagctctgcc  4140
tcccggttc ataccattct cctgtctcag cctcccaagt agctgggact acaggcaccc  4200
accaccacgc ctggctaaat gttttgtattt tttagtagag acggggtttc accatgttag  4260
ccaggatggt ctcgatctcc tgacctcgtg atccgcctac cttggcctcc caaagtgctg  4320
ggattacaag cgtgagccac cgtgcctggc ctggccaggc tgtcttgaac tcctgacctc  4380
aagtgatgtg cccgcctcgg cctcccaaaa tgttgggatt acagatgtga gtcactatgc  4440
ccggccagaa catttcttac taatttcaag tcttgatgct ggtcaatatc acctagttaa  4500
atgaataaca acctaaaatt ggtgtgtagg atggaatttg agagagtaga cagagcagtt  4560
ttatataatt ggaagttatt ctagcaactg ccagtccagt gttctgcttc cacatctgca  4620
gtggtggaac tcctagagag ctcgcttcag tggggagaca gggctggaga gagggtcagt  4680
gctatctatg tagggtgtaa tctgtaagtc agcttttgaa atggggtgcc ctctactttg  4740
aatatctcga tactgtacta ataaagtaac agaactctcc tatgccagaa atatagaaat  4800
ttttcatgct cttctaaaaa tctagaagtg gcaattttcc atttaactaa agatttgatg  4860
tcttttagga cttggcagat gaacttgctc ttgttgatgt catcgaagac aaattgaagg  4920
gagagatgat ggatctccaa catggcagcc ttttccttag aacaccaaag attgtctctg  4980
gcaaaggttg atttcaacaa gtttatatta taatccatgc ttgacttaaa ttcttttttcc  5040
agatggtctc catttgttgc ttagggtaga gtgcagttgc acaattatgg ctcaccacag  5100
cctcgaaccc tgggctcaag caatcctcct tccacttcat tacccccctcc ccctcacaaa  5160
gaaactggga ctagggta tgctaccatg cccggctaat ttttttactt tttgtagaga  5220
tggggaccca ctgtgttgcc caggcctgtc ttgaaccact gggctcaagt gatcctccct  5280
ccttagcctt ccgaagtact gggattgcag gtgtgaacca ctgtgcccgg ctttagactt  5340
aaatgtttta tcaggcttga aatcctagct cttttaaagat tttgttttaa atgccgggtg  5400
caagagcctg ggaacaattt cacttaggtg cctgtgaata tcaaagtttc aatttctggc  5460
aaatggttta aaatagaaat ccaatttgtc catgctatgc aaaccatctg aattagaatg  5520
taatgagtaa agcttaaacc ttaggtctgt attttaaccac attgtgttac ttacttgccc  5580
ccacatcctt tcacacacga agttgagaat agggtaaata aatgagcctg ttcagctaat  5640
actcttggct tgaccctttc acacttaaca gcaccagcca agaaacctga atgtgagccc  5700
aaatagtgtc tattttgata cctgaaaatc actggccacc ttgctgatgg gcaactccct  5760
tcatcactgg tttaactctc ttgtgccata gggtatctag aagcaaaata tgtttgttaa  5820
gtgtaaagct gtctctgctt aaaaacaagt ccccctaccca ccaccaccac acacacacac  5880
acacacacac acacacacac acacacacac acacacacac gaaattgcct gttcctgggc  5940
tgataggaca ccagttaagt agaaacagga gtatggaaga gtgtgaacgt tgagcttggg  6000
gatcaaaaat ttgaggatat gtaagaaatt aataggagaa tcaaataata aacttgatttt  6060
cctccagctc tccctaattg tagttacata aagttacaac ttgactaaaa ctacaaggaa  6120
gatgttgaca tgctcttcct ccatttaaga agccataatg ataaaactct aagaacaaga  6180
aaggtttgtg gagcatttat ggaacaaatt tttgctgcct aggtaaaatt tattctaaag  6240
gccttaatct ggtcattatt ccccttttct ctagactata atgtaactgc aaactccaag  6300
ctggtcatta tcacggctgg ggcacgtcag caagagggag aaagccgtct taatttggtc  6360
cagcgtaacg tgaacatctt taaattcatc attcctaatg ttgtaaaata cagcccgaac  6420
tgcaagttgc ttattgtttc aaatccaggt gaggcttttg actgcataaa aattgacaag  6480
ctatagtaaa actgatagta tatgatatat atattatata tatttaaat attttgaaat  6540
atttaaaaa atacatttt aaaaatattt tcgaatatta ttttaaaata tatatatata  6600
ttttgaggcg gagttttgct cttgtcgccc aggttggagt gcagtggcgc aatctgggct  6660
cactgcaacc tctgcctcat gggttcaagc gattcttttg cctcagcctc tcaagtagct  6720
gggattataa gcgcctgcca ccacacatgg ctaatttttt atatttttag tagagacagg  6780
gtttcaccat gttggccagg ctggtttga actcctggcc tcaagcagtc catctgcctc  6840
ccaaagtgct aggattacag gcgtgagcca ccgtgcccag ccacgcatat ttattgattc  6900
atttattttt cttttttttt tttttttttt tttgagacgg agtcttgctc tgtcaccctg  6960
gctggagtac agtggcttga tcttggctca ctgcaagctc cgcctcccgg ttcatgcca  7020
ttctcctgcc tcagcctccc gagtagctgg gactacaggt gcccaccacg acgcctggct  7080
aatttttgt attttagta gagacggggt ttcatcagtt tagctccagg ggtctcgatc  7140
tcctgacctc gtgatctgcc cgccttggcc tcccaaagtg ctgggattac aggcgtgagc  7200
caccgtgcct ggtgattcat ttattttca tgtttcattt cccttctaag gagatttgtg  7260
tgtgtgtgtt tttgttttt taataatttt aaaacattaa agggaataca atgcctttaa  7320
atgtagttgg agcttaaaat tacctgccca agatcttgga taagggataa gtttgtgaat  7380
aattgttatt tctcttttt tttttttttt tttttgagaca gtctcacttt gtagctcagg  7440
ctggagtgca gtggttcgat cttggctcac tgcaacctct gcctcctggg ttcaagcaat  7500
tctcctgcct cagcctccca gagctgggat tacaggcac gtgccaccat gctcggctaa  7560
ttttgaagt tttagtagaa aggggttca ccatgttgcc caggctggtc tcaaattcct  7620
gagctcaggt gatccatctg cctcagcctc ccaaagtatt aggattacag gcgtgagcca  7680
ccgtgcccgg gcccataatt gtctcttagt tgataaacag tttattttca taaactgtt  7740
actatacttt tttttttgaga gcatgtctca ctctgtcgcc caagctggag ggcaatggga  7800
tgatcatggc agctttgacc tactaggctc aggtgatcct tcttcctcag cctcttaagt  7860
agctaggact acaggcgtgc accaaatatgc ctggctagtt tgttaaaagt ttttttgtag  7920
agatggggtt ttgctatgtt gcccaggctg gtcttgaact gctggcctca ggcagtcctc  7980
ccacctcagc ctcccaaagt gttgggataa caggtgtgag ttgtcatgcc cagccaaaac  8040
```

```
tacttttttga ataattaatg gacttgatat acatagtgta gaggcttaaa aatattaaca   8100
aaattattgg ttagccatga tcaatatcaa gatcctgaaa agccatatat ctggagtagc   8160
ctattattat ctaatgatca cctagtatct ggttaagtgt tttcttcata gtaggtatat   8220
cttttttgtg tgtagggaga ggataatggg tgattttttat tttctccttt ttcatagtgg  8280
atatccttgac ctacgtgggct tggaagataa gtggttttcc caaaaaccgt gttattggaa 8340
gcggttgcaa tctggattca gcccgattcc gttacctaat gggggaaagg ctggagttc   8400
acccattaag ctgtcatggg tgggtccttg gggaacatgg agattccagt ggtaagcata   8460
agttattttc ttttgtttt tgaaaagatt atataaaaag tcgatgggca ttatattatt    8520
caattagagc ctaatcaaat atccattcag taggatggaa tggtttcccg aaatctagca   8580
tttttgtataa ttatatgtta agaattgtta agattgttgc cattttatat ggcattttat  8640
ggcgagggg acgggaaatg aaatttctct tcttaccatg gatatcttaa gactgtagtt   8700
cttaggatgt cttcagtcat ttaatatcac agctgtttat acctgacttg tactgcctgg   8760
ccctgaaaag atgagcaaat ccaaatgcac aaaagttata ttatcacagt tgaaaatgt    8820
tatgattagg ttctgtatgc taagaaaacc cccttactgt tctcatacta tctttatatt   8880
tcaaatatac atgggttaaa catttcaatt ggctagagaa acaggttaga atacagttaa   8940
aattcttagt tttacataat gtaagtaaat gaaaatctaa tctaaaagtg agtaatgact   9000
acattagtag tcttgaccat ctaccaaaat tgagtattct tcctccgaag ataagagaat   9060
taggaaaatg aatcacaatt actaatctgt tggtacatga aaataaatgt agtctgtact   9120
atttcttta gtgcctgtat ggagtggaat gaatgttgct ggtgtctctc tgaagactct   9180
gcacccagat ttagggactg ataaagataa ggaacagtgg aaagaggttc acaagcaggt   9240
ggttgagagg taataaatct ttcaatttgg caacacagaa tattaacatt tactatttt    9300
atttaaaagg ttaaaattgt aatagtattt gcatttgaga acttttttgtt agaaaactg  9360
tgtggttttt ttgtttttgtt ttgtttgaga cagaatcttg cccttcgca caggctgcag   9420
tgcagtggcg caatcttggc tcactgcaac ctctgcctcc cgggttcagg cgattctcct   9480
gcctcagcct cctgggtacc tgggactaca ggcatatgcc atgacgcccg ctaattttt    9540
tgtattttta gtagagatgg ggtttcacca tgttagccaa aaaaaaaaga atgtgcctca   9600
ccttgcaagg cccaggccct aggatcactt gagctcagga gttcaaggcc agcctgggca   9660
acagggcaaa accctgtctc tacaataaat acacaaatta gccaggcatg gtggtgagca   9720
cctgtggtcc tagctacttg agaggctgag gcaggaggat cgcatgagcc tgggaggtca   9780
aggctgcagt gaagcgagat cctgccactg cactccagga cctgctagcc tgggtgacag   9840
agtaagagcc tgtctcaaag gaaaaaaaaa attattgaaa tagggaagct ttcaacttgg   9900
tggcattatt tacctttgtg gtcctgtgtg gacctcaggt ctatagaatt aaaaaatgaa   9960
tcatagccgg gcatggtggc tcatgcctgt aatcccagca ctttgggagg ccgaggcagg  10020
cagatcacga ggtcaggaga tggagaccat cctggctgaa acggtgaaac cccgtctcta  10080
ctaaaaatac aaaaaattag ccgggcgtgg tggcaggcgc ctgtagtccc agctactcgg  10140
gaggctgagg caggagaatg gcatgaaccc ggtagttgga gcttgcagtg agccgagatc  10200
gcgccactgc actccagcct gggcgacaga gcgagactcc gtctcaaaaa aaaagaatc   10260
ataatcttta gttcataaca tattcttgtg attggtcaag caaggccctc ttgtttgtat  10320
ttgttttaatt aaataaaacc tgtgaaccca ccacccagct caagaaagaa acacaatatc  10380
tgtcaaataa cattgttgaa tcagaattta gtattctgct ggtgtttgga aataagtgga   10440
ttctgtgctc tttcccccag ctatccctct gtccccctca cgctcccact tgagataatc  10500
ctgagttaag gatgctatgt tatcttggat ttcttttttaa aattcaatat tatatttta   10560
agaattatcc aattttttt acaagtagct atagttttatt tttcgatagc tgtgtaatat  10620
tccattgtat cagtataccaa tgatttatcc attcttctgt tggaggacat tggaaagatt  10680
gtcatgtttt tgctgttact aacagtactg ttaatgaata tccctgtaca taatatccta  10740
gcatacatgt gtgcaagggt tattcttggt ataatgcaac attgtggcat tatttactgt  10800
aaaatgtgta ttaatgaaaa ctttgttttt cttcttttct cccaccctgc tttttctgcc  10860
tttacctatg gtttcctatc atacagtgct tatgaggtga tcaaactcaa aggctacaca  10920
tcctgggcta ttggactctc tgtagcagat ttggcagaga gtaatgaa gaatcttagg   10980
cgggtgcacc cagtttccac catgattaag gtaggtctat gtagtgatac gctgcatttg  11040
aatgcttttt gctggcttt taaaaaagat tcttctgaga aagattaata caagtcttcc   11100
attactgact taagtgaaat aaattaatgt acccacagct tacctttttt gaaagaaatg  11160
gttgagcttt aggattaatg tccattaggc ctgttcaaca catagatact tgataatttg  11220
actacaaaaa agtcttgttc aattatgctg aggtaggtgg aagactataa aagaaataaa  11280
ctatttctcc attgggggaaa atagaaatta tattcaagtt agcattatgt tactatttt   11340
aatgactttc ttttatacta ttaattaaat cataactgaa cacctggaaa ggaatttcta  11400
cttatcaaag tttttttattt ttttgagaca gtctccctct gtcacccagg ctgcagtgca  11460
gtggccgatc tcggctcacc gcaacctctg cctcccaggt ttaagcgatt cttctgcctc  11520
agcctcctaa gtagctggga ctacaggtgc gtgccaccac gcccggctac ttttttgtatt  11580
tttagtagag atggagtttc accatattgg ctaggctggt ctcgaactcc tgaccttgtg  11640
atccacccgc ctcggcctcc ccgaatgctg ggattcagg tgtgagccac cgcacctggc   11700
ctcaagttgt attttaaaat cttcataatt aggccacaca cagtgactga cagctgtaat  11760
gccagcactt tggaaggcca agggcaggag aattgcttga gcccaggtgt ttgagaccac  11820
cctaggcagt atagtgaaat cttgcctctg ttaaaaaaaaa aaaaaaaaaa aaaggccatg  11880
tgcgggcagc tgatgcctgt aatcccagca ctttgggagg ccaaggggtg gatcacctga  11940
ggtcagtagt tcaagaccag cctgaccaac atggtgaaac cctgtctcta ctaaaaatac  12000
agaattagcc aggtgtggtg gcaggcgcct gtaatcccag ctacttggga gactgaggca  12060
gaaatcac ttgaacccag gaggtggagg ttgcagtgag ctgagatcgc accattgcac   12120
tccagcctgg gcaacaagag tgaaactcca tctcaaaaga aaaaaaaaag cgctgggct   12180
ctgtggctca tgcttgtaac cccagcactt tgggaggcca agaggtggat cacctggagt  12240
caagaatttg agaccaacct ggccaacatg tgaaaccccc atctactacta aacatacaaa  12300
aattagccaa gtgtggtggc gcacgcctgt agtcccagaa ggctgaagca ggagaattac  12360
ttgaaccctg gaggtggagg ttgcggtgag ctgagatcgt gccactgcac tccagcctgg  12420
gcgacagaga gactctgc ctcaaaaaaaa aattaaaaaa aaaagctt ataattatag    12480
agactgtaag tctgggaaa cctgggaatg catagacaaa atgtgagatt tttttttttt   12540
catttcatct tcaggtgtctt tacgaataaa aggatgatgt cttccttagt gttccttgca  12600
tttttgggaca gaatgaaatc tcagaccttg tgaaggtgac tctgacttct gaggaagagg  12660
cccgtttgaa aagagtgca gatacacttt ggggatcca aaaggagctg caattttaaa   12720
gtcttctgat gtcatatcat ttcactgtct aggctacaac aggattctag gtggaggttg   12780
```

```
tgcatgttgt cctttttatc tgatctgtga ttaaagcagt aatattttaa gatggactgg   12840
gaaaaacatc aactcctgaa gttagaaata agaatggttt gtaaaatcca cagctatatc   12900
ctgatgctgg atggtattaa tcttgtgtag tcttcaactg gttagtgtga aatagttctg   12960
ccacctctga cgcaccactg ccaatgctgt acgtactgca tttgcccctt gagccaggtg   13020
gatgtttacc gtgtgttata taacttcctg gctccttcac tgaacatgcc tagtccaaca   13080
tttttttccca gtgagtcaca tcctgggatc cagtgtataa atccaatatc atgtcttgtg   13140
cataattctt ccaaaggatc ttattttgtg aactatatca gtagtgtaca ttaccatata   13200
atgtaaaaag atctacatac aaacaatgca accaactatc caagtgttat accaactaaa   13260
acccccaata aaccttgaac agtgactact ttggttaatt cattatatta agatataaag   13320
tcataaagct gctagttatt atattaattt ggaaatatta ggctattctt gggcaaccct   13380
gcaacgattt tttctaacag ggatattatt gactaatagc agaggatgta atagtcaact   13440
gagttgtatt ggtaccactt ccattgtaag tcccaaagta ttatatattt gataataatg   13500
ctaatcataa ttggaaagta acattctata tgtaaatgta aaatttattt gccaactgaa   13560
tataggcaat gatagtgtgt cactataggg aacacagatt tttgagatct tgtcctctgg   13620
aagctggtaa caattaaaaa caatcttaag gcagggtgca gtggctcatg cctataatcc   13680
cagcactttg ggaagcccag gtgggctgat cactggaggc caggaattgg ggaccagcct   13740
ggccaacaca caaaaacccc atctgttaaa aaaacaaaaa aaaccaaaaa aaaacaagta   13800
accttggtgg atgtctactc aagttttctg cacattttt tgaaaataca actgtgaccc   13860
tta                                                                 13863

SEQ ID NO: 1173        moltype = DNA  length = 124
FEATURE                Location/Qualifiers
misc_feature           1..124
                       note = Synthetic
source                 1..124
                       mol_type = other DNA
                       organism = synthetic construct
SEQUENCE: 1173
gtgctgcagc cgctgccgcc gattccggat ctcattgcca cgcgccccg acgaccgccc       60
gacgtgcatt cccggtacgg tagggccctg cgcgcacggc gccagaggga tgggcgggta      120
gagc                                                                    124

SEQ ID NO: 1174        moltype = DNA  length = 350
FEATURE                Location/Qualifiers
misc_feature           1..350
                       note = Synthetic
source                 1..350
                       mol_type = other DNA
                       organism = synthetic construct
SEQUENCE: 1174
ccagcaatta gtctgatttc cgcccacctt tccgagcggg aaggagagcc acaaagcgcg       60
catgcgcgcg gatcaccgca ggctcctgtg ccttgggctt gagctttgtg gcagttaatg      120
gcttttctgc acgtatctct ggtgtttact tgagaagcct ggctgtgtcc ttgctgtagg      180
agccggagta gctcagagtg atcttgtctg aggaaaggcc agcccacctt ggggttaata      240
aaccgcgatg ggtgaaccct caggaggcta tacttacacc caaacgtcga tattccttt       300
ccacgctaag gtatgggcct tcactcttca cagaccctgt cattaggcct                  350

SEQ ID NO: 1175        moltype = DNA  length = 250
FEATURE                Location/Qualifiers
misc_feature           1..250
                       note = Synthetic
source                 1..250
                       mol_type = other DNA
                       organism = synthetic construct
SEQUENCE: 1175
aataaacatt aaagaagctg tagtgacact aaatgttttt cctcctatag attccttttg       60
gttccaagtc caatatggca actctaaagg atcagctgat ttataatctt ctaaaggaag      120
aacagaccc ccagaataag attacagttg ttggggttgg tgctgttggc atggcctgtg       180
ccatcagtat cttaatgaag gtaagtgaga gtctaccaca ctggaagccc ataccttgac      240
cccatcctct                                                              250

SEQ ID NO: 1176        moltype = DNA  length = 218
FEATURE                Location/Qualifiers
misc_feature           1..218
                       note = Synthetic
source                 1..218
                       mol_type = other DNA
                       organism = synthetic construct
SEQUENCE: 1176
aatctagaag tggcaatttt ccatttaact aaagatttga tgtctttag gacttggcag        60
atgaacttgc tcttgttgat gtcatcgaag acaaattgaa gggagagatg atggatctcc      120
aacatgcag cctttttcctt agaacaccaa agattgtctc tggcaaaggt tgatttcaac      180
aagtttatat tataatccat gcttgactta aattctttt                              218

SEQ ID NO: 1177        moltype = DNA  length = 274
FEATURE                Location/Qualifiers
misc_feature           1..274
                       note = Synthetic
source                 1..274
```

```
SEQUENCE: 1177
aaaatttatt ctaaaggcct taatctggtc attattcccc ttttctctag actataatgt    60
aactgcaaac tccaagctgg tcattatcac ggctggggca cgtcagcaag agggagaaag   120
ccgtcttaat ttggtccagc gtaacgtgaa catctttaaa ttcatcattc ctaatgttat   180
aaaatacagc ccgaactgca agttgcttat tgtttcaaat ccaggtgagg cttttgactg   240
cataaaaatt gacaagctat agtaaaactg atag                               274

SEQ ID NO: 1178        moltype = DNA   length = 274
FEATURE                Location/Qualifiers
misc_feature           1..274
                       note = Synthetic
source                 1..274
                       mol_type = other DNA
                       organism = synthetic construct
SEQUENCE: 1178
gtgtgtaggg agaggataat gggtgatttt tattttctcc tttttcatag tggatatctt    60
gacctacgtg gcttggaaga taagtggttt tcccaaaaac cgtgttattg gaagcggttg   120
caatctggat tcagcccgat tccgttacct aatgggggaa aggctgggag ttcacccatt   180
aagctgtcat gggtgggtcc ttggggaaca tggagattcc agtggtaagc ataagttatt   240
ttcttttgt ttttgaaaag attatataaa aagt                                274

SEQ ID NO: 1179        moltype = DNA   length = 218
FEATURE                Location/Qualifiers
misc_feature           1..218
                       note = Synthetic
source                 1..218
                       mol_type = other DNA
                       organism = synthetic construct
SEQUENCE: 1179
ctaatctgtt ggtacatgaa aataaatgta gtctgtacta tttcttttag tgcctgtatg    60
gagtggaatg aatgttgctg gtgtctctct gaagactctg cacccagatt tagggactga   120
taaagataag gaacagtgga aagaggttca caagcaggtg gttgagaggt aataaatctt   180
tcaatttggc aacacagaat attaacattt actatttt                           218

SEQ ID NO: 1180        moltype = DNA   length = 224
FEATURE                Location/Qualifiers
misc_feature           1..224
                       note = Synthetic
source                 1..224
                       mol_type = other DNA
                       organism = synthetic construct
SEQUENCE: 1180
ttctcccacc ctgctttttc tgcctttacc tatggtttcc tatcatacag tgcttatgag    60
gtgatcaaac tcaaaggcta cacatcctgg gctattggac tctctgtagc agatttggca   120
gagtataa tgaagaatct taggcgggtg cacccagttt ccaccatgat taaggtaggt   180
ctatgtagtg atacgctgca tttgaatgct ttttgctggc tttt                    224

SEQ ID NO: 1181        moltype = DNA   length = 1359
FEATURE                Location/Qualifiers
misc_feature           1..1359
                       note = Synthetic
source                 1..1359
                       mol_type = other DNA
                       organism = synthetic construct
SEQUENCE: 1181
ggaatgcata gacaaaatgt gagattttt ttttttcatt tcatcttcag ggtctttacg     60
gaataaagga tgatgtcttc cttagtgttc cttgcatttt gggacagaat ggaatctcag   120
accttgtgaa ggtgactctg acttctgagg aagaggcccg tttgaagaag agtgcagata   180
cactttgggg gatccaaaag gagctgcaat tttaaagtct tctgatgtca tatcatttca   240
ctgtctaggc tacaacagga ttctaggtgg aggttgtgca tgttgtcctt tttatctgat   300
ctgtgattaa agcagtaata ttttaagatg gactgggaaa aacatcaact cctgaagtta   360
gaaataagaa tggtttgtaa aatccacagc tatatcctga tgctggatgg tattaatctt   420
gtgtagtctt caactggtta gtgtgaaata gttctgccac ctctgacgca ccactgccaa   480
tgctgtacgt actgcatttg cccttgagc caggtggatg tttaccgtgt gttatataac   540
ttcctggctc cttcactgaa catgcctagt ccaacatttt ttcccagtga gtcacatcct   600
gggatccagt gtataaatcc aatatcatgt cttgtgcata attcttccaa aggatcttat   660
tttgtgaact atatcagtag tgtacattac catataatgt aaaaagatct acatacaaac   720
aatgcaacca actatccaag tgttatacca actaaaaccc ccaataaacc ttgaacagtg   780
actactttgg ttaattcatt atattaagat ataaagtcat aaagctgcta gttattatat   840
taatttggaa atattaggct attccttggc aaccctgcaa cgattttttc taacagggat   900
attattgact aatagcagag gatgtaatag tcaactgagt tgtattggta ccacttccat   960
tgtaagtccc aaagtattat atatttgata ataatgctaa tcataattgg aaagtaacat  1020
tctatatgta aatgtaaaat ttatttgcca actgaatata ggcaatgata gtgtgtcact  1080
ataggaaaca cagatttttg agatcttgtc ctctggaagc tggtaacaat taaaaacaat  1140
cttaaggcag ggtgcagtgg ctcatgccta atcccagc actttgggaa gcccaggtgg  1200
gctgatcact ggaggccagg aattgggac cagcctggcc aacacaacaa acccccatct  1260
gttaaaaaaa caaaacaaaa ccaaaaaaaa caagtaacct tggtggatgt ctactcaagt  1320
```

```
tttctgcaca ttttctgaa atacaactg tgaccctta                                1359

SEQ ID NO: 1182         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1182
tctcaacgat agtcagacat gtgtcctcag tgacac                                 36

SEQ ID NO: 1183         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1183
ttttaacaac actcaggcat gtgtccacag tgacac                                 36

SEQ ID NO: 1184         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1184
ttgaacggat actcagacat gtgtttccag tgacac                                 36

SEQ ID NO: 1185         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1185
tgccctcaat agtcagatgt gtgtccacag tgacac                                 36

SEQ ID NO: 1186         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1186
tctcaatgat acttagatac gtgtcctcag tgacac                                 36

SEQ ID NO: 1187         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1187
tctcaatgat actcagacat gtgtccccag tgacac                                 36

SEQ ID NO: 1188         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1188
tctcaatgat actaagacat gtgtcctcag tgacac                                 36

SEQ ID NO: 1189         moltype = RNA   length = 36
FEATURE                 Location/Qualifiers
misc_feature            1..36
                        note = Synthetic
source                  1..36
                        mol_type = other RNA
                        organism = synthetic construct
```

-continued

```
SEQUENCE: 1189
tctcaactat actcagacat gtgtcctcag tgacac                                36

SEQ ID NO: 1190         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1190
tctcaacgat actcagacat gtgtcctcag tgacac                                36

SEQ ID NO: 1191         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1191
tctcaacgat actaagatat gtgtcctcag cgacac                                36

SEQ ID NO: 1192         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1192
tctcaacgat actaagatat gtgtccccag tgacac                                36

SEQ ID NO: 1193         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1193
tctcaacgat actaagatat gtgtccacag tgacac                                36

SEQ ID NO: 1194         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1194
tctcaacaat actcagacat gtgtccccag tgacac                                36

SEQ ID NO: 1195         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1195
tctcaacaat actaaggcat gtgtccccag tgaccc                                36

SEQ ID NO: 1196         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1196
tctcaaagat actcagacac gtgtccccag tgacac                                36

SEQ ID NO: 1197         moltype = RNA   length = 36
FEATURE                 Location/Qualifiers
misc_feature            1..36
                        note = Synthetic
source                  1..36
                        mol_type = other RNA
```

```
                           organism = synthetic construct
SEQUENCE: 1197
tctcaaaaat actcagacat gtgtcctcag tgacac                                 36

SEQ ID NO: 1198         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1198
gcgaaacaac agtcagacat gtgtccccag tgacac                                 36

SEQ ID NO: 1199         moltype = RNA   length = 36
FEATURE                 Location/Qualifiers
misc_feature            1..36
                        note = Synthetic
source                  1..36
                        mol_type = other RNA
                        organism = synthetic construct
SEQUENCE: 1199
cctcaacgat attaagacat gtgtccgcag tgacac                                 36

SEQ ID NO: 1200         moltype = RNA   length = 22
FEATURE                 Location/Qualifiers
misc_feature            1..22
                        note = Synthetic
source                  1..22
                        mol_type = other RNA
                        organism = synthetic construct
SEQUENCE: 1200
agacatgtgt cctcagtgac ac                                                22

SEQ ID NO: 1201         moltype = DNA   length = 3222
FEATURE                 Location/Qualifiers
misc_feature            1..3222
                        note = Synthetic
source                  1..3222
                        mol_type = other DNA
                        organism = synthetic construct
SEQUENCE: 1201
atggcttcca tctctaggcc atacggcacc aagctgcgac cggacgcacg gaagaaggag        60
atgctcgata agttctttaa tacactgact aagggtcagc gcgtgttcgc agacctggcc       120
ctgtgcatct atggctccct gaccctggag atggccaagt ctctggagcc agaaagtgat       180
tcagaactgg tgtgcgctat tgggtggttt cggctggtgg acaagaccat ctggtccaag       240
gatggcatca agcaggagaa tctggtgaaa cagtacgaag cctattccgg aaaggaggct       300
tctgaagtgg tcaaaacata cctgaacagc cccagctccg acaagtacgt gtggatcgat       360
tgcaggcaga aattcctgag gtttcagcgc gagctcggca ctcgcaacct gtccgaggac       420
ttcgaatgta tgctctttga acagtacatt agactgacca agggcgagat cgaagggtat       480
gccgctattt caaatatgtt cggaaacggc gagaaggaag accggagcaa gaaaagaatg       540
tacgctacac ggatgaaaga ttggctggag gcaaacgaaa atatcacttg ggagcagtat       600
agagaggccc tgaagaacca gctgaatgct aaaaaacctgg agcaggttgt ggccaattac       660
```
(Note: line 660 may read "aaaaacctgg" — reproduced as seen)
```
aaggggaacc tggcggggc agaccccttc tttaagtata gcttctccaa agagggaatg        720
gtgagcagga aagaacatgc acagcagctc gacaagttca aaaccgtcct gaagaacaaa       780
gcccgggacc tgaattttcc aaacaaggag aagctgaagc agtacctgga ggccgaaatc       840
ggcattccgg tcgacgctaa cgtgtactcc cagatgttct ctaacggggt gagtgaggtc       900
cagcctaaga ccacacggaa tatgtctttt agtaacgaga actggatct gctcactgaa        960
ctgaaggacc tgaacaaggg cgatgggttc gagtacgacc gagaagtgct gaacgggttc      1020
tttgactccg agctccacac taccgaggat aagtttaata tcacctctag gtacctggga      1080
ggcgacaaat caaaccgcct gagcaaactc tataagatct ggaagaaaga gggtgtggac      1140
tgcgaggaag gcattcagca gttctgtgaa gccgtcaaag ataagatggg ccagatcccc      1200
attcgaaatg tgctgaagta cctgtggcag ttccggagaa cagtcagtgc cgaggatttt      1260
gaagcagccg ctaaggctaa ccatctggag gaaaagatca gcccacccga agcccaccca      1320
atcgtgatta gcaataggta ctgggcttt gggacttccg cactggtggg aaacattatg      1380
cccgcagaca gaggcatca gggagagtat gccggtcaga atttcaaaat gtggctggag      1440
gctgaactgc actacgatgg caagaaagca agcaccatc tgccttttta taacgcccgc      1500
ttctttgagg aagtgtactg ctatcacccc tctgtcgccg agatcactcc tttcaaaacc      1560
aagcagtttg gctgtgaaat cggaaggac attccaatt acgtgagcgt cgctctgaag      1620
gacaatccgt ataagaaagc aaccaaacga atcctgcgtg caatctacaa tcccgtcgcc      1680
aacacaactg cgcgttgataa gaccacaaac tgcagcttca tgatcaaacg cgagaatgac      1740
gaatataagc tggtcatcaa ccgaaaaatt tccgtggatc ggcctaagag aatcgaagtg      1800
ggcaggacaa ttatggggta cgaccgcaat cagacagcta gcgatactta ttggattggc      1860
cggctggtgc cacctggaac ccggggcgca taccgcatcg gagagtggag cgtccagtat      1920
attaagtccg ggcctgtcct gtctagtact cagggagtta acaattccac taccgaccag      1980
ctggtgtaca acggcatgcc atcaagctcc agcggttca aggcctggaa gaaagccaga      2040
atggcttta tccgaaaact cattcgtcag ctgaatgacg agggactgga atctaagggt      2100
caggattata tccccgagaa cccttctagt ttcgatgtgc gggcgaaac cctgtacgtc      2160
tttaacagta attatctgaa ggccctggtg agcaaacaca gaaaggccaa gaaacctgtt      2220
```

```
gaggggatcc tggacgagat tgaagcctgg acatctaaag acaaggattc atgcagcctg   2280
atgcggctga gcagcctgag cgatgcttcc atgcagggaa tcgccagcct gaagagtctg   2340
attaacagct acttcaacaa gaatggctgt aaaaccatcg aggacaaaga aaagtttaat   2400
cccgtgctgt atgccaagct ggttgaggtg aacagcggga gaacaaacaa gcggtctgag   2460
aaagtgggaa gaatcgcagg tagtctggag cagctggccc tgctgaacag ggttgaggtg   2520
gtcatcggcg aagctgacct gggggaggtc gaaaaaggaa gagtaagaa acagaattca   2580
cggaacatgg attggtgcgc aaagcaggtg gcacagcggc tggagtacaa actggccttc   2640
catggaatcg gttactttgg agtgaacccc atgtatacca gccaccagga ccctttcgaa   2700
cataggcgcg tggctgatca catcgtcatg cgagcacgtt ttgaggaagt caacgtggag   2760
aacattgccg aatggcacgt gcgaaatttc tcaaactacc tgcgtgcaga cagcggcact   2820
gggctgtact ataagcaggc caccatggac ttcctgaaaa cattacggtct ggaggaacac   2880
gctgagggcc tggaaaataa gaaaatcaag ttctatgact ttagaaagat cctggaggat   2940
aaaaacctga caagcgtgat cattccaaag aggggcgggg catctacat ggccaccaac   3000
ccagtgacat ccgactctac cccgattaca tacgccggca gacttataa taggtgtaac   3060
gctgatgagg tggcagccgc taatatcgtt atttctgtgc tggctccccg cagtaagaaa   3120
aacgaggaac aggacgatat ccctctgatt accaagaaag ccgagagtaa gtcaccaccg   3180
aaagaccgga agagatcaaa aacaagccag ctgcctcaga aa                      3222

SEQ ID NO: 1202        moltype = AA   length = 1074
FEATURE                Location/Qualifiers
REGION                 1..1074
                       note = Synthetic
source                 1..1074
                       mol_type = protein
                       organism = synthetic construct
SEQUENCE: 1202
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF PKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KPNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SVDRPKRIEV   600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074

SEQ ID NO: 1203        moltype = AA   length = 1074
FEATURE                Location/Qualifiers
REGION                 1..1074
                       note = Synthetic
source                 1..1074
                       mol_type = protein
                       organism = synthetic construct
SEQUENCE: 1203
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID   120
CRQKFLRFQR ELGTRNLSED FECMLFEQYI RLTKGEIEGY AAISNMFGNG EKEDRSKKRM   180
YATRMKDWLE ANENITWEQY REALKNQLNA KNLEQVVANY KGNAGGADPF PKYSFSKEGM   240
VSKKEHAQQL DKFKTVLKNK ARDLNFPNKE KLKQYLEAEI GIPVDANVYS QMFSNGVSEV   300
QPKTTRNMSF SNEKLDLLTE LKDLNKGDGF EYAREVLNGF FDSELHTTED KPNITSRYLG   360
GDKSNRLSKL YKIWKKEGVD CEEGIQQFCE AVKDKMGQIP IRNVLKYLWQ FRETVSAEDF   420
EAAAKANHLE EKISRVKAHP IVISNRYWAF GTSALVGNIM PADKRHQGEY AGQNFKMWLE   480
AELHYDGKKA KHHLPFYNAR FFEEVYCYHP SVAEITPFKT KQFGCEIGKD IPDYVSVALK   540
DNPYKKATKR ILRAIYNPVA NTTGVDKTTN CSFMIKREND EYKLVINRKI SDRPKRIEV    600
GRTIMGYDRN QTASDTYWIG RLVPPGTRGA YRIGEWSVQY IKSGPVLSST QGVNNSTTDQ   660
LVYNGMPSSS ERFKAWKKAR MAFIRKLIRQ LNDEGLESKG QDYIPENPSS FDVRGETLYV   720
FNSNYLKALV SKHRKAKKPV EGILDEIEAW TSKDKDSCSL MRLSSLSDAS MQGIASLKSL   780
INSYFNKNGC KTIEDKEKFN PVLYAKLVEV EQRRTNKRSE KVGRIAGSLE QLALLNGVEV   840
VIGEADLGEV EKGKSKKQNS RNMDWCAKQV AQRLEYKLAF HGIGYFGVNP MYTSHQDPFE   900
HRRVADHIVM RARFEEVNVE NIAEWHVRNF SNYLRADSGT GLYYKQATMD FLKHYGLEEH   960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 1204        moltype = AA   length = 1074
FEATURE                Location/Qualifiers
REGION                 1..1074
                       note = Synthetic
source                 1..1074
                       mol_type = protein
                       organism = synthetic construct
```

-continued

```
SEQUENCE: 1204
MASISRPYGT KLRPDARKKE MLDKFFNTLT KGQRVFADLA LCIYGSLTLE MAKSLEPESD      60
SELVCAIGWF RLVDKTIWSK DGIKQENLVK QYEAYSGKEA SEVVKTYLNS PSSDKYVWID     120
CRQKFLRFQR ELGTRNLSED FECMLFEQYI RLTKGEIEGY AAISNMFGNG EKEDRSKKRM     180
YATRMKDWLE ANENITWEQY REALKNQLNA KNLEQVVANY KGNAGGADPF FKYSFSKEGM     240
VSKKEHAQQL DKFKTVLKNK ARDLNFPNKE KLKQYLEAEI GIPVDANVYS QMFSNGVSEV     300
QPKTTRNMSF SNEKLDLLTE LKDLNKGDGF EYAREVLNGF FDSELHTTED KFNITSRYLG     360
GDKSNRLSKL YKIWKKEGVD CEEGIQQFCE AVKDKMGQIP IRNVLKYLWQ FRETVSAEDF     420
EAAAKANHLE EKISRVKAHP IVISNRYWAF GTSALVGNIM PADKRHQGEY AGQNFKMWLR     480
AELHYDGKKA KHHLPFYNAR FFEEVYCYHP SVAEITPFKT KQFGCEIGKD IPDYVSVALK     540
DNPYKKATKR ILRAIYNPVA NTTRVDKTTN CSFMIKREND EYKLVINRKI SRDRPKRIEV     600
GRTIMGYDRN QTASDYWIG RLVPPGTRGA YRIGEWSVQY IKSGPVLSST QGVNNSTTDQ      660
LVYNGMPSSS ERFKAWKKAR MAFIRKLIRQ LNDEGLESKG QDYIPENPSS FDVRGETLYV     720
FNSNYLKALV SKHRKAKKPV EGILDEIEAW TSKDKDSCSL MRLSSLSDAS MQGIASLKSL     780
INSYFNKNGC KTIEDKEKFN PVLYAKLVEV EQRRTNKRSE KVGRIAGSLE QLALLNGVEV     840
VIGEADLGEV EKGKSKKQNS RNMDWCAKQV AQRLEYKLAF HGIGYFGVNP MYTSHQDPFE     900
HRRVADHIVM RARFEEVNVE NIAEWHVRNF SNYLRADSGT GLYYKQATMD FLKHYGLEEH     960
AEGLENKKIK FYDFRKILED KNLTSVIIPK RGGRIYMATN PVTSDSTPIT YAGKTYNRCN    1020
ADEVAAANIV ISVLAPRSKK NREQDDIPLI TKKAESKSPP KDRKRSKTSQ LPQK          1074

SEQ ID NO: 1205           moltype = RNA   length = 36
FEATURE                   Location/Qualifiers
misc_feature              1..36
                          note = Synthetic
source                    1..36
                          mol_type = other RNA
                          organism = synthetic construct
SEQUENCE: 1205
gttggaatga ctaattttg tgcccaccgt tggcac                                   36

SEQ ID NO: 1206           moltype = RNA   length = 24
FEATURE                   Location/Qualifiers
misc_feature              1..24
                          note = Synthetic
source                    1..24
                          mol_type = other RNA
                          organism = synthetic construct
SEQUENCE: 1206
aattttgtg cccatcgttg gcac                                                24

SEQ ID NO: 1207           moltype = RNA   length = 23
FEATURE                   Location/Qualifiers
misc_feature              1..23
                          note = Synthetic
source                    1..23
                          mol_type = other RNA
                          organism = synthetic construct
SEQUENCE: 1207
atttttgtgc ccatcgttgg cac                                                23

SEQ ID NO: 1208           moltype = RNA   length = 36
FEATURE                   Location/Qualifiers
misc_feature              1..36
                          note = Synthetic
source                    1..36
                          mol_type = other RNA
                          organism = synthetic construct
SEQUENCE: 1208
ctagcaatga cctaatagtg tgtccttagt tgacat                                  36

SEQ ID NO: 1209           moltype = RNA   length = 36
FEATURE                   Location/Qualifiers
misc_feature              1..36
                          note = Synthetic
source                    1..36
                          mol_type = other RNA
                          organism = synthetic construct
SEQUENCE: 1209
cctacaatac ctaagaaatc cgtcctaagt tgacgg                                  36

SEQ ID NO: 1210           moltype = RNA   length = 22
FEATURE                   Location/Qualifiers
misc_feature              1..22
                          note = Synthetic
source                    1..22
                          mol_type = other RNA
                          organism = synthetic construct
SEQUENCE: 1210
atagtgtgtc cttagttgac at                                                 22
```

```
SEQ ID NO: 1211           moltype = AA   length = 1093
FEATURE                   Location/Qualifiers
REGION                    1..1093
                          note = Synthetic
source                    1..1093
                          mol_type = protein
                          organism = synthetic construct
SEQUENCE: 1211
MSNKEKNASE TRKAYTTKMI PRSHDRMKLL GNFMDYLMDG TPIFFELWNQ FGGGIDRDII    60
SGTANKDKIS DDLLLAVNWF KVMPINSKPQ GVSPSNLANL FQQYSGSEPD IQAQEYFASN   120
FDTEKHQWKD MRVEYERLLA ELQLSRSDMH HDLKLMYKEK CIGLSLSTAH YITSVMFGTG   180
AKNNRQTKHQ FYSKVIQLLE ESTQINSVEQ LASIILKAGD CDSYRKLRIR CSRKGATPSI   240
LKIVQDYELG TNHDDEVNVP SLIANLKEKL GRFEYECEWK CMEKIKAFLA SKVGPYYLGS   300
YSAMLENALS PIKGMTTKNC KFVLKQIDAK NDIKYENEPF GKIVEGFFDS PYFESDTNVK   360
WVLHPHHIGE SNIKTLWEDL NAIHSKYEED IASLSEDKKE KRIKVYQGDV CQTINTYCEE   420
VGKEAKTPLV QLLRYLYSRK DDIAVDKIID GITFLSKKHK VEKQKINPVI QKYPSFNFGN   480
NSKLLGKIIS PKDKLKHNLK CNRNQVDNYI WIEIKVLNTK TMRWEKHHYA LSSTRFLEEV   540
YYPATSENPP DALAARFRTK TNGYEGKPAL SAEQIEQIRS APVGLRKVKK RQMRLEAARQ   600
QNLLPRYTWG KDFNINICKR GNNFEVTLAT KVKKKKEKNY KVVLGYDANI VRKNTYAAIE   660
AHANGDGVID YNDLPVKPIE SGFVTVESQV RDKSYDQLSY NGVKLLYCKP HVESRRSFLE   720
KYRNGTMKDN RGNNIQIDFM KDFEAIADDE TSLYYFNMKY CKLLQSSIRN HSSQAKEYRE   780
EIFELLRDGK LSVLKLSSLS NLSFVMFKVA KSLIGTYFGH LLKKPKNSKS DVKAPPITDE   840
DKQKADPEMF ALRLALEEKR LNKVKSKKEV IANKIVAKAL ELRDKYGPVL IKGENISDTT   900
KKGKKSSTNS FLMDWLARGV ANKVKEMVMM HQGLEFVEVN PNFTSHQDPF VHKNPENTFR   960
ARYSRCTPSE LTEKNRKEIL SFLSDKPSKR PTNAYYNEGA MAFLATYGLK KNDVLGVSLE  1020
KFKQIMANIL HQRSEDQLLF PSRGGMFYLA TYKLDADATS VNWNGKQFWV CNADLVAAYN  1080
VGLVDIQKDF KKK                                                    1093

SEQ ID NO: 1212           moltype = AA   length = 1098
FEATURE                   Location/Qualifiers
REGION                    1..1098
                          note = Synthetic
source                    1..1098
                          mol_type = protein
                          organism = synthetic construct
SEQUENCE: 1212
MSISNNNILP YNPKLLPDDR KHKMLVDTFN QLDLIRNNLH DMIIALYGAL KYDNIKQFAS    60
KEKPHISADA LCSINWFRLV KTNERKPAIE SNQIISKFIQ YSGHTPDKYA LSHITGNHEP   120
SHKWIDCREY AINYARIMHL SFSQFQDLAT ACLNCKILIL NGTLTSSWAW GANSALFGGS   180
DKENFSVKAK ILNSFIENLK DEMNTTKFQV VEKVCQQIGS SDAADLFDLY RSTVKDGNRG   240
PATGRNPKVM NLFSQDGEIS SEQREDFIES FQKVMQEKNS KQIIPHLDKL KYHLVKQSGL   300
YDIYSWAAAI KNANSTIVAS NSSNLNTILN KTEKQQTFEE LRKDEKIVAC SKILLSVNDT   360
LPEDLHYNPS TSNLGKNLDV FFDLLNENSV HTIENKEEKN KIVKECVNQY MEECKGLNKP   420
PMPVLLTFIS DYAHKHQAQD FLSAAKMNFI DLKIKSIKVV PTVHGSSPYT WISNLSKKNK   480
DGKMIRTPNS SLIGWIIPPE EIHDQKFAGQ NPIIWAVLRV YCNNKWEMHH FPPFSDSRFFT   540
EVYAYKPNLP YLPGGENRSK RFGYRHSTNL SNESRQILLD KSKYAKANKS VLRCMENMTH   600
NVVFDPKTSL NIRIKTDKNN SPVLDDKGRI TFVMQINHRI LEKYNNTKIE IGDRILAYDQ   660
NQSENHTYAI LQRTEEGSHA HQFNGWYVRV LETGKVTSIV QGLSGPIDQL NYDGMPVTSH   720
KFNCWQADRS AFVSQFASLK ISETETFDEA YQAINAQGAY TWNLFYLRIL RKALRVCHME   780
NINQFREEIL AISKNRLSPM SLGSLSQNSL KMIRAFKSII NCYMSRMSFV DELQKKEGDL   840
ELHTIMRLTD NKLNDKRVEK INRASSFLTN KAHSMGCKMI VGESDLPVAD SKTSKKQNVD   900
RMDWCARALS HKVEYACKLM GLAYRGIPAY MSSHQDPLVH LVESKRSVLR PRFVVADKSD   960
VKQHHLDNLR RMLNSKTKVG TAVYYREAVE LMCEELGIHK TDMAKGKVSL SDFVDKFIGE  1020
KAIFPQRGGR FYMSTKRLTT GAKLICYSGS DVWLSDADEI AAINIGMFVV CDQTGAFKKK  1080
KKEKLDDEEC DILPFRPM                                               1098

SEQ ID NO: 1213           moltype = RNA   length = 43
FEATURE                   Location/Qualifiers
misc_feature              1..43
                          note = Synthetic
source                    1..43
                          mol_type = other RNA
                          organism = synthetic construct
SEQUENCE: 1213
agaaatccgt ctttcattga cggccttcat taagatactg atg                    43

SEQ ID NO: 1214           moltype = RNA   length = 43
FEATURE                   Location/Qualifiers
misc_feature              1..43
                          note = Synthetic
source                    1..43
                          mol_type = other RNA
                          organism = synthetic construct
SEQUENCE: 1214
agaaatccgt ctttcattga cggtaggact tggcagatga act                    43

SEQ ID NO: 1215           moltype = RNA   length = 43
FEATURE                   Location/Qualifiers
```

```
misc_feature            1..43
                        note = Synthetic
source                  1..43
                        mol_type = other RNA
                        organism = synthetic construct
SEQUENCE: 1215
agaaatccgt ctttcattga cggatctgcc aagtcctaaa aga            43

SEQ ID NO: 1216         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1216
agaaatccgt ctttcattga cgggatgtct tttaggactt ggc            43

SEQ ID NO: 1217         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1217
agaaatccgt ctttcattga cggatgtctt ttaggacttg gca            43

SEQ ID NO: 1218         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1218
agaaatccgt ctttcattga cggggacttg gcagatgaac ttg            43

SEQ ID NO: 1219         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1219
agaaatccgt ctttcattga cggaaatcaa cctttgccag aga            43

SEQ ID NO: 1220         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1220
agaaatccgt ctttcattga cggttgaaat caacctttgc cag            43

SEQ ID NO: 1221         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1221
agaaatccgt ctttcattga cggttcatag tggatatctt gac            43

SEQ ID NO: 1222         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1222
agaaatccgt ctttcattga cggctccttt ttcatagtgg ata            43

SEQ ID NO: 1223         moltype = RNA   length = 43
```

```
FEATURE                 Location/Qualifiers
misc_feature            1..43
                        note = Synthetic
source                  1..43
                        mol_type = other RNA
                        organism = synthetic construct
SEQUENCE: 1223
agaaatccgt ctttcattga cggtccttttt tcatagtgga tat            43

SEQ ID NO: 1224         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1224
agaaatccgt ctttcattga cggtcatagt ggatatcttg acc            43

SEQ ID NO: 1225         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1225
agaaatccgt ctttcattga cggcatagtg gatatcttga cct            43

SEQ ID NO: 1226         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1226
agaaatccgt ctttcattga cggatagtgg atatcttgac cta            43

SEQ ID NO: 1227         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1227
agaaatccgt ctttcattga cggggtaacg gaatcgggct gaa            43

SEQ ID NO: 1228         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1228
agaaatccgt ctttcattga cggccactgg aatctccatg ttc            43

SEQ ID NO: 1229         moltype = RNA   length = 43
FEATURE                 Location/Qualifiers
misc_feature            1..43
                        note = Synthetic
source                  1..43
                        mol_type = other RNA
                        organism = synthetic construct
SEQUENCE: 1229
agaaatccgt ctttcattga cggtgcttac cactggaatc tcc            43

SEQ ID NO: 1230         moltype = DNA   length = 999
FEATURE                 Location/Qualifiers
misc_feature            1..999
                        note = Synthetic
source                  1..999
                        mol_type = other DNA
                        organism = synthetic construct
SEQUENCE: 1230
atggcaactc taaaggatca gctgatttat aatcttctaa aggaagaaca gaccccccag   60
aataagatta cagttgttgg ggttggtgct gttggcatgg cctgtgccat cagtatctta  120
```

```
atgaaggact tggcagatga acttgctctt gttgatgtca tcgaagacaa attgaaggga   180
gagatgatgg atctccaaca tggcagcctt ttccttagaa caccaaagat tgtctctggc   240
aaagactata atgtaactgc aaactccaag ctggtcatta tcacggctgg ggcacgtcag   300
caagagggag aaagccgtct taatttggtc agcgtaacg tgaacatctt taaattcatc    360
attcctaatg ttgtaaaata cagcccgaac tgcaagttgc ttattgtttc aaatccagtg   420
gatatcttga cctacgtggc ttggaagata agtggttttc ccaaaaaccg tgttattgga   480
agcggttgca atctgattc agcccgattc cgttacctaa tggggaaag ctgggagtt      540
cacccattaa gctgtcatgg gtgggtcctt ggggaacatg gagattccag tgtgcctgta   600
tggagtggaa tgaatgttgc tggtgtctct ctgaagactc tgcacccaga tttagggact   660
gataaagata aggaacagtg gaaagaggtt cacaagcagg tggttgagag tgcttatgag   720
gtgatcaaac tcaaaggcta cacatcctgg gctattggac tctctgtagc agatttggca   780
gagagtataa tgaagaatct taggcgggtg cacccagttt ccaccatgat taagggtctt   840
tacgggaataa aggatgatgt cttccttagt gttccttgca ttttgggaca gaatggaatc   900
tcagacccttg tgaaggtgac tctgacttct gaggaagagg cccgtttgaa gaagagtgca   960
gatacacttt ggggggatcca aaggagctg caatttttaa                          999

SEQ ID NO: 1231           moltype = DNA  length = 825
FEATURE                   Location/Qualifiers
misc_feature              1..825
                          note = Synthetic
source                    1..825
                          mol_type = other DNA
                          organism = synthetic construct
SEQUENCE: 1231
atggcaactc taaaggatca gctgatttat aatcttctaa aggaagaaca gaccccccag    60
aataagatta cagttgttgg ggttggtgct gttggcatgg cctgtgccat cagtatctta   120
atgaaggact tggcagatga acttgctctt gttgatgtca tcgaagacaa attgaaggga   180
gagatgatgg atctccaaca tggcagcctt ttccttagaa caccaaagat tgtctctggc   240
aaagtggata tcttgaccta cgtggcttgg aagataagtg gttttcccaa aaaccgtgtt   300
attggaagcg gttgcaatct ggattcagcc cgattccgtt acctaatggg gaaaggctg    360
ggagttcacc cattaagctg tcatgggtgg gtccttgggg aacatggaga ttccagtgtg   420
cctgtatgga gtggaatgaa tgttgctggt gtctctctga gactctgca cccagattta    480
gggactgata agataagga acagtggaaa gaggttcaca gcaggtggt tgagagtgct    540
tatgaggtga tcaaactcaa aggctacaca tcctgggcta ttggactctc tgtagcagat   600
ttggcagaga gtataatgaa gaatcttagg cgggtgcacc cagtttccac catgattaag   660
ggtctttacg gaataaagga tgatgtcttc cttagtgttc cttgcattttt gggacagaat   720
ggaatctcag accttgtgaa ggtgactctg acttctgagg aagaggcccg tttgaagaag   780
agtgcagata cactttgggg gatccaaaag gagctgcaat tttaa                   825

SEQ ID NO: 1232           moltype = DNA  length = 1086
FEATURE                   Location/Qualifiers
misc_feature              1..1086
                          note = Synthetic
source                    1..1086
                          mol_type = other DNA
                          organism = synthetic construct
SEQUENCE: 1232
atgggtgaac cctcaggagg ctatacttac acccaaacgt cgatattcct tttccacgct    60
aagattcctt ttggttccaa gtccaatatg gcaactctaa aggatcagct gatttataat   120
cttctaaagg aagaacagac cccccagaat aagattacag ttgttggggt tggtgctgtt   180
ggcatggcct gtgccatcag tatcttaatg aaggacttgg cagatgaact tgctcttgtt   240
gatgtcatcg aagacaaatt gaagggagag atgatggatc tccaacatgg cagccttttc   300
cttagaacac caaagattgt ctctggcaaa gactataatg taactgcaaa ctccaagctg   360
gtcattatca cggctgggc acgtcagcaa gagggagaaa gccgtcttaa tttggtccag   420
cgtaacgtga acatctttaa attcatcatt cctaatgttg taaaatacag cccgaactgc   480
aagttgctta ttgtttcaaa tccagtggat atcttgacct acgtggcttg gaagataagt   540
ggttttccca aaaaccgtgt tattggaagc ggttgcaatc tggattcagc ccgattccgt   600
tacctaatgg ggaaaggct gggagttcac ccattaagct gtcatgggtg gtccttggg     660
gaacatggag attccagtgt gcctgtatgg agtggaatga atgttgctgg tgtctctctg   720
aagactctgc acccagattt agggactgat aagataagg acagtggaaa gaggttcac    780
agcaggtggt tgagagtgct tatgaggtga tcaaactcaa aggctacaca tcctgggct    840
attggactct ctgtagcaga tttggcagag agtataatga gaatcttag cgggtgcac    900
ccagtttcca ccatgattaa gggtctttac gaataaagga tgatgtcttc cttagtgtt    960
ccttgcatttt gggacagaa tggaatctca gaccttgtga aggtgactct gacttctgag   1020
gaagaggccc gtttgaagaa gagtgcagat acactttggg ggatccaaaa ggagctgcaa  1080
ttttaa                                                               1086

SEQ ID NO: 1233           moltype = DNA  length = 825
FEATURE                   Location/Qualifiers
misc_feature              1..825
                          note = Synthetic
source                    1..825
                          mol_type = other DNA
                          organism = synthetic construct
SEQUENCE: 1233
atggcaactc taaaggatca gctgatttat aatcttctaa aggaagaaca gaccccccag    60
aataagatta cagttgttgg ggttggtgct gttggcatgg cctgtgccat cagtatctta   120
atgaaggact tggcagatga acttgctctt gttgatgtca tcgaagacaa attgaaggga   180
gagatgatgg atctccaaca tggcagcctt ttccttagaa caccaaagat tgtctctggc   240
```

```
aaagactata atgtaactgc aaactccaag ctggtcatta tcacggctgg ggcacgtcag    300
caagagggag aaagccgtct taatttggtc cagcgtaacg tgaacatctt taaattcatc    360
attcctaatg ttgtaaaata cagcccgaac tgcaagttgc ttattgtttc aaatccagtg    420
gatatcttga cctacgtggc ttggaagata agtggttttc ccaaaaaccg tgttattgga    480
agcggttgca atctggattc agcccgattc cgttacctaa tggggaaag gctgggagtt    540
cacccattaa gctgtcatgg gtgggtcctt ggggaacatg gagattccag tgtgcctgta    600
tggagtggaa tgaatgttgc tggtgtctct ctgaagactc tgcacccaga tttagggact    660
gataaagata aggaacagtg gaaagagtgc agatacactt tggggatcc aaaaggagct    720
gcaattttaa agtcttctga tgtcatatca tttcactgtc taggctacaa caggattcta    780
ggtggaggtt gtgcatgttg tcctttttat ctgatctgtg attaa                    825

SEQ ID NO: 1234         moltype = DNA  length = 726
FEATURE                 Location/Qualifiers
misc_feature            1..726
                        note = Synthetic
source                  1..726
                        mol_type = other DNA
                        organism = synthetic construct
SEQUENCE: 1234
atggcaactc taaggatca gctgatttat aatcttctaa aggaagaaca gaccccccag     60
aataagatta cagttgttgg ggttggtgct gttggcatgg cctgtgccat cagtatctta   120
atgaaggact tggcagatga acttgctctt gttgatgtca tcgaagacaa attgaaggga   180
gagatgatgg atctccaaca tggcagcctt ttccttagaa caccaaagat tgtctctggc   240
aaagactata atgtaactgc aaactccaag ctggtcatta tcacggctgg ggcacgtcag   300
caagagggag aaagccgtct taatttggtc cagcgtaacg tgaacatctt taaattcatc   360
attcctaatg ttgtaaaata cagcccgaac tgcaagttgc ttattgtttc aaatccagtg   420
gatatcttga cctacgtggc ttggaagata agtggttttc ccaaaaaccg tgttattgga   480
agcggttgca atctggattc agcccgattc cgttacctaa tggggaaag gctgggagtt   540
cacccattaa gctgtcatgg gtgggtcctt ggggaacatg gagattccag tgtgcctgta   600
tggagtggaa tgaatgttgc tggtgtctct ctgaagactc tgcacccaga tttagggact   660
gataaagata aggaacagtg gaaagaggtt cacaagcagg tggttgagag ggtctttacg   720
gaataa                                                              726

SEQ ID NO: 1235         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1235
agaaatccgt ctttcattga cgggatgaca tcaacaagag caa                      43

SEQ ID NO: 1236         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1236
ccttcattaa gatactgatg                                                20

SEQ ID NO: 1237         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1237
taggacttgg cagatgaact                                                20

SEQ ID NO: 1238         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1238
atctgccaag tcctaaaaga                                                20

SEQ ID NO: 1239         moltype = DNA  length = 20
FEATURE                 Location/Qualifiers
misc_feature            1..20
                        note = Synthetic
source                  1..20
                        mol_type = other DNA
```

```
                              organism = synthetic construct
SEQUENCE: 1239
gatgacatca acaagagcaa                                                    20

SEQ ID NO: 1240           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1240
gatgtctttt aggacttggc                                                    20

SEQ ID NO: 1241           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1241
atgtctttta ggacttggca                                                    20

SEQ ID NO: 1242           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1242
ggacttggca gatgaacttg                                                    20

SEQ ID NO: 1243           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1243
aaatcaacct tgccagaga                                                     20

SEQ ID NO: 1244           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1244
ttgaaatcaa cctttgccag                                                    20

SEQ ID NO: 1245           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1245
ttcatagtgg atatcttgac                                                    20

SEQ ID NO: 1246           moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 1246
ctccttttc atagtggata                                                     20

SEQ ID NO: 1247           moltype = DNA   length = 20
FEATURE                   Location/Qualifiers
misc_feature              1..20
                          note = Synthetic
source                    1..20
```

-continued

```
                         mol_type = other DNA
                         organism = synthetic construct
SEQUENCE: 1247
tcctttttca tagtggatat                                                    20

SEQ ID NO: 1248          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1248
tcatagtgga tatcttgacc                                                    20

SEQ ID NO: 1249          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1249
catagtggat atcttgacct                                                    20

SEQ ID NO: 1250          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1250
atagtggata tcttgaccta                                                    20

SEQ ID NO: 1251          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1251
ggtaacggaa tcgggctgaa                                                    20

SEQ ID NO: 1252          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1252
ccactggaat ctccatgttc                                                    20

SEQ ID NO: 1253          moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 1253
tgcttaccac tggaatctcc                                                    20

SEQ ID NO: 1254          moltype = RNA  length = 43
FEATURE                  Location/Qualifiers
misc_feature             1..43
                         note = Synthetic
modified_base            40..43
                         mod_base = OTHER
                         note = modified with phosphorothioate
modified_base            40..42
                         mod_base = OTHER
                         note = modified with 2'-O-methylation
source                   1..43
                         mol_type = other RNA
                         organism = synthetic construct
SEQUENCE: 1254
```
agaaatccgt ctttcattga cggtaggact tggcagatga act					43

SEQ ID NO: 1255			moltype = RNA   length = 43
FEATURE				Location/Qualifiers
misc_feature			1..43
				note = Synthetic
modified_base			1..4
				mod_base = OTHER
				note = modified with phosphorothioate
modified_base			1..3
				mod_base = OTHER
				note = modified with 2'-O-methylation
modified_base			40..43
				mod_base = OTHER
				note = modified with phosphorothioate
source				1..43
				mol_type = other RNA
				organism = synthetic construct
modified_base			40..42
				mod_base = OTHER
				note = modified with 2'-O-methylation
SEQUENCE: 1255
agaaatccgt ctttcattga cggtaggact tggcagatga act					43

SEQ ID NO: 1256			moltype = RNA   length = 43
FEATURE				Location/Qualifiers
misc_feature			1..43
				note = Synthetic
modified_base			40..43
				mod_base = OTHER
				note = modified with phosphorothioate
source				1..43
				mol_type = other RNA
				organism = synthetic construct
modified_base			40..42
				mod_base = OTHER
				note = modified with 2'-O-methylation
SEQUENCE: 1256
agaaatccgt ctttcattga cgggatgaca tcaacaagag caa					43

SEQ ID NO: 1257			moltype = RNA   length = 43
FEATURE				Location/Qualifiers
misc_feature			1..43
				note = Synthetic
modified_base			1..4
				mod_base = OTHER
				note = modified with phosphorothioate
modified_base			1..3
				mod_base = OTHER
				note = modified with 2'-O-methylation
modified_base			40..43
				mod_base = OTHER
				note = modified with phosphorothioate
modified_base			40..42
				mod_base = OTHER
				note = modified with 2'-O-methylation
source				1..43
				mol_type = other RNA
				organism = synthetic construct
SEQUENCE: 1257
agaaatccgt ctttcattga cgggatgaca tcaacaagag caa					43

SEQ ID NO: 1258			moltype = RNA   length = 43
FEATURE				Location/Qualifiers
misc_feature			1..43
				note = Synthetic
modified_base			40..43
				mod_base = OTHER
				note = modified with phosphorothioate
modified_base			40..42
				mod_base = OTHER
				note = modified with 2'-O-methylation
source				1..43
				mol_type = other RNA
				organism = synthetic construct
SEQUENCE: 1258
agaaatccgt ctttcattga cggtcatagt ggatatcttg acc					43

SEQ ID NO: 1259			moltype = RNA   length = 43

| FEATURE | Location/Qualifiers |
|---|---|
| misc_feature | 1..43 |
| | note = Synthetic |
| modified_base | 1..4 |
| | mod_base = OTHER |
| | note = modified with phosphorothioate |
| modified_base | 1..3 |
| | mod_base = OTHER |
| | note = modified with 2'-O-methylation |
| modified_base | 40..43 |
| | mod_base = OTHER |
| | note = modified with phosphorothioate |
| modified_base | 40..42 |
| | mod_base = OTHER |
| | note = modified with 2'-O-methylation |
| source | 1..43 |
| | mol_type = other RNA |
| | organism = synthetic construct |

SEQUENCE: 1259
agaaatccgt ctttcattga cggtcatagt ggatatcttg acc                43

| SEQ ID NO: 1260 | moltype = RNA  length = 43 |
|---|---|
| FEATURE | Location/Qualifiers |
| misc_feature | 1..43 |
| | note = Synthetic |
| modified_base | 40..43 |
| | mod_base = OTHER |
| | note = modified with phosphorothioate |
| modified_base | 40..42 |
| | mod_base = OTHER |
| | note = modified with 2'-O-methylation |
| source | 1..43 |
| | mol_type = other RNA |
| | organism = synthetic construct |

SEQUENCE: 1260
agaaatccgt ctttcattga cggttcatag tggatatctt gac                43

| SEQ ID NO: 1261 | moltype = RNA  length = 43 |
|---|---|
| FEATURE | Location/Qualifiers |
| misc_feature | 1..43 |
| | note = Synthetic |
| modified_base | 1..4 |
| | mod_base = OTHER |
| | note = modified with phosphorothioate |
| modified_base | 1..3 |
| | mod_base = OTHER |
| | note = modified with 2'-O-methylation |
| modified_base | 40..43 |
| | mod_base = OTHER |
| | note = modified with phosphorothioate |
| modified_base | 40..42 |
| | mod_base = OTHER |
| | note = modified with 2'-O-methylation |
| source | 1..43 |
| | mol_type = other RNA |
| | organism = synthetic construct |

SEQUENCE: 1261
agaaatccgt ctttcattga cggttcatag tggatatctt gac                43

| SEQ ID NO: 1262 | moltype = RNA  length = 43 |
|---|---|
| FEATURE | Location/Qualifiers |
| misc_feature | 1..43 |
| | note = Synthetic |
| modified_base | 40..43 |
| | mod_base = OTHER |
| | note = modified with phosphorothioate |
| modified_base | 40..42 |
| | mod_base = OTHER |
| | note = modified with 2'-O-methylation |
| source | 1..43 |
| | mol_type = other RNA |
| | organism = synthetic construct |

SEQUENCE: 1262
agaaatccgt ctttcattga cggcatagtg gatatcttga cct                43

| SEQ ID NO: 1263 | moltype = RNA  length = 43 |
|---|---|
| FEATURE | Location/Qualifiers |
| misc_feature | 1..43 |
| | note = Synthetic |

```
modified_base           1..4
                        mod_base = OTHER
                        note = modified with phosphorothioate
modified_base           40..43
                        mod_base = OTHER
                        note = modified with phosphorothioate
source                  1..43
                        mol_type = other RNA
                        organism = synthetic construct
modified_base           40..42
                        mod_base = OTHER
                        note = modified with 2'-O-methylation
modified_base           1..3
                        mod_base = OTHER
                        note = modified with 2'-O-methylation
SEQUENCE: 1263
agaaatccgt ctttcattga cggcatagtg gatatcttga cct              43

SEQ ID NO: 1264         moltype = DNA  length = 122
FEATURE                 Location/Qualifiers
misc_feature            1..122
                        note = Synthetic
source                  1..122
                        mol_type = other DNA
                        organism = synthetic construct
SEQUENCE: 1264
ttttccttag aacaccaaag attgtctctg gcaaagacta taatgtaact gcaaactcca   60
agctggtcat tatcacggct ggggcacgtc agcaagaggg agaaagccgt cttaatttgg  120
tc                                                                 122

SEQ ID NO: 1265         moltype = RNA  length = 3213
FEATURE                 Location/Qualifiers
misc_feature            1..3213
                        note = Synthetic
source                  1..3213
                        mol_type = other RNA
                        organism = synthetic construct
SEQUENCE: 1265
atgagctccg ccatcaagtc ctacaagtct gtgctgcggc caaacgagag aaagaatcag   60
ctgctgaagt ccaccatcca gtgcctggag gacggctccg ccttcttttt caagatgctg  120
cagggcctgt tggcggcat cacccccgag atcgtgagat tcagcacaga gcaggagaag  180
cagcagcagg atatcgccct gtggtgtgcc gtgaattggt tcaggcctgt gagccaggac  240
tccctgaccc acacaatcgc ctccgataac ctggtggaga gtttgagga gtactatgcc  300
ggcacagcca gcgacgccat caagcagtac ttcagcgcct ccatcggcga gtcctactat  360
tggaatgact gccgccagca gtactatgat ctgtgtcggg agctgggcgt ggaggtgtct  420
gacctgaccc acgatctgga gatcctgtgc gggagaagt gtctggccgt ggccacagag  480
agcaaccaga acaattctat catcagcgtg ctgtttggga ccggcgagaa ggaggatagg  540
tctgtgaagc tgcgcatcac aaagaagatc ctggaggcca tcagcaacct gaaggagatc  600
ccaaagaatg tggcccccat ccaggagatc atcctgaatg tggccaaggc caccaaggag  660
acattcgac aggtgtacgc aggaaacctg ggagcaccat ccaccctgga gaagtttatc  720
gccaaggacg gccagaagga gttcgatctg aagaagctgc agacagacct gaagaaagtg  780
atccggggca gtctaagga gagagattgg tgctgtcagg aggagctgag gagctacgtg  840
gagcagaata ccatccagta tgacctgtgg gcctggggcg agatgttcaa caaggccac  900
accgccctga gatcaagtc cacaagaaac tacaattttg ccaagcagag gctggagcag  960
ttcaaggaga tccagtctct gaacaatctg ctggtggtga agaagctgaa cgactttttc 1020
gatagcgagt ttttctccgg cgaggagacc tacacaatct gcgtgcacca cctgggcggc 1080
aaggacctgt ccaagctgta aaggcctgg gaggacgatc ccgccgatcc tgagaatgcc 1140
atcgtggtgc tgtgcgacga tctgaagaac aattttaaga aggagcctat caggaacatc 1200
ctgcgctaca tcttcaccat ccgccaggag tgtagcgcaa aggacatcct ggcagcagca 1260
aagtacaatc agcagctgga tcggtataag agccagaagg ccaacccatc cgtgctgggc 1320
aatcagggct ttacctggac aaacgccgtg atcctgccag agaaggccca gcggaacgac 1380
agacccaatt ctctggatct gcgcatctgg ctgtacctga gctgcggca ccctgacggc 1440
agatggaaga agcaccacat cccattctac gatacccggt ttttccagga gatctatgcc 1500
gccggcaata gccctgtgga cacctgtcag tttaggacag cccgcttcgg ctatcacctg 1560
cctaagctga ccgatcagac agccatccgc gtgaacaaga agcacgtgaa ggcagcaaag 1620
accgaggcac ggatcagact ggccatccag cagggcacac tgccagtgtc caatctgaag 1680
atcaccgaga tctccgccac aatcaactct aagggccagg tgcgcatccc cgtgaagttt 1740
cgggtgggaa ggcagaaggg aaccctgcag atcgcgacc ggttctgcgg ctacgatcag 1800
aaccagacag cctctcacgc ctatagcctg tgggaggtgg tgaaggaggg ccagtaccac 1860
aaggagctgg gctgttttgt gcgcttcatc tctagcggcg acatcgtgtc catcaccgag 1920
aaccggggca atcagtttga tcagctgtct tatgagggcc tggcctaccc ccagtatgcc 1980
gactggaaa agaaggcctc caagttcgtg tctctgtggc agatcaccaa gaagaacaag 2040
aagaaggaga tcgtgacagt ggaggccaag gagaagtttg acgccatctg caagtaccag 2100
cctaggctgt ataagttcaa caaggagtac gcctatctgg tcgtggatat cgtgagaggc 2160
aagagcctgg tggagctgca gcagatcagg caggagatct ttcgcttcat cgagcaggac 2220
tgtgagtgta cccgcctggg atctctgagc ctgtccaccc tggagacagt gaaggccgtg 2280
aagggcatca tctactccta ttttctacca gccctgaatg cctctaagaa caatcccatc 2340
agcgacgagc agcggaagga gtttgatcct gagctgttcg ccctgctgga gaagctggag 2400
ctgatcagga ctcggaagaa gaagcagaag gtggagagaa tcgccaatag cctgatcag 2460
```

```
acatgcctgg agaacaatat caagttcatc aggggcgagg gcgacctgtc caccacaaac 2520
aatgccacca agaagaaggc caactctagg agcatggatt ggctggccag aggcgtgttt 2580
aataagatcc ggcagctggc cccaatgcac aacatcaccc tgttcggctg cggcagcctg 2640
tacacatccc accaggaccc tctggtgcac agaaacccag ataaggccat gaagtgtaga 2700
tgggcagcaa tcccagtgaa ggacatcggc gattgggtgc tgagaaagct gtcccagaac 2760
ctgagggcca agaatcgggg caccggcgag tactatcacc agggcgtgaa ggagttcctg 2820
tctcactatg agctgcagga cctggaggag gagctgctga agtggcggtc tgatagaaag 2880
agcaacatcc cttgctgggt gctgcagaat agactggccg agaagctggg caacaaggag 2940
gccgtggtgt acatcccagt gaggggcggc cgcatctatt ttgcaaccca caggtggca  3000
acaggagccg tgagcatcgt gttcgaccag aagcaagtgt gggtgtgtaa tgcagatcac 3060
gtggcagcag caaacatcgc actgaccggc aagggcatcg gcgagcagtc ctctgacgag 3120
gagaaccccg atggctccag gatcaagctg cagctgacat ctaaaaggcc ggcggccacg 3180
aaaaaggccg gccaggcaaa aaagaaaaag taa                              3213

SEQ ID NO: 1266       moltype = RNA   length = 3213
FEATURE               Location/Qualifiers
misc_feature          1..3213
                      note = Synthetic
source                1..3213
                      mol_type = other RNA
                      organism = synthetic construct
SEQUENCE: 1266
atgagctccg ccatcaagtc ctacaagtct gtgctgcggc aaacgagag aaagaatcag  60
ctgctgaagt ccaccatcca gtgcctggag gacggctccg ccttctttt caagatgctg  120
cagggcctgt ttggcggcat cacccccgag atcgtgagat tcagcacaga gcaggagaag  180
cagcagcagg atatcgccct gtggtgtgcc gtgaattgtc aggcctgtg gagccaggac  240
tccctgaccc acacaatcgc ctccgataac ctggtggaga agtttgagga gtactatggc  300
ggcacagcca gcgacgccat caagcagtac ttcagcgcct ccatcggcga gtcctactat  360
tggaatgact gccgccagca gtactatgat ctgtgtcggg agctgggcgt ggaggtgtct  420
gacctgaccc acgatctgga gatcctgtgc cgggagaag gtctggccgt ggccacagag  480
agcaaccaga acaattctat catcagcgtg ctgtttggca ccggcgagaa ggaggatagg  540
tctgtgaagc tgcgcatcac aaagaagatc ctggaggcca tcagcaacct gaaggagatc  600
ccaaagaatg tggccccat ccaggagatc atcctgaatg tggccaaggc caccaaggag  660
acattcagac aggtgtacgc aggaaacctg ggagcaccat ccaccctgga gaagtttat  720
gccaaggacg gccagaagga gttcgatctg aagaagctgc agacagacct gaagaaagtg  780
atccggggca agtctaagga gagagattgg tgctgtcagg aggagctgag gagctacgtg  840
gagcagaata ccatccagta tgacctgtgg gcctggggcg agatgttcaa caaggccac  900
accgccctga agatcaagtc cacagaaaac tacaattttg ccaagcagag gctggagcag  960
ttcaaggaga tccagtctct gaacatctgc tggttggtga agaagctgaa cgacttttt  1020
gatagcgagt ttttctccgg cgaggagacc tacaatctgc gtgcacca cctgggcggc  1080
aaggacctgt ccaagctgta taggcctgg gaggacgatc ccgcgatcc tgagaatgcc  1140
atcgtggtgc tgtgcgacga tctgaagaac aatttttaaga aggagcctat caggaacatc  1200
ctgcgctaca tcttcaccat ccgccaggag tgtagcgaca gcagcagca              1260
aagtacaatc agcagctgga tcggtataag agccagaagg ccaacccatc cgtgctgggc  1320
aatcagggct ttacctggac aaacgccgtg atcctgccag agaaggccca gcggaacgac  1380
agacccaatt ctctggatct cgcatctgg ctgtacctga agctgcggca ccctgacggc  1440
agatgaagaa agcaccacat cccattctac gatacccgt ttttccagga gatctatgcc  1500
gccggcaata gccctgtgga cacctgtcag tttaggacac cccgcttcgg ctatcacctg  1560
cctaagctga ccgatcagac agccatccgc gtgaacaaga agcacgtgaa ggcagcaaag  1620
accgaggcac ggatcagact ggccatccag cagggcacac tgccagtgtc caatctgaag  1680
atcaccgaga tctccgccac aatcaactct aagggccagg tgcgcatccc cgtgaagttt  1740
cgggtgggaa ggcagaaggg aaccctgcag atcggcgacc ggttctgcgg ctacgatcag  1800
aaccagacag cctctcacgc ctatagcctg tgggaggtgg tgaaggaggg ccagtaccac  1860
aaggagctgc ggtgtcgggt gcgcttcatc tctagcggcg acatcgtgtc catcaccgag  1920
aaccggggca atcagtttga tcagctgtct tatgagggcc tggcctaccc ccagtatgcc  1980
gactgagaa agaaggcctc caagttcgtg tctctgtggc agatcaccaa gaagaacaag  2040
aagaaggaga tcgtgacagt ggaggccaag gagaagtttg acgccatctg caagtaccag  2100
cctaggctgt ataagttcaa caaggagtac gcctatctgc tgcgggatat cgtgagaggc  2160
aagagcctgg tggagctgca gcagatcagg caggagatct ttcgcttcat cgagcaggac  2220
tgtggagtga cccgcctggg atctctgagc ctgtccaccc tggagacagt gaaggccgtg  2280
aagggcatca tctactccta ttttttctaca gccctgaatg cctctaagaa caatcccatc  2340
agcgacgagc agcggaagga gtttgatcct gagctgttcg ccctgctgga gaagctggag  2400
ctgatcagga ctcggaagaa gaagcagaag gtggagagaa tcgccaatag cctgatccag  2460
acatgcctgg agaacaatat caagttcatc aggggcgagg gcgacctgtc caccacaaac  2520
aatgccacca agaagaaggc caactctagg agcatggatt ggctggccag aggcgtgttt  2580
aataagatcc ggcagctggc cccaatgcac aacatcaccc tgttcggctg cggcagcctg  2640
tacacatccc accaggaccc tctggtgcac agaaacccag ataaggccat gaagtgtaga  2700
tgggcagcaa tcccagtgaa ggacatcggc gattgggtgc tgagaaagct gtcccagaac  2760
ctgagggcca agaatcgggg caccggcgag tactatcacc agggcgtgaa ggagttcctg  2820
tctcactatg agctgcagga cctggaggag gagctgctga agtggcggtc tgatagaaag  2880
agcaacatcc cttgctgggt gctgcagaat agactggccg agaagctggg caacaaggag  2940
gccgtggtgt acatcccagt gaggggcggc cgcatctatt ttgcaaccca caggtggca   3000
acaggagccg tgagcatcgt gttcgaccag aagcaagtgt gggtgtgtaa tgcagatcac  3060
gtggcagcag caaacatcgc actgaccggc aagggcatcg gcgagcagtc ctctgacgag  3120
gagaaccccg atggctccag gatcaagctg cagctgacat ctaaaaggcc ggcggccacg  3180
aaaaaggccg gccaggcaaa aaagaaaaag taa                               3213

SEQ ID NO: 1267       moltype = RNA   length = 43
FEATURE               Location/Qualifiers
```

```
misc_feature            1..43
                        note = Synthetic
modified_base           40..43
                        mod_base = OTHER
                        note = modified with phosphorothioate
modified_base           40..42
                        mod_base = OTHER
                        note = modified with 2'-O-methylation
source                  1..43
                        mol_type = other RNA
                        organism = synthetic construct
SEQUENCE: 1267
agaaatccgt ctttcattga cggtaggact tggcagatga act                    43

SEQ ID NO: 1268         moltype = RNA   length = 43
FEATURE                 Location/Qualifiers
misc_feature            1..43
                        note = Synthetic
modified_base           1..4
                        mod_base = OTHER
                        note = modified with phosphorothioate
modified_base           1..3
                        mod_base = OTHER
                        note = modified with 2'-O-methylation
modified_base           40..43
                        mod_base = OTHER
                        note = modified with phosphorothioate
modified_base           40..42
                        mod_base = OTHER
                        note = modified with 2'-O-methylation
source                  1..43
                        mol_type = other RNA
                        organism = synthetic construct
SEQUENCE: 1268
agaaatccgt ctttcattga cggtaggact tggcagatga act                    43

SEQ ID NO: 1269         moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 1269
taggacttgg cagatgaact                                              20

SEQ ID NO: 1270         moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 1270
gatgacatca acaagagcaa                                              20

SEQ ID NO: 1271         moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 1271
ttcatagtgg atatcttgac                                              20

SEQ ID NO: 1272         moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 1272
tcatagtgga tatcttgacc                                              20

SEQ ID NO: 1273         moltype = RNA   length = 20
FEATURE                 Location/Qualifiers
misc_feature            1..20
```

```
                         note       = Synthetic
source                   1..20
                         mol_type   = other RNA
                         organism   = synthetic construct
SEQUENCE: 1273
catagtggat atcttgacct                                              20
```

GENE EDITING SYSTEMS COMPRISING AN RNA GUIDE TARGETING LACTATE DEHYDROGENASE A (LDHA) AND USES THEREOF

CROSS REFERENCE TO RELATED APPLICATIONS

The present application is a continuation of U.S. Nonprovisional application Ser. No. 17/832,114, filed Jun. 3, 2022, which claims the benefit under 35 U.S.C. § 119(e) of U.S. Provisional Application No. 63/197,067, filed Jun. 4, 2021, U.S. Provisional Application No. 63/225,214, filed Jul. 23, 2021, U.S. Provisional Application No. 63/292,912, filed Dec. 22, 2021, and U.S. Provisional Application No. 63/300,743, filed Jan. 19, 2022, the contents of each of which are incorporated by reference herein in their entirety.

SEQUENCE LISTING

The instant application contains a Sequence Listing which has been filed electronically in XML format and is hereby incorporated by reference in its entirety. Said XML copy, created on Mar. 21, 2023, is named 116928-0046-0003US01_SUBSEQ.xml and is 1,680,046 bytes in size.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

The present disclosure is based, at least in part, on the development of a system for genetic editing of a lactate dehydrogenase A (LDHA) gene. The system involves a Cas12i polypeptide such as a Cas12i2 polypeptide and an RNA guide mediating cleavage at a genetic site within the LDHA gene by the CRISPR nuclease polypeptide. As reported herein, the gene editing system disclosed herein has achieved successful editing of LDHA gene with high editing efficiency and accuracy.

Without being bound by theory, the gene editing system disclosed herein may exhibit one or more of the following advantageous features. Compared to SpCas9 and Cas12a, Cas12i effectors are smaller (1033 to 1093aa) which, in conjunction with their short mature crRNA (40-43 nt), is preferable in terms of delivery and cost of synthesis. Cas12i cleavage results in larger deletions compared to the small deletions and +1 insertions induced by Cas9 cleavage. Cas12i PAM sequences also differ from those of Cas9. Therefore, larger and different portions of genetic sites of interest can be disrupted with a Cas12i polypeptide and RNA guide compared to Cas9. Using an unbiased approach of tagmentation-based tag integration site sequencing (TTISS), more potential off-target sites with a higher number of unique integration events were identified for SpCas9 compared to Cas12i2. See WO/2021/202800. Therefore, Cas12i such as Cas12i2 may be more specific than Cas9.

Accordingly, provided herein are gene editing systems for editing LDHA gene, pharmaceutical compositions or kits comprising such, methods of using the gene editing systems to produce genetically modified cells, and the resultant cells thus produced. Also provided herein are uses of the gene editing systems disclosed herein, the pharmaceutical compositions and kits comprising such, and/or the genetically modified cells thus produced for treating primary hyperoxaluria (PH) in a subject.

In some aspects, the present disclosure features system for genetic editing of a hydroxyacid oxidase 1 (LDHA) gene, comprising (i) a Cas12i polypeptide or a first nucleic acid encoding the Cas12i polypeptide, and (ii) an RNA guide or a second nucleic acid encoding the RNA guide. The RNA guide comprises a spacer sequence specific to a target sequence within an LDHA gene, the target sequence being adjacent to a protospacer adjacent motif (PAM) comprising the motif of 5'-TTN-3', which is located 5' to the target sequence.

In some embodiments, the Cas12i is a Cas12i2 polypeptide. In other embodiments, the Cas12i is a Cas12i4 polypeptide.

In some embodiments, the Cas12i polypeptide is a Cas12i2 polypeptide comprising an amino acid sequence at least 95% identical to SEQ ID NO: 1166. In some instances, the Cas12i2 polypeptide may comprise one or more mutations relative to SEQ ID NO: 1166. In some examples, the one or more mutations in the Cas12i2 polypeptide are at positions D581, G624, F626, P868, I926, V1030, E1035, and/or S1046 of SEQ ID NO: 1166. In some examples, the one or more mutations are amino acid substitutions, which optionally is D581R, G624R, F626R, P868T, I926R, V1030G, E1035R, S1046G, or a combination thereof.

In one example, the Cas12i2 polypeptide comprises mutations at positions D581, D911, I926, and V1030 (e.g., amino acid substitutions of D581R, D911R, I926R, and V1030G). In another example, the Cas12i2 polypeptide comprises mutations at positions D581, I926, and V1030 (e.g., amino acid substitutions of D581R, I926R, and V1030G). In yet another example, the Cas12i2 polypeptide comprises mutations at positions D581, I926, V1030, and S1046 (e.g., amino acid substitutions of D581R, I926R, V1030G, and S1046G). In still another example, the Cas12i2 polypeptide comprises mutations at positions D581, G624, F626, I926, V1030, E1035, and S1046 (e.g., amino acid substitutions of D581R, G624R, F626R, I926R, V1030G, E1035R, and S1046G). In another example, the Cas12i2 polypeptide comprises mutations at positions D581, G624, F626, P868, I926, V1030, E1035, and S1046 (e.g., amino acid substitutions of D581R, G624R, F626R, P868T, I926R, V1030G, E1035R, and S1046G).

Exemplary Cas12i2 polypeptides for use in any of the gene editing systems disclosed herein may comprise the amino acid sequence of any one of SEQ ID NOs: 1167-1171. In one example, the exemplary Cas12i2 polypeptide for use in any of the gene editing systems disclosed herein comprises the amino acid sequence of SEQ ID NO: 1168. In another example, the exemplary Cas12i2 polypeptide for use in any of the gene editing systems disclosed herein comprises the amino acid sequence of SEQ ID NO: 1171.

In some embodiments, the gene editing system may comprise the first nucleic acid encoding the Cas12i polypeptide (e.g., the Cas12i2 polypeptide). In some instances, the first nucleic acid is located in a first vector (e.g., a viral vector such as an adeno-associated viral vector or AAV vector). In some instances, the first nucleic acid is a messenger RNA (mRNA). In some instances, the coding sequence for the Cas12i polypeptide is codon optimized.

In some embodiments, the target sequence may be within exon 1 or exon 2 of the LDHA gene. In some examples, the target sequence comprises 5'-TAGGACTTGGCAGAT- GAACT-3' (SEQ ID NO: 1237), 5'-GATGACAT-CAACAAGAGCAA-3' (SEQ ID NO: 1239), 5'-TTCAT-AGTGGATATCTTGAC-3' (SEQ ID NO: 1245), 5'-TCATAGTGGATATCTTGACC-3' (SEQ ID NO: 1248), or 5'-CATAGTGGATATCTTGACCT-3' (SEQ ID NO: 1249). In some examples, the target sequence may comprise SEQ ID NO: 1248.

In some embodiments, the spacer sequence may be 20-30-nucleotide in length. In some examples, the spacer sequence is 20-nucleotide in length. In some examples, the spacer sequence comprises 5'-UAGGACUUGGCAGAUGAACU-3' (SEQ ID NO: 1269); 5'-GAUGACAU-CAACAAGAGCAA-3' (SEQ ID NO: 1270); 5'-UU-CAUAGUGGAUAUCUUGAC-3' (SEQ ID NO: 1271); 5'-UCAUAGUGGAUAUCUUGACC-3' (SEQ ID NO: 1272); or 5'-CAUAGUGGAUAUCUUGACCU-3' (SEQ ID NO: 1273). In some examples, the spacer sequence may comprise SEQ ID NO: 1272.

In some embodiments, the RNA guide comprises the spacer and a direct repeat sequence. In some examples, the direct repeat sequence is 23-36-nucleotide in length. In one example, the direct repeat sequence is at least 90% identical to any one of SEQ ID NOs: 1-10 or a fragment thereof that is at least 23-nucleotide in length. In some specific examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUU-CAUUGACGG-3' (SEQ ID NO: 10).

In specific examples, the RNA guide may comprise the nucleotide sequence of 5'-AGAAAUCCGUCUUU-CAUUGACGGUAGGACUUGGCAGAUGAACU-3' (SEQ ID NO: 1214), 5'-AGAAAUCCGUCUUU-CAUUGACGGGAUGACAUCAACAAGAGCAA-3' (SEQ ID NO: 1235), 5'-AGAAAUCCGUCUUU-CAUUGACGGUUCAUAGUGGAUAUCUUGAC-3' (SEQ ID NO: 1221), 5'-AGAAAUCCGUCUUU-CAUUGACGGUCAUAGUGGAUAUCUUGACC-3' (SEQ ID NO: 1224), or 5'-AGAAAUCCGUCUUU-CAUUGACGGCAUAGUGGAUAUCUUGACCU-3' (SEQ ID NO: 1225). In one example, the RNA guide may comprise SEQ ID NO: 1224.

In some embodiments, the system may comprise the second nucleic acid encoding the RNA guide. In some examples, the nucleic acid encoding the RNA guide may be located in a viral vector. In some examples, the viral vector comprises the both the first nucleic acid encoding the Cas12i polypeptide (e.g., the Cas12i2 polypeptide) and the second nucleic acid encoding the RNA guide.

In some embodiments, any of the systems described herein may comprise the first nucleic acid encoding the Cas12i polypeptide (e.g., the Cas12i2 polypeptide), which is located in a first vector, and the second nucleic acid encoding the RNA guide, which is located on a second vector. In some examples, the first and/or second vector is a viral vector. In some specific examples, the first and second vectors are the same vector.

In some embodiments, any of the systems described herein may comprise one or more lipid nanoparticles (LNPs), which encompass the Cas12i polypeptide (e.g., the Cas12i2 polypeptide) or the first nucleic acid encoding the Cas12i polypeptide, the RNA guide or the second nucleic acid encoding the RNA guide, or both.

In some embodiments, the system described herein may comprise a LNP, which encompass the Cas12i polypeptide (e.g., the Cas12i2 polypeptide) or the first nucleic acid encoding the Cas12i polypeptide, and a viral vector comprising the second nucleic acid encoding the RNA guide. In some examples, the viral vector is an AAV vector. In other embodiments, the system described herein may comprise a LNP, which encompass the RNA guide or the second nucleic acid encoding the RNA guide, and a viral vector comprising the first nucleic acid encoding the Cas12i polypeptide. In some examples, the viral vector is an AAV vector.

In some aspects, the present disclosure also provides a pharmaceutical composition comprising any of the gene editing systems disclosed herein, and a kit comprising the components of the gene editing system.

In other aspects, the present disclosure also features a method for editing a lactate dehydrogenase A (LDHA) gene in a cell, the method comprising contacting a host cell with any of the systems disclosed herein to genetically edit the LDHA gene in the host cell. In some examples, the host cell is cultured in vitro. In other examples, the contacting step is performed by administering the system for editing the LDHA gene to a subject comprising the host cell.

Also within the scope of the present disclosure is a cell comprising a disrupted a lactate dehydrogenase A (LDHA) gene, which can be produced by contacting a host cell with the system disclosed herein genetically edit the LDHA gene in the host cell.

Still in other aspects, the present disclosure provides a method for treating primary hyperoxaluria (PH) in a subject. The method may comprise administering to a subject in need thereof any of the systems for editing a lactate dehydrogenase A (LDHA) gene or any of the cells disclosed herein.

In some embodiments, the subject may be a human patient having the PH. In some examples, the PH is PH1, PH2, or PH3. In a specific example, the PH is PH1.

Also provided herein is an RNA guide, comprising (i) a spacer sequence as disclosed herein that is specific to a target sequence in a lactate dehydrogenase A (LDHA) gene, wherein the target sequence is adjacent to a protospacer adjacent motif (PAM) comprising the motif of 5'-TTN-3', which is located 5' to the target sequence; and (ii) a direct repeat sequence.

In some embodiments, the spacer may be 20-30-nucleotide in length. In some examples, the spacer is 20-nucleotide in length.

In some embodiments, the direct repeat sequence may be 23-36-nucleotide in length. In some examples, the direct repeat sequence is 23-nucleotide in length.

In some embodiments, the target sequence may be within exon 3 or exon 5 of the LDHA gene. In some examples, the target sequence comprises 5'-TAGGACTTGGCAGAT-GAACT-3' (SEQ ID NO: 1237), 5'-GATGACAT-CAACAAGAGCAA-3' (SEQ ID NO: 1239), 5'-TTCAT-AGTGGATATCTTGAC-3' (SEQ ID NO: 1245), 5'-TCATAGTGGATATCTTGACC-3' (SEQ ID NO: 1248), or 5'-CATAGTGGATATCTTGACCT-3' (SEQ ID NO: 1249). In some examples, the target sequence may comprise SEQ ID NO: 1248.

In some embodiments, the spacer sequence may comprise 5'-AGGACUUGGCAGAUGAACU-3' (SEQ ID NO: 1269); 5'-GAUGACAUCAACAAGAGCAA-3' (SEQ ID NO: 1270); 5'-UUCAUAGUGGAUAUCUUGAC-3' (SEQ ID NO: 1271); 5'-UCAUAGUGGAUAUCUUGACC-3' (SEQ ID NO: 1272); or 5'-CAUAGUGGAUAUCUUGACCU-3 (SEQ ID NO: 1273). In some examples, the spacer sequence may comprise SEQ ID NO: 1272.

In some embodiments, the direct repeat sequence may be at least 90% identical to any one of SEQ ID NOs: 1-10 or a fragment thereof that is at least 23-nucleotide in length. In some examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUU-CAUUGACGG-3' (SEQ ID NO: 10).

In some embodiments, the RNA guide may comprise the nucleotide sequence of 5'-AGAAAUCCGUCUUU-CAUUGACGGUAGGACUUGGCAGAUGAACU-3' (SEQ ID NO: 1214), 5'-AGAAAUCCGUCUUU-CAUUGACGGGAUGACAUCAACAAGAGCAA-3' (SEQ ID NO: 1235), 5'-AGAAAUCCGUCUUU-CAUUGACGGUUCAUAGUGGAUAUCUUGAC-3' (SEQ ID NO: 1221), 5'-AGAAAUCCGUCUUU-CAUUGACGGUCAUAGUGGAUAUCUUGACC-3' (SEQ ID NO: 1224), or 5'-AGAAAUCCGUCUUU-CAUUGACGGCAUAGUGGAUAUCUUGACCU-3' (SEQ ID NO: 1225). In some examples, the RNA guide may comprise SEQ ID NO: 1224.

Also provided herein are any of the gene editing systems disclosed herein, pharmaceutical compositions or kits comprising such, or genetically modified cells generated by the gene editing system for use in treating PH in a subject, as well as uses of the gene editing systems disclosed herein, pharmaceutical compositions or kits comprising such, or genetically modified cells generated by the gene editing system for manufacturing a medicament for treatment of PH in a subject.

The details of one or more embodiments of the invention are set forth in the description below. Other features or advantages of the present invention will be apparent from the following drawings and detailed description of several embodiments, and also from the appended claims.

DETAILED DESCRIPTION

Figure 1:
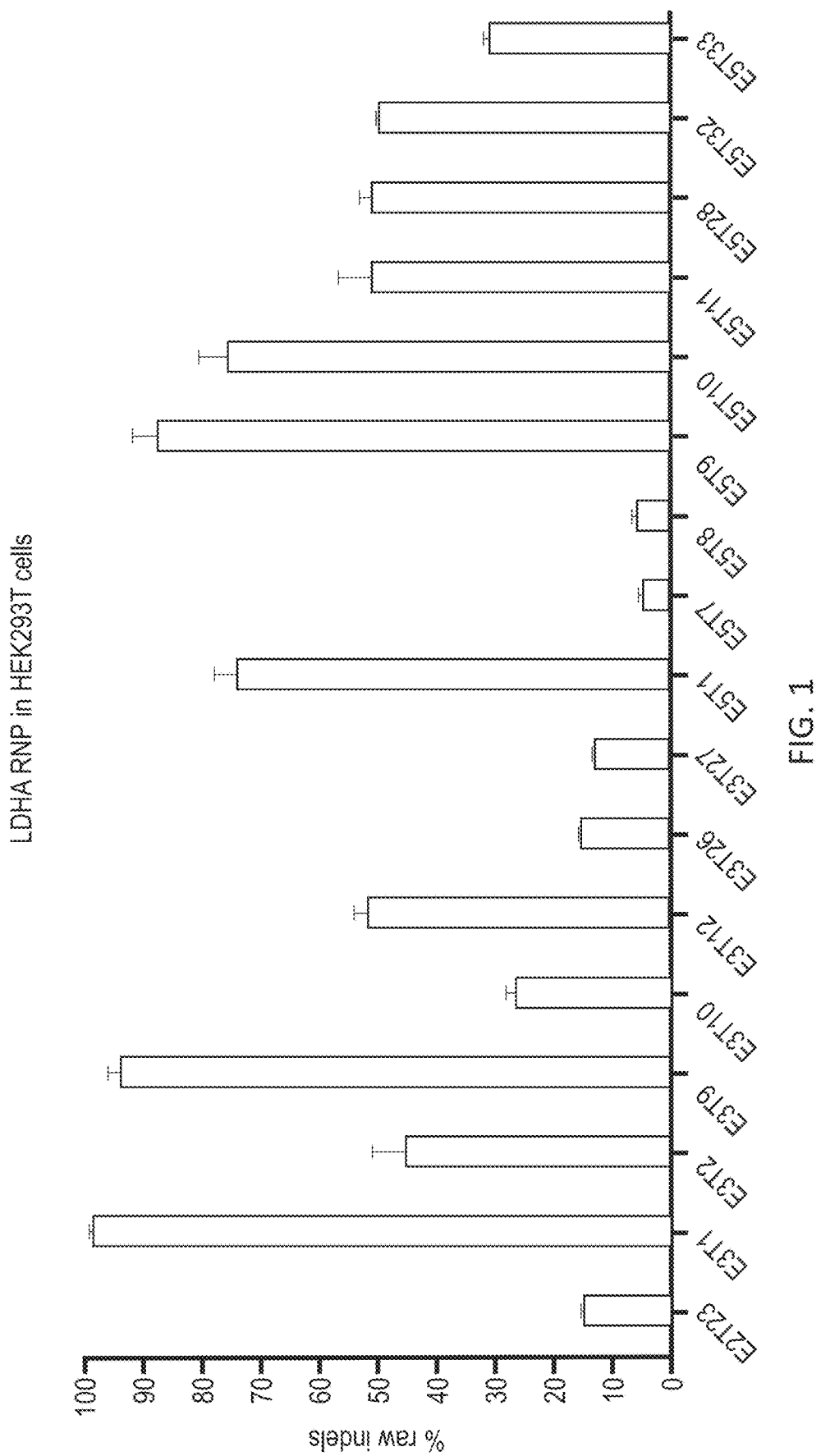
FIG. 1 is a graph showing the ability of RNPs prepared with a Cas12i2 polypeptide and a crRNA to edit the LDHA gene in HEK293 cells. The darker grey bars represent target sequences with perfect homology to both rhesus macaque (*Macaca* mulatta) and crab-eating macaque (*Macaca fascicularis*) sequences.

The present disclosure relates to a system for genetic editing of a lactate dehydrogenase A (LDHA) gene, which comprises (i) a Cas12i polypeptide or a first nucleic acid encoding the Cas12i2 polypeptide; and (ii) an RNA guide or a second nucleic acid encoding the RNA guide, wherein the RNA guide comprises a spacer sequence specific to a target sequence within an LDHA gene, the target sequence being adjacent to a protospacer adjacent motif (PAM) comprising the motif of 5'-TTN-3', which is located 5' to the target sequence. Also provided in the present disclosure are a pharmaceutical composition or a kit comprising such system as well as uses thereof. Further disclosed herein are a method for editing a LDHA gene in a cell, a cell so produced that comprises a disrupted a LDHA gene, a method of treating primary hyperoxaluria (PH) in a subject, and an RNA guide that comprises (i) a spacer that is specific to a target sequence in a LDHA gene, wherein the target sequence is adjacent to a protospacer adjacent motif (PAM) comprising the motif of 5'-TTN-3', which is located 5' to the target sequence; and (ii) a direct repeat sequence as well as uses thereof.

The Cas12i polypeptide for use in the gene editing system disclosed herein may be a Cas12i2 polypeptide, e.g., a wild-type Cas12i polypeptide or a variant thereof as those disclosed herein. In some examples, the Cas12i2 polypeptide comprises an amino acid sequence at least 95% identical to SEQ ID NO: 922 and comprises one or more mutations relative to SEQ ID NO: 922. In other examples, the Cas12i polypeptide may be a Cas12i4 polypeptide, which is also disclosed herein.

Definitions

The present disclosure will be described with respect to particular embodiments and with reference to certain Figures, but the disclosure is not limited thereto but only by the claims. Terms as set forth hereinafter are generally to be understood in their common sense unless indicated otherwise.

As used herein, the term "activity" refers to a biological activity. In some embodiments, activity includes enzymatic activity, e.g., catalytic ability of a Cas12i polypeptide. For example, activity can include nuclease activity.

As used herein the term "LDHA" refers to "lactate dehydrogenase A." LDHA is an enzyme that catalyzes the inter-conversion of pyruvate and L-lactate with concomitant inter-conversion of NADH and NAD+. LDHA plays roles in development, as well as invasion and metastasis of cancer. Many cancers are characterized by higher LDHA levels than normal tissues. SEQ ID NO: 1172 as set forth herein provides an example of an LDHA gene sequence.

As used herein, the term "Cas12i polypeptide" (also referred to herein as Cas12i) refers to a polypeptide that binds to a target sequence on a target nucleic acid specified by an RNA guide, wherein the polypeptide has at least some amino acid sequence homology to a wild-type Cas12i polypeptide. In some embodiments, the Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 1-5 and 11-18 of U.S. Pat. No. 10,808,245, which is incorporated by reference for the subject matter and purpose referenced herein. In some embodiments, a Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 8, 2, 11, and 9 of the present application. In some embodiments, a Cas12i polypeptide of the disclosure is a Cas12i2 polypeptide as described in WO/2021/202800, the relevant disclosures of which are incorporated by reference for the subject matter and purpose referenced herein. In some embodiments, the Cas12i polypeptide cleaves a target nucleic acid (e.g., as a nick or a double strand break).

As used herein, the term "complex" refers to a grouping of two or more molecules. In some embodiments, the complex comprises a polypeptide and a nucleic acid molecule interacting with (e.g., binding to, coming into contact with, adhering to) one another. For example, the term "complex" can refer to a grouping of an RNA guide and a polypeptide (e.g., a Cas12i polypeptide). Alternatively, the term "complex" can refer to a grouping of an RNA guide, a polypeptide, and the complementary region of a target sequence. In another example, the term "complex" can refer to a grouping of an LDHA-targeting RNA guide and a Cas12i polypeptide.

As used herein, the term "protospacer adjacent motif" or "PAM" refers to a DNA sequence adjacent to a target sequence (e.g., an LDHA target sequence) to which a complex comprising an RNA guide (e.g., an LDHA-targeting RNA guide) and a Cas12i polypeptide binds. In a double-stranded DNA molecule, the strand containing the PAM motif is called the "PAM-strand" and the complementary strand is called the "non-PAM strand." The RNA guide binds to a site in the non-PAM strand that is complementary to a target sequence disclosed herein. In some embodiments, the PAM strand is a coding (e.g., sense) strand. In other embodiments, the PAM strand is a non-coding (e.g., antisense) strand. Since an RNA guide binds the non-PAM strand via base-pairing, the non-PAM strand is also known as the target strand, while the PAM strand is also known as the non-target strand.

As used herein, the term "target sequence" refers to a DNA fragment adjacent to a PAM motif (on the PAM strand). The complementary region of the target sequence is on the non-PAM strand. A target sequence may be immediately adjacent to the PAM motif. Alternatively, the target sequence and the PAM may be separately by a small sequence segment (e.g., up to 5 nucleotides, for example, up to 4, 3, 2, or 1 nucleotide). A target sequence may be located at the 3' end of the PAM motif or at the 5' end of the PAM motif, depending upon the CRISPR nuclease that recognizes the PAM motif, which is known in the art. For example, a target sequence is located at the 3' end of a PAM motif for a Cas12i polypeptide (e.g., a Cas12i2 polypeptide such as those disclosed herein). In some embodiments, the target sequence is a sequence within an LDHA gene sequence, including, but not limited to the sequence set forth in SEQ ID NO: 1172.

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences (i.e., immediately adjacent). In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides. In some embodiments, a first sequence is adjacent to a second sequence if the two sequences are separated by up to 2 nucleotides, up to 5 nucleotides, up to 8 nucleotides, up to 10 nucleotides, up to 12 nucleotides, or up to 15 nucleotides. In some embodiments, a first sequence is adjacent to a second sequence if the two sequences are separated by 2-5 nucleotides, 4-6 nucleotides, 4-8 nucleotides, 4-10 nucleotides, 6-8 nucleotides, 6-10 nucleotides, 6-12 nucleotides, 8-10 nucleotides, 8-12 nucleotides, 10-12 nucleotides, 10-15 nucleotides, or 12-15 nucleotides.

As used herein, the term "spacer" or "spacer sequence" is a portion in an RNA guide that is the RNA equivalent of the target sequence (a DNA sequence). The spacer contains a sequence capable of binding to the non-PAM strand via base-pairing at the site complementary to the target sequence (in the PAM strand). Such a spacer is also known as specific to the target sequence. In some instances, the spacer may be at least 75% identical to the target sequence (e.g., at least 80%, at least 85%, at least 90%, at least 95%, at least 98%, or at least 99%), except for the RNA-DNA sequence difference. In some instances, the spacer may be 100% identical to the target sequence except for the RNA-DNA sequence difference.

As used herein, the term "RNA guide" or "RNA guide sequence" refers to any RNA molecule or a modified RNA molecule that facilitates the targeting of a polypeptide (e.g., a Cas12i polypeptide) described herein to a target sequence (e.g., a sequence of an LDHA gene). For example, an RNA guide can be a molecule that is designed to include sequences that are complementary to a specific nucleic acid sequence (e.g., an LDHA nucleic acid sequence). An RNA guide may comprise a DNA targeting sequence (i.e., a spacer sequence) and a direct repeat (DR) sequence. In some instances, the RNA guide can be a modified RNA molecule comprising one or more deoxyribonucleotides, for example, in a DNA-binding sequence contained in the RNA guide, which binds a sequence complementary to the target sequence. In some examples, the DNA-binding sequence may contain a DNA sequence or a DNA/RNA hybrid sequence. The terms CRISPR RNA (crRNA), pre-crRNA and mature crRNA are also used herein to refer to an RNA guide.

As used herein, the term "complementary" refers to a first polynucleotide (e.g., a spacer sequence of an RNA guide) that has a certain level of complementarity to a second polynucleotide (e.g., the complementary sequence of a target sequence) such that the first and second polynucleotides can form a double-stranded complex via base-pairing to permit an effector polypeptide that is complexed with the first polynucleotide to act on (e.g., cleave) the second polynucleotide. In some embodiments, the first polynucleotide may be substantially complementary to the second polynucleotide, i.e., having at least about 80%, 81%, 82%, 83%, 84%, 85%, 86%, 87%, 88%, 89%, 90%, 91%, 92%, 93%, 94%, 95%, 96%, 97%, 98%, or 99% complementarity to the second polynucleotide. In some embodiments, the first polynucleotide is completely complementary to the second polynucleotide, i.e., having 100% complementarity to the second polynucleotide.

The "percent identity" (a.k.a., sequence identity) of two nucleic acids or of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, word-length-12 to obtain nucleotide sequences homologous to the nucleic acid molecules of the present disclosure. BLAST protein searches can be performed with the XBLAST program, score=50, word length=3 to obtain amino acid sequences homologous to the protein molecules of the present disclosure. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein, the term "edit" refers to one or more modifications introduced into a target nucleic acid, e.g., within the LDHA gene. The edit can be one or more substitutions, one or more insertions, one or more deletions, or a combination thereof. As used herein, the term "substitution" refers to a replacement of a nucleotide or nucleotides with a different nucleotide or nucleotides, relative to a reference sequence. As used herein, the term "insertion" refers to a gain of a nucleotide or nucleotides in a nucleic acid sequence, relative to a reference sequence. As used herein, the term "deletion" refers to a loss of a nucleotide or nucleotides in a nucleic acid sequence, relative to a reference sequence.

No particular process is implied in how to make a sequence comprising a deletion. For instance, a sequence comprising a deletion can be synthesized directly from individual nucleotides. In other embodiments, a deletion is made by providing and then altering a reference sequence. The nucleic acid sequence can be in a genome of an organism. The nucleic acid sequence can be in a cell. The nucleic acid sequence can be a DNA sequence. The deletion can be a frameshift mutation or a non-frameshift mutation. A deletion described herein refers to a deletion of up to several kilobases.

As used herein, the terms "upstream" and "downstream" refer to relative positions within a single nucleic acid (e.g., DNA) sequence in a nucleic acid molecule. "Upstream" and "downstream" relate to the 5' to 3' direction, respectively, in which RNA transcription occurs. A first sequence is upstream of a second sequence when the 3' end of the first sequence occurs before the 5' end of the second sequence. A first sequence is downstream of a second sequence when the 5' end of the first sequence occurs after the 3' end of the second sequence. In some embodiments, the 5'-NTTN-3' or 5'-TTN-3' sequence is upstream of an indel described herein, and a Cas12i-induced indel is downstream of the 5'-NTTN-3' or 5'-TTN-3' sequence.

I. Gene Editing Systems

In some aspects, the present disclosure provides gene editing systems comprising an RNA guide targeting an LDHA gene or a portion of the LDHA gene. Such a gene editing system can be used to edit the LDHA target gene, e.g., to disrupt the LDHA gene.

Lactate dehydrogenase (LDH) is an enzyme found in nearly every cell that regulates both the homeostasis of lactate and pyruvate, and of glyoxylate and oxalate metabolism. LDH is comprised of 4 polypeptides that form a tetramer. Five isozymes of LDH differing in their subunit composition and tissue distribution have been identified. The two most common forms of LDH are the muscle (M) form encoded by the LDHA gene, and the heart (H) form encoded by LDHB gene. In the peroxisome of liver cells, LDH is the key enzyme responsible for converting glyoxalate to oxalate which is then secreted into the plasma and excreted by the kidneys. As LDH is key in the final step of oxalate production, reduction of LDHA can reduce hepatic LDH and prevent calcium oxalate crystal deposition.

In some embodiments, the RNA guide is comprised of a direct repeat component and a spacer component. In some embodiments, the RNA guide binds a Cas12i polypeptide. In some embodiments, the spacer component is specific to an LDHA target sequence, wherein the LDHA target sequence is adjacent to a 5'-NTTN-3' or 5'-TTN-3' PAM sequence as described herein. In the case of a double-stranded target, the RNA guide binds to a first strand of the target (i.e., the non-PAM strand) and a PAM sequence as described herein is present in the second, complementary strand (i.e., the PAM strand).

In some embodiments, the present disclosure described herein comprises compositions comprising a complex, wherein the complex comprises an RNA guide targeting LDHA. In some embodiments, the present disclosure comprises a complex comprising an RNA guide and a Cas12i polypeptide. In some embodiments, the RNA guide and the Cas12i polypeptide bind to each other in a molar ratio of about 1:1. In some embodiments, a complex comprising an RNA guide and a Cas12i polypeptide binds to an LDHA target sequence. In some embodiments, a complex comprising an RNA guide targeting LDHA and a Cas12i polypeptide binds to an LDHA target sequence at a molar ratio of about 1:1. In some embodiments, the complex comprises enzymatic activity, such as nuclease activity, that can cleave the LDHA target sequence. The RNA guide, the Cas12i polypeptide, and the LDHA target sequence, either alone or together, do not naturally occur. In some embodiments, the RNA guide in the complex comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 1213-1229. In some embodiments, the RNA guide has a sequence of any one of SEQ ID NOs: 1213-1229.

In some embodiments, the present disclosure described herein comprises compositions comprising an RNA guide as described herein and/or an RNA encoding a Cas12i polypeptide as described herein. In some embodiments, the RNA guide and the RNA encoding a Cas12i polypeptide are comprised together within the same composition. In some embodiments, the RNA guide and the RNA encoding a Cas12i polypeptide are comprised within separate compositions. In some embodiments, the RNA guide comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 1213-1229. In some embodiments, the RNA guide has a sequence of any one of SEQ ID NOs: 1213-1229.

Use of the gene editing systems disclosed herein has advantages over those of other known nuclease systems. Cas12i polypeptides are smaller than other nucleases. For example, Cas12i2 is 1,054 amino acids in length, whereas *S. pyogenes* Cas9 (SpCas9) is 1,368 amino acids in length, *S. thermophilus* Cas9 (StCas9) is 1,128 amino acids in length, FnCpf1 is 1,300 amino acids in length, AsCpf1 is 1,307 amino acids in length, and LbCpf1 is 1,246 amino acids in length. Cas12i RNA guides, which do not require a trans-activating CRISPR RNA (tracrRNA), are also smaller than Cas9 RNA guides. The smaller Cas12i polypeptide and RNA guide sizes are beneficial for delivery. Compositions comprising a Cas12i polypeptide also demonstrate decreased off-target activity compared to compositions comprising an SpCas9 polypeptide. See WO/2021/202800, the relevant disclosures of which are incorporated by reference for the subject matter and purpose referenced herein. Furthermore, indels induced by compositions comprising a Cas12i polypeptide differ from indels induced by compositions comprising an SpCas9 polypeptide. For example, SpCas9 polypeptides primarily induce insertions and deletions of 1 nucleotide in length. However, Cas12i polypeptides induce larger deletions, which can be beneficial in disrupting a larger portion of a gene such as LDHA.

Also provided herein is a system for genetic editing of an LDHA gene, which comprises (i) a Cas12i polypeptide (e.g., a Cas12i2 polypeptide) or a first nucleic acid encoding the Cas12i polypeptide (e.g., a Cas12i2 polypeptide comprises an amino acid sequence at least 95% identical to SEQ ID NO: 1166, which may comprise one or more mutations relative to SEQ ID NO: 1166); and (ii) an RNA guide or a second nucleic acid encoding the RNA guide, wherein the RNA guide comprises a spacer sequence specific to a target sequence within an LDHA gene (e.g., within exon 3 or exon 5 of the LDHA gene), the target sequence being adjacent to a protospacer adjacent motif (PAM) comprising the motif of 5'-TTN-3' (5'-NTTN-3'), which is located 5' to the target sequence.

A. RNA Guides

In some embodiments, the gene editing system described herein comprises an RNA guide targeting an LDHA gene, e.g., targeting exon 3 or exon 5 of the LDHA gene. In some embodiments, the gene editing system described herein comprises two or more (e.g., 2, 3, 4, 5, 6, 7, 8, 9, or more) RNA guides targeting LDHA.

The RNA guide may direct the Cas12i polypeptide contained in the gene editing system as described herein to an LDHA target sequence. Two or more RNA guides may direct two or more separate Cas12i polypeptides (e.g., Cas12i polypeptides having the same or different sequence) as described herein to two or more (e.g., 2, 3, 4, 5, 6, 7, 8, 9, or more) LDHA target sequences.

Those skilled in the art reading the below examples of particular kinds of RNA guides will understand that, in some embodiments, an RNA guide is LDHA target-specific. That is, in some embodiments, an RNA guide binds specifically to one or more LDHA target sequences (e.g., within a cell) and not to non-targeted sequences (e.g., non-specific DNA or random sequences within the same cell).

In some embodiments, the RNA guide comprises a spacer sequence followed by a direct repeat sequence, referring to the sequences in the 5' to 3' direction. In some embodiments, the RNA guide comprises a first direct repeat sequence followed by a spacer sequence and a second direct repeat sequence, referring to the sequences in the 5' to 3' direction. In some embodiments, the first and second direct repeats of such an RNA guide are identical. In some embodiments, the first and second direct repeats of such an RNA guide are different.

In some embodiments, the spacer sequence and the direct repeat sequence(s) of the RNA guide are present within the same RNA molecule. In some embodiments, the spacer and direct repeat sequences are linked directly to one another. In some embodiments, a short linker is present between the spacer and direct repeat sequences, e.g., an RNA linker of 1, 2, or 3 nucleotides in length. In some embodiments, the spacer sequence and the direct repeat sequence(s) of the RNA guide are present in separate molecules, which are joined to one another by base pairing interactions.

Additional information regarding exemplary direct repeat and spacer components of RNA guides is provided as follows.

(i). Direct Repeat

In some embodiments, the RNA guide comprises a direct repeat sequence. In some embodiments, the direct repeat sequence of the RNA guide has a length of between 12-100, 13-75, 14-50, or 15-40 nucleotides (e.g., 15, 16, 17, 18, 19, 20, 21, 22, 23, 24, 25, 26, 27, 28, 29, 30, 31, 32, 33, 34, 35, 36, 37, 38, 39, or 40 nucleotides).

In some embodiments, the direct repeat sequence is a sequence of Table 1 or a portion of a sequence of Table 1. The direct repeat sequence can comprise nucleotide 1 through nucleotide 36 of any one of SEQ ID NOs: 1, 2, 3, 4, 5, 6, 7, or 8. The direct repeat sequence can comprise nucleotide 2 through nucleotide 36 of any one of SEQ ID NOs: 1, 2, 3, 4, 5, 6, 7, or 8. The direct repeat sequence can comprise nucleotide 3 through nucleotide 36 of any one of SEQ ID NOs: 1, 2, 3, 4, 5, 6, 7, or 8. The direct repeat sequence can comprise nucleotide 4 through nucleotide 36 of any one of SEQ ID NOs: 1, 2, 3, 4, 5, 6, 7, or 8. The direct repeat sequence can comprise nucleotide 5 through nucleotide 36 of any one of SEQ ID NOs: 1, 2, 3, 4, 5, 6, 7, or 8. The direct repeat sequence can comprise nucleotide 6 through nucleotide 36 of any one of SEQ ID NOs: 1, 2, 3, 4, 5, 6, 7, or 8. The direct repeat sequence can comprise nucleotide 7 through nucleotide 36 of any one of SEQ ID NOs: 1, 2, 3, 4, 5, 6, 7, or 8. The direct repeat sequence can comprise nucleotide 8 through nucleotide 36 of any one of SEQ ID NOs: 1, 2, 3, 4, 5, 6, 7, or 8. The direct repeat sequence can comprise nucleotide 9 through nucleotide 36 of any one of SEQ ID NOs: 1, 2, 3, 4, 5, 6, 7, or 8. The direct repeat sequence can comprise nucleotide 10 through nucleotide 36 of any one of SEQ ID NOs: 1, 2, 3, 4, 5, 6, 7, or 8. The direct repeat sequence can comprise nucleotide 11 through nucleotide 36 of any one of SEQ ID NOs: 1, 2, 3, 4, 5, 6, 7, or 8. The direct repeat sequence can comprise nucleotide 12 through nucleotide 36 of any one of SEQ ID NOs: 1, 2, 3, 4, 5, 6, 7, or 8. The direct repeat sequence can comprise nucleotide 13 through nucleotide 36 of any one of SEQ ID NOs: 1, 2, 3, 4, 5, 6, 7, or 8. The direct repeat sequence can comprise nucleotide 14 through nucleotide 36 of any one of SEQ ID NOs: 1, 2, 3, 4, 5, 6, 7, or 8. The direct repeat sequence can comprise nucleotide 1 through nucleotide 34 of SEQ ID NO: 9. The direct repeat sequence can comprise nucleotide 2 through nucleotide 34 of SEQ ID NO: 9. The direct repeat sequence can comprise nucleotide 3 through nucleotide 34 of SEQ ID NO: 9. The direct repeat sequence can comprise nucleotide 4 through nucleotide 34 of SEQ ID NO: 9. The direct repeat sequence can comprise nucleotide 5 through nucleotide 34 of SEQ ID NO: 9. The direct repeat sequence can comprise nucleotide 6 through nucleotide 34 of SEQ ID NO: 9. The direct repeat sequence can comprise nucleotide 7 through nucleotide 34 of SEQ ID NO: 9. The direct repeat sequence can comprise nucleotide 8 through nucleotide 34 of SEQ ID NO: 9. The direct repeat sequence can comprise nucleotide 9 through nucleotide 34 of SEQ ID NO: 9. The direct repeat sequence can comprise nucleotide 10 through nucleotide 34 of SEQ ID NO: 9. The direct repeat sequence can comprise nucleotide 11 through nucleotide 34 of SEQ ID NO: 9. The direct repeat sequence can comprise nucleotide 12 through nucleotide 34 of SEQ ID NO: 9. In some embodiments, the direct repeat sequence is set forth in SEQ ID NO: 10. In some embodiments, the direct repeat sequence comprises a portion of the sequence set forth in SEQ ID NO: 10.

In some embodiments, the direct repeat sequence has at least 90% identity (e.g., at least 90%, 91%, 92%, 93%, 94%, 95%, 96%, 97%, 98% or 99% identity) to a sequence of Table 1 or a portion of a sequence of Table 1. The direct repeat sequence can have at least 90% identity to a sequence comprising nucleotide 1 through nucleotide 36 of any one of SEQ ID NOs: 1, 2, 3, 4, 5, 6, 7, or 8. The direct repeat sequence can have at least 90% identity to a sequence comprising 2 through nucleotide 36 of any one of SEQ ID NOs: 1, 2, 3, 4, 5, 6, 7, or 8. The direct repeat sequence can have at least 90% identity to a sequence comprising 3 through nucleotide 36 of any one of SEQ ID NOs: 1, 2, 3, 4, 5, 6, 7, or 8. The direct repeat sequence can have at least 90% identity to a sequence comprising 4 through nucleotide 36 of any one of SEQ ID NOs: 1, 2, 3, 4, 5, 6, 7, or 8. The direct repeat sequence can have at least 90% identity to a sequence comprising 5 through nucleotide 36 of any one of SEQ ID NOs: 1, 2, 3, 4, 5, 6, 7, or 8. The direct repeat sequence can have at least 90% identity to a sequence comprising 6 through nucleotide 36 of any one of SEQ ID NOs: 1, 2, 3, 4, 5, 6, 7, or 8. The direct repeat sequence can have at least 90% identity to a sequence comprising 7 through nucleotide 36 of any one of SEQ ID NOs: 1, 2, 3, 4, 5, 6, 7, or 8. The direct repeat sequence can have at least 90% identity to a sequence comprising 8 through nucleotide 36 of any one of SEQ ID NOs: 1, 2, 3, 4, 5, 6, 7, or 8. The direct repeat sequence can have at least 90% identity to a sequence comprising 9 through nucleotide 36 of any one of SEQ ID NOs: 1, 2, 3, 4, 5, 6, 7, or 8. The direct repeat sequence can have at least 90% identity to a sequence comprising 10 through nucleotide 36 of any one of SEQ ID NOs: 1, 2, 3, 4, 5, 6, 7, or 8. The direct repeat sequence can have at least 90% identity to a sequence comprising 11 through nucleotide 36 of any one of SEQ ID NOs: 1, 2, 3, 4, 5, 6, 7, or 8. The direct repeat sequence can have at least 90% identity to a sequence comprising 12 through nucleotide 36 of any one of SEQ ID NOs: 1, 2, 3, 4, 5, 6, 7, or 8. The direct repeat sequence can have at least 90% identity to a sequence comprising 13 through nucleotide 36 of any one of SEQ ID NOs: 1, 2, 3, 4, 5, 6, 7, or 8. The direct repeat sequence can have at least 90% identity to a sequence comprising 14 through nucleotide 36 of any one of SEQ ID NOs: 1, 2, 3, 4, 5, 6, 7, or 8. The direct repeat sequence can have at least 90% identity to a sequence comprising 1 through nucleotide 34 of SEQ ID NO: 9. The direct repeat sequence can have at least 90% identity to a sequence comprising 2 through nucleotide 34 of SEQ ID NO: 9. The direct repeat sequence can have at least 90% identity to a sequence comprising 3 through nucleotide 34 of SEQ ID NO: 9. The direct repeat sequence can have at least 90% identity to a sequence comprising 4 through nucleotide 34 of SEQ ID NO: 9. The direct repeat sequence can have at least 90% identity to a sequence comprising 5 through nucleotide 34 of SEQ ID NO: 9. The direct repeat sequence can have at least 90% identity to a sequence comprising 6 through nucleotide 34 of SEQ ID NO: 9. The direct repeat sequence can have at least 90% identity to a sequence comprising 7 through nucleotide 34 of SEQ ID NO: 9. The direct repeat sequence can have at least 90% identity to a sequence comprising 8 through nucleotide 34 of SEQ ID NO: 9. The direct repeat sequence can have at least 90% identity to a sequence comprising 9 through nucleotide 34 of SEQ ID NO: 9. The direct repeat sequence can have at least 90% identity to a sequence comprising 10 through nucleotide 34 of SEQ ID NO: 9. The direct repeat sequence can have at least 90% identity to a sequence comprising 11 through nucleotide 34 of SEQ ID NO: 9. The direct repeat sequence can have at least 90% identity to a sequence comprising 12 through nucleotide 34 of SEQ ID NO: 9. In some embodiments, the direct repeat sequence has at least 90% identity (e.g., at least 90%, 91%, 92%, 93%, 94%, 95%, 96%, 97%, 98% or 99% identity) to SEQ ID NO: 10. In some embodiments, the direct repeat sequence has at least 90% identity to a portion of the sequence set forth in SEQ ID NO: 10.

In some embodiments, compositions comprising a Cas12i2 polypeptide and an RNA guide comprising the direct repeat of SEQ ID NO: 10 and a spacer length of 20 nucleotides are capable of introducing indels into an LDHA target sequence. See, e.g., Example 1, where indels were measured at seventeen LDHA target sequences following delivery of an RNA guide and a Cas12i2 polypeptide of SEQ ID NO: 1168 to HEK293T cells by RNP; Example 2, where indels were measured at four LDHA target sequences following delivery of an RNA guide and a Cas12i2 polypeptide of SEQ ID NO: 1168 to HepG2 cells by RNP; and Example 3, where indels were measured at three LDHA target sequences following delivery of an RNA guide and a Cas12i2 polypeptide of SEQ ID NO: 1168 primary hepatocytes by RNP.

In some embodiments, the direct repeat sequence is at least 90% identical to the reverse complement of any one of SEQ ID NOs: 1-10. In some embodiments, the direct repeat sequence is the reverse complement of any one of SEQ ID NOs: 1-10.

TABLE 1

Cas12i2 Direct Repeat Sequences

| Sequence Identifier | Direct Repeat Sequence |
|---|---|
| SEQ ID NO: 1 | GUUGCAAAACCCAAGAAAUCCGUCUUUCAUUGACGG |
| SEQ ID NO: 2 | AAUAGCGGCCCUAAGAAAUCCGUCUUUCAUUGACGG |
| SEQ ID NO: 3 | AUUGGAACUGGCGAGAAAUCCGUCUUUCAUUGACGG |
| SEQ ID NO: 4 | CCAGCAACACCUAAGAAAUCCGUCUUUCAUUGACGG |
| SEQ ID NO: 5 | CGGCGCUCGAAUAGGAAAUCCGUCUUUCAUUGACGG |
| SEQ ID NO: 6 | GUGGCAACACCUAAGAAAUCCGUCUUUCAUUGACGG |
| SEQ ID NO: 7 | GUUGCAACACCUAAGAAAUCCGUCUUUCAUUGACGG |
| SEQ ID NO: 8 | GUUGCAAUGCCUAAGAAAUCCGUCUUUCAUUGACGG |
| SEQ ID NO: 9 | GCAACACCUAAGAAAUCCGUCUUUCAUUGACGGG |
| SEQ ID NO: 10 | AGAAAUCCGUCUUUCAUUGACGG |

In some embodiments, the direct repeat sequence is a sequence of Table 2 or a portion of a sequence of Table 2. The direct repeat sequence can comprise nucleotide 1 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 2 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 3 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 4 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 5 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 6 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 7 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 8 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 9 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 10 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 11 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 12 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 13 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can comprise nucleotide 14 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199.

In some embodiments, the direct repeat sequence has at least 95% identity (e.g., at least 95%, 96%, 97%, 98% or 99% identity) to a sequence of Table 2 or a portion of a sequence of Table 2. The direct repeat sequence can have at least 95% identity to a sequence comprising nucleotide 1 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 2 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 3 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 4 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 5 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 6 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 7 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 8 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 9 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 10 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 11 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 12 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 95% identity to a sequence comprising 13 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199.

In some embodiments, the direct repeat sequence has at least 90% identity (e.g., at least 90%, 91%, 92%, 93%, 94%, 95%, 96%, 97%, 98% or 99% identity) to a sequence of Table 2 or a portion of a sequence of Table 2. The direct repeat sequence can have at least 90% identity to a sequence comprising nucleotide 1 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 2 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 3 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 4 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 5 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 6 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 7 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 8 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 9 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 10 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 11 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 12 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199. The direct repeat sequence can have at least 90% identity to a sequence comprising 13 through nucleotide 36 of any one of SEQ ID NOs: 1182, 1183, 1184, 1185, 1186, 1187, 1188, 1189, 1190, 1191, 1192, 1193, 1194, 1195, 1196, 1197, 1198, or 1199.

In some embodiments, the direct repeat sequence is at least 90% identical to the reverse complement of any one of SEQ ID NOs: 1182, 1183, 1184, 1185, 1186, 1187, 1188, 1189, 1190, 1191, 1192, 1193, 1194, 1195, 1196, 1197, 1198, or 1199. In some embodiments, the direct repeat sequence is at least 95% identical to the reverse complement of any one of SEQ ID NOs: 1182, 1183, 1184, 1185, 1186, 1187, 1188, 1189, 1190, 1191, 1192, 1193, 1194, 1195, 1196, 1197, 1198, or 1199. In some embodiments, the direct repeat sequence is the reverse complement of any one of SEQ ID NOs: 1182, 1183, 1184, 1185, 1186, 1187, 1188, 1189, 1190, 1191, 1192, 1193, 1194, 1195, 1196, 1197, 1198, or 1199.

In some embodiments, the direct repeat sequence is at least 90% identical to SEQ ID NO: 1200 or a portion of SEQ ID NO: 1200. In some embodiments, the direct repeat sequence is at least 95% identical to SEQ ID NO: 1200 or a portion of SEQ ID NO: 1200. In some embodiments, the direct repeat sequence is 100% identical to SEQ ID NO: 1200 or a portion of SEQ ID NO: 1200.

TABLE 2

Cas12i4 Direct Repeat Sequences

| Sequence Identifier | Direct Repeat Sequence |
|---|---|
| SEQ ID NO: 1182 | UCUCAACGAUAGUCAGACAUGUGUCCUCAGUGACAC |
| SEQ ID NO: 1183 | UUUUAACAACACUCAGGCAUGUGUCCACAGUGACAC |
| SEQ ID NO: 1184 | UUGAACGGAUACUCAGACAUGUGUUUCCAGUGACAC |
| SEQ ID NO: 1185 | UGCCCUCAAUAGUCAGAUGUGUGUCCACAGUGACAC |
| SEQ ID NO: 1186 | UCUCAAUGAUACUUAGAUACGUGUCCUCAGUGACAC |
| SEQ ID NO: 1187 | UCUCAAUGAUACUCAGACAUGUGUCCCCAGUGACAC |
| SEQ ID NO: 1188 | UCUCAAUGAUACUAAGACAUGUGUCCUCAGUGACAC |
| SEQ ID NO: 1189 | UCUCAACUAUACUCAGACAUGUGUCCUCAGUGACAC |
| SEQ ID NO: 1190 | UCUCAACGAUACUCAGACAUGUGUCCUCAGUGACAC |
| SEQ ID NO: 1191 | UCUCAACGAUACUAAGAUAUGUGUCCUCAGCGACAC |
| SEQ ID NO: 1192 | UCUCAACGAUACUAAGAUAUGUGUCCCCAGUGACAC |
| SEQ ID NO: 1193 | UCUCAACGAUACUAAGAUAUGUGUCCACAGUGACAC |
| SEQ ID NO: 1194 | UCUCAACAAUACUCAGACAUGUGUCCCCAGUGACAC |
| SEQ ID NO: 1195 | UCUCAACAAUACUAAGGCAUGUGUCCCCAGUGACCC |
| SEQ ID NO: 1196 | UCUCAAGAUACUCAGACACGUGUCCCCAGUGACAC |
| SEQ ID NO: 1197 | UCUCAAAAAUACUCAGACAUGUGUCCUCAGUGACAC |
| SEQ ID NO: 1198 | GCGAAACAACAGUCAGACAUGUGUCCCCAGUGACAC |
| SEQ ID NO: 1199 | CCUCAACGAUAUUAAGACAUGUGUCCGCAGUGACAC |
| SEQ ID NO: 1200 | AGACAUGUGUCCUCAGUGACAC |

In some embodiments, the direct repeat sequence is a sequence of Table 3 or a portion of a sequence of Table 3. In some embodiments, the direct repeat sequence has at least 95% identity (e.g., at least 95%, 96%, 97%, 98% or 99% identity) to a sequence of Table 3 or a portion of a sequence of Table 3. In some embodiments, the direct repeat sequence has at least 90% identity (e.g., at least 90%, 91%, 92%, 93%, 94%, 95%, 96%, 97%, 98% or 99% identity) to a sequence of Table 3 or a portion of a sequence of Table 3. In some embodiments, the direct repeat sequence is at least 90% identical to the reverse complement of any one of SEQ ID NOs: 1205-1207. In some embodiments, the direct repeat sequence is at least 95% identical to the reverse complement of any one of SEQ ID NOs: 1205-1207. In some embodiments, the direct repeat sequence is the reverse complement of any one of SEQ ID NOs: 1205-1207.

TABLE 3

Cas12i1 Direct Repeat Sequences

| Sequence Identifier | Direct Repeat Sequence |
|---|---|
| SEQ ID NO: 1205 | GUUGGAAUGACUAAUUUUUGUGCCCACCGUUGGCAC |
| SEQ ID NO: 1206 | AAUUUUUGUGCCCAUCGUUGGCAC |
| SEQ ID NO: 1207 | AUUUUUGUGCCCAUCGUUGGCAC |

In some embodiments, the direct repeat sequence is a sequence of Table 4 or a portion of a sequence of Table 4. In some embodiments, the direct repeat sequence has at least 95% identity (e.g., at least 95%, 96%, 97%, 98% or 99% identity) to a sequence of Table 4 or a portion of a sequence of Table 4. In some embodiments, the direct repeat sequence has at least 90% identity (e.g., at least 90%, 91%, 92%, 93%, 94%, 95%, 96%, 97%, 98% or 99% identity) to a sequence of Table 4 or a portion of a sequence of Table 4. In some embodiments, the direct repeat sequence is at least 90% identical to the reverse complement of any one of SEQ ID NOs: 1208-1210. In some embodiments, the direct repeat sequence is at least 95% identical to the reverse complement of any one of SEQ ID NOs: 1208-1210. In some embodiments, the direct repeat sequence is the reverse complement of any one of SEQ ID NOs: 1208-1210.

TABLE 4

Cas12i3 Direct Repeat Sequences

| Sequence Identifier | Direct Repeat Sequence |
|---|---|
| SEQ ID NO: 1208 | CUAGCAAUGACCUAAUAGUGUGUCCUUAGUUGACAU |
| SEQ ID NO: 1209 | CCUACAAUACCUAAGAAAUCCGUCCUAAGUUGACGG |
| SEQ ID NO: 1210 | AUAGUGUGUCCUUAGUUGACAU |

In some embodiments, a direct repeat sequence described herein comprises a uracil (U). In some embodiments, a direct repeat sequence described herein comprises a thymine (T). In some embodiments, a direct repeat sequence according to Tables 1~4 comprises a sequence comprising a thymine in one or more places indicated as uracil in Tables 1-4.

(ii). Spacer Sequence

In some embodiments, the RNA guide comprises a DNA targeting or spacer sequence. In some embodiments, the spacer sequence of the RNA guide has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and is complementary to a non-PAM strand sequence). In some embodiments, the spacer sequence is designed to be complementary to a specific DNA strand, e.g., of a genomic locus.

In some embodiments, the RNA guide spacer sequence is substantially identical to a complementary strand of a target sequence. In some embodiments, the RNA guide comprises a sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., target sequence. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide comprises a spacer sequence that has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and at least 80%, at least 90%, at least 95%, at least 96%, at least 97%, at least 98%, at least 99% complementary to a region on the non-PAM strand that is complementary to the target sequence. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a region on the non-PAM strand that is complementary to the target. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In some embodiments, the spacer sequence is a sequence of Table 5 or a portion of a sequence of Table 5. It should be understood that an indication of SEQ ID NOs: 588-1164 should be considered as equivalent to a listing of SEQ ID NOs: 588-1164, with each of the intervening numbers present in the listing, i.e., 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, and 1164.

The spacer sequence can comprise nucleotide 1 through nucleotide 16 of any one of SEQ ID NOs: 588-1164. The spacer sequence can comprise nucleotide 1 through nucleotide 17 of any one of SEQ ID NOs: 588-1164. The spacer sequence can comprise nucleotide 1 through nucleotide 18 of any one of SEQ ID NOs: 588-1164. The spacer sequence can comprise nucleotide 1 through nucleotide 19 of any one of SEQ ID NOs: 588-1164. The spacer sequence can comprise nucleotide 1 through nucleotide 20 of any one of SEQ ID NOs: 588-1164. The spacer sequence can comprise nucleotide 1 through nucleotide 21 of any one of SEQ ID NOs: 588-1164. The spacer sequence can comprise nucleotide 1 through nucleotide 22 of any one of SEQ ID NOs: 588-1164. The spacer sequence can comprise nucleotide 1 through nucleotide 23 of any one of SEQ ID NOs: 588-1164. The spacer sequence can comprise nucleotide 1 through nucleotide 24 of any one of SEQ ID NOs: 588-1164. The spacer sequence can comprise nucleotide 1 through nucleotide 25 of any one of SEQ ID NOs: 588-1164. The spacer sequence can comprise nucleotide 1 through nucleotide 26 of any one of SEQ ID NOs: 588-1164. The spacer sequence can comprise nucleotide 1 through nucleotide 27 of any one of SEQ ID NOs: 588-1164. The spacer sequence can comprise nucleotide 1 through nucleotide 28 of any one of SEQ ID NOs: 588-1164. The spacer sequence can comprise nucleotide 1 through nucleotide 29 of any one of SEQ ID NOs: 588-1164. The spacer sequence can comprise nucleotide 1 through nucleotide 30 of any one of SEQ ID NOs: 588-1164.

In some embodiments, the spacer sequence has at least 90% identity (e.g., at least 90%, 91%, 92%, 93%, 94%, 95%, 96%, 97%, 98% or 99% identity) to a sequence of Table 5 or a portion of a sequence of Table 5. The spacer sequence can have at least 90% identity to a sequence comprising nucleotide 1 through nucleotide 16 of any one of SEQ ID NOs: 588-1164. The spacer sequence can have at least 90% identity to a sequence comprising nucleotide 1 through nucleotide 17 of any one of SEQ ID NOs: 588-1164. The spacer sequence can have at least 90% identity to a sequence comprising nucleotide 1 through nucleotide 18 of any one of SEQ ID NOs: 588-1164. The spacer sequence can have at least 90% identity to a sequence comprising nucleotide 1 through nucleotide 19 of any one of SEQ ID NOs: 588-1164. The spacer sequence can have at least 90% identity to a sequence comprising nucleotide 1 through nucleotide 20 of any one of SEQ ID NOs: 588-1164. The spacer sequence can have at least 90% identity to a sequence comprising nucleotide 1 through nucleotide 21 of any one of SEQ ID NOs: 588-1164. The spacer sequence can have at least 90% identity to a sequence comprising nucleotide 1 through nucleotide 22 of any one of SEQ ID NOs: 588-1164. The spacer sequence can have at least 90% identity to a sequence comprising nucleotide 1 through nucleotide 23 of any one of SEQ ID NOs: 588-1164. The spacer sequence can have at least 90% identity to a sequence comprising nucleotide 1 through nucleotide 24 of any one of SEQ ID NOs: 588-1164. The spacer sequence can have at least 90% identity to a sequence comprising nucleotide 1 through nucleotide 25 of any one of SEQ ID NOs: 588-1164. The spacer sequence can have at least 90% identity to a sequence comprising nucleotide 1 through nucleotide 26 of any one of SEQ ID NOs: 588-1164. The spacer sequence can have at least 90% identity to a sequence comprising nucleotide 1 through nucleotide 27 of any one of SEQ ID NOs: 588-1164. The spacer sequence can have at least 90% identity to a sequence comprising nucleotide 1 through nucleotide 28 of any one of SEQ ID NOs: 588-1164. The spacer sequence can have at least 90% identity to a sequence comprising nucleotide 1 through nucleotide 29 of any one of SEQ ID NOs: 588-1164. The spacer sequence can have at least 90% identity to a sequence comprising nucleotide 1 through nucleotide 30 of any one of 588-1164.

TABLE 5

Target and Spacer Sequences

| LDHA | Strand | PAM* | SEQ ID NO | Target Sequence | SEQ ID NO | Spacer Sequence |
|---|---|---|---|---|---|---|
| LDHA_exon1 | + | ATTC | 11 | CGGATCTCATTGCCACGCGCCCCGACGAC | 588 | CGGAUCUCAUUGCCACGCGCCCCGACGAC |
| LDHA_exon1 | + | ATTG | 12 | CCACGCGCCCCGACGACCGCCCGACGTGC | 589 | CCACGCGCCCCGACGACCGCCCGACGUGC |
| LDHA_exon1 | + | ATTC | 13 | CCGGTACGGTAGGGCCCTGCGCGCACGGCG | 590 | CCGGUACGGUAGGGCCCUGCGCGCACGGCG |
| LDHA_exon2 | + | CTTG | 14 | CTGTAGGAGCCGGAGTAGCTCAGAGTGATC | 591 | CUGUAGGAGCCGGAGUAGCUCAGAGUGAUC |
| LDHA_exon2 | + | CTTA | 15 | CACCCAAACGTCGATATTCCTTTTCCACGC | 592 | CACCCAAACGUCGAUAUUCCUUUUCCACGC |
| LDHA_exon2 | + | GTTA | 16 | ATAAACCGCGATGGGTGAACCCTCAGGAGG | 593 | AUAAACCGCGAUGGGUGAACCCUCAGGAGG |
| LDHA_exon2 | + | CTTG | 17 | GGGTTAATAAACCGCGATGGGTGAACCCTC | 594 | GGGUUAAUAAACCGCGAUGGGUGAACCCUC |
| LDHA_exon2 | + | TTTA | 18 | CTTGAGAAGCCTGGCTGTGTCCTTGCTGTA | 595 | CUUGAGAAGCCUGGCUGUGUCCUUGCUGUA |
| LDHA_exon2 | + | GTTT | 19 | ACTTGAGAAGCCTGGCTGTGTCCTTGCTGT | 596 | ACUUGAGAAGCCUGGCUGUGUCCUUGCUGU |
| LDHA_exon2 | + | TTTC | 20 | TGCACGTATCTCTGGTGTTTACTTGAGAAG | 597 | UGCACGUAUCUCUGGUGUUUACUUGAGAAG |
| LDHA_exon2 | + | TTTT | 21 | CTGCACGTATCTCTGGTGTTTACTTGAGAA | 598 | CUGCACGUAUCUCUGGUGUUUACUUGAGAA |
| LDHA_exon2 | + | GTTA | 22 | ATGGCTTTTCTGCACGTATCTCTGGTGTTT | 599 | AUGGCUUUUCUGCACGUAUCUCUGGUGUUU |
| LDHA_exon2 | + | ATTC | 23 | CTTTTCCACGCTAAGGTATGGGCCTTCACT | 600 | CUUUUCCACGCUAAGGUAUGGGCCUUCACU |
| LDHA_exon2 | + | TTTG | 24 | TGGCAGTTAATGGCTTTTCTGCACGTATCT | 601 | UGGCAGUUAAUGGCUUUUCUGCACGUAUCU |
| LDHA_exon2 | + | GTTT | 25 | GTGGCAGTTAATGGCTTTTCTGCACGTATC | 602 | GUGGCAGUUAAUGGCUUUUCUGCACGUAUC |
| LDHA_exon2 | + | CTTG | 26 | AGCTTTGTGGCAGTTAATGGCTTTTCTGCA | 603 | AGCUUUGUGGCAGUUAAUGGCUUUUCUGCA |
| LDHA_exon2 | + | CTTG | 27 | GGCTTGAGCTTTGTGGCAGTTAATGGCTTT | 604 | GGCUUGAGCUUUGUGGCAGUUAAUGGCUUU |
| LDHA_exon2 | + | TTTC | 28 | CGAGCGGGAAGGAGAGCCCACAAAGCGCGCA | 605 | CGAGCGGGAAGGAGAGCCACAAAGCGCGCA |
| LDHA_exon2 | + | CTTG | 29 | AGAAGCCTGGCTGTGTCCTTGCTGTAGGAG | 606 | AGAAGCCUGGCUGUGUCCUUGCUGUAGGAG |
| LDHA_exon2 | + | CTTT | 30 | TCTGCACGTATCTCTGGTGTTTACTTGAGA | 607 | UCUGCACGUAUCUCUGGUGUUUACUUGAGA |
| LDHA_exon2 | + | CTTG | 31 | TCTGAGGAAAGGCCAGCCCCACTTGGGGTT | 608 | UCUGAGGAAAGGCCAGCCCCACUUGGGGUU |
| LDHA_exon2 | + | TTTT | 32 | CCACGCTAAGGTATGGGCCTTCACTCTTCA | 609 | CCACGCUAAGGUAUGGGCCUUCACUCUUCA |
| LDHA_exon2 | + | TTTC | 33 | CGCCCACCTTTCCGAGCGGGAAGGAGAGCC | 610 | CGCCCACCUUUCCGAGCGGGAAGGAGAGCC |
| LDHA_exon2 | – | CTTC | 34 | CCGCTCGGAAAGGTGGGCGGAAATCAGACT | 611 | CCGCUCGGAAAGGUGGGCGGAAAUCAGACU |
| LDHA_exon2 | – | TTTG | 35 | TGGCTCTCCTTCCCGCTCGGAAAGGTGGGC | 612 | UGGCUCUCCUUCCCGCUCGGAAAGGUGGGC |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon2 | - | CTTT | 36 | GTGGCTCTCCTTCCCG CTCGGAAAGGTGGG | 613 | GUGGCUCUCCUUCCCGC UCGGAAAGGUGGG |
| LDHA_exon2 | - | ATTA | 37 | ACTGCCACAAAGCTCA AGCCCAAGGCACAG | 614 | ACUGCCACAAAGCUCAA GCCCAAGGCACAG |
| LDHA_exon2 | - | CTTC | 38 | TCAAGTAAACACCAGA GATACGTGCAGAAA | 615 | UCAAGUAAACACCAGAG AUACGUGCAGAAA |
| LDHA_exon2 | - | TTTC | 39 | CTCAGACAAGATCACT CTGAGCTACTCCGG | 616 | CUCAGACAAGAUCACUC UGAGCUACUCCGG |
| LDHA_exon2 | - | CTTT | 40 | CCTCAGACAAGATCAC TCTGAGCTACTCCG | 617 | CCUCAGACAAGAUCACU CUGAGCUACUCCG |
| LDHA_exon2 | - | ATTA | 41 | ACCCCAAGTGGGGCTG GCCTTTCCTCAGAC | 618 | ACCCCAAGUGGGGCUGG CCUUUCCUCAGAC |
| LDHA_exon2 | - | TTTA | 42 | TTAACCCCAAGTGGGG CTGGCCTTTCCTCA | 619 | UUAACCCCAAGUGGGGC UGGCCUUUCCUCA |
| LDHA_exon2 | - | GTTT | 43 | ATTAACCCCAAGTGGG GCTGGCCTTTCCTC | 620 | AUUAACCCCAAGUGGGG CUGGCCUUUCCUC |
| LDHA_exon2 | - | GTTC | 44 | ACCCATCGCGGTTTAT TAACCCCAAGTGGG | 621 | ACCCAUCGCGGUUUAUU AACCCCAAGUGGG |
| LDHA_exon2 | - | TTTG | 45 | GGTGTAAGTATAGCCT CCTGAGGGTTCACC | 622 | GGUGUAAGUAUAGCCUC CUGAGGGUUCACC |
| LDHA_exon2 | - | GTTT | 46 | GGGTGTAAGTATAGCC TCCTGAGGGTTCAC | 623 | GGGUGUAAGUAUAGCCU CCUGAGGGUUCAC |
| LDHA_exon2 | - | CTTA | 47 | GCGTGGAAAAGGAATA TCGACGTTTGGGTG | 624 | GCGUGGAAAAGGAAUAU CGACGUUUGGGUG |
| LDHA_exon2 | + | TTTC | 48 | CACGCTAAGGTATGGG CCTTCACTCTTCAC | 625 | CACGCUAAGGUAUGGGC CUUCACUCUUCAC |
| LDHA_exon2 | + | GTTT | 49 | TCCACGCTAAGGTATG GGCCTTCACTCTTC | 626 | UCCACGCUAAGGUAUGG GCCUUCACUCUUC |
| LDHA_exon2 | + | ATTT | 50 | CCGCCCACCTTTCCGA GCGGGAAGGAGAGC | 627 | CCGCCCACCUUUCCGAG CGGGAAGGAGAGC |
| LDHA_exon2 | + | GTTT | 51 | CCGAGCGGGAAGGAGA GCCACAAAGCGCGC | 628 | CCGAGCGGGAAGGAGAG CCACAAAGCGCGC |
| LDHA_exon2 | + | ATTA | 52 | GTCTGATTTCCGCCCA CCTTTCCGAGCGGG | 629 | GUCUGAUUUCCGCCCAC CUUUCCGAGCGGG |
| LDHA_exon2 | + | CTTC | 53 | ACAGACCCTGTCATTA GGCCT | 630 | ACAGACCCUGUCAUUAG GCCU |
| LDHA_exon2 | + | CTTC | 54 | ACTCTTCACAGACCCT GTCATTAGGCCT | 631 | ACUCUUCACAGACCCUG UCAUUAGGCCU |
| LDHA_exon3 |  | ATTT | 55 | AGTGTCACTACAGCTT CTTTAATGTTTATT | 632 | AGUGUCACUACAGCUUC UUUAAUGUUUAUU |
| LDHA_exon3 | + | GTTG | 56 | TTGGGGTTGGTGCTGT TGGCATGGCCTGTG | 633 | UUGGGGUUGGUGCUGUU GGCAUGGCCUGUG |
| LDHA_exon3 | + | CTTC | 57 | TAAAGGAAGAACAGAC CCCCCAGAATAAGA | 634 | UAAAGGAAGAACAGACC CCCCAGAAUAAGA |
| LDHA_exon3 | + | TTTA | 58 | TAATCTTCTAAAGGAA GAACAGACCCCCCA | 635 | UAAUCUUCUAAAGGAAG AACAGACCCCCCA |
| LDHA_exon3 | + | ATTT | 59 | ATAATCTTCTAAAGGA AGAACAGACCCCCC | 636 | AUAAUCUUCUAAAGGAA GAACAGACCCCCC |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon3 | + | GTTC | 60 | CAAGTCCAATATGGCAACTCTAAAGGATCA | 637 | CAAGUCCAAUAUGGCAACUCUAAAGGAUCA |
| LDHA_exon3 | + | TTTG | 61 | GTTCCAAGTCCAATATGGCAACTCTAAAGG | 638 | GUUCCAAGUCCAAUAUGGCAACUCUAAAGG |
| LDHA_exon3 | + | TTTT | 62 | GGTTCCAAGTCCAATATGGCAACTCTAAAG | 639 | GGUUCCAAGUCCAAUAUGGCAACUCUAAAG |
| LDHA_exon3 | + | CTTT | 63 | TGGTTCCAAGTCCAATATGGCAACTCTAAA | 640 | UGGUUCCAAGUCCAAUAUGGCAACUCUAAA |
| LDHA_exon3 | + | ATTC | 64 | CTTTTGGTTCCAAGTCCAATATGGCAACTC | 641 | CUUUUGGUUCCAAGUCCAAUAUGGCAACUC |
| LDHA_exon3 | + | TTTC | 65 | CTCCTATAGATTCCTTTTGGTTCCAAGTCC | 642 | CUCCUAUAGAUUCCUUUUGGUUCCAAGUCC |
| LDHA_exon3 | + | TTTT | 66 | CCTCCTATAGATTCCTTTTGGTTCCAAGTC | 643 | CCUCCUAUAGAUUCCUUUUGGUUCCAAGUC |
| LDHA_exon3 | + | TTTT | 67 | TCCTCCTATAGATTCCTTTTGGTTCCAAGT | 644 | UCCUCCUAUAGAUUCCUUUUGGUUCCAAGU |
| LDHA_exon3 | + | GTTT | 68 | TTCCTCCTATAGATTCCTTTTGGTTCCAAG | 645 | UUCCUCCUAUAGAUUCCUUUUGGUUCCAAG |
| LDHA_exon3 | + | ATTA | 69 | AAGAAGCTGTAGTGACACTAAATGTTTTC | 646 | AAGAAGCUGUAGUGACACUAAAUGUUUUC |
| LDHA_exon3 | + | GTTG | 70 | GGGTTGGTGCTGTTGGCATGGCCTGTGCCA | 647 | GGGUUGGUGCUGUUGGCAUGGCCUGUGCCA |
| LDHA_exon3 | + | GTTG | 71 | GTGCTGTTGGCATGGCCTGTGCCATCAGTA | 648 | GUGCUGUUGGCAUGGCCUGUGCCAUCAGUA |
| LDHA_exon3 | + | ATTA | 72 | CAGTTGTTGGGGTTGGTGCTGTTGGCATGG | 649 | CAGUUGUUGGGGUUGGUGCUGUUGGCAUGG |
| LDHA_exon3 | + | CTTA | 73 | ATGAAGGTAAGTGAGAGTCTACCACACTGG | 650 | AUGAAGGUAAGUGAGAGUCUACCACACUGG |
| LDHA_exon3 | - | GTTG | 74 | GAACCAAAAGGAATCTATAGGAGGAAAAAC | 651 | GAACCAAAAGGAAUCUAUAGGAGGAAAAAC |
| LDHA_exon3 | - | ATTG | 75 | GACTTGGAACCAAAAGGAATCTATAGGAGG | 652 | GACUUGGAACCAAAAGGAAUCUAUAGGAGG |
| LDHA_exon3 | - | GTTG | 76 | CCATATTGGACTTGGAACCAAAAGGAATCT | 653 | CCAUAUUGGACUUGGAACCAAAAGGAAUCU |
| LDHA_exon3 | + | GTTG | 77 | GCATGGCCTGTGCCATCAGTATCTTAATGA | 654 | GCAUGGCCUGUGCCAUCAGUAUCUUAAUGA |
| LDHA_exon3 | - | CTTT | 78 | AGAGTTGCCATATTGGACTTGGAACCAAAA | 655 | AGAGUUGCCAUAUUGGACUUGGAACCAAAA |
| LDHA_exon3 | - | ATTA | 79 | TAAATCAGCTGATCCTTTAGAGTTGCCATA | 656 | UAAAUCAGCUGAUCCUUUAGAGUUGCCAUA |
| LDHA_exon3 | - | TTTA | 80 | GAAGATTATAAATCAGCTGATCCTTTAGAG | 657 | GAAGAUUAUAAAUCAGCUGAUCCUUUAGAG |
| LDHA_exon3 | - | CTTT | 81 | AGAAGATTATAAATCAGCTGATCCTTTAGA | 658 | AGAAGAUUAUAAAUCAGCUGAUCCUUUAGA |
| LDHA_exon3 | - | TTTA | 82 | GAGTTGCCATATTGGACTTGGAACCAAAAG | 659 | GAGUUGCCAUAUUGGACUUGGAACCAAAAG |
| LDHA_exon3 | - | GTTC | 83 | TTCCTTTAGAAGATTATAAATCAGCTGATC | 660 | UUCCUUUAGAAGAUUAUAAAUCAGCUGAUC |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon3 | - | ATTC | 84 | TGGGGGGTCTGTTCTT CCTTTAGAAGATTA | 661 | UGGGGGGUCUGUUCUUC CUUUAGAAGAUUA |
| LDHA_exon3 | - | CTTA | 85 | TTCTGGGGGTCTGTT CTTCCTTTAGAAGA | 662 | UUCUGGGGGUCUGUUC UUCCUUUAGAAGA |
| LDHA_exon3 | - | ATTA | 86 | AGATACTGATGGCACA GGCCATGCCAACAG | 663 | AGAUACUGAUGGCACAG GCCAUGCCAACAG |
| LDHA_exon3 | - | CTTC | 87 | ATTAAGATACTGATGG CACAGGCCATGCCA | 664 | AUUAAGAUACUGAUGGC ACAGGCCAUGCCA |
| LDHA_exon3 | - | CTTA | 88 | CCTTCATTAAGATACT GATGGCACAGGCCA | 665 | CCUUCAUUAAGAUACUG AUGGCACAGGCCA |
| LDHA_exon3 | - | CTTC | 89 | CAGTGTGGTAGACTCT CACTTACCTTCATT | 666 | CAGUGUGGUAGACUCUC ACUUACCUUCAUU |
| LDHA_exon3 | - | CTTC | 90 | CTTTAGAAGATTATAA ATCAGCTGATCCTT | 667 | CUUUAGAAGAUUAUAAA UCAGCUGAUCCUU |
| LDHA_exon3 | - | TTTA | 91 | GTGTCACTACAGCTTC TTTAATGTTTATT | 668 | GUGUCACUACAGCUUCU UUAAUGUUUAUU |
| LDHA_exon4 | - | GTTC | 92 | TAAGGAAAAGGCTGCC ATGTTGGAGATCCA | 669 | UAAGGAAAAGGCUGCCA UGUUGGAGAUCCA |
| LDHA_exon4 | - | GTTG | 93 | GAGATCCATCATCTCT CCCTTCAATTTGTC | 670 | GAGAUCCAUCAUCUCUC CCUUCAAUUUGUC |
| LDHA_exon4 | - | CTTC | 94 | AATTTGTCTTCGATGA CATCAACAAGAGCA | 671 | AAUUUGUCUUCGAUGAC AUCAACAAGAGCA |
| LDHA_exon4 | - | GTTC | 95 | ATCTGCCAAGTCCTAA AAGACATCAAATCT | 672 | AUCUGCCAAGUCCUAAA AGACAUCAAAUCU |
| LDHA_exon4 | - | TTTG | 96 | TCTTCGATGACATCAA CAAGAGCAAGTTCA | 673 | UCUUCGAUGACAUCAAC AAGAGCAAGUUCA |
| LDHA_exon4 | - | CTTC | 97 | GATGACATCAACAAGA GCAAGTTCATCTGC | 674 | GAUGACAUCAACAAGAG CAAGUUCAUCUGC |
| LDHA_exon4 | - | CTTT | 98 | AGTTAAATGGAAAATT GCCACTTCTAGATT | 675 | AGUUAAAUGGAAAAUUG CCACUUCUAGAUU |
| LDHA_exon4 | - | ATTT | 99 | GTCTTCGATGACATCA ACAAGAGCAAGTTC | 676 | GUCUUCGAUGACAUCAA CAAGAGCAAGUUC |
| LDHA_exon4 | - | CTTT | 100 | GGTGTTCTAAGGAAAA GGCTGCCATGTTGG | 677 | GGUGUUCUAAGGAAAAG GCUGCCAUGUUGG |
| LDHA_exon4 | - | TTTG | 101 | GTGTTCTAAGGAAAAG GCTGCCATGTTGGA | 678 | GUGUUCUAAGGAAAAGG CUGCCAUGUUGGA |
| LDHA_exon4 | - | CTTT | 102 | GCCAGAGACAATCTTT GGTGTTCTAAGGAA | 679 | GCCAGAGACAAUCUUUG GUGUUCUAAGGAA |
| LDHA_exon4 | + | ATTT | 103 | TCCATTTAACTAAAGA TTTGATGTCTTTTA | 680 | UCCAUUUAACUAAAGAU UUGAUGUCUUUUA |
| LDHA_exon4 | + | TTTT | 104 | CCATTTAACTAAAGAT TTGATGTCTTTTAG | 681 | CCAUUUAACUAAAGAUU UGAUGUCUUUUAG |
| LDHA_exon4 | + | TTTC | 105 | CATTTAACTAAAGATT TGATGTCTTTTAGG | 682 | CAUUUAACUAAAGAUUU GAUGUCUUUUAGG |
| LDHA_exon4 | + | ATTT | 106 | AACTAAAGATTTGATG TCTTTTAGGACTTG | 683 | AACUAAAGAUUUGAUGU CUUUUAGGACUUG |
| LDHA_exon4 | + | ATTT | 107 | GATGTCTTTTAGGACT TGGCAGATGAACTT | 684 | GAUGUCUUUUAGGACUU GGCAGAUGAACUU |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon4 | + | TTTG | 108 | ATGTCTTTTAGGACTTGGCAGATGAACTTG | 685 | AUGUCUUUUAGGACUUGGCAGAUGAACUUG |
| LDHA_exon4 | + | CTTT | 109 | TAGGACTTGGCAGATGAACTTGCTCTTGTT | 686 | UAGGACUUGGCAGAUGAACUUGCUCUUGUU |
| LDHA_exon4 | + | TTTT | 110 | AGGACTTGGCAGATGAACTTGCTCTTGTTG | 687 | AGGACUUGGCAGAUGAACUUGCUCUUGUUG |
| LDHA_exon4 | + | TTTA | 111 | GGACTTGGCAGATGAACTTGCTCTTGTTGA | 688 | GGACUUGGCAGAUGAACUUGCUCUUGUUGA |
| LDHA_exon4 | + | CTTG | 112 | GCAGATGAACTTGCTCTTGTTGATGTCATC | 689 | GCAGAUGAACUUGCUCUUGUUGAUGUCAUC |
| LDHA_exon4 | + | CTTG | 113 | CTCTTGTTGATGTCATCGAAGACAAATTGA | 690 | CUCUUGUUGAUGUCAUCGAAGACAAAUUGA |
| LDHA_exon4 | + | CTTG | 114 | TTGATGTCATCGAAGACAAATTGAAGGGAG | 691 | UUGAUGUCAUCGAAGACAAAUUGAAGGGAG |
| LDHA_exon4 | + | GTTG | 115 | ATGTCATCGAAGACAAATTGAAGGGAGAGA | 692 | AUGUCAUCGAAGACAAAUUGAAGGGAGAGA |
| LDHA_exon4 | + | ATTG | 116 | AAGGGAGAGATGATGGATCTCCAACATGGC | 693 | AAGGGAGAGAUGAUGGAUCUCCAACAUGGC |
| LDHA_exon4 | + | CTTT | 117 | TCCTTAGAACACCAAAGATTGTCTCTGGCA | 694 | UCCUUAGAACACCAAAGAUUGUCUCUGGCA |
| LDHA_exon4 | + | TTTT | 118 | CCTTAGAACACCAAAGATTGTCTCTGGCAA | 695 | CCUUAGAACACCAAAGAUUGUCUCUGGCAA |
| LDHA_exon4 | + | TTTC | 119 | CTTAGAACACCAAAGATTGTCTCTGGCAAA | 696 | CUUAGAACACCAAAGAUUGUCUCUGGCAAA |
| LDHA_exon4 | + | CTTA | 120 | GAACACCAAAGATTGTCTCTGGCAAAGGTT | 697 | GAACACCAAAGAUUGUCUCUGGCAAAGGUU |
| LDHA_exon4 | + | ATTG | 121 | TCTCTGGCAAAGGTTGATTTCAACAAGTTT | 698 | UCUCUGGCAAAGGUUGAUUUCAACAAGUUU |
| LDHA_exon4 | + | GTTG | 122 | ATTTCAACAAGTTTATATTATAATCCATGC | 699 | AUUUCAACAAGUUUAUAUUAUAAUCCAUGC |
| LDHA_exon4 | + | ATTT | 123 | CAACAAGTTTATATTATAATCCATGCTTGA | 700 | CAACAAGUUUAUAUUAUAAUCCAUGCUUGA |
| LDHA_exon4 | + | TTTC | 124 | AACAAGTTTATATTATAATCCATGCTTGAC | 701 | AACAAGUUUAUAUUAUAAUCCAUGCUUGAC |
| LDHA_exon4 | + | GTTT | 125 | ATATTATAATCCATGCTTGACTTAAATTCT | 702 | AUAUUAUAAUCCAUGCUUGACUUAAAUUCU |
| LDHA_exon4 | + | TTTA | 126 | TATTATAATCCATGCTTGACTTAAATTCTT | 703 | UAUUAUAAUCCAUGCUUGACUUAAAUUCUU |
| LDHA_exon4 | - | ATTT | 127 | AAGTCAAGCATGGATTATAATATAAACTTG | 704 | AAGUCAAGCAUGGAUUAUAAUAUAAACUUG |
| LDHA_exon4 | - | TTTA | 128 | AGTCAAGCATGGATTATAATATAAACTTGT | 705 | AGUCAAGCAUGGAUUAUAAUAUAAACUUGU |
| LDHA_exon4 | - | ATTA | 129 | TAATATAAACTTGTTGAAATCAACCTTTGC | 706 | UAAUAUAAACUUGUUGAAAUCAACCUUUGC |
| LDHA_exon4 | - | CTTG | 130 | TTGAAATCAACCTTTGCCAGAGACAATCTT | 707 | UUGAAAUCAACCUUUGCCAGAGACAAUCUU |
| LDHA_exon4 | - | GTTG | 131 | AAATCAACCTTTGCCAGAGACAATCTTTGG | 708 | AAAUCAACCUUUGCCAGAGACAAUCUUUGG |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon4 | - | TTTG | 132 | CCAGAGACAATCTTTGGTGTTCTAAGGAAA | 709 | CCAGAGACAAUCUUUGGUGUUCUAAGGAAA |
| LDHA_exon4 | + | TTTA | 133 | ACTAAAGATTTGATGTCTTTTAGGACTTGG | 710 | ACUAAAGAUUUGAUGUCUUUUAGGACUUGG |
| LDHA_exon4 | + | ATTA | 134 | TAATCCATGCTTGACTTAAATTCTTT | 711 | UAAUCCAUGCUUGACUUAAAUUCUUU |
| LDHA_exon4 | - | TTTA | 135 | GTTAAATGGAAAATTGCCACTTCTAGATT | 712 | GUUAAAUGGAAAAUUGCCACUUCUAGAUU |
| LDHA_exon4 | - | GTTA | 136 | AATGGAAAATTGCCACTTCTAGATT | 713 | AAUGGAAAAUUGCCACUUCUAGAUU |
| LDHA_exon5 | + | ATTT | 137 | ATTCTAAAGGCCTTAATCTGGTCATTATTC | 714 | AUUCUAAAGGCCUUAAUCUGGUCAUUAUUC |
| LDHA_exon5 | - | ATTA | 138 | TAGTCTAGAGAAAGGGGAATAATGACCAG | 715 | UAGUCUAGAGAAAGGGGAAUAAUGACCAG |
| LDHA_exon5 | + | TTTT | 139 | GACTGCATAAAAATTGACAAGCTATAGTAA | 716 | GACUGCAUAAAAAUUGACAAGCUAUAGUAA |
| LDHA_exon5 | + | GTTT | 140 | TGACTGCATAAAAATTGACAAGGTATAGTA | 717 | UGACUGCAUAAAAAUUGACAAGCUAUAGUA |
| LDHA_exon5 | + | TTTG | 141 | AAATCCAGGTGAGGCTTTTGACTGCATAAA | 718 | AAAUCCAGGUGAGGCUUUUGACUGCAUAAA |
| LDHA_exon5 | + | GTTT | 142 | CAAATCCAGGTGAGGCTTTTGACTGCATAA | 719 | CAAAUCCAGGUGAGGCUUUUGACUGCAUAA |
| LDHA_exon5 | + | ATTG | 143 | TTTCAAATCCAGGTGAGGCTTTTGACTGCA | 720 | UUUCAAAUCCAGGUGAGGCUUUUGACUGCA |
| LDHA_exon5 | + | GTTA | 144 | TTGTTTCAAATCCAGGTGAGGCTTTTGACT | 721 | UUGUUUCAAAUCCAGGUGAGGCUUUUGACU |
| LDHA_exon5 | + | GTTG | 145 | CTTATTGTTTCAAATCCAGGTGAGGCTTTT | 722 | CUUAUUGUUUCAAAUCCAGGUGAGGCUUUU |
| LDHA_exon5 | + | GTTG | 146 | TAAAATACAGCCCGAACTGCAAGTTGCTTA | 723 | UAAAAUACAGCCCGAACUGCAAGUUGCUUA |
| LDHA_exon5 | + | ATTC | 147 | CTAATGTTGTAAAATACAGCCCGAACTGCA | 724 | CUAAUGUUGUAAAAUACAGCCCGAACUGCA |
| LDHA_exon5 | + | ATTC | 148 | ATCATTCCTAATGTTGTAAAATACAGCCCG | 725 | AUCAUUCCUAAUGUUGUAAAAUACAGCCCG |
| LDHA_exon5 | + | TTTA | 149 | AATTCATCATTCCTAATGTTGTAAAATACA | 726 | AAUUCAUCAUUCCUAAUGUUGUAAAAUACA |
| LDHA_exon5 | + | TTTG | 150 | ACTGCATAAAAATTGACAAGCTATAGTAAA | 727 | ACUGCAUAAAAAUUGACAAGCUAUAGUAAA |
| LDHA_exon5 | + | GTTT | 151 | AAATTCATCATTCCTAATGTTGTAAAATAC | 728 | AAAUUCAUCAUUCCUAAUGUUGUAAAAUAC |
| LDHA_exon5 | + | ATTT | 152 | GGTCCAGCGTAACGTGAACATCTTTAAATT | 729 | GGUCCAGCGUAACGUGAACAUCUUUAAAUU |
| LDHA_exon5 | + | CTTA | 153 | ATTTGGTCCAGCGTAACGTGAACATCTTTA | 730 | AUUUGGUCCAGCGUAACGUGAACAUCUUUA |
| LDHA_exon5 | + | ATTA | 154 | TCACGGCTGGGGCACGTCAGCAAGAGGGAG | 731 | UCACGGCUGGGGCACGUCAGCAAGAGGGAG |
| LDHA_exon5 | + | TTTC | 155 | TCTAGACTATAATGTAACTGCAAACTCCAA | 732 | UCUAGACUAUAAUGUAACUGCAAACUCCAA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon5 | + | TTTT | 156 | CTCTAGACTATAATGTAACTGCAAACTCCA | 733 | CUCUAGACUAUAAUGUAACUGCAAACUCCA |
| LDHA_exon5 | + | CTTT | 157 | TCTCTAGACTATAATGTAACTGCAAACTCC | 734 | UCUCUAGACUAUAAUGUAACUGCAAACUCC |
| LDHA_exon5 | + | ATTC | 158 | CCCTTTTCTCTAGACTATAATGTAACTGCA | 735 | CCCUUUUCUCUAGACUAUAAUGUAACUGCA |
| LDHA_exon5 | + | ATTA | 159 | TTCCCCTTTTCTCTAGACTATAATGTAACT | 736 | UUCCCCUUUUCUCUAGACUAUAAUGUAACU |
| LDHA_exon5 | + | CTTA | 160 | ATCTGGTCATTATTCCCCTTTTCTCTAGAC | 737 | AUCUGGUCAUUAUUCCCCUUUUCUCUAGAC |
| LDHA_exon5 | + | ATTC | 161 | TAAAGGCCTTAATCTGGTCATTATTCCCCT | 738 | UAAAGGCCUUAAUCUGGUCAUUAUUCCCCU |
| LDHA_exon5 | + | TTTA | 162 | TTCTAAAGGCCTTAATCTGGTCATTATTCC | 739 | UUCUAAAGGCCUUAAUCUGGUCAUUAUUCC |
| LDHA_exon5 | + | TTTG | 163 | GTCCAGCGTAACGTGAACATCTTTAAATTC | 740 | GUCCAGCGUAACGUGAACAUCUUUAAAUUC |
| LDHA_exon5 | - | TTTT | 164 | ACTATAGCTTGTCAATTTTTATGCAGTCAA | 741 | ACUAUAGCUUGUCAAUUUUUAUGCAGUCAA |
| LDHA_exon5 | - | GTTT | 165 | TACTATAGCTTGTCAATTTTTATGCAGTCA | 742 | UACUAUAGCUUGUCAAUUUUUAUGCAGUCA |
| LDHA_exon5 | - | ATTT | 166 | AAAGATGTTCACGTTACGCTGGACCAAATT | 743 | AAAGAUGUUCACGUUACGCUGGACCAAAUU |
| LDHA_exon5 | - | GTTT | 167 | GCAGTTACATTATAGTCTAGAGAAAAGGGG | 744 | GCAGUUACAUUAUAGUCUAGAGAAAAGGGG |
| LDHA_exon5 | - | CTTG | 168 | GAGTTTGCAGTTACATTATAGTCTAGAGAA | 745 | GAGUUUGCAGUUACAUUAUAGUCUAGAGAA |
| LDHA_exon5 | - | CTTG | 169 | CTGACGTGCCCCAGCCGTGATAATGACCAG | 746 | CUGACGUGCCCCAGCCGUGAUAAUGACCAG |
| LDHA_exon5 | - | TTTC | 170 | TCCCTCTTGCTGACGTGCCCCAGCCGTGAT | 747 | UCCCUCUUGCUGACGUGCCCCAGCCGUGAU |
| LDHA_exon5 | - | CTTT | 171 | CTCCCTCTTGCTGACGTGCCCCAGCCGTGA | 748 | CUCCCUCUUGCUGACGUGCCCCAGCCGUGA |
| LDHA_exon5 | - | ATTA | 172 | AGACGGCTTTCTCCCTCTTGCTGACGTGCC | 749 | AGACGGCUUUCUCCCUCUUGCUGACGUGCC |
| LDHA_exon5 | - | GTTA | 173 | CGCTGGACCAAATTAAGACGGCTTTCTCCC | 750 | CGCUGGACCAAAUUAAGACGGCUUUCUCCC |
| LDHA_exon5 | - | GTTC | 174 | ACGTTACGCTGGACCAAATTAAGACGGCTT | 751 | ACGUUACGCUGGACCAAAUUAAGACGGCUU |
| LDHA_exon5 | - | TTTA | 175 | AAGATGTTCACGTTACGCTGGACCAAATTA | 752 | AAGAUGUUCACGUUACGCUGGACCAAAUUA |
| LDHA_exon5 | - | TTTA | 176 | CTATAGCTTGTCAATTTTTATGCAGTCAAA | 753 | CUAUAGCUUGUCAAUUUUUAUGCAGUCAAA |
| LDHA_exon5 | - | ATTA | 177 | GGAATGATGAATTTAAAGATGTTCACGTTA | 754 | GGAAUGAUGAAUUUAAAGAUGUUCACGUUA |
| LDHA_exon5 | - | TTTA | 178 | CAACATTAGGAATGATGAATTTAAAGATGT | 755 | CAACAUUAGGAAUGAUGAAUUUAAAGAUGU |
| LDHA_exon5 | - | TTTT | 179 | ACAACATTAGGAATGATGAATTTAAAGATG | 756 | ACAACAUUAGGAAUGAUGAAUUUAAAGAUG |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon5 | - | ATTT | 180 | TACAACATTAGGAATGATGAATTTAAAGAT | 757 | UACAACAUUAGGAAUGAUGAAUUUAAAGAU |
| LDHA_exon5 | - | GTTC | 181 | GGGCTGTATTTTACAACATTAGGAATGATG | 758 | GGGCUGUAUUUUACAACAUUAGGAAUGAUG |
| LDHA_exon5 | - | CTTG | 182 | CAGTTCGGGCTGTATTTTACAACATTAGGA | 759 | CAGUUCGGGCUGUAUUUUACAACAUUAGGA |
| LDHA_exon5 | - | TTTG | 183 | AAACAATAAGCAACTTGCAGTTCGGGCTGT | 760 | AAACAAUAAGCAACUUGCAGUUCGGGCUGU |
| LDHA_exon5 | - | ATTT | 184 | GAAACAATAAGCAACTTGCAGTTCGGGCTG | 761 | GAAACAAUAAGCAACUUGCAGUUCGGGCUG |
| LDHA_exon5 | - | TTTA | 185 | TGCAGTCAAAAGCCTCACCTGGATTTGAAA | 762 | UGCAGUCAAAAGCCUCACCUGGAUUUGAAA |
| LDHA_exon5 | - | TTTT | 186 | ATGCAGTCAAAAGCCTCACCTGGATTTGAA | 763 | AUGCAGUCAAAAGCCUCACCUGGAUUUGAA |
| LDHA_exon5 | - | TTTT | 187 | TATGCAGTCAAAAGCCTCACCTGGATTTGA | 764 | UAUGCAGUCAAAAGCCUCACCUGGAUUUGA |
| LDHA_exon5 | - | ATTT | 188 | TTATGCAGTCAAAAGCCTCACCTGGATTTG | 765 | UUAUGCAGUCAAAAGCCUCACCUGGAUUUG |
| LDHA_exon5 | - | CTTG | 189 | TCAATTTTTATGCAGTCAAAAGCCTCACCT | 766 | UCAAUUUUUAUGCAGUCAAAAGCCUCACCU |
| LDHA_exon5 | - | TTTG | 190 | CAGTTACATTATAGTCTAGAGAAAAGGGGA | 767 | CAGUUACAUUAUAGUCUAGAGAAAAGGGGA |
| LDHA_exon5 | - | GTTA | 191 | CATTATAGTCTAGAGAAAAGGGGAATAATG | 768 | CAUUAUAGUCUAGAGAAAAGGGGAAUAAUG |
| LDHA_exon5 | + | ATTG | 192 | ACAAGCTATAGTAAAACTGATAG | 769 | ACAAGCUAUAGUAAAACUGAUAG |
| LDHA_exon5 | - | ATTA | 193 | AGGCCTTTAGAATAAATTTT | 770 | AGGCCUUUAGAAUAAAUUUU |
| LDHA_exon6 | - | GTTA | 194 | TCTTCCAAGCCACGTAGGTCAAGATATCCA | 771 | UCUUCCAAGCCACGUAGGUCAAGAUAUCCA |
| LDHA_exon6 | - | CTTG | 195 | CAAGCCACGTAGGTCAAGATATCCACTATG | 772 | CAAGCCACGUAGGUCAAGAUAUCCACUAUG |
| LDHA_exon6 | - | TTTG | 196 | GGAAAACCACTTATCTTCCAAGCCACGTAG | 773 | GGAAAACCACUUAUCUUCCAAGCCACGUAG |
| LDHA_exon6 | + | CTTG | 197 | ACCTACGTGGCTTGGAAGATAAGTGGTTTT | 774 | ACCUACGUGGCUUGGAAGAUAAGUGGUUUU |
| LDHA_exon6 | - | TTTT | 198 | TGGGAAAACCACTTATCTTCCAAGCCACGT | 775 | UGGGAAAACCACUUAUCUUCCAAGCCACGU |
| LDHA_exon6 | + | GTTA | 199 | CCTAATGGGGAAAGGCTGGGAGTTCACCC | 776 | CCUAAUGGGGAAAGGCUGGGAGUUCACCC |
| LDHA_exon6 | + | ATTC | 200 | CGTTACCTAATGGGGAAAGGCTGGGAGTT | 777 | CGUUACCUAAUGGGGAAAGGCUGGGAGUU |
| LDHA_exon6 | + | ATTC | 201 | AGCCCGATTCCGTTACCTAATGGGGAAAG | 778 | AGCCCGAUUCCGUUACCUAAUGGGGAAAG |
| LDHA_exon6 | + | GTTG | 202 | CAATCTGGATTCAGCCCGATTCCGTTACCT | 779 | CAAUCUGGAUUCAGCCCGAUUCCGUUACCU |
| LDHA_exon6 | + | ATTG | 203 | GAAGCGGTTGCAATCTGGATTCAGCCCGAT | 780 | GAAGCGGUUGCAAUCUGGAUUCAGCCCGAU |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon6 | + | TTTC | 204 | CCAAAAACCGTGTTATTGGAAGCGGTTGCA | 781 | CCAAAAACCGUGUUAUUGGAAGCGGUUGCA |
| LDHA_exon6 | + | TTTT | 205 | CCCAAAAACCGTGTTATTGGAAGCGGTTGC | 782 | CCCAAAAACCGUGUUAUUGGAAGCGGUUGC |
| LDHA_exon6 | + | GTTT | 206 | TCCCAAAAACCGTGTTATTGGAAGCGGTTG | 783 | UCCCAAAAACCGUGUUAUUGGAAGCGGUUG |
| LDHA_exon6 | + | CTTG | 207 | GAAGATAAGTGGTTTTCCCAAAAACCGTGT | 784 | GAAGAUAAGUGGUUUUCCCAAAAACCGUGU |
| LDHA_exon6 | + | TTTC | 208 | ATAGTGGATATCTTGACCTACGTGGCTTGG | 785 | AUAGUGGAUAUCUUGACCUACGUGGCUUGG |
| LDHA_exon6 | + | TTTT | 209 | CATAGTGGATATCTTGACCTACGTGGCTTG | 786 | CAUAGUGGAUAUCUUGACCUACGUGGCUUG |
| LDHA_exon6 | + | TTTT | 210 | TCATAGTGGATATCTTGACCTACGTGGCTT | 787 | UCAUAGUGGAUAUCUUGACCUACGUGGCUU |
| LDHA_exon6 | + | GTTT | 211 | TTCATAGTGGATATCTTGACCTACGTGGCT | 788 | UUCAUAGUGGAUAUCUUGACCUACGUGGCU |
| LDHA_exon6 | + | TTTC | 212 | TCCTTTTTCATAGTGGATATCTTGACCTAC | 789 | UCCUUUUUCAUAGUGGAUAUCUUGACCUAC |
| LDHA_exon6 | + | TTTT | 213 | CTCCTTTTTCATAGTGGATATCTTGACCTA | 790 | CUCCUUUUUCAUAGUGGAUAUCUUGACCUA |
| LDHA_exon6 | + | ATTT | 214 | TCTCCTTTTTCATAGTGGATATCTTGACCT | 791 | UCUCCUUUUUCAUAGUGGAUAUCUUGACCU |
| LDHA_exon6 | + | TTTA | 215 | TTTTCTCCTTTTTCATAGTGGATATCTTGA | 792 | UUUUCUCCUUUUUCAUAGUGGAUAUCUUGA |
| LDHA_exon6 | + | TTTT | 216 | ATTTTCTCCTTTTTCATAGTGGATATCTTG | 793 | AUUUUCUCCUUUUUCAUAGUGGAUAUCUUG |
| LDHA_exon6 | + | TTTT | 217 | TATTTTCTCCTTTTTCATAGTGGATATCTT | 794 | UAUUUUCUCCUUUUUCAUAGUGGAUAUCUU |
| LDHA_exon6 | + | ATTT | 218 | TTATTTTCTCCTTTTTCATAGTGGATATCT | 795 | UUAUUUUCUCCUUUUUCAUAGUGGAUAUCU |
| LDHA_exon6 | - | TTTT | 219 | GGGAAAACCACTTATCTTCCAAGCCACGTA | 796 | GGGAAAACCACUUAUCUUCCAAGCCACGUA |
| LDHA_exon6 | + | GTTC | 220 | ACCCATTAAGCTGTCATGGGTGGGTCCTTG | 797 | ACCCAUUAAGCUGUCAUGGGUGGGUCCUUG |
| LDHA_exon6 | + | ATTA | 221 | AGCTGTCATGGGTGGGTCCTTGGGGAACAT | 798 | AGCUGUCAUGGGUGGGUCCUUGGGGAACAU |
| LDHA_exon6 | + | GTTA | 222 | TTGGAAGCGGTTGCAATCTGGATTCAGCCC | 799 | UUGGAAGCGGUUGCAAUCUGGAUUCAGCCC |
| LDHA_exon6 | + | ATTC | 223 | CAGTGGTAAGCATAAGTTATTTTCTTTTTG | 800 | CAGUGGUAAGCAUAAGUUAUUUUCUUUUUG |
| LDHA_exon6 | - | GTTT | 224 | TTGGGAAAACCACTTATCTTCCAAGCCACG | 801 | UUGGGAAAACCACUUAUCUUCCAAGCCACG |
| LDHA_exon6 | - | CTTC | 225 | CAATAACACGGTTTTTGGGAAAACCACTTA | 802 | CAAUAACACGGUUUUUGGGAAAACCACUUA |
| LDHA_exon6 | - | ATTG | 226 | CAACCGCTTCCAATAACACGGTTTTTGGGA | 803 | CAACCGCUUCCAAUAACACGGUUUUUGGGA |
| LDHA_exon6 | - | ATTA | 227 | GGTAACGGAATCGGGCTGAATCCAGATTGC | 804 | GGUAACGGAAUCGGGCUGAAUCCAGAUUGC |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon6 | + | CTTG | 228 | GGGAACATGGAGATTCCAGTGGTAAGCATA | 805 | GGGAACAUGGAGAUUCCAGUGGUAAGCAUA |
| LDHA_exon6 | - | CTTT | 229 | CCCCCATTAGGTAACGGAATCGGGCTGAAT | 806 | CCCCCAUUAGGUAACGGAAUCGGGCUGAAU |
| LDHA_exon6 | - | CTTA | 230 | ATGGGTGAACTCCCAGCCTTTCCCCCATTA | 807 | AUGGGUGAACUCCCAGCCUUUCCCCCAUUA |
| LDHA_exon6 | - | GTTC | 231 | CCCAAGGACCCACCCATGACAGCTTAATGG | 808 | CCCAAGGACCCACCCAUGACAGCUUAAUGG |
| LDHA_exon6 | - | CTTA | 232 | CCACTGGAATCTCCATGTTCCCCAAGGACC | 809 | CCACUGGAAUCUCCAUGUUCCCCAAGGACC |
| LDHA_exon6 | - | CTTA | 233 | TGCTTACCACTGGAATCTCCATGTTCCCCA | 810 | UGCUUACCACUGGAAUCUCCAUGUUCCCCA |
| LDHA_exon6 | - | TTTC | 234 | AAAAACAAAAGAAAATAACTTATGCTTAC | 811 | AAAAACAAAAGAAAAUAACUUAUGCUUAC |
| LDHA_exon6 | - | TTTC | 235 | CCCCATTAGGTAACGGAATCGGGCTGAATC | 812 | CCCCAUUAGGUAACGGAAUCGGGCUGAAUC |
| LDHA_exon6 | + | TTTT | 236 | CTTTTGTTTTGAAAAGATTATATAAAAA | 813 | CUUUUGUUUUGAAAAGAUUAUAUAAAAA |
| LDHA_exon6 | - | CTTT | 237 | TCAAAACAAAAGAAAATAACTTATGCTT | 814 | UCAAAACAAAAGAAAAUAACUUAUGCUU |
| LDHA_exon6 | - | TTTA | 238 | TATAATCTTTTCAAAACAAAAGAAAATA | 815 | UAUAAUCUUUUCAAAACAAAAGAAAAUA |
| LDHA_exon6 | - | TTTT | 239 | ATATAATCTTTTCAAAACAAAAGAAAAT | 816 | AUAUAAUCUUUUCAAAACAAAAGAAAAU |
| LDHA_exon6 | - | TTTT | 240 | TATATAATCTTTTCAAAACAAAAGAAAA | 817 | UAUAUAAUCUUUUCAAAACAAAAGAAAA |
| LDHA_exon6 | - | CTTT | 241 | TTATATAATCTTTTCAAAAACAAAAGAAA | 818 | UUAUAUAAUCUUUUCAAAAACAAAAGAAA |
| LDHA_exon6 | + | TTTC | 242 | TTTTTGTTTTGAAAAGATTATATAAAAG | 819 | UUUUUGUUUUGAAAAGAUUAUAUAAAAG |
| LDHA_exon6 | + | GTTA | 243 | TTTTCTTTTGTTTTTGAAAGATTATATA | 820 | UUUUCUUUUGUUUUUGAAAAGAUUAUAUA |
| LDHA_exon6 | + | ATTT | 244 | TCTTTTGTTTTGAAAAGATTATATAAAA | 821 | UCUUUUGUUUUGAAAAGAUUAUAUAAAA |
| LDHA_exon6 | - | TTTT | 245 | CAAAAACAAAAGAAAATAACTTATGCTTA | 822 | CAAAAACAAAAGAAAAUAACUUAUGCUUA |
| LDHA_exon6 | + | TTTT | 246 | GAAAAGATTATATAAAAAGT | 823 | GAAAAGAUUAUAUAAAAAGU |
| LDHA_exon6 | + | TTTT | 247 | TGAAAAGATTATATAAAAAGT | 824 | UGAAAAGAUUAUAUAAAAAGU |
| LDHA_exon6 | + | GTTT | 248 | TTGAAAAGATTATATAAAAAGT | 825 | UUGAAAAGAUUAUAUAAAAAGU |
| LDHA_exon6 | + | TTTT | 249 | GTTTTTGAAAAGATTATATAAAAAGT | 826 | GUUUUUGAAAAGAUUAUAUAAAAAGU |
| LDHA_exon6 | + | TTTT | 250 | TGTTTTTGAAAAGATTATATAAAAAGT | 827 | UGUUUUUGAAAAGAUUAUAUAAAAAGU |
| LDHA_exon6 | + | CTTT | 251 | TTGTTTTTGAAAAGATTATATAAAAAGT | 828 | UUGUUUUUGAAAAGAUUAUAUAAAAAGU |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon6 | + | TTTG | 252 | TTTTTGAAAAGATTATATAAAAAGT | 829 | UUUUUGAAAAGAUUAUAUAAAAAGU |
| LDHA_exon7 | + | GTTG | 253 | AGAGGTAATAAATCTTTCAATTTGGCAACA | 830 | AGAGGUAAUAAAUCUUUCAAUUUGGCAACA |
| LDHA_exon7 | + | GTTG | 254 | GTACATGAAAATAAATGTAGTCTGTACTAT | 831 | GUACAUGAAAAUAAAUGUAGUCUGUACUAU |
| LDHA_exon7 | + | TTTC | 255 | AATTTGGCAACACAGAATATTAACATTTAC | 832 | AAUUUGGCAACACAGAAUAUUAACAUUUAC |
| LDHA_exon7 | + | GTTC | 256 | ACAAGCAGGTGGTTGAGAGGTAATAAATCT | 833 | ACAAGCAGGUGGUUGAGAGGUAAUAAAUCU |
| LDHA_exon7 | + | ATTT | 257 | GGCAACACAGAATATTAACATTTACTATTT | 834 | GGCAACACAGAAUAUUAACAUUUACUAUUU |
| LDHA_exon7 | + | CTTT | 258 | CAATTTGGCAACACAGAATATTAACATTTA | 835 | CAAUUUGGCAACACAGAAUAUUAACAUUUA |
| LDHA_exon7 | + | TTTA | 259 | GGGACTGATAAAGATAAGGAACAGTGGAAA | 836 | GGGACUGAUAAAGAUAAGGAACAGUGGAAA |
| LDHA_exon7 | + | CTTT | 260 | TAGTGCCTGTATGGAGTGGAATGAATGTTG | 837 | UAGUGCCUGUAUGGAGUGGAAUGAAUGUUG |
| LDHA_exon7 | + | GTTG | 261 | CTGGTGTCTCTCTGAAGACTCTGCACCCAG | 838 | CUGGUGUCUCUCUGAAGACUCUGCACCCAG |
| LDHA_exon7 | + | TTTA | 262 | GTGCCTGTATGGAGTGGAATGAATGTTGCT | 839 | GUGCCUGUAUGGAGUGGAAUGAAUGUUGCU |
| LDHA_exon7 | + | TTTT | 263 | AGTGCCTGTATGGAGTGGAATGAATGTTGC | 840 | AGUGCCUGUAUGGAGUGGAAUGAAUGUUGC |
| LDHA_exon7 | + | TTTC | 264 | TTTTAGTGCCTGTATGGAGTGGAATGAATG | 841 | UUUUAGUGCCUGUAUGGAGUGGAAUGAAUG |
| LDHA_exon7 | + | ATTT | 265 | CTTTTAGTGCCTGTATGGAGTGGAATGAAT | 842 | CUUUUAGUGCCUGUAUGGAGUGGAAUGAAU |
| LDHA_exon7 | + | TTTG | 266 | GCAACACAGAATATTAACATTTACTATTTT | 843 | GCAACACAGAAUAUUAACAUUUACUAUUUU |
| LDHA_exon7 | + | ATTT | 267 | AGGGACTGATAAAGATAAGGAACAGTGGAA | 844 | AGGGACUGAUAAAGAUAAGGAACAGUGGAA |
| LDHA_exon7 | - | GTTA | 268 | ATATTCTGTGTTGCCAAATTGAAAGATTTA | 845 | AUAUUCUGUGUUGCCAAAUUGAAAGAUUUA |
| LDHA_exon7 | - | TTTA | 269 | TCAGTCCCTAAATCTGGGTGCAGAGTCTTC | 846 | UCAGUCCCUAAAUCUGGGUGCAGAGUCUUC |
| LDHA_exon7 | - | GTTG | 270 | CCAAATTGAAAGATTTATTACCTCTCAACC | 847 | CCAAAUUGAAAGAUUUAUUACCUCUCAACC |
| LDHA_exon7 | - | ATTC | 271 | TGTGTTGCCAAATTGAAGATTTATTACCT | 848 | UGUGUUGCCAAAUUGAAAGAUUUAUUACCU |
| LDHA_exon7 | - | ATTC | 272 | CACTCCATACAGGCACTAAAAGAAATAGTA | 849 | CACUCCAUACAGGCACUAAAAGAAAUAGUA |
| LDHA_exon7 | - | CTTC | 273 | AGAGAGACACCAGCAACATTCATTCCACTC | 850 | AGAGAGACACCAGCAACAUUCAUUCCACUC |
| LDHA_exon7 | - | CTTT | 274 | ATCAGTCCCTAAATCTGGGTGCAGAGTCTT | 851 | AUCAGUCCCUAAAUCUGGGUGCAGAGUCUU |
| LDHA_exon7 | - | CTTA | 275 | TCTTTATCAGTCCCTAAATCTGGGTGCAGA | 852 | UCUUUAUCAGUCCCUAAAUCUGGGUGCAGA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon7 | - | GTTC | 276 | CTTATCTTTATCAGTCCCTAAATCTGGGTG | 853 | CUUAUCUUUAUCAGUCCCUAAAUCUGGGUG |
| LDHA_exon7 | - | ATTC | 277 | ATTCCACTCCATACAGGCACTAAAAGAAAT | 854 | AUUCCACUCCAUACAGGCACUAAAAGAAAU |
| LDHA_exon7 | - | CTTT | 278 | CCACTGTTCCTTATCTTTATCAGTCCCTAA | 855 | CCACUGUUCCUUAUCUUUAUCAGUCCCUAA |
| LDHA_exon7 | - | CTTG | 279 | TGAACCTCTTTCCACTGTTCCTTATCTTTA | 856 | UGAACCUCUUUCCACUGUUCCUUAUCUUUA |
| LDHA_exon7 | - | ATTA | 280 | CCTCTCAACCACCTGCTTGTGAACCTCTTT | 857 | CCUCUCAACCACCUGCUUGUGAACCUCUUU |
| LDHA_exon7 | - | TTTA | 281 | TTACCTCTCAACCACCTGCTTGTGAACCTC | 858 | UUACCUCUCAACCACCUGCUUGUGAACCUC |
| LDHA_exon7 | - | ATTT | 282 | ATTACCTCTCAACCACCTGCTTGTGAACCT | 859 | AUUACCUCUCAACCACCUGCUUGUGAACCU |
| LDHA_exon7 | - | TTTC | 283 | CACTGTTCCTTATCTTTATCAGTCCCTAAA | 860 | CACUGUUCCUUAUCUUUAUCAGUCCCUAAA |
| LDHA_exon7 | - | ATTG | 284 | AAAGATTATTACCTCTCAACCACCTGCTT | 861 | AAAGAUUAUUACCUCUCAACCACCUGCUU |
| LDHA_exon7 | - | TTTA | 285 | TTTTCATGTACCAACAGATTAG | 862 | UUUUCAUGUACCAACAGAUUAG |
| LDHA_exon7 | - | ATTT | 286 | ATTTTCATGTACCAACAGATTAG | 863 | AUUUUCAUGUACCAACAGAUUAG |
| LDHA_exon8 | + | ATTG | 287 | GACTCTCTGTAGCAGATTTGGCAGAGAGTA | 864 | GACUCUCUGUAGCAGAUUUGGCAGAGAGUA |
| LDHA_exon8 | + | CTTA | 288 | TGAGGTGATCAAACTCAAAGGCTACACATC | 865 | UGAGGUGAUCAAACUCAAAGGCUACACAUC |
| LDHA_exon8 | + | TTTC | 289 | CTATCATACAGTGCTTATGAGGTGATCAAA | 866 | CUAUCAUACAGUGCUUAUGAGGUGAUCAAA |
| LDHA_exon8 | + | GTTT | 290 | CCTATCATACAGTGCTTATGAGGTGATCAA | 867 | CCUAUCAUACAGUGCUUAUGAGGUGAUCAA |
| LDHA_exon8 | + | CTTT | 291 | ACCTATGGTTTCCTATCATACAGTGCTTAT | 868 | ACCUAUGGUUUCCUAUCAUACAGUGCUUAU |
| LDHA_exon8 | + | TTTC | 292 | TGCCTTTACCTATGGTTTCCTATCATACAG | 869 | UGCCUUUACCUAUGGUUUCCUAUCAUACAG |
| LDHA_exon8 | + | TTTT | 293 | CTGCCTTTACCTATGGTTTCCTATCATACA | 870 | CUGCCUUUACCUAUGGUUUCCUAUCAUACA |
| LDHA_exon8 | + | ATTT | 294 | GGCAGAGAGTATAATGAAGAATCTTAGGCG | 871 | GGCAGAGAGUAUAAUGAAGAAUCUUAGGCG |
| LDHA_exon8 | + | TTTA | 295 | CCTATGGTTTCCTATCATACAGTGCTTATG | 872 | CCUAUGGUUUCCUAUCAUACAGUGCUUAUG |
| LDHA_exon8 | + | TTTG | 296 | GCAGAGAGTATAATGAAGAATCTTAGGCGG | 873 | GCAGAGAGUAUAAUGAAGAAUCUUAGGCGG |
| LDHA_exon8 | - | CTTC | 297 | ATTATACTCTCTGCCAAATCTGCTACAGAG | 874 | AUUAUACUCUCUGCCAAAUCUGCUACAGAG |
| LDHA_exon8 | + | GTTT | 298 | CCACCATGATTAAGGTAGGTCTATGTAGTG | 875 | CCACCAUGAUUAAGGUAGGUCUAUGUAGUG |
| LDHA_exon8 | + | TTTC | 299 | CACCATGATTAAGGTAGGTCTATGTAGTGA | 876 | CACCAUGAUUAAGGUAGGUCUAUGUAGUGA |

TABLE 5-continued

Target and Spacer Sequences

| LDHA | Strand | PAM* | SEQ ID NO | Target Sequence | SEQ ID NO | Spacer Sequence |
| --- | --- | --- | --- | --- | --- | --- |
| LDHA_exon8 | + | ATTA | 300 | AGGTAGGTCTATGTAGTGATACGCTGCATT | 877 | AGGUAGGUCUAUGUAGUGAUACGCUGCAUU |
| LDHA_exon8 | - | ATTC | 301 | AAATGCAGCGTATCACTACATAGACCTACC | 878 | AAAUGCAGCGUAUCACUACAUAGACCUACC |
| LDHA_exon8 | - | CTTA | 302 | ATCATGGTGGAAACTGGGTGCACCCGCCTA | 879 | AUCAUGGUGGAAACUGGGUGCACCCGCCUA |
| LDHA_exon8 | - | ATTC | 303 | TTCATTATACTCTCTGCCAAATCTGCTACA | 880 | UUCAUUAUACUCUCUGCCAAAUCUGCUACA |
| LDHA_exon8 | - | ATTA | 304 | TACTCTCTGCCAAATCTGCTACAGAGAGTC | 881 | UACUCUCUGCCAAAUCUGCUACAGAGAGUC |
| LDHA_exon8 | - | CTTT | 305 | GAGTTTGATCACCTCATAAGCACTGTATGA | 882 | GAGUUUGAUCACCUCAUAAGCACUGUAUGA |
| LDHA_exon8 | - | TTTG | 306 | AGTTTGATCACCTCATAAGCACTGTATGAT | 883 | AGUUUGAUCACCUCAUAAGCACUGUAUGAU |
| LDHA_exon8 | + | TTTT | 307 | TCTGCCTTTACCTATGGTTTCCTATCATAC | 884 | UCUGCCUUUACCUAUGGUUUCCUAUCAUAC |
| LDHA_exon8 | + | CTTA | 308 | GGCGGGTGCACCCAGTTTCCACCATGATTA | 885 | GGCGGGUGCACCCAGUUUCCACCAUGAUUA |
| LDHA_exon8 | + | CTTT | 309 | TTCTGCCTTTACCTATGGTTTCCTATCATA | 886 | UUCUGCCUUUACCUAUGGUUUCCUAUCAUA |
| LDHA_exon8 | - | TTTG | 310 | ATCACCTCATAAGCACTGTATGATAGGAAA | 887 | AUCACCUCAUAAGCACUGUAUGAUAGGAAA |
| LDHA_exon8 | - | GTTT | 311 | GATCACCTCATAAGCACTGTATGATAGGAA | 888 | GAUCACCUCAUAAGCACUGUAUGAUAGGAA |
| LDHA_exon8 | + | ATTT | 312 | GAATGCTTTTGCTGGCTTTTT | 889 | GAAUGCUUUUGCUGGCUUUU |
| LDHA_exon8 | + | TTTG | 313 | AATGCTTTTGCTGGCTTTT | 890 | AAUGCUUUUGCUGGCUUUU |
| LDHA_exon9 | + | CTTC | 314 | TGAGGAAGAGGCCCGTTTGAAGAAGAGTGC | 891 | UGAGGAAGAGGCCCGUUUGAAGAAGAGUGC |
| LDHA_exon9 | - | TTTC | 315 | CAAATTAATATAATAACTAGCAGCTTTATG | 892 | CAAAUUAAUAUAAUAACUAGCAGCUUUAUG |
| LDHA_exon9 | - | ATTA | 316 | ATATAATAACTAGCAGCTTTATGACTTTAT | 893 | AUAUAAUAACUAGCAGCUUUAUGACUUUAU |
| LDHA_exon9 | - | CTTT | 317 | ATGACTTTATATCTTAAATATAATGAATTAA | 894 | AUGACUUUAUAUCUUAAUAUAAUGAAUUAA |
| LDHA_exon9 | - | TTTA | 318 | TGACTTTATATCTTAATATAATGAATTAAC | 895 | UGACUUUAUAUCUUAAUAUAAUGAAUUAAC |
| LDHA_exon9 | - | CTTT | 319 | ATATCTTAATATAATGAATTAACCAAAGTA | 896 | AUAUCUUAAUAUAAUGAAUUAACCAAAGUA |
| LDHA_exon9 | - | TTTA | 320 | TATCTTAATATAATGAATTAACCAAAGTAG | 897 | UAUCUUAAUAUAAUGAAUUAACCAAAGUAG |
| LDHA_exon9 | - | CTTA | 321 | ATATAATGAATTAACCAAAGTAGTCACTGT | 898 | AUAUAAUGAAUUAACCAAAGUAGUCACUGU |
| LDHA_exon9 | - | ATTA | 322 | ACCAAAGTAGTCACTGTTCAAGGTTTATTG | 899 | ACCAAAGUAGUCACUGUUCAAGGUUUAUUG |
| LDHA_exon9 | - | GTTC | 323 | AAGGTTTATTGGGGGTTTTAGTTGGTATAA | 900 | AAGGUUUAUUGGGGGUUUUAGUUGGUAUAA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | GTTT | 324 | ATTGGGGGTTTTAGTTGGTATAACACTTGG | 901 | AUUGGGGUUUUAGUUGGUAUAACACUUGG |
| LDHA_exon9 | - | TTTA | 325 | TTGGGGGTTTTAGTTGGTATAACACTTGGA | 902 | UUGGGGUUUUAGUUGGUAUAACACUUGGA |
| LDHA_exon9 | - | ATTG | 326 | GGGGTTTTAGTTGGTATAACACTTGGATAG | 903 | GGGGUUUUAGUUGGUAUAACACUUGGAUAG |
| LDHA_exon9 | - | GTTT | 327 | TAGTTGGTATAACACTTGGATAGTTGGTTG | 904 | UAGUUGGUAUAACACUUGGAUAGUUGGUUG |
| LDHA_exon9 | - | ATTT | 328 | CCAAATTAATATAATAACTAGCAGCTTTAT | 905 | CCAAAUUAAUAUAAUAACUAGCAGCUUUAU |
| LDHA_exon9 | - | TTTT | 329 | AGTTGGTATAACACTTGGATAGTTGGTTGC | 906 | AGUUGGUAUAACACUUGGAUAGUUGGUUGC |
| LDHA_exon9 | - | GTTG | 330 | GTATAACACTTGGATAGTTGGTTGCATTGT | 907 | GUAUAACACUUGGAUAGUUGGUUGCAUUGU |
| LDHA_exon9 | - | CTTG | 331 | GATAGTTGGTTGCATTGTTTGTATGTAGAT | 908 | GAUAGUUGGUUGCAUUGUUUGUAUGUAGAU |
| LDHA_exon9 | - | GTTG | 332 | GTTGCATTGTTTGTATGTAGATCTTTTTAC | 909 | GUUGCAUUGUUUGUAUGUAGAUCUUUUUAC |
| LDHA_exon9 | - | GTTG | 333 | CATTGTTTGTATGTAGATCTTTTTACATTA | 910 | CAUUGUUUGUAUGUAGAUCUUUUUACAUUA |
| LDHA_exon9 | - | ATTG | 334 | TTTGTATGTAGATCTTTTTACATTATATGG | 911 | UUUGUAUGUAGAUCUUUUUACAUUAUAUGG |
| LDHA_exon9 | - | GTTT | 335 | GTATGTAGATCTTTTTACATTATATGGTAA | 912 | GUAUGUAGAUCUUUUUACAUUAUAUGGUAA |
| LDHA_exon9 | - | TTTG | 336 | TATGTAGATCTTTTTACATTATATGGTAAT | 913 | UAUGUAGAUCUUUUUACAUUAUAUGGUAAU |
| LDHA_exon9 | - | CTTT | 337 | TTACATTATATGGTAATGTACACTACTGAT | 914 | UUACAUUAUAUGGUAAUGUACACUACUGAU |
| LDHA_exon9 | - | TTTT | 338 | TACATTATATGGTAATGTACACTACTGATA | 915 | UACAUUAUAUGGUAAUGUACACUACUGAUA |
| LDHA_exon9 | - | TTTT | 339 | ACATTATATGGTAATGTACACTACTGATAT | 916 | ACAUUAUAUGGUAAUGUACACUACUGAUAU |
| LDHA_exon9 | - | TTTA | 340 | CATTATATGGTAATGTACACTACTGATATA | 917 | CAUUAUAUGGUAAUGUACACUACUGAUAUA |
| LDHA_exon9 | - | ATTA | 341 | TATGGTAATGTACACTACTGATATAGTTCA | 918 | UAUGGUAAUGUACACUACUGAUAUAGUUCA |
| LDHA_exon9 | - | GTTC | 342 | ACAAATAAGATCCTTTGGAAGAATTATGC | 919 | ACAAAUAAGAUCCUUUGGAAGAAUUAUGC |
| LDHA_exon9 | - | CTTT | 343 | GGAAGAATTATGCACAAGACATGATATTGG | 920 | GGAAGAAUUAUGCACAAGACAUGAUAUUGG |
| LDHA_exon9 | - | TTTA | 344 | GTTGGTATAACACTTGGATAGTTGGTTGCA | 921 | GUUGGUAUAACACUUGGAUAGUUGGUUGCA |
| LDHA_exon9 | - | GTTG | 345 | CCCAAGAATAGCCTAATATTTCCAAATTAA | 922 | CCCAAGAAUAGCCUAAUAUUUCCAAAUUAA |
| LDHA_exon9 | - | GTTG | 346 | CAGGGTTGCCCAAGAATAGCCTAATATTTC | 923 | CAGGGUUGCCCAAGAAUAGCCUAAUAUUUC |
| LDHA_exon9 | - | GTTA | 347 | GAAAAAATCGTTGCAGGGTTGCCCAAGAAT | 924 | GAAAAAAUCGUUGCAGGGUUGCCCAAGAAU |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | ATTG | 348 | TTTTTAATTGTTACCAGCTTCCAGAGGACA | 925 | UUUUUAAUUGUUACCAGCUUCCAGAGGACA |
| LDHA_exon9 | - | GTTT | 349 | TTAATTGTTACCAGCTTCCAGAGGACAAGA | 926 | UUAAUUGUUACCAGCUUCCAGAGGACAAGA |
| LDHA_exon9 | - | TTTT | 350 | TAATTGTTACCAGCTTCCAGAGGACAAGAT | 927 | UAAUUGUUACCAGCUUCCAGAGGACAAGAU |
| LDHA_exon9 | - | TTTT | 351 | AATTGTTACCAGCTTCCAGAGGACAAGATC | 928 | AAUUGUUACCAGCUUCCAGAGGACAAGAUC |
| LDHA_exon9 | - | TTTA | 352 | ATTGTTACCAGCTTCCAGAGGACAAGATCT | 929 | AUUGUUACCAGCUUCCAGAGGACAAGAUCU |
| LDHA_exon9 | - | ATTG | 353 | TTACCAGCTTCCAGAGGACAAGATCTCAAA | 930 | UUACCAGCUUCCAGAGGACAAGAUCUCAAA |
| LDHA_exon9 | - | GTTA | 354 | CCAGCTTCCAGAGGACAAGATCTCAAAAAT | 931 | CCAGCUUCCAGAGGACAAGAUCUCAAAAAU |
| LDHA_exon9 | - | GTTG | 355 | CAGAGGACAAGATCTCAAAAATCTGTGTTC | 932 | CAGAGGACAAGAUCUCAAAAAUCUGUGUUC |
| LDHA_exon9 | - | GTTG | 356 | CCTATAGTGACACACTATCATTGCCTATAT | 933 | CCUAUAGUGACACACUAUCAUUGCCUAUAU |
| LDHA_exon9 | - | ATTG | 357 | CCTATATTCAGTTGGCAAATAAATTTTACA | 934 | CCUAUAUUCAGUUGGCAAAUAAAUUUUACA |
| LDHA_exon9 | - | ATTG | 358 | AGTTGGCAAATAAATTTTACATTTACATAT | 935 | AGUUGGCAAAUAAAUUUUACAUUUACAUAU |
| LDHA_exon9 | - | GTTG | 359 | GCAAATAAATTTTACATTTACATATAGAAT | 936 | GCAAAUAAAUUUUACAUUUACAUAUAGAAU |
| LDHA_exon9 | - | ATTT | 360 | TACATTTACATATAGAAATGTTACTTTCCAA | 937 | UACAUUUACAUAUAGAAUGUUACUUUCCAA |
| LDHA_exon9 | - | TTTT | 361 | ACATTTACATATAGAATGTTACTTTCCAAT | 938 | ACAUUUACAUAUAGAAUGUUACUUUCCAAU |
| LDHA_exon9 | - | TTTG | 362 | GAAGAATTATGCACAAGACATGATATTGGA | 939 | GAAGAAUUAUGCACAAGACAUGAUAUUGGA |
| LDHA_exon9 | - | TTTA | 363 | CATTTACATATAGAATGTTACTTTCCAATT | 940 | CAUUUACAUAUAGAAUGUUACUUUCCAAUU |
| LDHA_exon9 | - | TTTA | 364 | CATATAGAATGTTACTTTCCAATTATGATT | 941 | CAUAUAGAAUGUUACUUUCCAAUUAUGAUU |
| LDHA_exon9 | - | GTTA | 365 | CTTTCCAATTATGATTAGCATTATTATCAA | 942 | CUUUCCAAUUAUGAUUAGCAUUAUUAUCAA |
| LDHA_exon9 | - | CTTT | 366 | CCAATTATGATTAGCATTATTATCAAATAT | 943 | CCAAUUAUGAUUAGCAUUAUUAUCAAAUAU |
| LDHA_exon9 | - | TTTC | 367 | CAATTATGATTAGCATTATTATCAAATATA | 944 | CAAUUAUGAUUAGCAUUAUUAUCAAAUAUA |
| LDHA_exon9 | - | ATTA | 368 | TGATTAGCATTATTATCAAATATATAATAC | 945 | UGAUUAGCAUUAUUAUCAAAUAUAUAAUAC |
| LDHA_exon9 | - | ATTA | 369 | GCATTATTATCAAATATATAATACTTTGGG | 946 | GCAUUAUUAUCAAAUAUAUAAUACUUUGGG |
| LDHA_exon9 | - | ATTA | 370 | TTATCAAATATATAATACTTTGGGACTTAC | 947 | UUAUCAAAUAUAUAAUACUUUGGGACUUAC |
| LDHA_exon9 | - | ATTA | 371 | TCAAATATATAATACTTTGGGACTTACAAT | 948 | UCAAAUAUAUAAUACUUUGGGACUUACAAU |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | CTTT | 372 | GGGACTTACAATGGAAGTGGTACCAATACA | 949 | GGGACUUACAAUGGAAGUGGUACCAAUACA |
| LDHA_exon9 | - | TTTG | 373 | GGACTTACAATGGAAGTGGTACCAATACAA | 950 | GGACUUACAAUGGAAGUGGUACCAAUACAA |
| LDHA_exon9 | - | CTTA | 374 | CAATGGAAGTGGTACCAATACAACTCAGTT | 951 | CAAUGGAAGUGGUACCAAUACAACUCAGUU |
| LDHA_exon9 | - | GTTG | 375 | ACTATTACATCCTCTGCTATTAGTCAATAA | 952 | ACUAUUACAUCCUCUGCUAUUAGUCAAUAA |
| LDHA_exon9 | - | ATTA | 376 | CATCCTCTGCTATTAGTCAATAATATCCCT | 953 | CAUCCUCUGCUAUUAGUCAAUAAUAUCCCU |
| LDHA_exon9 | - | ATTA | 377 | GTCAATAATATCCCTGTTAGAAAAAATCGT | 954 | GUCAAUAAUAUCCCUGUUAGAAAAAAUCGU |
| LDHA_exon9 | - | ATTT | 378 | ACATATAGAATGTTACTTTCCAATTATGAT | 955 | ACAUAUAGAAUGUUACUUUCCAAUUAUGAU |
| LDHA_exon9 | - | ATTA | 379 | TGCACAAGACATGATATTGGATTTATACAC | 956 | UGCACAAGACAUGAUAUUGGAUUUAUACAC |
| LDHA_exon9 | - | ATTG | 380 | GATTTATACACTGGATCCCAGGATGTGACT | 957 | GAUUUAUACACUGGAUCCCAGGAUGUGACU |
| LDHA_exon9 | - | ATTT | 381 | ATACACTGGATCCCAGGATGTGACTCACTG | 958 | AUACACUGGAUCCCAGGAUGUGACUCACUG |
| LDHA_exon9 | - | CTTC | 382 | AAACGGGCCTCTTCCTCAGAAGTCAGAGTC | 959 | AAACGGGCCUCUUCCUCAGAAGUCAGAGUC |
| LDHA_exon9 | - | CTTC | 383 | CTCAGAAGTCAGAGTCACCTTCACAAGGTC | 960 | CUCAGAAGUCAGAGUCACCUUCACAAGGUC |
| LDHA_exon9 | - | CTTC | 384 | ACAAGGTCTGAGATTCCATTCTGTCCCAAA | 961 | ACAAGGUCUGAGAUUCCAUUCUGUCCCAAA |
| LDHA_exon9 | - | ATTC | 385 | CATTCTGTCCCAAAATGCAAGGAACACTAA | 962 | CAUUCUGUCCCAAAAUGCAAGGAACACUAA |
| LDHA_exon9 | - | ATTC | 386 | TGTCCCAAAATGCAAGGAACACTAAGGAAG | 963 | UGUCCCAAAAUGCAAGGAACACUAAGGAAG |
| LDHA_exon9 | - | CTTT | 387 | ATTCCGTAAAGACCCTGAAGATGAAATGAA | 964 | AUUCCGUAAAGACCCUGAAGAUGAAAUGAA |
| LDHA_exon9 | - | TTTA | 388 | TTCCGTAAAGACCCTGAAGATGAAATGAAA | 965 | UUCCGUAAAGACCCUGAAGAUGAAAUGAAA |
| LDHA_exon9 | - | ATTC | 389 | CGTAAAGACCCTGAAGATGAAATGAAAAAA | 966 | CGUAAAGACCCUGAAGAUGAAAUGAAAAAA |
| LDHA_exon9 | + | TTTG | 390 | GGACAGAATGGAATCTCAGACCTTGTGAAG | 967 | GGACAGAAUGGAAUCUCAGACCUUGUGAAG |
| LDHA_exon9 | + | TTTT | 391 | GGGACAGAATGGAATCTCAGACCTTGTGAA | 968 | GGGACAGAAUGGAAUCUCAGACCUUGUGAA |
| LDHA_exon9 | + | ATTT | 392 | TGGGACAGAATGGAATCTCAGACCTTGTGA | 969 | UGGGACAGAAUGGAAUCUCAGACCUUGUGA |
| LDHA_exon9 | + | CTTG | 393 | CATTTGGGACAGAATGGAATCTCAGACCT | 970 | CAUUUGGGACAGAAUGGAAUCUCAGACCU |
| LDHA_exon9 | + | GTTC | 394 | CTTGCATTTGGGACAGAATGGAATCTCAG | 971 | CUUGCAUUUGGGACAGAAUGGAAUCUCAG |
| LDHA_exon9 | + | CTTC | 395 | CTTAGTGTTCCTTGCATTTTGGGACAGAAT | 972 | CUUAGUGUUCCUUGCAUUUUGGGACAGAAU |

TABLE 5-continued

Target and Spacer Sequences

| LDHA | Strand | PAM* | SEQ ID NO | Target Sequence | SEQ ID NO | Spacer Sequence |
| --- | --- | --- | --- | --- | --- | --- |
| LDHA_exon9 | - | CTTC | 396 | TTCAAACGGGCCTCTTCCTCAGAAGTCAGA | 973 | UUCAAACGGGCCUCUUCCUCAGAAGUCAGA |
| LDHA_exon9 | + | TTTA | 397 | CGGAATAAAGGATGATGTCTTCCTTAGTGT | 974 | CGGAAUAAAGGAUGAUGUCUUCCUUAGUGU |
| LDHA_exon9 | + | CTTC | 398 | AGGGTCTTTACGGAATAAAGGATGATGTCT | 975 | AGGGUCUUUACGGAAUAAAGGAUGAUGUCU |
| LDHA_exon9 | + | TTTC | 399 | ATCTTCAGGGTCTTTACGGAATAAAGGATG | 976 | AUCUUCAGGGUCUUUACGGAAUAAAGGAUG |
| LDHA_exon9 | + | ATTT | 400 | CATCTTCAGGGTCTTTACGGAATAAAGGAT | 977 | CAUCUUCAGGGUCUUUACGGAAUAAAGGAU |
| LDHA_exon9 | + | TTTC | 401 | ATTTCATCTTCAGGGTCTTTACGGAATAAA | 978 | AUUUCAUCUUCAGGGUCUUUACGGAAUAAA |
| LDHA_exon9 | + | TTTT | 402 | CATTTCATCTTCAGGGTCTTTACGGAATAA | 979 | CAUUUCAUCUUCAGGGUCUUUACGGAAUAA |
| LDHA_exon9 | + | TTTT | 403 | TCATTTCATCTTCAGGGTCTTTACGGAATA | 980 | UCAUUUCAUCUUCAGGGUCUUUACGGAAUA |
| LDHA_exon9 | + | TTTT | 404 | TTCATTTCATCTTCAGGGTCTTTACGGAAT | 981 | UUCAUUUCAUCUUCAGGGUCUUUACGGAAU |
| LDHA_exon9 | + | TTTT | 405 | TTTCATTTCATCTTCAGGGTCTTTACGGAA | 982 | UUUCAUUUCAUCUUCAGGGUCUUUACGGAA |
| LDHA_exon9 | + | TTTT | 406 | TTTTCATTTCATCTTCAGGGTCTTTACGGA | 983 | UUUUCAUUUCAUCUUCAGGGUCUUUACGGA |
| LDHA_exon9 | + | TTTT | 407 | TTTTTCATTTCATCTTCAGGGTCTTTACGG | 984 | UUUUUCAUUUCAUCUUCAGGGUCUUUACGG |
| LDHA_exon9 | + | TTTT | 408 | TTTTTTCATTTCATCTTCAGGGTCTTTACG | 985 | UUUUUUCAUUUCAUCUUCAGGGUCUUUACG |
| LDHA_exon9 | + | TTTT | 409 | TTTTTTTCATTTCATCTTCAGGGTCTTTAC | 986 | UUUUUUUCAUUUCAUCUUCAGGGUCUUUAC |
| LDHA_exon9 | + | TTTT | 410 | TTTTTTTTCATTTCATCTTCAGGGTCTTTA | 987 | UUUUUUUUCAUUUCAUCUUCAGGGUCUUUA |
| LDHA_exon9 | + | ATTT | 411 | TTTTTTTTTCATTTCATCTTCAGGGTCTTT | 988 | UUUUUUUUUCAUUUCAUCUUCAGGGUCUUU |
| LDHA_exon9 | + | CTTT | 412 | ACGGAATAAAGGATGATGTCTTCCTTAGTG | 989 | ACGGAAUAAAGGAUGAUGUCUUCCUUAGUG |
| LDHA_exon9 | - | CTTA | 413 | AGATTGTTTTAATTGTTACCAGCTTCCAG | 990 | AGAUUGUUUUAAUUGUUACCAGCUUCCAG |
| LDHA_exon9 | - | TTTG | 414 | GATCCCCCAAAGTGTATCTGCACTCTTCTT | 991 | GAUCCCCCAAAGUGUAUCUGCACUCUUCUU |
| LDHA_exon9 | - | CTTT | 415 | TGGATCCCCCAAAGTGTATCTGCACTCTTC | 992 | UGGAUCCCCCAAAGUGUAUCUGCACUCUUC |
| LDHA_exon9 | - | TTTA | 416 | TACACTGGATCCCAGGATGTGACTCACTGG | 993 | UACACUGGAUCCCAGGAUGUGACUCACUGG |
| LDHA_exon9 | - | GTTG | 417 | GACTAGGCATGTTCAGTGAAGGAGCCAGGA | 994 | GACUAGGCAUGUUCAGUGAAGGAGCCAGGA |
| LDHA_exon9 | - | GTTC | 418 | AGTGAAGGAGCCAGGAAGTTATATAACACA | 995 | AGUGAAGGAGCCAGGAAGUUAUAUAACACA |
| LDHA_exon9 | - | GTTA | 419 | TATAACACACGGTAAACATCCACCTGGCTC | 996 | UAUAACACACGGUAAACAUCCACCUGGCUC |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | ATTG | 420 | GCAGTGGTGCGTCAGAGGTGGCAGAACTAT | 997 | GCAGUGGUGCGUCAGAGGUGGCAGAACUAU |
| LDHA_exon9 | - | ATTT | 421 | CACACTAACCAGTTGAAGACTACACAAGAT | 998 | CACACUAACCAGUUGAAGACUACACAAGAU |
| LDHA_exon9 | - | TTTC | 422 | ACACTAACCAGTTGAAGACTACACAAGATT | 999 | ACACUAACCAGUUGAAGACUACACAAGAUU |
| LDHA_exon9 | - | GTTG | 423 | AAGACTACACAAGATTAATACCATCCAGCA | 1000 | AAGACUACACAAGAUUAAUACCAUCCAGCA |
| LDHA_exon9 | - | ATTA | 424 | ATACCATCCAGCATCAGGATATAGCTGTGG | 1001 | AUACCAUCCAGCAUCAGGAUAUAGCUGUGG |
| LDHA_exon9 | - | ATTT | 425 | TACAAACCATTCTTATTTCTAACTTCAGGA | 1002 | UACAAACCAUUCUUAUUUCUAACUUCAGGA |
| LDHA_exon9 | - | TTTT | 426 | ACAAACCATTCTTATTTCTAACTTCAGGAG | 1003 | ACAAACCAUUCUUAUUUCUAACUUCAGGAG |
| LDHA_exon9 | - | TTTA | 427 | CAAACCATTCTTATTTCTAACTTCAGGAGT | 1004 | CAAACCAUUCUUAUUUCUAACUUCAGGAGU |
| LDHA_exon9 | - | ATTC | 428 | TTATTTCTAACTTCAGGAGTTGATGTTTTT | 1005 | UUAUUUCUAACUUCAGGAGUUGAUGUUUUU |
| LDHA_exon9 | - | CTTA | 429 | TTTCTAACTTCAGGAGTTGATGTTTTCCC | 1006 | UUUCUAACUUCAGGAGUUGAUGUUUUUCCC |
| LDHA_exon9 | - | TTTT | 430 | GGATCCCCCAAAGTGTATCTGCACTCTTCT | 1007 | GGAUCCCCCAAAGUGUAUCUGCACUCUUCU |
| LDHA_exon9 | - | ATTT | 431 | CTAACTTCAGGAGTTGATGTTTTTCCCAGT | 1008 | CUAACUUCAGGAGUUGAUGUUUUUCCCAGU |
| LDHA_exon9 | - | CTTC | 432 | AGGAGTTGATGTTTTTCCCAGTCCATCTTA | 1009 | AGGAGUUGAUGUUUUUCCCAGUCCAUCUUA |
| LDHA_exon9 | - | GTTG | 433 | ATGTTTTTCCCAGTCCATCTTAAAATATTA | 1010 | AUGUUUUUCCCAGUCCAUCUUAAAAUAUUA |
| LDHA_exon9 | - | GTTT | 434 | TTCCCAGTCCATCTTAAAATATTACTGCTT | 1011 | UUCCCAGUCCAUCUUAAAAUAUUACUGCUU |
| LDHA_exon9 | - | TTTT | 435 | TCCCAGTCCATCTTAAAATATTACTGCTTT | 1012 | UCCCAGUCCAUCUUAAAAUAUUACUGCUUU |
| LDHA_exon9 | - | TTTT | 436 | CCCAGTCCATCTTAAAATATTACTGCTTTA | 1013 | CCCAGUCCAUCUUAAAAUAUUACUGCUUUA |
| LDHA_exon9 | - | TTTC | 437 | CCAGTCCATCTTAAAATATTACTGCTTTAA | 1014 | CCAGUCCAUCUUAAAAUAUUACUGCUUUAA |
| LDHA_exon9 | - | CTTA | 438 | AAATATTACTGCTTTAATCACAGATCAGAT | 1015 | AAAUAUUACUGCUUUAAUCACAGAUCAGAU |
| LDHA_exon9 | - | ATTA | 439 | CTGCTTTAATCACAGATCAGATAAAAGGA | 1016 | CUGCUUUAAUCACAGAUCAGAUAAAAGGA |
| LDHA_exon9 | - | CTTT | 440 | AATCACAGATCAGATAAAAGGACAACATG | 1017 | AAUCACAGAUCAGAUAAAAGGACAACAUG |
| LDHA_exon9 | - | TTTA | 441 | ATCACAGATCAGATAAAAAGGACAACATGC | 1018 | AUCACAGAUCAGAUAAAAGGACAACAUGC |
| LDHA_exon9 | - | GTTG | 442 | TAGCCTAGACAGTGAAATGATATGACATCA | 1019 | UAGCCUAGACAGUGAAAUGAUAUGACAUCA |
| LDHA_exon9 | - | CTTT | 443 | AAAATTGCAGCTCCTTTTGGATCCCCCAAA | 1020 | AAAAUUGCAGCUCCUUUUGGAUCCCCCAAA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | TTTA | 444 | AAATTGCAGCTCCTTTTGGATCCCCCAAAG | 1021 | AAAUUGCAGCUCCUUUUGGAUCCCCCAAAG |
| LDHA_exon9 | - | ATTG | 445 | CAGCTCCTTTTGGATCCCCAAAGTGTATC | 1022 | CAGCUCCUUUUGGAUCCCCAAAGUGUAUC |
| LDHA_exon9 | - | TTTC | 446 | TAACTTCAGGAGTTGATGTTTTTCCCAGTC | 1023 | UAACUUCAGGAGUUGAUGUUUUUCCCAGUC |
| LDHA_exon9 | + | CTTG | 447 | TGAAGGTGACTCTGACTTCTGAGGAAGAGG | 1024 | UGAAGGUGACUCUGACUUCUGAGGAAGAGG |
| LDHA_exon9 | - | ATTA | 448 | TAGGCATGAGCCACTGCACCCTGCCTTAAG | 1025 | UAGGCAUGAGCCACUGCACCCUGCCUUAAG |
| LDHA_exon9 | - | ATTC | 449 | CTGGCCTCCAGTGATCAGCCCACCTGGGCT | 1026 | CUGGCCUCCAGUGAUCAGCCCACCUGGGCU |
| LDHA_exon9 | + | GTTA | 450 | TATAACTTCCTGGCTCCTTCACTGAACATG | 1027 | UAUAACUUCCUGGCUCCUUCACUGAACAUG |
| LDHA_exon9 | + | CTTC | 451 | CTGGCTCCTTCACTGAACATGCCTAGTCCA | 1028 | CUGGCUCCUUCACUGAACAUGCCUAGUCCA |
| LDHA_exon9 | + | CTTC | 452 | ACTGAACATGCCTAGTCCAACATTTTTTCC | 1029 | ACUGAACAUGCCUAGUCCAACAUUUUUUCC |
| LDHA_exon9 | + | ATTT | 453 | TTTCCCAGTGAGTCACATCCTGGGATCCAG | 1030 | UUUCCCAGUGAGUCACAUCCUGGGAUCCAG |
| LDHA_exon9 | + | TTTT | 454 | TTCCCAGTGAGTCACATCCTGGGATCCAGT | 1031 | UUCCCAGUGAGUCACAUCCUGGGAUCCAGU |
| LDHA_exon9 | + | TTTT | 455 | TCCCAGTGAGTCACATCCTGGGATCCAGTG | 1032 | UCCCAGUGAGUCACAUCCUGGGAUCCAGUG |
| LDHA_exon9 | + | TTTT | 456 | CCCAGTGAGTCACATCCTGGGATCCAGTGT | 1033 | CCCAGUGAGUCACAUCCUGGGAUCCAGUGU |
| LDHA_exon9 | + | TTTC | 457 | CCAGTGAGTCACATCCTGGGATCCAGTGTA | 1034 | CCAGUGAGUCACAUCCUGGGAUCCAGUGUA |
| LDHA_exon9 | + | CTTG | 458 | TGCATAATTCTTCCAAAGGATCTTATTTG | 1035 | UGCAUAAUUCUUCCAAAGGAUCUUAUUUG |
| LDHA_exon9 | + | ATTC | 459 | TTCCAAAGGATCTTATTTTGTGAACTATAT | 1036 | UUCCAAAGGAUCUUAUUUUGUGAACUAUAU |
| LDHA_exon9 | + | CTTC | 460 | CAAAGGATCTTATTTTGTGAACTATATCAG | 1037 | CAAAGGAUCUUAUUUUGUGAACUAUAUCAG |
| LDHA_exon9 | + | CTTA | 461 | TTTTGTGAACTATATCAGTAGTGTACATTA | 1038 | UUUUGUGAACUAUAUCAGUAGUGUACAUUA |
| LDHA_exon9 | + | ATTT | 462 | TGTGAACTATATCAGTAGTGTACATTACCA | 1039 | UGUGAACUAUAUCAGUAGUGUACAUUACCA |
| LDHA_exon9 | + | TTTT | 463 | GTGAACTATATCAGTAGTGTACATTACCAT | 1040 | GUGAACUAUAUCAGUAGUGUACAUUACCAU |
| LDHA_exon9 | + | TTTA | 464 | CCGTGTGTTATATAACTTCCTGGCTCCTTC | 1041 | CCGUGUGUUAUAUAACUUCCUGGCUCCUUC |
| LDHA_exon9 | + | TTTG | 465 | TGAACTATATCAGTAGTGTACATTACCATA | 1042 | UGAACUAUAUCAGUAGUGUACAUUACCAUA |
| LDHA_exon9 | + | GTTA | 466 | TACCAACTAAAACCCCCAATAAACCTTGAA | 1043 | UACCAACUAAAACCCCAAUAAACCUUGAA |
| LDHA_exon9 | + | CTTG | 467 | AACAGTGACTACTTTGGTTAATTCATTATA | 1044 | AACAGUGACUACUUUGGUUAAUUCAUUAUA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | + | CTTT | 468 | GGTTAATTCATTATATTAAGATATAAAGTC | 1045 | GGUUAAUUCAUUAUAUUAAGAUAUAAAGUC |
| LDHA_exon9 | + | TTTG | 469 | GTTAATTCATTATATTAAGATATAAAGTCA | 1046 | GUUAAUUCAUUAUAUUAAGAUAUAAAGUCA |
| LDHA_exon9 | + | GTTA | 470 | ATTCATTATATTAAGATATAAAGTCATAAA | 1047 | AUUCAUUAUAUUAAGAUAUAAAGUCAUAAA |
| LDHA_exon9 | + | ATTC | 471 | ATTATATTAAGATATAAAGTCATAAAGCTG | 1048 | AUUAUAUUAAGAUAUAAAGUCAUAAAGCUG |
| LDHA_exon9 | + | ATTA | 472 | TATTAAGATATAAAGTCATAAAGCTGCTAG | 1049 | UAUUAAGAUAUAAAGUCAUAAAGCUGCUAG |
| LDHA_exon9 | + | ATTA | 473 | AGATATAAAGTCATAAAGCTGCTAGTTATT | 1050 | AGAUAUAAAGUCAUAAAGCUGCUAGUUAUU |
| LDHA_exon9 | + | GTTA | 474 | TTATATTAATTTGGAAATATTAGGCTATTC | 1051 | UUAUAUUAAUUUGGAAAUAUUAGGCUAUUC |
| LDHA_exon9 | + | ATTA | 475 | TATTAATTTGGAAATATTAGGCTATTCTTG | 1052 | UAUUAAUUUGGAAAUAUUAGGCUAUUCUUG |
| LDHA_exon9 | + | ATTA | 476 | ATTTGGAAATATTAGGCTATTCTTGGGCAA | 1053 | AUUUGGAAAUAUUAGGCUAUUCUUGGGCAA |
| LDHA_exon9 | + | ATTT | 477 | GGAAATATTAGGCTATTCTTGGGCAACCCT | 1054 | GGAAAUAUUAGGCUAUUCUUGGGCAACCCU |
| LDHA_exon9 | + | TTTG | 478 | GAAATATTAGGCTATTCTTGGGCAACCCTG | 1055 | GAAAUAUUAGGCUAUUCUUGGGCAACCCUG |
| LDHA_exon9 | + | ATTA | 479 | GGCTATTCTTGGGCAACCCTGCAACGATTT | 1056 | GGCUAUUCUUGGGCAACCCUGCAACGAUUU |
| LDHA_exon9 | + | ATTA | 480 | CCATATAATGTAAAAAGATCTACATACAAA | 1057 | CCAUAUAAUGUAAAAAGAUCUACAUACAAA |
| LDHA_exon9 | + | ATTC | 481 | TTGGGCAACCCTGCAACGATTTTTTCTAAC | 1058 | UUGGGCAACCCUGCAACGAUUUUUUCUAAC |
| LDHA_exon9 | + | GTTT | 482 | ACCGTGTGTTATATAACTTCCTGGCTCCTT | 1059 | ACCGUGUGUUAUAUAACUUCCUGGCUCCUU |
| LDHA_exon9 | + | TTTG | 483 | CCCCTTGAGCCAGGTGGATGTTTACCGTGT | 1060 | CCCCUUGAGCCAGGUGGAUGUUUACCGUGU |
| LDHA_exon9 | + | GTTT | 484 | GAAGAAGAGTGCAGATACACTTTGGGGAT | 1061 | GAAGAAGAGUGCAGAUACACUUUGGGGAU |
| LDHA_exon9 | + | TTTG | 485 | AAGAAGAGTGCAGATACACTTTGGGGATC | 1062 | AAGAAGAGUGCAGAUACACUUUGGGGAUC |
| LDHA_exon9 | + | GTTT | 486 | GGGGGATCCAAAAGGAGCTGCAATTTTAAA | 1063 | GGGGGAUCCAAAAGGAGCUGCAAUUUUAAA |
| LDHA_exon9 | + | TTTG | 487 | GGGGATCCAAAAGGAGCTGCAATTTTAAAG | 1064 | GGGGAUCCAAAAGGAGCUGCAAUUUUAAAG |
| LDHA_exon9 | + | ATTT | 488 | TAAAGTCTTCTGATGTCATATCATTTCACT | 1065 | UAAAGCUUCUGAUGUCAUAUCAUUUCACU |
| LDHA_exon9 | + | TTTT | 489 | AAAGTCTTCTGATGTCATATCATTTCAGTG | 1066 | AAAGUCUUCUGAUGUCAUAUCAUUUCACUG |
| LDHA_exon9 | + | TTTA | 490 | AAGTCTTCTGATGTCATATCATTTCACTGT | 1067 | AAGUCUUCUGAUGUCAUAUCAUUUCACUGU |
| LDHA_exon9 | + | CTTC | 491 | TGATGTCATATCATTTCACTGTCTAGGCTA | 1068 | UGAUGUCAUAUCAUUUCACUGUCUAGGCUA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | + | ATTT | 492 | CACTGTCTAGGCTACAACAGGATTCTAGGT | 1069 | CACUGUCUAGGCUACAACAGGAUUCUAGGU |
| LDHA_exon9 | + | TTTG | 493 | ACTGTCTAGGCTACAACAGGATTCTAGGTG | 1070 | ACUGUCUAGGCUACAACAGGAUUCUAGGUG |
| LDHA_exon9 | + | ATTC | 494 | TAGGTGGAGGTTGTGCATGTTGTCCTTTTT | 1071 | UAGGUGGAGGUUGUGCAUGUUGUCCUUUUU |
| LDHA_exon9 | + | GTTG | 495 | TGCATGTTGTCCTTTTTATCTGATCTGTGA | 1072 | UGCAUGUUGUCCUUUUUAUCUGAUCUGUGA |
| LDHA_exon9 | + | GTTG | 496 | TCCTTTTTATCTGATCTGTGATTAAAGCAG | 1073 | UCCUUUUUAUCUGAUCUGUGAUUAAAGCAG |
| LDHA_exon9 | + | GTTT | 497 | TTATCTGATCTGTGATTAAAGCAGTAATAT | 1074 | UUAUCUGAUCUGUGAUUAAAGCAGUAAUAU |
| LDHA_exon9 | + | GTTG | 498 | AGCCAGGTGGATGTTTACCGTGTGTTATAT | 1075 | AGCCAGGUGGAUGUUUACCGUGUGUUAUAU |
| LDHA_exon9 | + | TTTT | 499 | TATCTGATCTGTGATTAAAGCAGTAATATT | 1076 | UAUCUGAUCUGUGAUUAAAGCAGUAAUAUU |
| LDHA_exon9 | + | TTTA | 500 | TCTGATCTGTGATTAAAGCAGTAATATTTT | 1077 | UCUGAUCUGUGAUUAAAGCAGUAAUAUUUU |
| LDHA_exon9 | + | ATTA | 501 | AAGCAGTAATATTTTAAGATGGACTGGGAA | 1078 | AAGCAGUAAUAUUUUAAGAUGGACUGGGAA |
| LDHA_exon9 | + | ATTT | 502 | TAAGATGGACTGGGAAAAACATCAACTCCT | 1079 | UAAGAUGGACUGGGAAAAACAUCAACUCCU |
| LDHA_exon9 | + | TTTT | 503 | AAGATGGACTGGGAAAAACATCAACTCCTG | 1080 | AAGAUGGACUGGGAAAAACAUCAACUCCUG |
| LDHA_exon9 | + | TTTA | 504 | AGATGGACTGGGAAAAACATCAACTCCTGA | 1081 | AGAUGGACUGGGAAAAACAUCAACUCCUGA |
| LDHA_exon9 | + | GTTA | 505 | GAAATAAGAATGGTTTGTAAAATCCACAGC | 1082 | GAAAUAAGAAUGGUUUGUAAAAUCCACAGC |
| LDHA_exon9 | + | GTTT | 506 | GTAAAATCCACAGCTATATCCTGATGCTGG | 1083 | GUAAAAUCCACAGCUAUAUCCUGAUGCUGG |
| LDHA_exon9 | + | TTTG | 507 | TAAAATCCACAGCTATATCCTGATGCTGGA | 1084 | UAAAAUCCACAGCUAUAUCCUGAUGCUGGA |
| LDHA_exon9 | + | ATTA | 508 | ATCTTGTGTAGTCTTCAACTGGTTAGTGTG | 1085 | AUCUUGUGUAGUCUUCAACUGGUUAGUGUG |
| LDHA_exon9 | + | CTTG | 509 | TGTAGTCTTCAACTGGTTAGTGTGAAATAG | 1086 | UGUAGUCUUCAACUGGUUAGUGUGAAAUAG |
| LDHA_exon9 | + | CTTC | 510 | AACTGGTTAGTGTGAAATAGTTCTGCCACC | 1087 | AACUGGUUAGUGUGAAAUAGUUCUGCCACC |
| LDHA_exon9 | + | GTTA | 511 | GTGTGAAATAGTTCTGCCACCTCTGACGCA | 1088 | GUGUGAAAUAGUUCUGCCACCUCUGACGCA |
| LDHA_exon9 | + | GTTC | 512 | TGCCACCTCTGACGCACCCACTGCCAATGCT | 1089 | UGCCACCUCUGACGCACCACUGCCAAUGCU |
| LDHA_exon9 | + | ATTT | 513 | GCCCCTTGAGCCAGGTGGATGTTACCGTG | 1090 | GCCCCUUGAGCCAGGUGGAUGUUUACCGUG |
| LDHA_exon9 | + | TTTT | 514 | ATCTGATCTGTGATTAAAGCAGTAATATTT | 1091 | AUCUGAUCUGUGAUUAAAGCAGUAAUAUUU |
| LDHA_exon9 | − | CTTC | 515 | CCAAAGTGCTGGGATTATAGGCATGAGCCA | 1092 | CCAAAGUGCUGGGAUUAUAGGCAUGAGCCA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | + | CTTG | 516 | GGCAACCCTGCAACGATTTTTTCTAACAGG | 1093 | GGCAACCCUGCAACGAUUUUUUCUAACAGG |
| LDHA_exon9 | + | TTTT | 517 | TTCTAACAGGGATATTATTGACTAATAGCA | 1094 | UUCUAACAGGGAUAUUAUUGACUAAUAGCA |
| LDHA_exon9 | - | ATTT | 518 | TCAGAAAAATGTGCAGAAAACTTGAGTAGA | 1095 | UCAGAAAAAUGUGCAGAAAACUUGAGUAGA |
| LDHA_exon9 | - | TTTT | 519 | CAGAAAAATGTGCAGAAAACTTGAGTAGAC | 1096 | CAGAAAAAUGUGCAGAAAACUUGAGUAGAC |
| LDHA_exon9 | - | TTTC | 520 | AGAAAAATGTGCAGAAAACTTGAGTAGACA | 1097 | AGAAAAAUGUGCAGAAAACUUGAGUAGACA |
| LDHA_exon9 | - | CTTG | 521 | AGTAGACATCCACCAAGGTTACTTGTTTTT | 1098 | AGUAGACAUCCACCAAGGUUACUUGUUUUU |
| LDHA_exon9 | - | GTTA | 522 | CTTGTTTTTTTGGTTTTGTTTTGTTTTT | 1099 | CUUGUUUUUUUGGUUUUGUUUUGUUUUU |
| LDHA_exon9 | - | CTTG | 523 | TTTTTTTGGTTTTGTTTTGTTTTTTAAC | 1100 | UUUUUUUGGUUUUGUUUUGUUUUUUAAC |
| LDHA_exon9 | - | GTTT | 524 | TTTTTGGTTTTGTTTTGTTTTTTAACAGA | 1101 | UUUUUGGUUUUGUUUUGUUUUUUAACAGA |
| LDHA_exon9 | - | TTTT | 525 | TTTTGGTTTTGTTTTGTTTTTTAACAGAT | 1102 | UUUUGGUUUUGUUUUGUUUUUUAACAGAU |
| LDHA_exon9 | - | TTTT | 526 | TTTGGTTTTGTTTTGTTTTTTAACAGATG | 1103 | UUUGGUUUUGUUUUGUUUUUUAACAGAUG |
| LDHA_exon9 | - | TTTT | 527 | TTGGTTTTGTTTTGTTTTTTAACAGATGG | 1104 | UUGGUUUUGUUUUGUUUUUUAACAGAUGG |
| LDHA_exon9 | - | TTTT | 528 | TGGTTTTGTTTTGTTTTTTAACAGATGGG | 1105 | UGGUUUUGUUUUGUUUUUUAACAGAUGGG |
| LDHA_exon9 | - | TTTT | 529 | GGTTTTGTTTTGTTTTTTAACAGATGGGG | 1106 | GGUUUUGUUUUGUUUUUUAACAGAUGGGG |
| LDHA_exon9 | - | TTTG | 530 | GTTTTGTTTTGTTTTTTAACAGATGGGGT | 1107 | GUUUUGUUUUGUUUUUUAACAGAUGGGGU |
| LDHA_exon9 | - | GTTT | 531 | TGTTTTGTTTTTTAACAGATGGGGTTTTG | 1108 | UGUUUUGUUUUUUAACAGAUGGGGUUUUG |
| LDHA_exon9 | - | GTTG | 532 | TATTTTCAGAAAAATGTGCAGAAAACTTGA | 1109 | UAUUUUCAGAAAAAUGUGCAGAAAACUUGA |
| LDHA_exon9 | - | TTTT | 533 | GTTTTGTTTTTTAACAGATGGGGTTTTGT | 1110 | GUUUUGUUUUUUAACAGAUGGGGUUUUGU |
| LDHA_exon9 | - | GTTT | 534 | TGTTTTTTTAACAGATGGGGTTTTGTTGTG | 1111 | UGUUUUUUUAACAGAUGGGGUUUUGUUGUG |
| LDHA_exon9 | - | TTTT | 535 | GTTTTTTAACAGATGGGGTTTTGTTGTGT | 1112 | GUUUUUUAACAGAUGGGGUUUUGUUGUGU |
| LDHA_exon9 | - | TTTG | 536 | TTTTTTAACAGATGGGGTTTTGTTGTGTT | 1113 | UUUUUUAACAGAUGGGGUUUUGUUGUGUU |
| LDHA_exon9 | - | GTTT | 537 | TTTTAACAGATGGGGTTTTGTTGTGTTGGC | 1114 | UUUUAACAGAUGGGGUUUUGUUGUGUUGGC |
| LDHA_exon9 | - | TTTT | 538 | TTTAACAGATGGGGTTTTGTTGTGTTGGCC | 1115 | UUUAACAGAUGGGGUUUUGUUGUGUUGGCC |
| LDHA_exon9 | - | TTTT | 539 | TTAACAGATGGGGTTTTGTTGTGTTGGCCA | 1116 | UUAACAGAUGGGGUUUUGUUGUGUUGGCCA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | - | TTTT | 540 | TAACAGATGGGGTTTTGTTGTGTTGGCCAG | 1117 | UAACAGAUGGGGUUUUGUUGUGUUGGCCAG |
| LDHA_exon9 | - | TTTT | 541 | AACAGATGGGGTTTTGTTGTGTTGGCCAGG | 1118 | AACAGAUGGGGUUUUGUUGUGUUGGCCAGG |
| LDHA_exon9 | - | TTTA | 542 | ACAGATGGGGTTTTGTTGTGTTGGCCAGGC | 1119 | ACAGAUGGGGUUUUGUUGUGUUGGCCAGGC |
| LDHA_exon9 | - | GTTT | 543 | TGTTGTGTTGGCCAGGCTGGTCCCCAATTC | 1120 | UGUUGUGUUGGCCAGGCUGGUCCCCAAUUC |
| LDHA_exon9 | - | TTTT | 544 | GTTGTGTTGGCCAGGCTGGTCCCCAATTCC | 1121 | GUUGUGUUGGCCAGGCUGGUCCCCAAUUCC |
| LDHA_exon9 | - | TTTG | 545 | TTGTGTTGGCCAGGCTGGTCCCCAATTCCT | 1122 | UUGUGUUGGCCAGGCUGGUCCCCAAUUCCU |
| LDHA_exon9 | - | GTTG | 546 | TGTTGGCCAGGCTGGTCCCCAATTCCTGGC | 1123 | UGUUGGCCAGGCUGGUCCCCAAUUCCUGGC |
| LDHA_exon9 | - | GTTG | 547 | GCCAGGCTGGTCCCCAATTCCTGGCCTCCA | 1124 | GCCAGGCUGGUCCCCAAUUCCUGGCCUCCA |
| LDHA_exon9 | - | TTTG | 548 | TTTTGTTTTTTAACAGATGGGGTTTTGTT | 1125 | UUUUGUUUUUUAACAGAUGGGGUUUUGUU |
| LDHA_exon9 | + | ATTT | 549 | TTTCTAACAGGGATATTATTGACTAATAGC | 1126 | UUUCUAACAGGGAUAUUAUUGACUAAUAGC |
| LDHA_exon9 | + | TTTG | 550 | TGCACATTTTTCTGAAAATACAACTGTGAC | 1127 | UGCACAUUUUUCUGAAAAUACAACUGUGAC |
| LDHA_exon9 | + | GTTT | 551 | TCTGCACATTTTTCTGAAAATACAACTGTG | 1128 | UCUGCACAUUUUUCUGAAAAUACAACUGUG |
| LDHA_exon9 | + | TTTT | 552 | TCTAACAGGGATATTATTGACTAATAGCAG | 1129 | UCUAACAGGGAUAUUAUUGACUAAUAGCAG |
| LDHA_exon9 | + | TTTT | 553 | CTAACAGGGATATTATTGACTAATAGCAGA | 1130 | CUAACAGGGAUAUUAUUGACUAAUAGCAGA |
| LDHA_exon9 | + | TTTG | 554 | TAACAGGGATATTATTGACTAATAGCAGAG | 1131 | UAACAGGGAUAUUAUUGACUAAUAGCAGAG |
| LDHA_exon9 | + | ATTA | 555 | TTGACTAATAGCAGAGGATGTAATAGTCAA | 1132 | UUGACUAAUAGCAGAGGAUGUAAUAGUCAA |
| LDHA_exon9 | + | ATTG | 556 | ACTAATAGCAGAGGATGTAATAGTCAACTG | 1133 | ACUAAUAGCAGAGGAUGUAAUAGUCAACUG |
| LDHA_exon9 | + | GTTG | 557 | TATTGGTACCACTTCCATTGTAAGTCCCAA | 1134 | UAUUGGUACCACUUCCAUUGUAAGUCCCAA |
| LDHA_exon9 | + | ATTG | 558 | GTACCACTTCCATTGTAAGTCCCAAAGTAT | 1135 | GUACCACUUCCAUUGUAAGUCCCAAAGUAU |
| LDHA_exon9 | + | CTTC | 559 | CATTGTAAGTCCCAAAGTATTATATATTTG | 1136 | CAUUGUAAGUCCCAAAGUAUUAUAUAUUUG |
| LDHA_exon9 | + | ATTG | 560 | TAAGTCCCAAAGTATTATATATTTGATAAT | 1137 | UAAGUCCCAAAGUAUUAUAUAUUUGAUAAU |
| LDHA_exon9 | + | ATTA | 561 | TATATTTGATAATAATGCTAATCATAATTG | 1138 | UAUAUUUGAUAAUAAUGCUAAUCAUAAUUG |
| LDHA_exon9 | + | ATTT | 562 | GATAATAATGCTAATCATAATTGGAAAGTA | 1139 | GAUAAUAAUGCUAAUCAUAAUUGGAAAGUA |
| LDHA_exon9 | + | TTTG | 563 | ATAATAATGCTAATCATAATTGGAAAGTAA | 1140 | AUAAUAAUGCUAAUCAUAAUUGGAAAGUAA |

TABLE 5-continued

Target and Spacer Sequences

| LDHA | Strand | PAM* | SEQ ID NO | Target Sequence | SEQ ID NO | Spacer Sequence |
|---|---|---|---|---|---|---|
| LDHA_exon9 | + | ATTG | 564 | GAAAGTAACATTCTAT ATGTAAATGTAAAA | 1141 | GAAAGUAACAUUCUAUA UGUAAAUGUAAAA |
| LDHA_exon9 | + | ATTG | 565 | TATATGTAAATGTAAA ATTTATTTGCCAAC | 1142 | UAUAUGUAAAUGUAAA UUUAUUUGCCAAC |
| LDHA_exon9 | + | TTTT | 566 | CTGCACATTTTTCTGA AAATACAACTGTGA | 1143 | CUGCACAUUUUUCUGAA AAUACAACUGUGA |
| LDHA_exon9 | + | ATTT | 567 | ATTTGCCAACTGAATA TAGGCAATGATAGT | 1144 | AUUUGCCAACUGAAUAU AGGCAAUGAUAGU |
| LDHA_exon9 | + | ATTT | 568 | GCCAACTGAATATAGG CAATGATAGTGTGT | 1145 | GCCAACUGAAUAUAGGC AAUGAUAGUGUGU |
| LDHA_exon9 | + | TTTG | 569 | CCAACTGAATATAGGC AATGATAGTGTGTC | 1146 | CCAACUGAAUAUAGGCA AUGAUAGUGUGUC |
| LDHA_exon9 | + | ATTT | 570 | TTGAGATCTTGTCCTC TGGAAGCTGGTAAC | 1147 | UUGAGAUCUUGUCCUCU GGAAGCUGGUAAC |
| LDHA_exon9 | + | TTTT | 571 | TGAGATCTTGTCCTCT GGAAGCTGGTAACA | 1148 | UGAGAUCUUGUCCUCUG GAAGCUGGUAACA |
| LDHA_exon9 | + | TTTT | 572 | GAGATCTTGTCCTCTG GAAGCTGGTAACAA | 1149 | GAGAUCUUGUCCUCUGG AAGCUGGUAACAA |
| LDHA_exon9 | + | TTTG | 573 | AGATCTTGTCCTCTGG AAGCTGGTAACAAT | 1150 | AGAUCUUGUCCUCUGGA AGCUGGUAACAAU |
| LDHA_exon9 | + | GTTG | 574 | TCCTCTGGAAGCTGGT AACAATTAAAAACA | 1151 | UCCUCUGGAAGCUGGUA ACAAUUAAAAACA |
| LDHA_exon9 | + | ATTA | 575 | AAAACAATCTTAAGGC AGGGTGCAGTGGCT | 1152 | AAAACAAUCUUAAGGCA GGGUGCAGUGGCU |
| LDHA_exon9 | + | CTTA | 576 | AGGCAGGGTGCAGTGG CTCATGCCTATAAT | 1153 | AGGCAGGGUGCAGUGGC UCAUGCCUAUAAU |
| LDHA_exon9 | + | CTTT | 577 | GGGAAGCCCAGGTGGG CTGATCACTGGAGG | 1154 | GGGAAGCCCAGGUGGGC UGAUCACUGGAGG |
| LDHA_exon9 | + | TTTG | 578 | GGAAGCCCAGGTGGGC TGATCACTGGAGGC | 1155 | GGAAGCCCAGGUGGGCU GAUCACUGGAGGC |
| LDHA_exon9 | + | ATTG | 579 | GGGACCAGCCTGGCCA ACACAACAAAACCC | 1156 | GGGACCAGCCUGGCCAA CACAACAAAACCC |
| LDHA_exon9 | + | GTTA | 580 | AAAAACAAAACAAAA CCAAAAAAACAAG | 1157 | AAAAAACAAAACAAAC CAAAAAAACAAG |
| LDHA_exon9 | + | GTTG | 581 | GTGGATGTCTACTCAA GTTTTCTGCACATT | 1158 | GUGGAUGUCUACUCAAG UUUUCUGCACAUU |
| LDHA_exon9 | + | TTTA | 582 | TTTGCCAACTGAATAT AGGCAATGATAGTG | 1159 | UUUGCCAACUGAAUAUA GGCAAUGAUAGUG |
| LDHA_exon9 | + | CTTA | 583 | GTGTTCCTTGCATTTT GGGACAGAATGGAA | 1160 | GUGUUCCUUGCAUUUUG GGACAGAAUGGAA |
| LDHA_exon9 | + | ATTT | 584 | TTCTGAAAATACAACT GTGACCCTTA | 1161 | UUCUGAAAAUACAACUG UGACCCUUA |
| LDHA_exon9 | + | TTTT | 585 | TCTGAAAATACAACTG TGACCCTTA | 1162 | UCUGAAAAUACAACUGU GACCCUUA |
| LDHA_exon9 | + | TTTT | 586 | CTGAAAATACAACTGT GACCCTTA | 1163 | CUGAAAAUACAACUGUG ACCCUUA |
| LDHA_exon9 | + | TTTC | 587 | TGAAAATACAACTGTG ACCCTTA | 1164 | UGAAAAUACAACUGUGA CCCUUA |

*The 3' three nucleotides represent the 5'-TTN-3' motif.

The present disclosure includes all combinations of the direct repeats and spacers listed above, consistent with the disclosure herein.

In some embodiments, a spacer sequence described herein comprises a uracil (U). In some embodiments, a spacer sequence described herein comprises a thymine (T). In some embodiments, a spacer sequence according to Table 5 comprises a sequence comprising a thymine in one or more places indicated as uracil in Table 5.

(iii). Exemplary RNA Guides

The present disclosure includes RNA guides that comprise any and all combinations of the direct repeats and spacers described herein (e.g., as set forth in Table 5, above). In some embodiments, the sequence of an RNA guide has at least 90% identity (e.g., at least 90%, 91%, 92%, 93%, 94%, 95%, 96%, 97%, 98%, or 99% identity) to a sequence of any one of SEQ ID NOs: 1213-1229. In some embodiments, an RNA guide has a sequence of any one of SEQ ID NOs: 1213-1229.

In some embodiments, exemplary RNA guides provided herein may comprise a spacer sequence of any one of SEQ ID NOs: 1269-1273. In one example, the RNA guide may comprise a spacer of SEQ ID NO: 1272. In another example, the RNA guide may comprise a spacer of SEQ ID NO: 1269. In still another example, the RNA guide may comprise a spacer of SEQ ID NO: 1270. In still another example, the RNA guide may comprise a spacer of SEQ ID NO: 1271. In yet another example, the RNA guide may comprise a spacer of SEQ ID NO: 1273.

Any of the exemplary RNA guides disclosed herein may comprise a direct sequence of any one of SEQ ID NOs:1-10 or a fragment thereof that is at least 23-nucleotide in length. In one example, the direct sequence may comprise SEQ ID NO: 10.

In specific examples, the RNA guides provide herein may comprise the nucleotide sequence of SEQ ID NOs: 1214, 1235, 1221, 1224 or 1225. In one example, the RNA guide provided herein comprise the nucleotide sequence of SEQ ID NO: 1224. In another example, the RNA guide provided herein comprise the nucleotide sequence of SEQ ID NO: 1214. In still another example, the RNA guide provided herein comprise the nucleotide sequence of SEQ ID NO: 1235. In still another example, the RNA guide provided herein comprise the nucleotide sequence of SEQ ID NO: 1221. In yet another example, the RNA guide provided herein comprise the nucleotide sequence of SEQ ID NO: 1225.

(iv). Modifications

The RNA guide may include one or more covalent modifications with respect to a reference sequence, in particular the parent polyribonucleotide, which are included within the scope of this invention.

Exemplary modifications can include any modification to the sugar, the nucleobase, the internucleoside linkage (e.g., to a linking phosphate/to a phosphodiester linkage/to the phosphodiester backbone), and any combination thereof. Some of the exemplary modifications provided herein are described in detail below.

The RNA guide may include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to RNA guide-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e., any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present disclosure, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotides (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

In some embodiments, one or more of the nucleotides of an RNA guide comprises a 2'-O-methyl phosphorothioate modification. In some embodiments, each of the first three nucleotides of the RNA guide comprises a 2'-O-methyl phosphorothioate modification. In some embodiments, each of the last four nucleotides of the RNA guide comprises a 2'-O-methyl phosphorothioate modification. In some embodiments, each of the first to last, second to last, and third to last nucleotides of the RNA guide comprises a 2'-O-methyl phosphorothioate modification, and wherein the last nucleotide of the RNA guide is unmodified. In some embodiments, each of the first three nucleotides of the RNA guide comprises a 2'-O-methyl phosphorothioate modification, and each of the first to last, second to last, and third to last nucleotides of the RNA guide comprises a 2'-O-methyl phosphorothioate modification.

When a gene editing system disclosed herein comprises nucleic acids encoding the Cas12i polypeptide disclosed herein, e.g., mRNA molecules, such nucleic acid molecules may contain any of the modifications disclosed herein, where applicable.

B. Cas12i Polypeptide

In some embodiments, the composition or system of the present disclosure includes a Cas12i polypeptide as described in WO/2019/178427, the relevant disclosures of which are incorporated by reference for the subject matter and purpose referenced herein.

In some embodiments, the composition of the present disclosure includes a Cas12i2 polypeptide described herein (e.g., a polypeptide comprising SEQ ID NO: 1166 and/or encoded by SEQ ID NO: 1165). In some embodiments, the Cas12i2 polypeptide comprises at least one RuvC domain.

A nucleic acid sequence encoding the Cas12i2 polypeptide described herein may be substantially identical to a reference nucleic acid sequence, e.g., SEQ ID NO: 1165. In some embodiments, the Cas12i2 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 1165. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency). See, e.g., Tijssen, "Hybridization with Nucleic Acid Probes. Part I. Theory and Nucleic Acid Preparation" (Laboratory Techniques in Biochemistry and Molecular Biology, Vol 24).

In some embodiments, the Cas12i2 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 1165.

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1166.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1166. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 1166 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the Cas12i2 polypeptide comprises a polypeptide having a sequence of SEQ ID NO: 1167, SEQ ID NO: 1168, SEQ ID NO: 1169, SEQ ID NO: 1170, or SEQ ID NO: 1171. In specific examples, the Cas12i2 polypeptide comprises a polypeptide having a sequence of SEQ ID NO: 1168 or SEQ ID NO: 1171.

In some examples, the Cas12i2 polypeptide may contain one or more mutations relative to SEQ ID NO: 1166, for example, at position D581, G624, F626, P868, I926, V1030, E1035, S1046, or any combination thereof. In some instances, the one or more mutations are amino acid substitutions, for example, D581R, G624R, F626R, P868T, I926R, V1030G, E1035R, S1046G, or a combination thereof.

In some examples, the Cas12i2 polypeptide contains mutations at positions D581, D911, I926, and V1030. Such a Cas12i2 polypeptide may contain amino acid substitutions of D581R, D911R, I926R, and V1030G (e.g., SEQ ID NO: 1167). In some examples, the Cas12i2 polypeptide contains mutations at positions D581, I926, and V1030. Such a Cas12i2 polypeptide may contain amino acid substitutions of D581R, I926R, and V1030G (e.g., SEQ ID NO: 1168). In some examples, the Cas12i2 polypeptide may contain mutations at positions D581, I926, V1030, and S1046. Such a Cas12i2 polypeptide may contain amino acid substitutions of D581R, I926R, V1030G, and S1046G (e.g., SEQ ID NO: 1169). In some examples, the Cas12i2 polypeptide may contain mutations at positions D581, G624, F626, I926, V1030, E1035, and S1046. Such a Cas12i2 polypeptide may contain amino acid substitutions of D581R, G624R, F626R, I926R, V1030G, E1035R, and S1046G (e.g., SEQ ID NO: 1170). In some examples, the Cas12i2 polypeptide may contain mutations at positions D581, G624, F626, P868, I926, V1030, E1035, and S1046. Such a Cas12i2 polypeptide may contain amino acid substitutions of D581R, G624R, F626R, P868T, I926R, V1030G, E1035R, and S1046G (e.g., SEQ ID NO: 1171).

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1167, SEQ ID NO: 1168, SEQ ID NO: 1169, SEQ ID NO: 1170, or SEQ ID NO: 1171. In some embodiments, a Cas12i2 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 1167, SEQ ID NO: 1168, SEQ ID NO: 1169, SEQ ID NO: 1170, or SEQ ID NO: 1171 maintains the amino acid changes (or at least 1, 2, 3 etc. of these changes) that differentiate the polypeptide from its respective parent/reference sequence.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1167, SEQ ID NO: 1168, SEQ ID NO: 1169, SEQ ID NO: 1170, or SEQ ID NO: 1171. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 1167, SEQ ID NO: 1168, SEQ ID NO: 1169, SEQ ID NO: 1170, or SEQ ID NO: 1171 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i4 polypeptide described herein (e.g., a polypeptide comprising SEQ ID NO: 1202 and/or encoded by SEQ ID NO: 1201). In some embodiments, the Cas12i4 polypeptide comprises at least one RuvC domain.

A nucleic acid sequence encoding the Cas12i4 polypeptide described herein may be substantially identical to a reference nucleic acid sequence, e.g., SEQ ID NO: 1201. In some embodiments, the Cas12i4 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 1201. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency).

In some embodiments, the Cas12i4 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 1201.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1202.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1202. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 1202 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the Cas12i4 polypeptide comprises a polypeptide having a sequence of SEQ ID NO: 1203 or SEQ ID NO: 1204.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1203 or SEQ ID NO: 1204. In some embodiments, a Cas12i4 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 1203 or SEQ ID NO: 1204 maintains the amino acid changes (or at least 1, 2, 3 etc. of these changes) that differentiate it from its respective parent/reference sequence.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1203 or SEQ ID NO: 1204. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 1203 or SEQ ID NO: 1204 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i1 polypeptide described herein (e.g., a polypeptide comprising SEQ ID NO: 1211). In some embodiments, the Cas12i4 polypeptide comprises at least one RuvC domain.

In some embodiments, the Cas12i1 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1211.

In some embodiments, the present disclosure describes a Cas12i1 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1211. Homology or identity can be determined by amino acid sequence alignment, e.g., using a program such as BLAST, ALIGN, or CLUSTAL, as described herein.

Also provided is a Cas12i1 polypeptide of the present disclosure having enzymatic activity, e.g., nuclease or endonuclease activity, and comprising an amino acid sequence which differs from the amino acid sequences of SEQ ID NO: 1211 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i3 polypeptide described herein (e.g., a polypeptide comprising SEQ ID NO: 1212). In some embodiments, the Cas12i4 polypeptide comprises at least one RuvC domain.

In some embodiments, the Cas12i3 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 1212.

In some embodiments, the present disclosure describes a Cas12i3 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 1212. Homology or identity can be determined by amino acid sequence alignment, e.g., using a program such as BLAST, ALIGN, or CLUSTAL, as described herein.

Also provided is a Cas12i3 polypeptide of the present disclosure having enzymatic activity, e.g., nuclease or endonuclease activity, and comprising an amino acid sequence which differs from the amino acid sequences of SEQ ID NO: 1212 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

Although the changes described herein may be one or more amino acid changes, changes to the Cas12i polypeptide may also be of a substantive nature, such as fusion of polypeptides as amino- and/or carboxyl-terminal extensions. For example, the Cas12i polypeptide may contain additional peptides, e.g., one or more peptides. Examples of additional peptides may include epitope peptides for labelling, such as a polyhistidine tag (His-tag), Myc, and FLAG. In some embodiments, the Cas12i polypeptide described herein can be fused to a detectable moiety such as a fluorescent protein (e.g., green fluorescent protein (GFP) or yellow fluorescent protein (YFP)).

In some embodiments, the Cas12i polypeptide comprises at least one (e.g., two, three, four, five, six, or more) nuclear localization signal (NLS). In some embodiments, the Cas12i polypeptide comprises at least one (e.g., two, three, four, five, six, or more) nuclear export signal (NES). In some embodiments, the Cas12i polypeptide comprises at least one (e.g., two, three, four, five, six, or more) NLS and at least one (e.g., two, three, four, five, six, or more) NES.

In some embodiments, the Cas12i polypeptide described herein can be self-inactivating. See, Epstein et al., "Engineering a Self-Inactivating CRISPR System for AAV Vectors," Mol. Ther., 24 (2016): S50, which is incorporated by reference in its entirety.

In some embodiments, the nucleotide sequence encoding the Cas12i polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/ and these tables can be adapted in a number of ways. See Nakamura et al. Nucl. Acids Res. 28:292 (2000), which is incorporated herein by reference in its entirety. Computer algorithms for codon optimizing a particular sequence for expression in a particular host cell are also available, such as Gene Forge (Aptagen; Jacobus, PA). In some examples, the nucleic acid encoding the Cas12i polypeptides such as Cas12i2 polypeptides as disclosed herein can be an mRNA molecule, which can be codon optimized.

Exemplary Cas12i polypeptide sequences and corresponding nucleotide sequences are listed in Table 6.

TABLE 6

Cas12i and LDHA Sequences

| SEQ ID NO | Sequence | Description |
|---|---|---|
| 1165 | ATGAGCAGCGCGATCAAAAGCTACAAGAGCGTTCTGCGTCCGAACGAGCGTAAGAA CCAACTGCTGAAAAGCACCATTCAGTGCCTGGAAGACGGTAGCGCGTTCTTTTTCA AGATGCTGCAAGGCCTGTTTGGTGGCATCACCCCGGAGATTGTTCGTTTCAGCACC GAACAGGAGAAACAGCAACAGGATATCGCGCTGTGGTGCGCGGTTAACTGGTTCCG TCCGGTGAGCCAAGACAGCCTGACCCACACCATTGCGAGCGATAACCTGGTGGAGA AGTTTGAGGAATACTATGGTGGCACCGCGAGCGACGCGATCAAACAGTACTTCAGC GCGAGCATTGGCGAAAGCTACTATTGGAACGACTGCCGTCAACAGTACTATGATCT GTGCCGTGAGCTGGGTGTTGAGGTGAGCGACCTGACCCATGATCTGGAGATCCTGT GCCGTGAAAAGTGCCTGGCGGTTGCGACCGAGAGCAACCAGAACAACAGCATCATT AGCGTTCTGTTTGGCACCGGCGAAAAAGAGGACCGTAGCGTGAAACTGCGTATCAC CAAGAAATTCTGGAGGCGATCAGCAACCTGAAAGAAATCCCGAAGAACGTTGCGC CGATTCAAGAGATCATTCTGAACGTGGCGAAAGCGACCAAGGAAACCTTCCGTCAG GTGTATGCGGGTAACCTGGGTGCGCCGAGCACCCTGGAGAAATTTATCGCGAAGGA CGGCCAAAAAGAGTTCGATCTGAAGAAACTGCAGACCGACCTGAAGAAAGTTATTC GTGGTAAAAGCAAGGAGCGTGATTGGTGCTGCCAGGAAGAGCTGCGTAGCTACGTG | Nucleotide sequence encoding parent Cas12i2 |

TABLE 6-continued

Cas12i and LDHA Sequences

| SEQ ID NO | Sequence | Description |
|---|---|---|
| | GAGCAAAACACCATCCAGTATGACCTGTGGGCGTGGGGCGAAATGTTCAACAAAGC<br>GCACACCGCGCTGAAAATCAAGAGCACCCGTAACTACAACTTTGCGAAGCAACGTC<br>TGGAACAGTTCAAAGAGATTCAGAGCCTGAACAACCTGCTGGTTGTGAAGAAGCTG<br>AACGACTTTTTCGATAGCGAATTTTTCAGCGGCGAGGAAACCTACACCATCTGCGT<br>TCACCATCTGGGTGGCAAGGACCTGAGCAAACTGTATAAGGCGTGGGAGGATGATC<br>CGGCGGACCCGGAAAACGCGATTGTGGTTCTGTGCGACGATCTGAAAAACAACTTT<br>AAGAAAGAGCCGATCCGTAACATTCTGCGTTACATCTTCACCATTCGTCAAGAATG<br>CAGCGCGCAGGACATCCTGGCGGCGGCGAAGTACAACCAACAGCTGGATCGTTATA<br>AAAGCCAAAAGGCGAACCCGAGCGTTCTGGGTAACCAGGGCTTTACCTGGACCAAC<br>GCGGTGATCCTGCCGGAGAAGGCGCAGCGTAACGACCGTCCGAACAGCCTGGATCT<br>GCGTATTTGGCTGTACCTGAAACTGCGTCACCCGGACGGTCGTTGGAAGAAACACC<br>ATATCCCGTTCTACGATACCCGTTTCTTCCAAGAAATTTATGCGGCGGGCAACAGC<br>CCGGTTGACACCTGCCAGTTTCGTACCCCGCGTTTCGGTTATCACCTGCCGAAACT<br>GACCGATCAGACCGCGATCCGTGTTAACAAGAAACATGTGAAAGCGGCGAAGACCG<br>AGGCGCGTATTCGTCTGGCGATCCAACAGGGCACCCTGCCGGTGAGCAACCTGAAG<br>ATCACCGAAATTAGCGCGACCATCAACAGCAAAGGTCAAGTGCGTATTCCGGTTAA<br>GTTTGACGTGGGTCGTCAAAAAGGCACCCTGCAGATCGGTGACCGTTTCTGCGGCT<br>ACGATCAAAACCAGACCGCGAGCCACGCGTATAGCCTGTGGGAAGTGGTTAAAGAG<br>GGTCAATACCATAAAGAGCTGGGCTGCTTTGTTCGTTTCATCAGCAGCGGTGACAT<br>CGTGAGCATTACCGAGAACCGTGGCAACCAATTTGATCAGCTGAGCTATGAAGGTC<br>TGGCGTACCCGCAATATGCGGACTGGCGTAAGAAAGCGAGCAAGTTCGTGAGCCTG<br>TGGCAGATCACCAAGAAAAACAAGAAAGAAGGAAATCGTGACCGTTGAAGCGAAAGA<br>GAAGTTTGACGCGATCTGCAAGTACCAGCCGCGTCTGTATAAATTCAACAAGGAGT<br>ACGCGTATCTGCTGCGTGATATTGTTCGTGGCAAAAGCCTGGTGGAACTGCAACAG<br>ATTCGTCAAGAGATCTTTCGTTTCATTGAACAGGACTGCGGTGTTACCCGTCTGGG<br>CAGCCTGAGCCTGAGCACCCTGGAAACCGTGAAAGCGGTTAAGGGTATCATTTACA<br>GCTATTTTAGCACCGCGCTGAACGCGAGCAAGAACAACCCGATCAGCGACGAACAG<br>CGTAAAGAGTTTGATCCGGAACTGTTCGCGCTGCTGGAAAAGCTGGAGCTGATTCG<br>TACCCGTAAAAAGAAACAAAAAGTGGAACGTATCGCGAACAGCCTGATTCAGACCT<br>GCCTGGAGAACAACATCAAGTTCATTCGTGGTGAAGGCGACCTGAGCACCACCAAC<br>AACGCGACCAAGAAAAAGGCGAACAGCCGTAGCATGGATTGGTTGGCGCGTGGTGT<br>TTTTAACAAAATCCGTCAACTGGCGCCGATGCACAACATTACCCTGTTCGGTTGCG<br>GCAGCCTGTACACCAGCCACCAGGACCCGCTGGTGCATCGTAACCCGGATAAAGCG<br>ATGAAGTGCCGTTGGGCGGCGATCCCGGTTAAGGACATTGGCGATTGGGTGCTGCG<br>TAAGCTGAGCCAAAACCTGCGTGCGAAAAACATCGGCACCGGCGAGTACTATCACC<br>AAGGTGTTAAAGAGTTCCTGAGCCATTATGAACTGCAGGACCTGGAGGAAGAGCTG<br>CTGAAGTGGCGTAGCGATCGTAAAAGCAACATTCCGTGCTGGGTGCTGCAGAACCG<br>TCTGGCGGAGAAGCTGGGCAACAAAGAAGCGGTGGTTTACATCCCGGTTCGTGGTG<br>GCCGTATTTATTTTGCGACCCACAAGGTGGCGACCGGTGCGGTGAGCATCGTTTTC<br>GACCAAAAACAAGTGTGGGTTTGCAACGCGGATCATGTTGCGGCGGCGAACATCGC<br>GCTGACCGTGAAGGGTATTGGCGAACAAAGCAGCGACGAAGAGAACCCGGATGGTA<br>GCCGTATCAAACTGCAGCTGACCAGC | |
| 1166 | MSSAIKSYKSVLRPNERKNQLLKSTIQCLEDGSAFFFKMLQGLFGGITPEIVRFST<br>EQEKQQQDIALWCAVNWFRPVSQDSLTHTIASDNLVEKFEEYYGGTASDAIKQYFS<br>ASIGESYYWNDCRQQYYDLCRELGVEVSDLTHDLEILCREKCLAVATESNQNNSII<br>SVLFGTGEKEDRSVKLRITKKILEAISNLKEIPKNVAPIQEIILNVAKATKETFRQ<br>VYAGNLGAPSTLEKFIAKDGQKEFDLKKLQTDLKKVIRGKSKERDWCCQEELRSYV<br>EQNTIQYDLWAWGEMFNKAHTALKIKSTRNYNFAKQRLEQFKEIQSLNNLLVVKKL<br>NDFFDSEFFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGNQGFTWTN<br>AVILPEKAQRNDRPNSLDLRIWLYLKLRHPDGRWKKHHIPFYDTRFFQEIYAAGNS<br>PVDTCQFRTPRFGYHLPKLTDQTAIRVNKKHVKAAKTEARIRLAIQQGTLPVSNLK<br>ITEISATINSKGQVRIPVKFDVGRQKGTLQIGDRFCGYDQNQTASHAYSLWEVVKE<br>GQYHKELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSLVELQQ<br>IRQEIFRFIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGEGDLSTTN<br>NATKKKANSRSMDWLARGVFNKIRQLAPMHNITLFGCGSLYTSHQDPLVHRNPDKA<br>MKCRWAAIPVKDIGDWVLRKLSQNLRAKNIGTGEYYHQGVKEFLSHYELQDLEEEL<br>LKWRSDRKSNIPCWVLQNRLAEKLGNKEAVVYIPVRGGRIYFATHKVATGAVSIVF<br>DQKQVWVCNADHVAAANIALTVKGIGEQSSDEENPDGSRIKLQLTS | Parent<br>Cas12i2<br>amino acid<br>sequence |
| 1167 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ | Variant<br>Cas12i2 of<br>SEQ ID<br>NO: 3 of<br>PCT/US20<br>21/025257 |

TABLE 6-continued

Cas12i and LDHA Sequences

| SEQ ID NO | Sequence | Description |
|---|---|---|
| | NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG RWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGSRIKL QLTS | |
| 1168 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG DWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGSRIKL QLTS | Variant Cas12i2 of SEQ ID NO: 4 of PCT/US2021/025257 |
| 1169 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG DWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGGRIKL QLTS | Variant Cas12i2 of SEQ ID NO: 5 of PCT/US2021/025257 |
| 1170 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELRCRVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR | Variant Cas12i2 of SEQ ID NO: 495 of PCT/US2021/025257 |

TABLE 6-continued

Cas12i and LDHA Sequences

| SEQ ID NO | Sequence | Description |
|---|---|---|
| | WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | |
| 1171 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELRCRVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLATMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | Variant Cas12i2 of SEQ ID NO: 496 of PCT/US20 21/025257 |
| 1201 | ATGGCTTCCATCTCTAGGCCATACGGCACCAAGCTGCGACCGGACGCACGGAAGAA<br>GGAGATGCTCGATAAGTTCTTTAATACACTGACTAAGGGTCAGCGCGTGTTCGCAG<br>ACCTGGCCCTGTGCATCTATGGCTCCCTGACCCTGGAGATGGCCAAGTCTCTGGAG<br>CCAGAAAGTGATTCAGAACTGGTGTGCGCTATTGGGTGGTTTCGGCTGGTGGACAA<br>GACCATCTGGTCCAAGGATGGCATCAAGCAGGAGAATCTGGTGAACAGTACGAAG<br>CCTATTCCGGAAAGGAGGCTTCTGAAGTGGTCAAAACATACCTGAACAGCCCCAGC<br>TCCGACAAGTACGTGTGGATCGATTGCAGGCAGAAATTCCTGAGGTTTCAGCGCGA<br>GCTCGGCACTCGCAACCTGTCCGAGGACTTCGAATGTATGCTCTTTGAACAGTACA<br>TTAGACTGACCAAGGGCGAGATCGAAGGGTATGCCGCTATTTCAAATATGTTCGGA<br>AACGGCGAGAAGGAAGACCGGAGCAAGAAAGAATGTACGCTACACGGATGAAAGA<br>TTGGCTGGAGGCAAACGAAAATATCACTTGGGAGCAGTATAGAGAGGCCCTGAAGA<br>ACCAGCTGAATGCTAAAAACCTGGAGCAGGTTGTGGCCAATTACAAGGGGAACGCT<br>GGCGGGCAGACCCCTTCTTTAAGTATAGCTTCTCCAAAGAGGGAATGGTGAGCAA<br>GAAAGAACATGCACAGCAGCTCGACAAGTTCAAAACCGTCCTGAAGAACAAAGCCC<br>GGGACCTGAATTTTCCAAACAAGGAGAAGCTGAAGCAGTACCTGGAGGCCGAAATC<br>GGCATTCCGGTCGACGCTAACGTGTACTCCCAGATGTTCTCTAACGGGGTGAGTGA<br>GGTCCAGCCTAAGACCACACGGAATATGTCTTTTAGTAACGAGAAACTGGATCTGC<br>TCACTGAACTGAAGGACCTGAACAAGGGCGATGGGTTCGAGTACGCCAGAGAAGTG<br>CTGAACGGGTTCTTTGACTCCGAGCTCCACACTACCGAGGATAAGTTTAATATCAC<br>CTCTAGGTACCTGGGAGGCGACAAATCAAACCGCCTGAGCAAACTCTATAAGATCT<br>GGAAGAAAGAGGGTGTGGACTGCGAGGAAGGCATTCAGCAGTTCTGTGAAGCCGTC<br>AAAGATAAGATGGGCCAGATCCCCATTCGAAATGTGCTGAAGTACCTGTGGCAGTT<br>CCGGGAGACAGTCAGTGCCGAGGATTTTGAAGCAGCCGCTAAGGCTAACCATCTGG<br>AGGAAAAGATCAGCCGGGTGAAAGCCCACCCAATCGTGATTAGCAATAGGTACTGG<br>GCTTTTGGGACTTCCGCACTGGTGGGAAACATTATGCCCGCAGACAAGAGGCATCA<br>GGGAGAGTATGCCGGTCAGAATTTCAAAATGTGGCTGGAGGCTGAACTGCACTACG<br>ATGGCAAGAAAGCAAAGCACCATCTGCCTTTTTATAACGCCCGCTTCTTTGAGGAA<br>GTGTACTGCTATCACCCCTCTGTCGCCGAGATCACTCCTTTCAAAACCAAGCAGTT<br>TGGCTGTGAAATCGGGAAGGACATTCCAGATTACGTGAGCGTCGCTCTGAAGGACA<br>ATCCGTATAAGAAAGCAACCAAACGAATCCTGCGTGCAATCTACAATCCCGTCGCC<br>AACACAACTGGCGTTGATAAGACCACAAACTGCAGCTTCATGATCAAACGCGAGAA<br>TGACGAATATAAGCTGGTCATCAACCGAAAAATTTCCGTGGATCGGCCTAAGAGAA<br>TCGAAGTGGGCAGGACAATTATGGGGTACGACCGCAATCAGACAGCTAGCGATACT<br>TATTGGATTGGCCGGCTGGTGCCACCTGGAACCCGGGGCGCATACCGCATCGGAGA<br>GTGGAGCGTCCAGTATATTAAGTCCGGGCCTGTCCTGTCTAGTACTCAGGGAGTTA<br>ACAATTCCACTACCGACCAGCTGGTGTACAACGGCATGCCATCAAGCTCCGAGCGG<br>TTCAAGGCCTGGAAGAAAGCCAGAATGGCTTTTATCCGAAAACTCATTCGTCAGCT<br>GAATGACGAGGGACTGGAATCTAAGGGTCAGGATTATATCCCCGAGAACCCTTCTA<br>GTTTCGATGTGCGGGGCGAAACCCTGTACGTCTTTAACAGTAATTATCTGAAGGCC<br>CTGGTGAGCAAACACAGAAAGGCCAAGAAACCTGTTGAGGGGATCCTGGACGAGAT<br>TGAAGCCTGGACATCTAAAGACAAGGATTCATGCAGCCTGATGCGGCTGAGCAGCC<br>TGAGCGATGCTTCCATGCAGGGAATCGCCAGCCTGAAGAGTCTGATTAACAGCTAC<br>TTCAACAAGAATGGCTGTAAAACCATCGAGGACAAAGAAAGTTTAATCCCGTGCT<br>GTATGCCAAGCTGGTTGAGGTGGAACAGCGGAGAACAAACAAGCGGTCTGAGAAAG<br>TGGGAAGAATCGCAGGTAGTCTGGAGCAGCTGGCCCTGCTGAACGGGGTTGAGGTG<br>GTCATCGGCAAGCTGACCTGGGGAGGTCGAAAAAGGAAAGAGTAAGAAACAGAA<br>TTCACGGAACATGGATTGGTGCGCAAAGCAGGTGGCACAGCGGCTGGAGTACAAAC | Nucleotide sequence encoding parent Cas12i4 |

TABLE 6-continued

Cas12i and LDHA Sequences

| SEQ ID NO | Sequence | Description |
|---|---|---|
| | TGGCCTTCCATGGAATCGGTTACTTTGGAGTGAACCCCATGTATACCAGCCACCAG<br>GACCCTTTCGAACATAGGCGCGTGGCTGATCACATCGTCATGCGAGCACGTTTTGA<br>GGAAGTCAACGTGGAGAACATTGCCGAATGGCACGTGCGAAATTTCTCAAACTACC<br>TGCGTGCAGACAGCGGCACTGGGCTGTACTATAAGCAGGCCACCATGGACTTCCTG<br>AAACATTACGGTCTGGAGGAACACGCTGAGGGCCTGGAAAATAAGAAAATCAAGTT<br>CTATGACTTTAGAAAGATCCTGGAGGATAAAAACCTGACAAGCGTGATCATTCCAA<br>AGAGGGGCGGGCGCATCTACATGGCCACCAACCCAGTGACATCCGACTCTACCCCG<br>ATTACATACGCCGGCAAGACTTATAATAGGTGTAACGCTGATGAGGTGGCAGCCGC<br>TAATATCGTTATTTCTGTGCTGGCTCCCCGCAGTAAGAAAAACGAGGAACAGGACG<br>ATATCCCTCTGATTACCAAGAAAGCCGAGAGTAAGTCACCACCGAAAGACCGGAAG<br>AGATCAAAAACAAGCCAGCTGCCTCAGAAA | |
| 1202 | MASISRPYGTKLRPDARKKEMLDKFFNTLTKGQRVFADLALCIYGSLTLEMAKSLE<br>PESDSELVCAIGWFRLVDKTIWSKDGIKQENLVKQYEAYSGKEASEVVKTYLNSPS<br>SDKYVWIDCRQKFLRFQRELGTRNLSEDFECMLFEQYIRLTKGEIEGYAAISNMFG<br>NGEKEDRSKKRMYATRMKDWLEANENITWEQYREALKNQLNAKNLEQVVANYKGNA<br>GGADPFFKYSFSKEGMVSKKEHAQQLDKFKTVLKNKARDLNFPNKEKLKQYLEAEI<br>GIPVDANVYSQMFSNGVSEVQPKTTRNMSFSNEKLDLLTELKDLNKGDGFEYAREV<br>LNGFFDSELHTTEDKFNITSRYLGGDKSNRLSKLYKIWKKEGVDCEEGIQQFCEAV<br>KDKMGQIPIRNVLKYLWQFRETVSAEDFEAAAKANHLEEKISRVKAHPIVISNRYW<br>AFGTSALVGNIMPADKRHQGEYAGQNFKMWLEAELHYDGKKAKHHLPFYNARFFEE<br>VYCYHPSVAEITPFKTKQFGCEIGKDIPDYVSVALKDNPYKKATKRILRAIYNPVA<br>NTTGVDKTTNCSFMIKRENDEYKLVINRKISVDRPKRIEVGRTIMGYDRNQTASDT<br>YWIGRLVPPGTRGAYRIGEWSVQYIKSGPVLSSTQGVNNSTTDQLVYNGMPSSSER<br>FKAWKKARMAFIRKLIRQLNDEGLESKGQDYIPENPSSFDVRGETLYVFNSNYLKA<br>LVSKHRKAKKPVEGILDEIEAWTSKDKDSCSLMRLSSLSDASMQGIASLKSLINSY<br>FNKNGCKTIEDKEKFNPVLYAKLVEVEQRRTNKRSEKVGRIAGSLEQLALLNGVEV<br>VIGEADLGEVEKGKSKKQNSRNMDWCAKQVAQRLEYKLAFHGIGYFGVNPMYTSHQ<br>DPFEHRRVADHIVMRARFEEVNVENIAEWHVRNFSNYLRADSGTGLYYKQATMDFL<br>KHYGLEEHAEGLENKKIKFYDFRKILEDKNLTSVIIPKRGGRIYMATNPVTSDSTP<br>ITYAGKTYNRCNADEVAAANIVISVLAPRSKKNEEQDDIPLITKKAESKSPPKDRK<br>RSKTSQLPQK | Parent<br>Cas12i4<br>amino acid<br>sequence |
| 1203 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLE AELHYDGKKA KHHLPFYNAR<br>FFEEVYCYHP SVAEITPFKT KQFGCEIGKD IPDYVSVALK DNPYKKATKR<br>ILRAIYNPVA NTTGVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN<br>PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD<br>FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | Variant<br>Cas12i4 A |
| 1204 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLR AELHYDGKKA KHHLPFYNAR<br>FFEEVYCYHP SVAEITPFKT KQFGCEIGKD IPDYVSVALK DNPYKKATKR<br>ILRAIYNPVA NTTRVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN<br>PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD | Variant<br>Cas12i4 B |

TABLE 6-continued

Cas12i and LDHA Sequences

| SEQ ID NO | Sequence | Description |
|---|---|---|
| | FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | |
| 1172 | GTGCTGCAGCCGCTGCCGCCGATTCCGGATCTCATTGCCACGCGCCCCGACGACC<br>GCCCGACGTGCATTCCCGGTACGGTAGGGCCCTGCGCGCACGGCGCCAGAGGGATG<br>GGCGGGTAGAGCCAACTGCCTCTGGTTCTGCTGGCCTCCGCTGCTCGCGAAGGGAT<br>TCCTGCTCCCGGGAGGTGTAGGAGCCGCTTTCCAGAAGCACAGCCCAGAGACGTCT<br>GGGCGGCGGCCCACACAACGCATGTGTTCGGAGCTCGCCGCGCTCTGCTTTTGCTC<br>TAAGCGGGAACCATGGCTTCTGGCCACGCTGGGGAACCGAGGAGGTGGCCGCACCC<br>AAGCAGGGGTCGAAAGCCCGGTGGATGCGGAACAAGGATATGATAGGCCTTAAGG<br>GTGGGGGATACCTCTGGGCTCGAAATCGGCGGGCGGTGCAAAACTCGAGGTCCAGT<br>TCTCGGAGCCCATAGAGCCAAAAAAGCCTCAGCTTGTCCGGGGCGGGTTCTTGAAA<br>GACGGAAAGCGGCTGAGTACCACGCGGCTTGCATTTTTCTCTTGGGACGCTCGAGA<br>GGTGGGCTCCGTGAGGGCAGCTGCTGCCTGCAGATTATAGGGAGCCCTTTGCGCAT<br>TTATTAAGAAGCTACTGGTGTATCTCGGGCTGCGCTAGGCACGGCGCATGCAAAGA<br>TGAAGCAGGCAGCATCCCAGCCCTTCCGCACCTCAGACGGTCAGTTGAGTAGGATC<br>CGCCGGTACCAACTCCTCCTTTTAACAAATAGGGAGACCGAAAGCTAGGAGACAGT<br>CAGGGATCTCTAAGTTCCCAGTGAGTAGGAGGCAGAGGTGAGGTGTAGAACTCGTT<br>TTTGCATGTCTCTCGCCTCTAGACGCACCCTTCCCTCATCCCATGCCCTCCCACCT<br>CCGCCCCTACATTAAAGGTAGCATTGGATCCCGGGGCCGTTCAGTGAAGCTAGCAG<br>GTGTCCGCAGGAACTCCCTTCCCCCTGCCAGGCTAGAAACCTTACAAGGCTGTCTA<br>GAAATAGCAGTGATTTGTAAGGAGAGACCCGGCTCCAGCTTGGTGACTCTGGGCTG<br>ACTGCCTGCCTAGAGGTCCTCTCGGATTTTTGCCCTTTGGAGTGGTGTCAAAACTA<br>GACGTGATACTTTGGGGATGCAGCCTGTGATATTTCCTCCAGCGAATGCAGTGCAG<br>GGTTGGATTAACAAGGTGGAAAGAATTCGAGGGTTCCACCAAGTAGCTATTAACTC<br>TAGGGCTGCAGGCCTCAGGCCTTCTGCAGCTATTTCTACACTCCCTGTACTGAAAC<br>TATTTCTTCATACTGGGCCTGACAGGCCTTTGCAACAAGGATCACGGCCGAAGCCA<br>CACCGTGCGCCTCCCTCCCGGTTGGTTAACAGGCCCTGGTTTCTAGTATTGCGATT<br>TAAAGTCTGGCGCTGGCTGCGCGCCAGACCTGGGAGGCTGCCAGCTAGGCTTCACG<br>TTGCTGGCGTCTGCTTCGGGGCATTCATTAGGTCTGAAGTCTGAATCCCAGCTCCC<br>TCCCTCTCACCCACTGAGCTGCATAGCTCCAGATTGCCTCTGCTTACGGGCGGGGC<br>TTCTCAGCCTTCTGCCTTCTGGCCGATGCCCGCTTCCCAACGGCCGGAGGCCGCT<br>AGACTAATCGGCTTCGCCCTGCGCGCTGTAATGCGCATGCGCACGCGCACAAGTTC<br>CTGGGCCCGCCCATCTTCCGGACTTGGGCGGGGCGTAAAAGCCGGGCGTTCGGAGG<br>ACCCAGCAATTAGTCTGATTTCCGCCCACCTTTCCGAGCGGGAAGGAGAGCCACAA<br>AGCGCGCATGCGCGCGGATCACCGCAGGCTCCTGTGCCTTGGGCTTGAGCTTTGTG<br>GCAGTTAATGGCTTTTCTGCACGTATCTCTGGTGTTTACTTGAGAAGCCTGGCTGT<br>GTCCTTGCTGTAGGAGCCGGAGTAGCTCAGAGTGATCTTGTCTGAGGAAAGGCCAG<br>CCCCACTTGGGGTTAATAAACCGCGATGGGTGAACCCTCAGGAGGCTATACTTACA<br>CCCAAACGTCGATATTCCTTTTCCACGCTAAGGTATGGCCTTCACTCTTCACAGA<br>CCCTGTCATTAGGCCTTTCAACTCTCTTTTGGCAACCATTAGGTTTTTTCCCCTCC<br>CTTTTTAGTCATCTCTAGTGATTTATAGTGGCAAATACCCCAAAGGAAGTAAAAT<br>AGCTTAAAAAAATCTCTTGGTTAATAAACATTAAAGAAGCTGTAGTGACACTAAAT<br>GTTTTTCCTCCTATAGATTCCTTTTGGTTCCAAGTCCAATATGGCAACTCTAAAGG<br>ATCAGCTGATTTATAATCTTCTAAAGGAAGAACAGACCCCCCAGAATAAGATTACA<br>GTTGTTGGGGTTGGTGCTGTTGGCATGGCCTGTGCCATCAGTATCTTAATGAAGGT<br>AAGTGAGAGTCTACCACACTGGAAGCCCATACCTTGACCCCATCCTCTACCCCCAC<br>TCCTACCCCTAGAACTGTATTATTACATTTCATGTAACAGTATTTAGATTTATGCA<br>CTCATTCGGATAACTTTCTGTGAAACAAACTTTTGAAATATGATAATACACCAAAA<br>GTGTATCTGAAATTAAAAAGAATCAAAGGTTGTCAGGCTGGAGACCCAGTTCCTAA<br>AATTCATTATTCTGTATTAACATGCATGGATTGACTACCAATGAAAAGGAAGGGTC<br>CATGATTTTAAATGAGCCAAAATTCTTTTAAAGTGATTTTTGAATTGAAAATGACA<br>ATTCAAAAATTGTCATTTATTGGTAAAATTATATGGGAAATCATAAGTTCTCCCAC<br>TCAAATCTCATTGCCCCTGTGCCTTGGATAGCAATTTTGTTATCAATTATGGAGCT<br>AAAATTTAATTAGAAAAAGAAATTGTGAGTAAAGCACTCCTTATTACACTATTGA<br>AAGCTGATTATATTTAAAAGAAATTGAGGCAGCTTACAACATTAAAATGTCTGAG<br>GCGGGGCACAGTGGCTCATGCTTGTAATGCCAGCACTTTAGGAGGCTGAGGTGGGT<br>GGATCACGAGGTCAGGAGATGGAGACCATCCTGGCTAACACGATGAAACCCCATCT<br>TTACTAGAAATACAAAAAATTAGCCGGGCGTGGTGGCATACGCCTATAGTCCCAGC<br>TACTTGGGAGGCTGAGGCAGGAGAATTGCTTGAACCCAGGAGGTGGAGGTGGCAGT<br>GACCCGAGATAGCACCACTCCACTCCAGCCTGGGCGACAGTGAGACTCCATCTCAA<br>AAAAAAAAATCTGAAGTTAAGATGTGGAGTGTCTAATAAAAGTAAAATGATGAATT<br>CTGGGTTCTAAATAGAAATGGATTCAAGTGAGAAGGGACTAAAGACAGAAATGAGC<br>TATGAAAAGGCCTCGTAACAACACAGGTGACTCTACATATGTTCTTAGGAAAGGCC<br>ACATAATACACCAACTTTTATTCCTTACCCACTAGATGAGAAATTGATGCTGTTTT<br>CCCCACACCTACAAACCGCCTATGTTTTTCTCTGTGATGGCCTCTGGCTCAGGTG<br>TGGGTAAGAAGAGTAACTGACACTCATTATATTGTGGATGATTTAGGGATAGATCT<br>GCAGCTTGAATAACTTTTGGTAACGATAGACCACATCCAGTTGTATTAAAGCTGTT<br>ATTGGTGCTCCTGGCCTGAAATGGACCTATGAACTTTGAGTTGCAACTATAAGGAT<br>ATTTTTTGCCAGTATTATACACTGCACAAACCTATTTATCCATAACTGTTAGTATT<br>GGTTCATATATGGAATCAACCAGGGAATAGTTCAGATTCCATCTCTGAAAGATGGG<br>CGGAAATCAGACTTTTTAACTTTTTAAGTTTTTTTTTTTGAGACGGAATCTCGCT<br>TTGTTGCCCTGGCTGGAGTGCAGTGGCACGATCTTGGCTCACTTGACCTCCTGGGT<br>TCAAGTGATTCTCCTGCCTCAGCCTCCCGAGTAGCTGGGACTACAGGCACCCACCG | LDHA |

TABLE 6-continued

Cas12i and LDHA Sequences

| SEQ ID NO | Sequence | Description |
|---|---|---|
| | CCACGCCTGGCTGATTTTTGTATTTTTAGTAGAGACAGGCCTTCACCATATTGGCC<br>AGGCTGGTCTTTTTTTTTTTTTTTTTTTTTTTCTGAGAAGGAGTCTCGCCGTG<br>TCGCCCAGGCTAGAGTGCAGTGGCGTGAACTCCGCTCACTGCTAGCTCTGCCTCCC<br>GGGTTCATACCATTCTCCTGTCTCAGCCTCCCAAGTAGCTGGGACTACAGGCACCC<br>ACCACCACGCCTGGCTAAATGTTTGTATTTTTAGTAGAGACGGGGTTTCACCATG<br>TTAGCCAGGATGGTCTCGATCTCCTGACCTCGTGATCCGCCTACCTTGGCCTCCCA<br>AAGTGCTGGGATTACAAGCGTGAGCCACCGTGCCTGGCCTGGCCAGGCTGTCTTGA<br>ACTCCTGACCTCAAGTGATGTGCCCGCCTCGGCCTCCCAAAGTGTTGGGATTACAG<br>ATGTGAGTCACTATGCCCGGCCAGAACATTTCTTACTAATTTCAAGTCTTGATGCT<br>GGTCAATATCACCTAGTTAAATGAATAACAACCTAAAATTGGTGTGTAGGATGGAA<br>TTTGAGAGAGTAGACAGAGCAGTTTTATATAATTGGAAGTTATTCTAGCAACTGCC<br>AGTCCAGTGTTCTGCTTCCACATCTGCAGTGGTGGAACTCCTATAGAGCTCGCTTC<br>AGTGGGGAGACAGGGCTGGAGAGAGGGTCAGTGCTATCTATGTAGGGTGTAATCTG<br>TAAGTCAGCTTTTGAAATGGGGTGCCCTCTACTTTGAATATCTCGATACTGTACTA<br>ATAAAGTAACAGAACTCTCCTATGCCAGAAATATAGAAATTTTTCATGCTCTTCTA<br>AAAATCTAGAAGTGGCAATTTTCCATTTAACTAAAGATTTGATGTCTTTTAGGACT<br>TGGCAGATGAACTTGCTCTTGTTGATGTCATCGAAGACAAATTGAAGGGAGAGATG<br>ATGGATCTCCAACATGGCAGCCTTTTCCTTAGAACACCAAAGATTGTCTCTGGCAA<br>AGGTTGATTTCAACAAGTTTATATTATAATCCATGCTTGACTTAAATTCTTTTTCC<br>AGATGGTCTCCATTTGTTGCTTAGGGTAGAGTGCAGTTGCACAATTATGGCTCACC<br>ACAGCCTCGAACCCTGGGCTCAAGCAATCCTCCTTCCACTTCATTACCCCCTCCCC<br>CTCACAAAGAAACTGGGACTATAGGGTATGCTACCATGCCCGGCTAATTTTTTTAC<br>TTTTTGTAGAGATGGGGACCCACTGTGTTGCCCAGGCCTGTCTTGAACCACTGGGC<br>TCAAGTGATCCTCCCTCCTTAGCCTTCCGAAGTACTGGGATTGCAGGTGTGAACCA<br>CTGTGCCCGGCTTTAGACTTAAATGTTTTATCAGGCTTGAAATCCTAGCTCTTTAA<br>AGATTTTGTTTTAAATGCCGGGTGCAAGAGCCTGGGAACAATTTCACTTAGGTGCC<br>TGTGAATATCAAAGTTTCAATTTCTGGCAAATGGTTTAAAATAGAAATCCAATTTG<br>TCCATGCTATGCAAACCATCTGAATTAGAATGTAATGAGTAAAGCTTAAACCTTAG<br>GTCTGTATTTAACCACATTGTGTTACTTACTTGCCCCCACATCCTTTCACACACGA<br>AGTTGAGAATAGGGTAAATAAATGAGCCTGTTCAGCTAATACTCTTGGCTTGACCC<br>TTTCACACTTAACAGCACCAGCCAAGAAACCTGAATGTGAGCCCAAATAGTGTCTA<br>TTTTGATACCTGAAAATCACTGGCCACCTTGCTGATGGGCAACTCCCTTCATCACT<br>GGTTTAACTCTCTTGTGCCATAGGGTATCTAGAAGCAAAATATGTTTGTTAAGTGT<br>AAAGCTGTCTCTGCTTAAAAACAAGTCCCCCTACCACCACCACCACACACACACAC<br>ACACACACACACACACACACACACACACACACACACACGAAATTGCCTGTTCCT<br>GGGCTGATAGGACACCAGTTAAGTAGAAACAGGAGTATGGAAGAGTGTGAACGTTG<br>AGCTTGGGGATCAAAAATTTGAGGATATGTAAGAAATTAATAGGAGAATCAAATAA<br>TAAAACTTGATTTCCTCCAGCTCTCCCTAATTGTAGTTACATAAAGTTACAACTTGA<br>CTAAAACTACAAGGAAGATGTTGACATGCTCTTCCTCCATTTAAGAAGCCATAATG<br>ATAAAACTCTAAGAACAAGAAAGGTTTGTGGAGCATTTATGGAACAAATTTTTGCT<br>GCCTAGGTAAAATTTATTCTAAAGGCCTTAATCTGGTCATTATTCCCCTTTTCTCT<br>AGACTATAATGTAACTGCAAACTCCAAGCTGGTCATTATCACGGCTGGGGCACGTC<br>AGCAAGAGGGAGAAAGCCGTCTTAATTTGGTCCAGCGTAACGTGAACATCTTTAAA<br>TTCATCATTCCTAATGTTGTAAAATACAGCCCGAACTGCAAGTTGCTTATTGTTTC<br>AAATCCAGGTGAGGCTTTTGACTGCATAAAAATTGACAAGCTATAGTAAAACTGAT<br>AGTATATGATATATATATTATATATATTTTAAATATTTTGAAATATTTTAAAAAAT<br>ACATTTTTAAAAATATTTTCGAATATTATTTTAAAATATATATATATATTTTGAGG<br>CGGAGTTTTGCTCTTGTCGCCCAGGTTGGAGTGCAGTGGCGCAATCTGGGCTCACT<br>GCAACCTCTGCCTCATGGGTTCAAGCGATTCTTTTGCCTCAGCCTCTCAAGTAGCT<br>GGGATTATAAGCGCCTGCCACCACACATGGCTAATTTTTTATATTTTTAGTAGAGA<br>CAGGGTTTCACCATGTTGGCCAGGCTGGTTTTGAACTCCTGGCCTCAAGCAGTCCA<br>TCTGCCTCCCAAAGTGCTAGGATTACAGGCGTGAGCCACCGTGCCCAGCCACGCAT<br>ATTTATTGATTCATTTATTTTCTTTTTTTTTTTTTTTTTGAGACGGAGTC<br>TTGCTCTGTCACCCTGGCTGGAGTACAGTGGCTTGATCTTGGCTCACTGCAAGCTC<br>CGCCTCCCGGGTTCATGCCATTCTCCTGCCTCAGCCTCCCGAGTAGCTGGGACTAC<br>AGGTGCCCACCACGACGCCTGGCTAATTTTTGTATTTTTAGTAGAGACGGGGTTT<br>CATCAGGTTAGCCAGGATGGTCTCGATCTCCTGACCTCGTGATCTGCCCGCCTTGG<br>CCTCCCAAAGTGCTGGGATTACAGGCGTGAGCCACCGTGCCTGGTGATTCATTTAT<br>TTTTCATGTTTCATTTCCCTTCTAAGGAGATTTGTGTGTGTGTTTTTTGTTTTT<br>TAATAATTTTAAAACATTAAAGGGAATACAATGCCTTTAAATGTAGTTGGAGCTTA<br>AAATTACCTGCCCAAGATCTTGGATAAGGGATAAGTTTGTGAATAATTGTTATTCT<br>CTTTTTTTTTTTTTTTTTTGAGACAGTCTCACTTTGTGCTCAGGCTGGAGTG<br>CAGTGGTTCGATCTTGGCTCACTGCAACCTCTGCCTCCTGGGTTCAAGCAATTCTC<br>CTGCCTCAGCCTCCCAAGAGCTGGGATTACAGGCACGTGCCACCATGCTCGGCTAA<br>TTTTTGAAGTTTTAGTAGAAAGGGGTTTCACCATGTTGCCCAGGCTGGTCTCAAAT<br>TCCTGAGCTCAGGTGATCCATCTGCCTCAGCCTCCCAAAGTATTAGGATTACAGGC<br>GTGAGCCACCGTGCCCGGCCCATAATTGTCTCTTAGTTGATAAACAGTTTATTTT<br>CATAAAACTGTTACTATACTTTTTTTTGAGAGCATGTCTCACTCTGTCGCCCAAG<br>CTGGAGGGCAATGGGATGATCATGGCAGCTTTGACCTACTAGGCTCAGGTGATCCT<br>TCTTCCTCAGCCTCTTAAGTAGCTAGGACTACAGGCGTGCACCAATATGCCTGCT<br>AGTTTGTTAAAAGTTTTTTTGTAGAGATGGGGTTTTGCTATGTTGCCCAGGCTGGT<br>CTTGAACTGCTGGCCTCAGGCAGTCCTCCCACCTCAGCCTCCCAAAGTGTTGGGAT<br>AACAGGTGTGAGTTGTCATGCCCAGCCAAAACTACTTTTTGAATAATTAATGGACT<br>TGATATACATAGTGTAGAGGCTTAAAAATATTAACAAAATTATTGGTTAGCCATGA<br>TCAATATCAAGATCCTGAAAAGCCATATATCTGGAGTAGCCTATTATTATCTAATG | |

TABLE 6-continued

Cas12i and LDHA Sequences

| SEQ ID NO | Sequence | Description |
|---|---|---|
| | ATCACCTAGTATCTGGTTAAGTGTTTTCTTCATAGTAGGTATATCTTTTTTGTGTG<br>TAGGGAGAGGATAATGGGTGATTTTTATTTTCTCCTTTTTCATAGTGGATATCTTG<br>ACCTACGTGGCTTGGAAGATAAGTGGTTTTCCCAAAAACCGTGTTATTGGAAGCGG<br>TTGCAATCTGGATTCAGCCCGATTCCGTTACCTAATGGGGGAAAGGCTGGGAGTTC<br>ACCCATTAAGCTGTCATGGGTGGGTCCTTGGGGAACATGGAGATTCCAGTGGTAAG<br>CATAAGTTATTTTCTTTTTGTTTTTGAAAAGATTATATAAAAAGTCGATGGGCATT<br>ATATTATTCAATTAGAGCCTAATCAAATATCCATTCAGTAGGATGGAATGGTTTCC<br>CGAAATCTAGCATTTTGTATAATTATATGTTAAGAATTGTTAAGATTGTTGCCATT<br>TTATATGGCATTTTATGGCGAGGGGGACGGGAAATGAAATTTCTCTTCTTACCATG<br>GATATCTTAAGACTGTAGTTCTTAGGATGTCTTCAGTCATTTAATATCACAGCTGT<br>TTATACCTGACTTGTACTGCCTGGCCCTGAAAAGATGAGCAAATCCAAATGCACAA<br>AAGTTATATTATCACAGTTGAAAAATGTTATGATTAGGTTCTGTATGCTAAGAAAA<br>CCCCCCTTATGTTCTCATACTATCTTTATATTTCAAATATACATGGGTTAAACATT<br>TCAATTGGCTAGAGAAACAGGTTAGAATACAGTTAAAATTCTTAGTTTTACATAAT<br>GTAAGTAAATGAAAATCTAATCTAAAAGTGAGTAATGACTACATTAGTAGTCTTGA<br>CCATCTACCAAAATTGAGTATTCTTCCTCCGAAGATAAGAGAATTAGGAAAATGAA<br>TCACAATTACTAATCTGTTGGTACATGAAAATAAATGTAGTCTGTACTATTTCTTT<br>TAGTGCCTGTATGGAGTGGAATGAATGTTGCTGGTGTCTCTCTGAAGACTCTGCAC<br>CCAGATTTAGGGACTGATAAAGATAAGGAACAGTGGAAAGAGGTTCACAAGCAGGT<br>GGTTGAGAGGTAATAAATCTTTCAATTTGGCAACACAGAATATTAACATTTACTAT<br>TTTTATTTAAAAGGTTAAAATTGTAATAGTATTTGCATTTGAGAACTTTTTGTTAG<br>AAAACTTGTGTGGTTTTTTTGTTTTGTTTTGTTTGAGACAGAATCTTGCCCTTTCG<br>CACAGGCTGCAGTGCAGTGGCGCAATCTTGGCTCACTGCAACCTCTGCCTCCCGGG<br>TTCAGGCGATTCTCCTGCCTCAGCCTCCTGGGTACCTGGGACTACAGGCATATGCC<br>ATGACGCCCGGCTAATTTTTTGTATTTTTAGTAGAGATGGGGTTTCACCATGTTAG<br>CCAAAAAAAAAGAATGTGCCTCACCTTGCAAGGCCCAGGCCCTAGGATCACTTGA<br>GCTCAGGAGTTCAAGGCCAGCCTGGGCAACAGGGCAAAACCCTGTCTCTACAATAA<br>ATACACAAATTAGCCAGGCATGGTGGTGAGCACCTGTGGTCCTAGCTACTTGAGAG<br>GCTGAGGCAGGAGGATCGCATGAGCCTGGGAGGTCAAGGCTGCAGTGAAGCGAGAT<br>CCTGCCACTGCACTCCAGAGCCTGCTAGCCTGGGTGACAGAGTAAGAGCCTGTCTC<br>AAAGGAAAAAAAAATTATTGAAATAGGGAAGCTTTCAACTTGGTGGCATTATTTA<br>CCTTTGTGGTCCTGTGTGGACCTCAGGTCTATAGAATTAAAAAATGAATCATAGCC<br>GGGCATGGTGGCTCATGCCTGTAATCCCAGCACTTTGGGAGGCCGAGGCAGGCAGA<br>TCACGAGGTCAGGAGATGGAGACCATCCTGGCTAACACGGTGAAACCCCGTCTCTA<br>CTAAAAATACAAAAAATTAGCCGGGCGTGGTGGCAGGCGCCTGTAGTCCCAGCTAC<br>TCGGGAGGCTGAGGCAGGAGAATGGCATGAACCCGGTAGTTGGAGCTTGCAGTGAG<br>CCGAGATCGCGCCACTGCACTCCAGCCTGGGCGACAGAGCGAGACTCCGTCTCAAA<br>AAAAAAAGAATCATAATCTTTAGTTCATAACATATTCTTGTGATTGGTCAAGCAAG<br>GCCCTCTTGTTTGTATTTGTTTAATTAAATAAAACCTGTGAACCCACCACCCAGCT<br>CAAGAAAGAAACACAATATCTGTCAAATAACATTGTTGAATCAGAATTTAGTATTC<br>TGCTGGTGTTTGGAAATAAGTGGATTCTGTGCTCTTTCCCCCAGCTATCCCTCTGT<br>CCCCCTCACGCTCCCACTTGAGATAATCCTGAGTTAAGGATGCTATGTTATCTTGG<br>ATTTCTTTTTAAAATTCAATATTATATTTTTAAGAATTATCCAATTTTTTTTACAA<br>GTAGCTATAGTTTATTTTTTGATAGCTGTGTAATATTCCATTGTATCAGTATACCA<br>TGATTTATCCATTCTTCTGTTGGAGGACATTGGAAAGATTGTCATGTTTTTGCTGT<br>TACTAACAGTACTGTTAATGAATATCCCTGTACATAATATCCTAGCATACATGTGT<br>GCAAGGGTTATTCTTGGTATAATGCAACATTGTGGCATTATTTACTGTAAAATGTG<br>TATTAATGAAAACTTTGTTTTTCTTTCTTTCTCCCACCCTGCTTTTTCTGCCTTTA<br>CCTATGGTTTCCTATCATACAGTGCTTATGAGGTGATCAAACTCAAAGGCTACACA<br>TCCTGGGCTATTGGACTCTCTGTAGCAGATTTGGCAGAGAGTATAATGAAGAATCT<br>TAGGCGGGTGCACCCAGTTTCCACCATGATTAAGGTAGGTCTATGTAGTGATACGC<br>TGCATTTGAATGCTTTTTGCTGGCTTTTTAAAAAAGATTCTTCTGAGAAAGATTAA<br>TACAAGTCTTCCATTACTGACTTAAGTGAAATAAATTAATGTACCCACAGCTTACC<br>TTTTTTGAAAGAAATGGTTGAGCTTTAGGATTAATGTCCATTAGGCCTGTTCAACA<br>CATAGATACTTGATAATTTGACTACAAAAAAGTCTTGTTCAATTATGCTGAGGTAG<br>GTGGAAGACTATAAAAGAAATAAACTATTTCTCCATTGGGGAAAATAGAAATTATA<br>TTCAAGTTAGCATTATGTTACTATTTTTAATGACTTTCTTTTATACTATTAATTAA<br>ATCATAACTGAACACCTGGAAAGGAATTTCTACTTATCAAAGTTTTTTATTTTTT<br>GAGACAGTCTCCCTCTGTCACCCAGGCTGCAGTGCAGTGGCCGATCTCGGCTCACC<br>GCAACCTCTGCCTCCCAGGTTTAAGCGATTCTTCTGCCTCAGCCTCCTAAGTAGCT<br>GGGACTACAGGTGCGTGCCACCACGCCCGGCTACTTTTTGTATTTTTAGTAGAGAT<br>GGAGTTTCACCATATTGGCTAGGCTGGTCTCGAACTCCTGACCTTGTGATCCACCC<br>GCCTCGGCCTCCCCGAATGCTGGGATTGCAGGTGTGAGCCACCGCACCTGGCCTCA<br>AGTTGTATTTTAAAATCTTCATAATTAGGCCACACACAGTGACTGACAGCTGTAAT<br>GCCAGCACTTTGGAAGGCCAAGGGCAGGAGAATTGCTTGAGCCCAGGTGTTTGAGA<br>CCACCCTAGGCAGTATAGTGGAGATCTTGCCTCTGTTAAAAAAAAAAAAAAAAAAA<br>AGGCCATGTGCGGGCAGCTGATGCCTGTAATCCCAGCACTTTGGGAGGCCAAGGGG<br>TGGATCACCTGAGGTCAGTAGTTCAAGACCAGCCTGACCAACATGGTGAAACCCTG<br>TCTCTACTAAAAATACAGAATTAGCCAGGTGTGGTGGCAGGCGCCTGTAATCCCAG<br>CTACTTGGGAGACTGAGGCAGAAGAATCACTTGAACCCAGGAGGTGGAGGTTGCAG<br>TGAGCTGAGATCGCACCATTGCACTCCAGCCTGGGCAACAAGAGTGAAACTCCATC<br>TCAAAAGAAAAAAAAAGCGGCTGGGCTCTGTGGCTCATGCTTGTAACCCCAGCAC<br>TTTGGGAGGCCAAGAGGTGGATCACCTGAGGTCAAGAATTTGAGACCAACCTGGCC<br>AACATGGTGAAACCCCATCTGTACTAAACATACAAAAATTAGCCAAGTGTGGTGGC<br>GCACGCCTGTAGTCCCAGAAGGCTGAAGCAGGAGAATTACTTGAACCCTGGGAGGTG</td> | |

TABLE 6-continued

Cas12i and LDHA Sequences

| SEQ ID NO | Sequence | Description |
|---|---|---|
| | GAGGTTGCGGTGAGCTGAGATCGTGCCACTGCACTCCAGCCTGGGCGACAGAGCGA<br>GACTCTGCCTCAAAAAAAAATTAAAAAAAAAAAGCTTTATAATTATAGAGACTGTA<br>AGTCTTGGGAAACCTGGGAATGCATAGACAAAATGTGAGATTTTTTTTTTTTCATT<br>TCATCTTCAGGGTCTTTACGGAATAAAGGATGATGTCTTCCTTAGTGTTCCTTGCA<br>TTTTGGGACAGAATGGAATCTCAGACCTTGTGAAGGTGACTCTGACTTCTGAGGAA<br>GAGGCCCGTTTGAAGAAGAGTGCAGATACACTTTGGGGGATCCAAAAGGAGCTGCA<br>ATTTTAAAGTCTTCTGATGTCATATCATTTCACTGTCTAGGCTACAACAGGATTCT<br>AGGTGGAGGTTGTGCATGTTGTCCTTTTTATCTGATCTGTGATTAAAGCAGTAATA<br>TTTTAAGATGGACTGGGAAAAACATCAACTCCTGAAGTTAGAAATAAGAATGGTTT<br>GTAAAATCCACAGCTATATCCTGATGCTGGATGGTATTAATCTTGTGTAGTCTTCA<br>ACTGGTTAGTGTGAAATAGTTCTGCCACCTCTGACGCACCACTGCCAATGCTGTAC<br>GTACTGCATTTGCCCCTTGAGCCAGGTGGATGTTTACCGTGTGTTATATAACTTCC<br>TGGCTCCTTCACTGAACATGCCTAGTCCAACATTTTTTCCCAGTGAGTCACATCCT<br>GGGATCCAGTGTATAAATCCAATATCATGTCTTGTGCATAATTCTTCCAAAGGATC<br>TTATTTTGTGAACTATATCAGTAGTGTACATTACCATATAATGTAAAAAGATCTAC<br>ATACAAACAATGCAACCAACTATCCAAGTGTTATACCAACTAAAACCCCCAATAAA<br>CCTTGAACAGTGACTACTTTGGTTAATTCATTATATTAAGATATAAAGTCATAAAG<br>CTGCTAGTTATTATATTAATTTGGAAATATTAGGCTATTCTTGGGCAACCCTGCAA<br>CGATTTTTTCTAACAGGGATATTATTGACTAATAGCAGAGGATGTAATAGTCAACT<br>GAGTTGTATTGGTACCACTTCCATTGTAAGTCCCAAAGTATTATATATTTGATAAT<br>AATGCTAATCATAATTGGAAAGTAACATTCTATATGTAAATGTAAAATTTATTTGC<br>CAACTGAATATAGGCAATGATAGTGTGTCACTATAGGGAACACAGATTTTTGAGAT<br>CTTGTCCTCTGGAAGCTGGTAACAATTAAAAACAATCTTAAGGCAGGGTGCAGTGG<br>CTCATGCCTATAATCCCAGCACTTTGGGAAGCCCAGGTGGGCTGATCACTGGAGGC<br>CAGGAATTGGGGACCAGCCTGGCCAACACAACAAAACCCCATCTGTTAAAAAACA<br>AAACAAACCAAAAAAAACAAGTAACCTTGGTGGATGTCTACTCAAGTTTTCTGCA<br>CATTTTTCTGAAAATACAACTGTGACCCTTA | |
| 1173 | GTGCTGCAGCCGCTGCCGCCGATTCCGGATCTCATTGCCACGCGCCCCCGACGACC<br>GCCCGACGTGCATTCCCGGTACGGTAGGGCCCTGCGCGCACGGCGCCAGAGGGATG<br>GGGGGGTAGAGC | LDHA<br>exon 1 |
| 1174 | CCAGCAATTAGTCTGATTTCCGCCCACCTTTCCGAGCGGGAAGGAGAGCCACAAAG<br>CGCGCATGCGCGCGGATCACCGCAGGCTCCTGTGCCTTGGGCTTGAGCTTTGTGGC<br>AGTTAATGGCTTTTCTGCACGTATCTCTGGTGTTTACTTGAGAAGCCTGGCTGTGT<br>CCTTGCTGTAGGAGCCGGAGTAGCTCAGAGTGATCTTGTCTGAGGAAAGGCCAGCC<br>CCACTTGGGGTTAATAAACCGCGATGGGTGAACCCTCAGGAGGCTATACTTACACC<br>CAAACGTCGATATTCCTTTTCCACGCTAAGGTATGGGCCTTCACTCTTCACAGACC<br>CTGTCATTAGGCCT | LDHA<br>exon 2 |
| 1175 | AATAAACATTAAAGAAGCTGTAGTGACACTAAATGTTTTTCCTCCTATAGATTCCT<br>TTTGGTTCCAAGTCCAATATGGCAACTCTAAAGGATCAGCTGATTTATAATCTTCT<br>AAAGGAAGAACAGACCCCCCAGAATAAGATTACAGTTGTTGGGGTTGGTGCTGTTG<br>GCATGGCCTGTGCCATCAGTATCTTAATGAAGGTAAGTGAGAGTCTACCACACTGG<br>AAGCCCATACCTTGACCCCATCCTCT | LDHA<br>exon 3 |
| 1176 | AATCTAGAAGTGGCAATTTTCCATTTAACTAAAGATTTGATGTCTTTTAGGACTTG<br>GCAGATGAACTTGCTCTTGTTGATGTCATCGAAGACAAATTGAAGGGAGAGATGAT<br>GGATCTCCAACATGGCAGCCTTTTCCTTAGAACACCAAAGATTGTCTCTGGCAAAG<br>GTTGATTTCAACAAGTTTATATTATAATCCATGCTTGACTTAAATTCTTT | LDHA<br>exon 4 |
| 1177 | AAAATTTATTCTAAAGGCCTTAATCTGGTCATTATTCCCCTTTTCTCTAGACTATA<br>ATGTAACTGCAAACTCCAAGCTGGTCATTATCACGGCTGGGGCACGTCAGCAAGAG<br>GGAGAAAGCCGTCTTAATTTGGTCCAGCGTAACGTGAACATCTTTAAATTCATCAT<br>TCCTAATGTTGTAAAATACAGCCCGAACTGCAAGTTGCTTATTGTTTCAAATCCAG<br>GTGAGGCTTTTGACTGCATAAAAATTGACAAGCTATAGTAAAACTGATAG | LDHA<br>exon 5 |
| 1178 | GTGTGTAGGGAGAGGATAATGGGTGATTTTTATTTTCTCCTTTTTCATAGTGGATA<br>TCTTGACCTACGTGGCTTGGAAGATAAGTGGTTTTCCCAAAAACCGTGTTATTGGA<br>AGCGGTTGCAATCTGGATTCAGCCCGATTCCGTTACCTAATGGGGGAAAGGCTGGG<br>AGTTCACCCATTAAGCTGTCATGGGTGGGTCCTTGGGGAACATGGAGATTCCAGTG<br>GTAAGCATAAGTTATTTTCTTTTTGTTTTTGAAAAGATTATATAAAAAGT | LDHA<br>exon 6 |
| 1179 | CTAATCTGTTGGTACATGAAAATAAATGTAGTCTGTACTATTTCTTTTAGTGCCTG<br>TATGGAGTGGAATGAATGTTGCTGGTGTCTCTCTGAAGACTCTGCACCCAGATTTA<br>GGGACTGATAAAGATAAGGAACAGTGGAAAGAGGTTCACAAGCAGGTGGTTGAGAG<br>GTAATAAATCTTTCAATTTGGCAACACAGAATATTAACATTTACTATTTT | LDHA<br>exon 7 |
| 1180 | TTCTCCCACCCTGCTTTTTCTGCCTTTACCTATGGTTTCCTATCATACAGTGCTTA<br>TGAGGTGATCAAACTCAAAGGCTACACATCCTGGGCTATTGGACTCTCTGTAGCAG<br>ATTTGGCAGAGAGTATAATGAAGAATCTTAGGCGGGTGCACCCAGTTTCCACCATG<br>ATTAAGGTAGGTCTATGTAGTGATACGCTGCATTTGAATGCTTTTTGCTGGCTTTT | LDHA<br>exon 8 |

TABLE 6-continued

Cas12i and LDHA Sequences

| SEQ ID NO | Sequence | Description |
|---|---|---|
| 1181 | GGAATGCATAGACAAAATGTGAGATTTTTTTTTTTCATTTCATCTTCAGGGTCTT<br>TACGGAATAAAGGATGATGTCTTCCTTAGTGTTCCTTGCATTTTGGGACAGAATGG<br>AATCTCAGACCTTGTGAAGGTGACTCTGACTTCTGAGGAAGAGGCCCGTTTGAAGA<br>AGAGTGCAGATACACTTTGGGGGATCCAAAAGGAGCTGCAATTTTAAAGTCTTCTG<br>ATGTCATATCATTTCACTGTCTAGGCTACAACAGGATTCTAGGTGGAGGTTGTGCA<br>TGTTGTCCTTTTTATCTGATCTGTGATTAAAGCAGTAATATTTTAAGATGGACTGG<br>GAAAAACATCAACTCCTGAAGTTAGAAATAAGAATGGTTTGTAAAATCCACAGCTA<br>TATCCTGATGCTGGATGGTATTAATCTTGTGTAGTCTTCAACTGGTTAGTGTGAAA<br>TAGTTCTGCCACCTCTGACGCACCACTGCCAATGCTGTACGTACTGCATTTGCCCC<br>TTGAGCCAGGTGGATGTTTACCGTGTGTTATATAACTTCCTGGCTCCTTCACTGAA<br>CATGCCTAGTCCAACATTTTTTCCCAGTGAGTCACATCCTGGGATCCAGTGTATAA<br>ATCCAATATCATGTCTTGTGCATAATTCTTCCAAAGGATCTTATTTTGTGAACTAT<br>ATCAGTAGTGTACATTACCATATAATGTAAAAGATCTACATACAAACAATGCAAC<br>CAACTATCCAAGTGTTATACCAACTAAAACCCCCAATAAACCTTGAACAGTGACTA<br>CTTTGGTTAATTCATTATATTAAGATATAAAGTCATAAAGCTGCTAGTTATTATAT<br>TAATTTGGAAATATTAGGCTATTCTTGGGCAACCCTGCAACGATTTTTTCTAACAG<br>GGATATTATTGACTAATAGCAGAGGATGTAATAGTCAACTGAGTTGTATTGGTACC<br>ACTTCCATTGTAAGTCCCAAAGTATTATATATTTGATAATAATGCTAATCATAATT<br>GGAAAGTAACATTCTATATGTAAATGTAAAATTTATTTGCCAACTGAATATAGGCA<br>ATGATAGTGTGTCACTATAGGGAACACAGATTTTTGAGATCTTGTCCTCTGGAAGC<br>TGGTAACAATTAAAAACAATCTTAAGGCAGGGTGCAGTGGCTCATGCCTATAATCC<br>CAGCACTTTGGGAAGCCCAGGTGGGCTGATCACTGGAGGCCAGGAATTGGGGACCA<br>GCCTGGCCAACACAACAAAACCCCATCTGTTAAAAAAACAAAACAAAACCAAAAAA<br>AACAAGTAACCTTGGTGGATGTCTACTCAAGTTTTCTGCACATTTTTCTGAAAATA<br>CAACTGTGACCCTTA | LDHA<br>exon 9 |
| 1211 | MSNKEKNASETRKAYTTKMIPRSHDRMKLLGNFMDYLMDGTPIFFELWNQFGGGID<br>RDIISGTANKDKISDDLLLAVNWFKVMPINSKPQGVSPSNLANLFQQYSGSEPDIQ<br>AQEYFASNFDTEKHQWKDMRVEYERLLAELQLSRSDMHHDLKLMYKEKCIGLSLST<br>AHYITSVMFGTGAKNNRQTKHQFYSKVIQLLEESTQINSVEQLASIILKAGDCDSY<br>RKLRIRCSRKGATPSILKIVQDYELGTNHDDEVNVPSLIANLKEKLGRFEYECEWK<br>CMEKIKAFLASKVGPYYLGSYSAMLENALSPIKGMTTKNCKFVLKQIDAKNDIKYE<br>NEPFGKIVEGFFDSPYFESDTNVKWVLHPHHIGESNIKTLWEDLNAIHSKYEEDIA<br>SLSEDKKEKRIKVYQGDVCQTINTYCEEVGKEAKTPLVQLLRYLYSRKDDIAVDKI<br>IDGITFLSKKHKVEKQKINPVIQKYPSFNFGNNSKLLGKIISPKDKLKHNLKCNRN<br>QVDNYIWIEIKVLNTKTMRWEKHHYALSSTRFLEEVYYPATSENPPDALAARFRTK<br>TNGYEGKPALSAEQIEQIRSAPVGLRKVKKRQMRLEAARQQNLLPRYTWGKDFNIN<br>ICKRGNNFEVTLATKVKKKKEKNYKVVLGYDANIVRKNTYAAIEAHANGDGVIDYN<br>DLPVKPIESGFVTVESQVRDKSYDQLSYNGVKLLYCKPHVESRRSFLEKYRNGTMK<br>DNRGNNIQIDFMKDFEAIADDETSLYYFNMKYCKLLQSSIRNHSSQAKEYREEIFE<br>LLRDGKLSVLKLSSLSNLSFVMFKVAKSLIGTYFGHLLKKPKNSKSDVKAPPITDE<br>DKQKADPEMFALRLALEEKRLNKVKSKKEVIANKIVAKALELRDKYGPVLIKGENI<br>SDTTKKGKKSSTNSFLMDWLARGVANKVKEMVMMHQGLEFVEVNPNFTSHQDPFVH<br>KNPENTFRARYSRCTPSELTEKNRKEILSFLSDKPSKRPTNAYYNEGAMAFLATYG<br>LKKNDVLGVSLEKFKQIMANILHQRSEDQLLFPSRGGMFYLATYKLDADATSVNWN<br>GKQFWVCNADLVAAYNVGLVDIQKDFKKK | (Cas12i1 of<br>SEQ ID<br>NO: 3 of<br>U.S. Pat.<br>No.<br>10,808,245) |
| 1212 | MSISNNNILPYNPKLLPDDRKHKMLVDTFNQLDLIRNNLHDMIIALYGALKYDNIK<br>QFASKEKPHISADALCSINWFRLVKTNERKPAIESNQIISKFIQYSGHTPDKYALS<br>HITGNHEPSHKWIDCREYAINYARIMHLSFSQFQDLATACLNCKILILNGTLTSSW<br>AWGANSALFGGSDKENFSVKAKILNSFIENLKDEMNTTKFQVVEKVCQQIGSSDAA<br>DLFDLYRSTVKDGNRGPATGRNPKVMNLFSQDGEISSEQREDFIESFQKVMQEKNS<br>KQIIPHLDKLKYHLVKQSGLYDIYSWAAAIKNANSTIVASNSSNLNTILNKTEKQQ<br>TFEELRKDEKIVACSKILLSVNDTLPEDLHYNPSTSNLGKNLDVFFDLLNENSVHT<br>IENKEEKNKIVKECVNQYMEECKGLNKPPMPVLLTFISDYAHKHQAQDFLSAAKMN<br>FIDLKIKSIKVVPTVHGSSPYTWISNLSKKNKDGKMIRTPNSSLIGWIIPPEEIHD<br>QKFAGQNPIIWAVLRVYCNNKWEMHHFPFSDSRFFTEVYAYKPNLPYLPGGENRSK<br>RFGYRHSTNLSNESRQILLDKSKYAKANKSVLRCMENMTHNVVFDPKTSLNIRIKT<br>DKNNSPVLDDKGRITFVMQINHRILEKYNNTKIEIGDRILAYDQNQSENHTYAILQ<br>RTEEGSHAHQFNGWYVRVLETGKVTSIVQGLSGPIDQLNYDGMPVTSHKFNCWQAD<br>RSAFVSQFASLKISETETFDEAYQAINAQGAYTWNLFYLRILRKALRVCHMENINQ<br>FREEILAISKNRLSPMSLGSLSQNSLKMIRAFKSIIINCYMSRMSFVDELQKKEGDL<br>ELHTIMRLTDNKLNDKRVEKINRASSFLTNKAHSMGCKMIVGESDLPVADSKTSKK<br>QNVDRMDWCARALSHKVEYACKLMGLAYRGIPAYMSSHQDPLVHLVESKRSVLRPR<br>FVVADKSDVKQHHLDNLRRMLNSKTKVGTAVYYREAVELMCEELGIHKTDMAKGKV<br>SLSDFVDKFIGEKAIFPQRGGRFYMSTKRLTTGAKLICYSGSDVWLSDADEIAAIN<br>IGMFVVCDQTGAFKKKKKEKLDDEECDILPFRPM | (Cas12i3 of<br>SEQ ID<br>NO: 14 of<br>U.S. Pat.<br>No.<br>10,808,245) |
| 1230 | ATGGCAACTCTAAAGGATCAGCTGATTTATAATCTTCTAAAGGAAGAACAGACCCC<br>CCAGAATAAGATTACAGTTGTTGGGGTTGGTGCTGTTGGCATGGCCTGTGCCATCA<br>GTATCTTAATGAAGGACTTGGCAGATGAACTTGCTCTTGTTGATGTCATCGAAGAC<br>AAATTGAAGGGAGAGATGATGGATCTCCAACATGGCAGCCTTTTCCTTAGAACACC<br>AAAGATTGTCTCTGGCAAAGACTATAATGTAACTGCAAACTCCAAGCTGGTCATTA<br>TCACGGCTGGGGCACGTCAGCAAGAGGGAGAAAGCCGTCTTAATTTGGTCCAGCGT | LDHA<br>isoform 1<br>cDNA |

TABLE 6-continued

Cas12i and LDHA Sequences

| SEQ ID NO | Sequence | Description |
|---|---|---|
| | AACGTGAACATCTTTAAATTCATCATTCCTAATGTTGTAAAATACAGCCCGAACTG<br>CAAGTTGCTTATTGTTTCAAATCCAGTGGATATCTTGACCTACGTGGCTTGGAAGA<br>TAAGTGGTTTTCCCAAAAACCGTGTTATTGGAAGCGGTTGCAATCTGGATTCAGCC<br>CGATTCCGTTACCTAATGGGGGAAAGGCTGGGAGTTCACCCATTAAGCTGTCATGG<br>GTGGGTCCTTGGGGAACATGGAGATTCCAGTGTGCCTGTATGGAGTGGAATGAATG<br>TTGCTGGTGTCTCTCTGAAGACTCTGCACCCAGATTTAGGGACTGATAAAGATAAG<br>GAACAGTGGAAAGAGGTTCACAAGCAGGTGGTTGAGAGTGCTTATGAGGTGATCAA<br>ACTCAAAGGCTACACATCCTGGGCTATTGGACTCTCTGTAGCAGATTTGGCAGAGA<br>GTATAATGAAGAATCTTAGGCGGGTGCACCCAGTTTCCACCATGATTAAGGGTCTT<br>TACGGAATAAAGGATGATGTCTTCCTTAGTGTTCCTTGCATTTTGGGACAGAATGG<br>AATCTCAGACCTTGTGAAGGTGACTCTGACTTCTGAGGAAGAGGCCCGTTTGAAGA<br>AGAGTGCAGATACACTTTGGGGGATCCAAAAGGAGCTGCAATTTTAA | |
| 1231 | ATGGCAACTCTAAAGGATCAGCTGATTTATAATCTTCTAAAGGAAGAACAGACCCC<br>CCAGAATAAGATTACAGTTGTTGGGGTTGGTGCTGTTGGCATGGCCTGTGCCATCA<br>GTATCTTAATGAAGGACTTGGCAGATGAACTTGCTCTTGTTGATGTCATCGAAGAC<br>AAATTGAAGGGAGAGATGATGGATCTCCAACATGGCAGCCTTTTCCTTAGAACACC<br>AAAGATTGTCTCTGGCAAAGTGGATATCTTGACCTACGTGGCTTGGAAGATAAGTG<br>GTTTTCCCAAAAACCGTGTTATTGGAAGCGGTTGCAATCTGGATTCAGCCCGATTC<br>CGTTACCTAATGGGGGAAAGGCTGGGAGTTCACCCATTAAGCTGTCATGGGTGGGT<br>CCTTGGGGAACATGGAGATTCCAGTGTGCCTGTATGGAGTGGAATGAATGTTGCTG<br>GTGTCTCTCTGAAGACTCTGCACCCAGATTTAGGGACTGATAAAGATAAGGAACAG<br>TGGAAAGAGGTTCACAAGCAGGTGGTTGAGAGTGCTTATGAGGTGATCAAACTCAA<br>AGGCTACACATCCTGGGCTATTGGACTCTCTGTAGCAGATTTGGCAGAGAGTATAA<br>TGAAGAATCTTAGGCGGGTGCACCCAGTTTCCACCATGATTAAGGGTCTTTACGGA<br>ATAAAGGATGATGTCTTCCTTAGTGTTCCTTGCATTTTGGGACAGAATGGAATCTC<br>AGACCTTGTGAAGGTGACTCTGACTTCTGAGGAAGAGGCCCGTTTGAAGAAGAGTG<br>CAGATACACTTTGGGGATCCAAAAGGAGCTGCAATTTTAA | LDHA<br>isoform 2<br>cDNA |
| 1232 | ATGGGTGAACCCTCAGGAGGCTATACTTACACCCAAACGTCGATATTCCTTTTCCA<br>CGCTAAGATTCCTTTTGGTTCCAAGTCCAATATGGCAACTCTAAAGGATCAGCTGA<br>TTTATAATCTTCTAAAGGAAGAACAGACCCCCCAGAATAAGATTACAGTTGTTGGG<br>GTTGGTGCTGTTGGCATGGCCTGTGCCATCAGTATCTTAATGAAGGACTTGGCAGA<br>TGAACTTGCTCTTGTTGATGTCATCGAAGACAAATTGAAGGGAGAGATGATGGATC<br>TCCAACATGGCAGCCTTTTCCTTAGAACACCAAAGATTGTCTCTGGCAAAGACTAT<br>AATGTAACTGCAAACTCCAAGCTGGTCATTATCACGGCTGGGGCACGTCAGCAAGA<br>GGGAGAAAGCCGTCTTAATTTGGTCCAGCGTAACGTGAACATCTTTAAATTCATCA<br>TTCCTAATGTTGTAAAATACAGCCCGAACTGCAAGTTGCTTATTGTTTCAAATCCA<br>GTGGATATCTTGACCTACGTGGCTTGGAAGATAAGTGGTTTTCCCAAAAACCGTGT<br>TATTGGAAGCGGTTGCAATCTGGATTCAGCCCGATTCCGTTACCTAATGGGGGAAA<br>GGCTGGGAGTTCACCCATTAAGCTGTCATGGGTGGGTCCTTGGGGAACATGGAGAT<br>TCCAGTGTGCCTGTATGGAGTGGAATGAATGTTGCTGGTGTCTCTCTGAAGACTCT<br>GCACCCAGATTTAGGGACTGATAAAGATAAGGAACAGTGGAAAGAGGTTCACAAGC<br>AGGTGGTTGAGAGTGCTTATGAGGTGATCAAACTCAAAGGCTACACATCCTGGGCT<br>ATTGGACTCTCTGTAGCAGATTTGGCAGAGAGTATAATGAAGAATCTTAGGCGGGT<br>GCACCCAGTTTCCACCATGATTAAGGGTCTTTACGGAATAAAGGATGATGTCTTCC<br>TTAGTGTTCCTTGCATTTTGGGACAGAATGGAATCTCAGACCTTGTGAAGGTGACT<br>CTGACTTCTGAGGAAGAGGCCCGTTTGAAGAAGAGTGCAGATACACTTTGGGGGAT<br>CCAAAAGGAGCTGCAATTTTAA | LDHA<br>isoform 3<br>cDNA |
| 1233 | ATGGCAACTCTAAAGGATCAGCTGATTTATAATCTTCTAAAGGAAGAACAGACCCC<br>CCAGAATAAGATTACAGTTGTTGGGGTTGGTGCTGTTGGCATGGCCTGTGCCATCA<br>GTATCTTAATGAAGGACTTGGCAGATGAACTTGCTCTTGTTGATGTCATCGAAGAC<br>AAATTGAAGGGAGAGATGATGGATCTCCAACATGGCAGCCTTTTCCTTAGAACACC<br>AAAGATTGTCTCTGGCAAAGACTATAATGTAACTGCAAACTCCAAGCTGGTCATTA<br>TCACGGCTGGGGCACGTCAGCAAGAGGGAGAAAGCCGTCTTAATTTGGTCCAGCGT<br>AACGTGAACATCTTTAAATTCATCATTCCTAATGTTGTAAAATACAGCCCGAACTG<br>CAAGTTGCTTATTGTTTCAAATCCAGTGGATATCTTGACCTACGTGGCTTGGAAGA<br>TAAGTGGTTTTCCCAAAAACCGTGTTATTGGAAGCGGTTGCAATCTGGATTCAGCC<br>CGATTCCGTTACCTAATGGGGGAAAGGCTGGGAGTTCACCCATTAAGCTGTCATGG<br>GTGGGTCCTTGGGGAACATGGAGATTCCAGTGTGCCTGTATGGAGTGGAATGAATG<br>TTGCTGGTGTCTCTCTGAAGACTCTGCACCCAGATTTAGGGACTGATAAAGATAAG<br>GAACAGTGGAAAGAGTGCAGATACACTTTGGGGGATCCAAAAGGAGCTGCAATTTT<br>AAAGTCTTCTGATGTCATATCATTTCACTGTCTAGGCTACAACAGGATTCTAGGTG<br>GAGGTTGTGCATGTTGTCCTTTTTATCTGATCTGTGATTAA | LDHA<br>isoform 4<br>cDNA |
| 1234 | ATGGCAACTCTAAAGGATCAGCTGATTTATAATCTTCTAAAGGAAGAACAGACCCC<br>CCAGAATAAGATTACAGTTGTTGGGGTTGGTGCTGTTGGCATGGCCTGTGCCATCA<br>GTATCTTAATGAAGGACTTGGCAGATGAACTTGCTCTTGTTGATGTCATCGAAGAC<br>AAATTGAAGGGAGAGATGATGGATCTCCAACATGGCAGCCTTTTCCTTAGAACACC<br>AAAGATTGTCTCTGGCAAAGACTATAATGTAACTGCAAACTCCAAGCTGGTCATTA<br>TCACGGCTGGGGCACGTCAGCAAGAGGGAGAAAGCCGTCTTAATTTGGTCCAGCGT<br>AACGTGAACATCTTTAAATTCATCATTCCTAATGTTGTAAAATACAGCCCGAACTG<br>CAAGTTGCTTATTGTTTCAAATCCAGTGGATATCTTGACCTACGTGGCTTGGAAGA<br>TAAGTGGTTTTCCCAAAAACCGTGTTATTGGAAGCGGTTGCAATCTGGATTCAGCC | LDHA<br>isoform 4<br>cDNA |

TABLE 6-continued

Cas12i and LDHA Sequences

| SEQ ID NO | Sequence | Description |
|---|---|---|
| | CGATTCCGTTACCTAATGGGGGAAAGGCTGGGAGTTCACCCATTAAGCTGTCATGG GTGGGTCCTTGGGGAACATGGAGATTCCAGTGTGCCTGTATGGAGTGGAATGAATG TTGCTGGTGTCTCTCTGAAGACTCTGCACCCAGATTTAGGGACTGATAAAGATAAG GAACAGTGGAAAGAGGTTCACAAGCAGGTGGTTGAGAGGGTCTTTACGGAATAA | |
| 1254 | rArGrArArArUrCrCrGrUrCrUrUrUrCrArUrGrArCrGrGrUrArGrGrArCrUrGrGrCrArGrArUrGmA*mA*mC*rU | 3' end modified RNA guide targeting LDHA sequence of SEQ ID NO: 1237 |
| 1255 | mA*mG*mA*rArArUrCrCrGrUrCrUrUrUrCrArUrGrArCrGrGrUrArGrGrArCrUrGrGrCrArGrArUrGmA*mA*mC*rU | 5' and 3' end modified RNA guide targeting LDHA sequence of SEQ ID NO: 1237 |
| 1256 | rArGrArArArUrCrCrGrUrCrUrUrUrCrArUrGrArCrGrGrGrArUrGrArCrArUrCrArArCrArArGrAmG*mC*mA*rA | 3' end modified RNA guide targeting LDHA sequence of SEQ ID NO: 1239 |
| 1257 | mA*mG*mA*rArArUrCrCrGrUrCrUrUrUrCrArUrGrArCrGrGrGrArUrGrArCrArUrCrArArCrArArGrAmG*mC*mA*rA | 5' and 3' end modified RNA guide targeting LDHA sequence of SEQ ID NO: 1239 |
| 1258 | rArGrArArArUrCrCrGrUrCrUrUrUrCrArUrGrArCrGrGrUrCrArUrArGrUrGrArUrArUrCrUrUmG*mA*mC*rC | 3' end modified RNA guide targeting LDHA sequence of SEQ ID NO: 1248 |
| 1259 | mA*mG*mA*rArArUrCrCrGrUrCrUrUrUrCrArUrGrArCrGrGrUrCrArUrArGrUrGrArUrArUrCrUrUmG*mA*mC*rC | 5' and 3' end modified RNA guide targeting LDHA sequence of SEQ ID NO: 1248 |
| 1260 | rArGrArArArUrCrCrGrUrCrUrUrUrCrArUrGrArCrGrGrUrCrArUrUrArGrUrGrGrArUrArUrCrUmU*mG*mA*rC | 3' end modified RNA guide targeting LDHA sequence of SEQ ID NO: 1245 |
| 1261 | mA*mG*mA*rArArUrCrCrGrUrCrUrUrUrCrArUrGrArCrGrGrUrUrCrArUrArGrUrGrGrArUrArUrCrUmU*mG*mA*rC | 5' and 3' end modified RNA guide |

TABLE 6-continued

Cas12i and LDHA Sequences

| SEQ ID NO | Sequence | Description |
|---|---|---|
| | | targeting LDHA sequence of SEQ ID NO: 1245 |
| 1262 | rArGrArArArUrCrCrGrUrCrUrUrUrCrArUrGrArCrGrGrCrArUrArG rUrGrGrArUrArUrCrUrUrGmA*mC*mC*rU | 3' end modified RNA guide targeting LDHA sequence of SEQ ID NO: 1249 |
| 1263 | mA*mG*mA*rArArUrCrCrGrUrCrUrUrUrCrArUrUrGrArCrGrGrCrArUr ArGrUrGrGrArUrArUrCrUrUrGmA*mC*mC*rU | 5' and 3' end modified RNA guide targeting LDHA sequence of SEQ ID NO: 1249 |

In some embodiments, the gene editing system disclosed herein may comprise a Cas12i polypeptide as disclosed herein. In other embodiments, the gene editing system may comprise a nucleic acid encoding the Cas12i polypeptide. For example, the gene editing system may comprise a vector (e.g., a viral vector such as an AAV vector, such as AAV1, AAV2, AAV3, AAV4, AAV5, AAV6, AAV7, AAV8, AAV9, AAVrh10, AAV11 and AAV12) encoding the Cas12i polypeptide. Alternatively, the gene editing system may comprise a mRNA molecule encoding the Cas12i polypeptide. In some instances, the mRNA molecule may be codon-optimized.

II. Preparation of Gene Editing System Components

The present disclosure provides methods for production of components of the gene editing systems disclosed herein, e.g., the RNA guide, methods for production of the Cas12i polypeptide, and methods for complexing the RNA guide and Cas12i polypeptide.

A. RNA Guide

In some embodiments, the RNA guide is made by in vitro transcription of a DNA template. Thus, for example, in some embodiments, the RNA guide is generated by in vitro transcription of a DNA template encoding the RNA guide using an upstream promoter sequence (e.g., a T7 polymerase promoter sequence).

In some embodiments, the DNA template encodes multiple RNA guides or the in vitro transcription reaction includes multiple different DNA templates, each encoding a different RNA guide. In some embodiments, the RNA guide is made using chemical synthetic methods. In some embodiments, the RNA guide is made by expressing the RNA guide sequence in cells transfected with a plasmid including sequences that encode the RNA guide. In some embodiments, the plasmid encodes multiple different RNA guides. In some embodiments, multiple different plasmids, each encoding a different RNA guide, are transfected into the cells. In some embodiments, the RNA guide is expressed from a plasmid that encodes the RNA guide and also encodes a Cas12i polypeptide. In some embodiments, the RNA guide is expressed from a plasmid that expresses the RNA guide but not a Cas12i polypeptide. In some embodiments, the RNA guide is purchased from a commercial vendor. In some embodiments, the RNA guide is synthesized using one or more modified nucleotide, e.g., as described above.

B. Cas12i Polypeptide

In some embodiments, the Cas12i polypeptide of the present disclosure can be prepared by (a) culturing bacteria which produce the Cas12i polypeptide of the present disclosure, isolating the Cas12i polypeptide, optionally, purifying the Cas12i polypeptide, and complexing the Cas12i polypeptide with an RNA guide. The Cas12i polypeptide can be also prepared by (b) a known genetic engineering technique, specifically, by isolating a gene encoding the Cas12i polypeptide of the present disclosure from bacteria, constructing a recombinant expression vector, and then transferring the vector into an appropriate host cell that expresses the RNA guide for expression of a recombinant protein that complexes with the RNA guide in the host cell. Alternatively, the Cas12i polypeptide can be prepared by (c) an in vitro coupled transcription-translation system and then complexing with an RNA guide.

In some embodiments, a host cell is used to express the Cas12i polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the Cas12i polypeptide. After expression of the Cas12i polypeptide, the host cells can be collected and Cas12i polypeptide purified from the cultures etc. according to conventional methods (for example, filtration, centrifugation, cell disruption, gel filtration chromatography, ion exchange chromatography, etc.).

In some embodiments, the methods for Cas12i polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the Cas12i polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the Cas12i polypeptide.

A variety of methods can be used to determine the level of production of a Cas12i polypeptide in a host cell. Such methods include, but are not limited to, for example, methods that utilize either polyclonal or monoclonal antibodies specific for the Cas12i polypeptide or a labeling tag as described elsewhere herein. Exemplary methods include, but are not limited to, enzyme-linked immunosorbent assays (ELISA), radioimmunoassays (MA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the Cas12i polypeptide in a cell, comprising providing a polyribonucleotide encoding the Cas12i polypeptide to a host cell wherein the polyribonucleotide encodes the Cas12i polypeptide, expressing the Cas12i polypeptide in the cell, and obtaining the Cas12i polypeptide from the cell.

The present disclosure further provides methods of in vivo expression of a Cas12i polypeptide in a cell, comprising providing a polyribonucleotide encoding the Cas12i polypeptide to a host cell wherein the polyribonucleotide encodes the Cas12i polypeptide and expressing the Cas12i polypeptide in the cell. In some embodiments, the polyribonucleotide encoding the Cas12i polypeptide is delivered to the cell with an RNA guide and, once expressed in the cell, the Cas12i polypeptide and the RNA guide form a complex. In some embodiments, the polyribonucleotide encoding the Cas12i polypeptide and the RNA guide are delivered to the cell within a single composition. In some embodiments, the polyribonucleotide encoding the Cas12i polypeptide and the RNA guide are comprised within separate compositions. In some embodiments, the host cell is present in a subject, e.g., a human patient.

C. Complexing

In some embodiments, an RNA guide targeting LDHA is complexed with a Cas12i polypeptide to form a ribonucleoprotein. In some embodiments, complexation of the RNA guide and Cas12i polypeptide occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the RNA guide does not dissociate from the Cas12i polypeptide at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours.

In some embodiments, the RNA guide and Cas12i polypeptide are complexed in a complexation buffer. In some embodiments, the Cas12i polypeptide is stored in a buffer that is replaced with a complexation buffer to form a complex with the RNA guide. In some embodiments, the Cas12i polypeptide is stored in a complexation buffer.

In some embodiments, the complexation buffer has a pH in a range of about 7.3 to 8.6. In one embodiment, the pH of the complexation buffer is about 7.3. In one embodiment, the pH of the complexation buffer is about 7.4. In one embodiment, the pH of the complexation buffer is about 7.5. In one embodiment, the pH of the complexation buffer is about 7.6. In one embodiment, the pH of the complexation buffer is about 7.7. In one embodiment, the pH of the complexation buffer is about 7.8. In one embodiment, the pH of the complexation buffer is about 7.9. In one embodiment, the pH of the complexation buffer is about 8.0. In one embodiment, the pH of the complexation buffer is about 8.1. In one embodiment, the pH of the complexation buffer is about 8.2. In one embodiment, the pH of the complexation buffer is about 8.3. In one embodiment, the pH of the complexation buffer is about 8.4. In one embodiment, the pH of the complexation buffer is about 8.5. In one embodiment, the pH of the complexation buffer is about 8.6.

In some embodiments, the Cas12i polypeptide can be overexpressed and complexed with the RNA guide in a host cell prior to purification as described herein. In some embodiments, mRNA or DNA encoding the Cas12i polypeptide is introduced into a cell so that the Cas12i polypeptide is expressed in the cell. In some embodiments, the RNA guide is also introduced into the cell, whether simultaneously, separately, or sequentially from a single mRNA or DNA construct, such that the ribonucleoprotein complex is formed in the cell.

III. Genetic Editing Methods

The disclosure also provides methods of modifying a target site within the LDHA gene. In some embodiments, the methods comprise introducing an LDHA-targeting RNA guide and a Cas12i polypeptide into a cell. The LDHA-targeting RNA guide and Cas12i polypeptide can be introduced as a ribonucleoprotein complex into a cell. The LDHA-targeting RNA guide and Cas12i polypeptide can be introduced on a nucleic acid vector. The Cas12i polypeptide can be introduced as an mRNA. The RNA guide can be introduced directly into the cell. In some embodiments, the composition described herein is delivered to a cell/tissue/liver/person to reduce LDHA in the cell/tissue/liver/person. In some embodiments, the composition described herein is delivered to a cell/tissue/liver/person to reduce oxalate production in the cell/tissue/liver/person. In some embodiments, the composition described herein is delivered to a cell/tissue/liver/person to correct calcium oxalate crystal deposition in the cell/tissue/liver/person. In some embodiments, the composition described herein is delivered to a person with primary hyperoxaluria.

Any of the gene editing systems disclosed herein may be used to genetically engineered an LDHA gene. The gene editing system may comprise a RNA guide and a Cas12i2 polypeptide. The RNA guide comprises a spacer sequence specific to a target sequence in the LDHA gene, e.g., specific to a region in exon 3 or exon 5 of the LDHA gene.

A. Target Sequence

In some embodiments, an RNA guide as disclosed herein is designed to be complementary to a target sequence that is adjacent to a 5'-TTN-3' PAM sequence or 5'-NTTN-3' PAM sequence.

In some embodiments, the target sequence is within an LDHA gene or a locus of an LDHA gene (e.g., exon 3 or exon 5), to which the RNA guide can bind via base pairing. In some embodiments, a cell has only one copy of the target sequence. In some embodiments, a cell has more than one copy, such as at least about any one of 2, 3, 4, 5, 10, 100, or more copies of the target sequence.

In some embodiments, the LDHA gene is a mammalian gene. In some embodiments, the LDHA gene is a human gene. For example, in some embodiments, the target sequence is within the sequence of SEQ ID NO: 1172 (or the reverse complement thereof). In some embodiments, the target sequence is within an exon of the LDHA gene set forth in SEQ ID NO: 1172, e.g., within a sequence of SEQ ID NO: 1173, 1174, 1175, 1176, 1177, 1178, 1179, 1180, or 1181 (or a reverse complement thereof). Target sequences within an exon region of the LDHA gene of SEQ ID NO: 1172 are set forth in Table 5. In some embodiments, the target sequence is within an intron of the LDHA gene set forth in SEQ ID NO: 1172 (or the reverse complement thereof). In some embodiments, the target sequence is within a variant (e.g., a polymorphic variant) of the LDHA gene sequence set forth in SEQ ID NO: 1172 (or the reverse complement thereof). In some embodiments, the LDHA gene sequence is a homolog of the sequence set forth in SEQ ID NO: 1172 (or the reverse complement thereof). For examples, in some embodiments, the LDHA gene sequence is a non-human LDHA sequence. In some embodiments, the LDHA gene sequence is a coding sequence set forth in any one of SEQ ID NOs: 1230-1234 (or the reverse complement thereof). In some embodiments, the LDHA gene sequence is a homolog of a coding sequence set forth in any one of SEQ ID NOs: 1230-1234 (or the reverse complement thereof).

In some embodiments, the target sequence is adjacent to a 5'-NTTN-3' PAM sequence or 5'-TTN-3' PAM sequence, wherein N is any nucleotide. The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5'-NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. The PAM sequence may be 5' to the target sequence.

The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5'-NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. In some embodiments, the RNA guide is designed to bind to a first strand of a double-stranded target nucleic acid (i.e., the non-PAM strand), and the 5'-NTTN-3' PAM sequence is present in the second, complementary strand (i.e., the PAM strand). In some embodiments, the RNA guide binds to a region on the non-PAM strand that is complementary to a target sequence on the PAM strand, which is adjacent to a 5'-NAAN-3' sequence.

In some embodiments, the target sequence is present in a cell. In some embodiments, the target sequence is present in the nucleus of the cell. In some embodiments, the target sequence is endogenous to the cell. In some embodiments, the target sequence is a genomic DNA. In some embodiments, the target sequence is a chromosomal DNA. In some embodiments, the target sequence is a protein-coding gene or a functional region thereof, such as a coding region, or a regulatory element, such as a promoter, enhancer, a 5' or 3' untranslated region, etc.

In some embodiments, the target sequence is present in a readily accessible region of the target sequence. In some embodiments, the target sequence is in an exon of a target gene. In some embodiments, the target sequence is across an exon-intron junction of a target gene. In some embodiments, the target sequence is present in a non-coding region, such as a regulatory region of a gene.

B. Gene Editing

In some embodiments, the Cas12i polypeptide has enzymatic activity (e.g., nuclease activity). In some embodiments, the Cas12i polypeptide induces one or more DNA double-stranded breaks in the cell. In some embodiments, the Cas12i polypeptide induces one or more DNA single-stranded breaks in the cell. In some embodiments, the Cas12i polypeptide induces one or more DNA nicks in the cell. In some embodiments, DNA breaks and/or nicks result in formation of one or more indels (e.g., one or more deletions).

In some embodiments, an RNA guide disclosed herein forms a complex with the Cas12i polypeptide and directs the Cas12i polypeptide to a target sequence adjacent to a 5'-NTTN-3' sequence. In some embodiments, the complex induces a deletion (e.g., a nucleotide deletion or DNA deletion) adjacent to the 5'-NTTN-3' sequence. In some embodiments, the complex induces a deletion adjacent to a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the complex induces a deletion adjacent to a T/C-rich sequence.

In some embodiments, the deletion is downstream of a 5'-NTTN-3' sequence. In some embodiments, the deletion is downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion is downstream of a T/C-rich sequence.

In some embodiments, the deletion alters expression of the LDHA gene. In some embodiments, the deletion alters function of the LDHA gene. In some embodiments, the deletion inactivates the LDHA gene. In some embodiments, the deletion is a frameshifting deletion. In some embodiments, the deletion is a non-frameshifting deletion. In some embodiments, the deletion leads to cell toxicity or cell death (e.g., apoptosis).

In some embodiments, the deletion starts within about 5 to about 15 nucleotides (e.g., about 3, 4, 5, 6, 7, 8, 9, 10, 11, 12, 13, 14, 15, 16, or 17 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence.

In some embodiments, the deletion starts within about 5 to about 10 nucleotides (e.g., about 3, 4, 5, 6, 7, 8, 9, 10, 11, or 12 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence.

In some embodiments, the deletion starts within about 10 to about 15 nucleotides (e.g., about 8, 9, 10, 11, 12, 13, 14, 15, 16, or 17 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) downstream of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) downstream of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides and ends within about 20 to about 25 nucleotides (e.g., about 17, 18, 19, 20, 21, 22, 23, 24, 25, 26, 27, or 28 nucleotides) (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion is up to about 40 nucleotides in length (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 40 nucleotides in length (e.g., about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 25 nucleotides in length (e.g., about 3, 4, 5, 6, 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 25 nucleotides in length (e.g., about 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 15 nucleotides in length (e.g., about 7, 8, 9, 10, 11, 12, 13, 14, 15, 16, or 17 nucleotides).

In some embodiments, the methods described herein are used to engineer a cell comprising a deletion as described herein in an LDHA gene. In some embodiments, the methods are carried out using a complex comprising a Cas12i enzyme as described herein and an RNA guide comprising a direct repeat and a spacer as described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 1213-1229. In some embodiments, an RNA guide has a sequence of any one of SEQ ID NOs: 1213-1229. In some embodiments, the RNA guide targeting LDHA is encoded in a plasmid. In some embodiments, the RNA guide targeting LDHA is synthetic or purified RNA. In some embodiments, the Cas12i polypeptide is encoded in a plasmid. In some embodiments, the Cas12i polypeptide is encoded by an RNA that is synthetic or purified.

C. Delivery

Components of any of the gene editing systems disclosed herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, adeno-associated virus (AAV)), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the Cas12i polypeptide, RNA guide, donor DNA, etc.), one or more transcripts thereof, and/or a pre-formed RNA guide/Cas12i polypeptide complex to a cell, where a ternary complex is formed. In some embodiments, an RNA guide and an RNA encoding a Cas12i polypeptide are delivered together in a single composition. In some embodiments, an RNA guide and an RNA encoding a Cas12i polypeptide are delivered in separate compositions. In some embodiments, an RNA guide and an RNA encoding a Cas12i polypeptide delivered in separate compositions are delivered using the same delivery technology. In some embodiments, an RNA guide and an RNA encoding a Cas12i polypeptide delivered in separate compositions are delivered using different delivery technologies. Exemplary intracellular delivery methods, include, but are not limited to: viruses, such as AAV, or virus-like agents; chemical-based transfection methods, such as those using calcium phosphate, dendrimers, liposomes, lipid nanoparticles, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnectofection or magnet assisted transfection, particle bombardment; and hybrid methods, such as nucleofection. In some embodiments, a lipid nanoparticle comprises an mRNA encoding a Cas12i polypeptide, an RNA guide, or an mRNA encoding a Cas12i polypeptide and an RNA guide. In some embodiments, the mRNA encoding the Cas12i polypeptide is a transcript of the nucleotide sequence set forth in SEQ ID NO: 1165 or SEQ ID NO: 1201 or a variant thereof. In some embodiments, the present application further provides cells produced by such methods, and organisms (such as animals, plants, or fungi) comprising or produced from such cells.

D. Genetically Modified Cells

Any of the gene editing systems disclosed herein can be delivered to a variety of cells. In some embodiments, the cell is an isolated cell. In some embodiments, the cell is in cell culture or a co-culture of two or more cell types. In some embodiments, the cell is ex vivo. In some embodiments, the cell is obtained from a living organism and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the cell is an archaeal cell or derived from an archaeal cell.

In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, CHO, and transgenic varieties thereof. Cell lines are available from a variety of sources known to those with skill in the art (see, e.g., the American Type Culture Collection (ATCC) (Manassas, Va.)). In some embodiments, the cell is an immortal or immortalized cell.

In some embodiments, the cell is a primary cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a differentiated cell. For example, in some embodiments, the differentiated cell is a liver cell (e.g., a hepatocyte), a biliary cell (e.g., a cholangiocyte), a stellate cell, a Kupffer cell, a liver sinusoidal endothelial cell, a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is an immune cell. In some embodiments, the immune cell is a T cell. In some embodiments, the immune cell is a B cell. In some embodiments, the immune cell is a Natural Killer (NK) cell. In some embodiments, the immune cell is a Tumor Infiltrating Lymphocyte (TIL). In some embodiments, the cell is a mammalian cell, e.g., a human cell or a murine cell. In some embodiments, the murine cell is derived from a wild-type mouse, an immunosuppressed mouse, or a disease-specific mouse model. In some embodiments, the cell is a cell within a living tissue, organ, or organism.

Any of the genetically modified cells produced using any of the gene editing system disclosed herein is also within the scope of the present disclosure. Such modified cells may comprise a disrupted LDHA gene.

Compositions, vectors, nucleic acids, RNA guides and cells disclosed herein may be used in therapy. Compositions, vectors, nucleic acids, RNA guides and cells disclosed herein may be used in methods of treating a disease or condition in a subject. In some embodiments, the disease or condition is primary hyperoxaluria (PH). In some embodiments, the PH is PH1, PH2, or PH3. Any suitable delivery or administration method known in the art may be used to deliver compositions, vectors, nucleic acids, RNA guides and cells disclosed herein. Such methods may involve contacting a target sequence with a composition, vector, nucleic acid, or RNA guide disclosed herein. Such methods may involve a method of editing an LDHA sequence as disclosed herein. In some embodiments, a cell engineered using an RNA guide disclosed herein is used for ex vivo gene therapy.

IV. Therapeutic Applications

Any of the gene editing systems or modified cells generated using such a gene editing system as disclosed herein may be used for treating a disease that is associated with the LDHA gene, for example, primary hyperoxaluria (PH). In some embodiments, the PH is PH1, PH2, or PH3. In specific examples, the target disease is PH1.

PH is a rare genetic disorder effecting subjects of all ages from infants to elderly. PH includes three subtypes involving genetic defects that alter the expression of three distinct proteins. PH1 involves alanine-glyoxylate aminotransferase, or AGT/AGT1. PH2 involves glyoxylate/hydroxypyruvate reductase, or GR/HPR, and PH3 involves 4-hydroxy-2-oxoglutarate aldolase, or HOGA.

In PH1, excess oxalate can also combine with calcium to form calcium oxalate in the kidney and other organs. Deposits of calcium oxalate can produce widespread deposition of calcium oxalate (nephrocalcinosis) or formation of kidney and bladder stones (urolithiasis) and lead to kidney damage. Common kidney complications in PH1 include blood in the urine (hematuria), urinary tract infections, kidney damage, and end-stage renal disease (ESRD). Over time, kidneys in patients with PH1 may begin to fail, and levels of oxalate may rise in the blood. Deposition of oxalate in tissues throughout the body, e.g., systemic oxalosis, may occur due to high blood levels of oxalate and can lead to complications in bone, skin, and eye. Patients with PH1 normally have kidney failure at an early age, with renal dialysis or dual kidney/liver organ transplant as the only treatment options.

In some embodiments, provided herein is a method for treating a target disease as disclosed herein (e.g., PH such as PH1) comprising administering to a subject (e.g., a human patient) in need of the treatment any of the gene editing systems disclosed herein. The gene editing system may be delivered to a specific tissue or specific type of cells where the gene edit is needed. The gene editing system may comprise LNPs encompassing one or more of the components, one or more vectors (e.g., viral vectors) encoding one or more of the components, or a combination thereof. Components of the gene editing system may be formulated to form a pharmaceutical composition, which may further comprise one or more pharmaceutically acceptable carriers.

In some embodiments, modified cells produced using any of the gene editing systems disclosed herein may be administered to a subject (e.g., a human patient) in need of the treatment. The modified cells may comprise a substitution, insertion, and/or deletion described herein. In some examples, the modified cells may include a cell line modified by a CRISPR nuclease, reverse transcriptase polypeptide, and editing template RNA (e.g., RNA guide and RT donor RNA). In some instances, the modified cells may be a heterogenous population comprising cells with different types of gene edits. Alternatively, the modified cells may comprise a substantially homogenous cell population (e.g., at least 80% of the cells in the whole population) comprising one particular gene edit in the LDHA gene. In some examples, the cells can be suspended in a suitable media.

In some embodiments, provided herein is a composition comprising the gene editing system or components thereof. Such a composition can be a pharmaceutical composition. A pharmaceutical composition that is useful may be prepared, packaged, or sold in a formulation suitable for oral, rectal, vaginal, parenteral, topical, pulmonary, intranasal, intralesional, buccal, ophthalmic, intravenous, intra-organ or another route of administration. A pharmaceutical composition of the disclosure may be prepared, packaged, or sold in bulk, as a single unit dose, or as a plurality of single unit doses. As used herein, a "unit dose" is discrete amount of the pharmaceutical composition (e.g., the gene editing system or components thereof), which would be administered to a subject or a convenient fraction of such a dosage such as, for example, one-half or one-third of such a dosage.

In some embodiments, a pharmaceutical composition comprising the gene editing system or components thereof as described herein may be administered to a subject in need thereof, e.g., one who suffers from a liver disease associated with the LDHA gene. In some instances, the gene editing system or components thereof may be delivered to specific cells or tissue (e.g., to liver cells), where the gene editing system could function to genetically modify the LDHA gene in such cells.

A formulation of a pharmaceutical composition suitable for parenteral administration may comprise the active agent (e.g., the gene editing system or components thereof or the modified cells) combined with a pharmaceutically acceptable carrier, such as sterile water or sterile isotonic saline. Such a formulation may be prepared, packaged, or sold in a form suitable for bolus administration or for continuous administration. Some injectable formulations may be prepared, packaged, or sold in unit dosage form, such as in ampules or in multi-dose containers containing a preservative. Some formulations for parenteral administration include, but are not limited to, suspensions, solutions, emulsions in oily or aqueous vehicles, pastes, and implantable sustained-release or biodegradable formulations. Some formulations may further comprise one or more additional ingredients including, but not limited to, suspending, stabilizing, or dispersing agents.

The pharmaceutical composition may be in the form of a sterile injectable aqueous or oily suspension or solution. This suspension or solution may be formulated according to the known art, and may comprise, in addition to the cells, additional ingredients such as the dispersing agents, wetting agents, or suspending agents described herein. Such sterile injectable formulation may be prepared using a non-toxic parenterally-acceptable diluent or solvent, such as water or saline. Other acceptable diluents and solvents include, but are not limited to, Ringer's solution, isotonic sodium chloride solution, and fixed oils such as synthetic mono- or di-glycerides. Other parentally-administrable formulations which that are useful include those which may comprise the cells in a packaged form, in a liposomal preparation, or as a component of a biodegradable polymer system. Some compositions for sustained release or implantation may comprise pharmaceutically acceptable polymeric or hydrophobic materials such as an emulsion, an ion exchange resin, a sparingly soluble polymer, or a sparingly soluble salt.

V. Kits and Uses Thereof

The present disclosure also provides kits that can be used, for example, to carry out a method described herein for genetical modification of the LDHA gene. In some embodiments, the kits include an RNA guide and a Cas12i polypeptide. In some embodiments, the kits include a polynucleotide that encodes such a Cas12i polypeptide, and optionally the polynucleotide is comprised within a vector, e.g., as described herein. The Cas12i polypeptide and the RNA guide (e.g., as a ribonucleoprotein) can be packaged within the same or other vessel within a kit or system or can be packaged in separate vials or other vessels, the contents of which can be mixed prior to use. The kits can additionally include, optionally, a buffer and/or instructions for use of the RNA guide and Cas12i polypeptide.

In some embodiments, the kit may be useful for research purposes. For example, in some embodiments, the kit may be useful to study gene function.

All references and publications cited herein are hereby incorporated by reference.

Additional Embodiments

Provided below are additional embodiments, which are also within the scope of the present disclosure.

Embodiment 1: A composition comprising an RNA guide, wherein the RNA guide comprises (i) a spacer sequence that is substantially complementary or complete complementary to a region on a non-PAM strand (the complementary sequence of a target sequence) within an LDHA gene and (ii) a direct repeat sequence; wherein the target sequence is adjacent to a protospacer adjacent motif (PAM) comprising the sequence 5'-NTTN-3'.

In Embodiment 1, the target sequence may be within exon 1, exon 2, exon 3, exon 4, exon 5, exon 6, exon 7, exon 8, or exon 9 of the LDHA gene. In some examples, the LDHA gene comprises the sequence of SEQ ID NO: 1172, the reverse complement of SEQ ID NO: 1172, a variant of SEQ ID NO: 1172, or the reverse complement of a variant of SEQ ID NO: 1172.

In Embodiment 1, the spacer sequence may comprise: (a) nucleotide 1 through nucleotide 16 of a sequence that is at least 90% identical to a sequence of any one of SEQ ID NOs: 588-1164; (b) nucleotide 1 through nucleotide 17 of a sequence that is at least 90% identical to a sequence of any one of SEQ ID NOs: 588-1164; (c) nucleotide 1 through nucleotide 18 of a sequence that is at least 90% identical to a sequence of any one of SEQ ID NOs: 588-1164; (d) nucleotide 1 through nucleotide 19 of a sequence that is at least 90% identical to a sequence of any one of SEQ ID NOs: 588-1164; (e) nucleotide 1 through nucleotide 20 of a sequence that is at least 90% identical to a sequence of any one of SEQ ID NOs: 588-1164; (f) nucleotide 1 through nucleotide 21 of a sequence that is at least 90% identical to a sequence of any one of SEQ ID NOs: 588-1164; (g) nucleotide 1 through nucleotide 22 of a sequence that is at least 90% identical to a sequence of any one of SEQ ID NOs: 588-1164; (h) nucleotide 1 through nucleotide 23 of a sequence that is at least 90% identical to a sequence of any one of SEQ ID NOs: 588-1164; (i) nucleotide 1 through nucleotide 24 of a sequence that is at least 90% identical to a sequence of any one of SEQ ID NOs: 588-1164; (j) nucleotide 1 through nucleotide 25 of a sequence that is at least 90% identical to a sequence of any one of SEQ ID NOs: 588-1164; (k) nucleotide 1 through nucleotide 26 of a sequence that is at least 90% identical to a sequence of any one of SEQ ID NOs: 588-1164; (l) nucleotide 1 through nucleotide 27 of a sequence that is at least 90% identical to a sequence of any one of SEQ ID NOs: 588-1164; (m) nucleotide 1 through nucleotide 28 of a sequence that is at least 90% identical to a sequence of any one of SEQ ID NOs: 588-1164; (n) nucleotide 1 through nucleotide 29 of a sequence that is at least 90% identical to a sequence of any one of SEQ ID NOs: 588-1164; or (o) nucleotide 1 through nucleotide 30 of a sequence that is at least 90% identical to a sequence of any one of SEQ ID NOs: 588-1164.

In any of the compositions of Embodiment 1, the spacer sequence may comprise: (a) nucleotide 1 through nucleotide 16 of any one of SEQ ID NOs: 588-1164; (b) nucleotide 1 through nucleotide 17 of any one of SEQ ID NOs: 588-1164; (c) nucleotide 1 through nucleotide 18 of any one of SEQ ID NOs: 588-1164; (d) nucleotide 1 through nucleotide 19 of any one of SEQ ID NOs: 588-1164; (e) nucleotide 1 through nucleotide 20 of any one of SEQ ID NOs: 588-1164; (f) nucleotide 1 through nucleotide 21 of any one of SEQ ID NOs: 588-1164; (g) nucleotide 1 through nucleotide 22 of any one of SEQ ID NOs: 588-1164; (h) nucleotide 1 through nucleotide 23 of any one of SEQ ID NOs: 588-1164; (i) nucleotide 1 through nucleotide 24 of any one of SEQ ID NOs: 588-1164; (j) nucleotide 1 through nucleotide 25 of any one of SEQ ID NOs: 588-1164; (k) nucleotide 1 through nucleotide 26 of any one of SEQ ID NOs: 588-1164; (l) nucleotide 1 through nucleotide 27 of any one of SEQ ID NOs: 588-1164; (m) nucleotide 1 through nucleotide 28 of any one of SEQ ID NOs: 588-1164; (n) nucleotide 1 through nucleotide 29 of any one of SEQ ID NOs: 588-1164; or (o) nucleotide 1 through nucleotide 30 of any one of SEQ ID NOs: 588-1164.

In any of the compositions of Embodiment 1, the direct repeat sequence may comprise: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 1182-1199; (b) nucleotide 2 through nucleotide 36 of a sequence that is at least 90% identical to a sequence of any one of SEQ ID NOs: 1182-1199; (c) nucleotide 3 through nucleotide 36 of a sequence that is at least 90% identical to a sequence of any one of SEQ ID NOs: 1182-1199; (d) nucleotide 4 through nucleotide 36 of a sequence that is at least 90% identical to a sequence of any one of SEQ ID NOs: 1182-1199; (e) nucleotide 5 through nucleotide 36 of a sequence that is at least 90% identical to a sequence of any one of SEQ ID NOs: 1182-1199; (f) nucleotide 6 through nucleotide 36 of a sequence that is at least 90% identical to a sequence of any one of SEQ ID NOs: 1182-1199; (g) nucleotide 7 through nucleotide 36 of a sequence that is at least 90% identical to a sequence of any one of SEQ ID NOs: 1182-1199; (h) nucleotide 8 through nucleotide 36 of a sequence that is at least 90% identical to a sequence of any one of SEQ ID NOs: 1182-1199; (i) nucleotide 9 through nucleotide 36 of a sequence that is at least 90% identical to a sequence of any one of SEQ ID NOs: 1182-1199; (j) nucleotide 10 through nucleotide 36 of a sequence that is at least 90% identical to a sequence of any one of SEQ ID NOs: 1182-1199; (k) nucleotide 11 through nucleotide 36 of a sequence that is at least 90% identical to a sequence of any one of SEQ ID NOs: 1182-1199; (l) nucleotide 12 through nucleotide 36 of a sequence that is at least 90% identical to a sequence of any one of SEQ ID NOs: 1182-1199; (m) nucleotide 13 through nucleotide 36 of a sequence that is at least 90% identical to a sequence of any one of SEQ ID NOs: 1182-1199; (n) nucleotide 14 through nucleotide 36 of a sequence that is at least 90% identical to a sequence of any one of SEQ ID NOs: 1182-1199; or (o) a sequence that is at least 90% identical to a sequence of SEQ ID NO: 1200 or a portion thereof.

In some examples, the direct repeat sequence comprises: (a) nucleotide 1 through nucleotide 36 of any one of SEQ ID NOs: 1182-1199; (b) nucleotide 2 through nucleotide 36 of any one of SEQ ID NOs: 1182-1199; (c) nucleotide 3 through nucleotide 36 of any one of SEQ ID NOs: 1182-1199; (d) nucleotide 4 through nucleotide 36 of any one of SEQ ID NOs: 1182-1199; (e) nucleotide 5 through nucleotide 36 of any one of SEQ ID NOs: 1182-1199; (f) nucleotide 6 through nucleotide 36 of any one of SEQ ID NOs: 1182-1199; (g) nucleotide 7 through nucleotide 36 of any one of SEQ ID NOs: 1182-1199; (h) nucleotide 8 through nucleotide 36 of any one of SEQ ID NOs: 1182-1199; (i) nucleotide 9 through nucleotide 36 of any one of SEQ ID NOs: 1182-1199; (j) nucleotide 10 through nucleotide 36 of any one of SEQ ID NOs: 1182-1199; (k) nucleotide 11 through nucleotide 36 of any one of SEQ ID NOs: 1182-1199; (l) nucleotide 12 through nucleotide 36 of any one of SEQ ID NOs: 1182-1199; (m) nucleotide 13 through nucleotide 36 of any one of SEQ ID NOs: 1182-1199; (n) nucleotide 14 through nucleotide 36 of any one of SEQ ID NOs: 1182-1199; or (o) SEQ ID NO: 1200 or a portion thereof.

In some examples, the direct repeat sequence comprises: (a) nucleotide 1 through nucleotide 36 of a sequence that is at least 90% identical to SEQ ID NO: 1205; (b) nucleotide 2 through nucleotide 36 of a sequence that is at least 90% identical to SEQ ID NO: 1205; (c) nucleotide 3 through nucleotide 36 of a sequence that is at least 90% identical to SEQ ID NO: 1205; (d) nucleotide 4 through nucleotide 36 of a sequence that is at least 90% identical to SEQ ID NO: 1205; (e) nucleotide 5 through nucleotide 36 of a sequence that is at least 90% identical to SEQ ID NO: 1205; (f) nucleotide 6 through nucleotide 36 of a sequence that is at least 90% identical to SEQ ID NO: 1205; (g) nucleotide 7 through nucleotide 36 of a sequence that is at least 90% identical to SEQ ID NO: 1205; (h) nucleotide 8 through nucleotide 36 of a sequence that is at least 90% identical to SEQ ID NO: 1205; (i) nucleotide 9 through nucleotide 36 of a sequence that is at least 90% identical to SEQ ID NO: 1205; (j) nucleotide 10 through nucleotide 36 of a sequence that is at least 90% identical to SEQ ID NO: 1205; (k) nucleotide 11 through nucleotide 36 of a sequence that is at least 90% identical to SEQ ID NO: 1205; (l) nucleotide 12 through nucleotide 36 of a sequence that is at least 90% identical to SEQ ID NO: 1205; (m) nucleotide 13 through nucleotide 36 of a sequence that is at least 90% identical to SEQ ID NO: 1205; (n) nucleotide 14 through nucleotide 36 of a sequence that is at least 90% identical to SEQ ID NO: 1205; or (o) a sequence that is at least 90% identical to a sequence of SEQ ID NO: 1206 or SEQ ID NO: 1207 or a portion thereof.

In some examples, the direct repeat sequence comprises: (a) nucleotide 1 through nucleotide 36 of SEQ ID NO: 1205; (b) nucleotide 2 through nucleotide 36 of SEQ ID NO: 1205; (c) nucleotide 3 through nucleotide 36 of SEQ ID NO: 1205; (d) nucleotide 4 through nucleotide 36 of SEQ ID NO: 1205; (e) nucleotide 5 through nucleotide 36 of SEQ ID NO: 1205; (f) nucleotide 6 through nucleotide 36 of SEQ ID NO: 1205; (g) nucleotide 7 through nucleotide 36 of SEQ ID NO: 1205; (h) nucleotide 8 through nucleotide 36 of SEQ ID NO: 1205; (i) nucleotide 9 through nucleotide 36 of SEQ ID NO: 1205; (j) nucleotide 10 through nucleotide 36 of SEQ ID NO: 1205; (k) nucleotide 11 through nucleotide 36 of SEQ ID NO: 1205; (l) nucleotide 12 through nucleotide 36 of SEQ ID NO: 1205; (m) nucleotide 13 through nucleotide 36 of SEQ ID NO: 1205; (n) nucleotide 14 through nucleotide 36 of SEQ ID NO: 1205; or (o) SEQ ID NO: 1206 or SEQ ID NO: 1207 or a portion thereof.

In some examples, the direct repeat sequence comprises: (a) nucleotide 1 through nucleotide 36 of a sequence that is at least 90% identical to a sequence of SEQ ID NO: 1208 or SEQ ID NO: 1209; (b) nucleotide 2 through nucleotide 36 of a sequence that is at least 90% identical to a sequence of SEQ ID NO: 1208 or SEQ ID NO: 1209; (c) nucleotide 3 through nucleotide 36 of a sequence that is at least 90% identical to a sequence of SEQ ID NO: 1208 or SEQ ID NO: 1209; (d) nucleotide 4 through nucleotide 36 of a sequence that is at least 90% identical to a sequence of SEQ ID NO: 1208 or SEQ ID NO: 1209; (e) nucleotide 5 through nucleotide 36 of a sequence that is at least 90% identical to a sequence of SEQ ID NO: 1208 or SEQ ID NO: 1209; (f) nucleotide 6 through nucleotide 36 of a sequence that is at least 90% identical to a sequence of SEQ ID NO: 1208 or SEQ ID NO: 1209; (g) nucleotide 7 through nucleotide 36 of a sequence that is at least 90% identical to a sequence of SEQ ID NO: 1208 or SEQ ID NO: 1209; (h) nucleotide 8 through nucleotide 36 of a sequence that is at least 90% identical to a sequence of SEQ ID NO: 1208 or SEQ ID NO: 1209; (i) nucleotide 9 through nucleotide 36 of a sequence that is at least 90% identical to a sequence of SEQ ID NO: 1208 or SEQ ID NO: 1209; (j) nucleotide 10 through nucleotide 36 of a sequence that is at least 90% identical to a sequence of SEQ ID NO: 1208 or SEQ ID NO: 1209; (k) nucleotide 11 through nucleotide 36 of a sequence that is at least 90% identical to a sequence of SEQ ID NO: 1208 or SEQ ID NO: 1209; (l) nucleotide 12 through nucleotide 36 of a sequence that is at least 90% identical to a sequence of SEQ ID NO: 1208 or SEQ ID NO: 1209; (m) nucleotide 13 through nucleotide 36 of a sequence that is at least 90% identical to a sequence of SEQ ID NO: 1208 or SEQ ID NO: 1209; (n) nucleotide 14 through nucleotide 36 of a sequence that is at least 90% identical to a sequence of SEQ ID NO: 1208 or SEQ ID NO: 1209; (o) nucleotide 15 through nucleotide 36 of a sequence that is at least 90% identical to a sequence of SEQ ID NO: 1208 or SEQ ID NO: 1209; or (p) a sequence that is at least 90% identical to a sequence of SEQ ID NO: 1210 or a portion thereof.

In some examples, the direct repeat sequence comprises: (a) nucleotide 1 through nucleotide 36 of SEQ ID NO: 1208 or SEQ ID NO: 1209; (b) nucleotide 2 through nucleotide 36 of SEQ ID NO: 1208 or SEQ ID NO: 1209; (c) nucleotide 3 through nucleotide 36 of SEQ ID NO: 1208 or SEQ ID NO: 1209; (d) nucleotide 4 through nucleotide 36 of SEQ ID NO: 1208 or SEQ ID NO: 1209; (e) nucleotide 5 through nucleotide 36 of SEQ ID NO: 1208 or SEQ ID NO: 1209; (f) nucleotide 6 through nucleotide 36 of SEQ ID NO: 1208 or SEQ ID NO: 1209; (g) nucleotide 7 through nucleotide 36 of SEQ ID NO: 1208 or SEQ ID NO: 1209; (h) nucleotide 8 through nucleotide 36 of SEQ ID NO: 1208 or SEQ ID NO: 1209; (i) nucleotide 9 through nucleotide 36 of SEQ ID NO: 1208 or SEQ ID NO: 1209; (j) nucleotide 10 through nucleotide 36 of SEQ ID NO: 1208 or SEQ ID NO: 1209; (k) nucleotide 11 through nucleotide 36 of SEQ ID NO: 1208 or SEQ ID NO: 1209; (l) nucleotide 12 through nucleotide 36 of SEQ ID NO: 1208 or SEQ ID NO: 1209; (m) nucleotide 13 through nucleotide 36 of SEQ ID NO: 1208 or SEQ ID NO: 1209; (n) nucleotide 14 through nucleotide 36 of SEQ ID NO: 1208 or SEQ ID NO: 1209; (o) nucleotide 15 through nucleotide 36 of SEQ ID NO: 1208 or SEQ ID NO: 1209; or (p) SEQ ID NO: 1210 or a portion thereof.

In some examples, the spacer sequence is substantially complementary to the complement of a sequence of any one of SEQ ID NOs: 11-587.

In any of the composition of Embodiment 1, the PAM may comprise the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence.

In some examples, the RNA guide has a sequence that is at least 90% identical to a sequence of any one of SEQ ID NOs: 1213-1229.

In some examples, the RNA guide has the sequence of any one of SEQ ID NOs: 1213-1229.

Embodiment 2: The composition of Embodiment 1 may further comprise a Cas12i polypeptide or a polyribonucleotide encoding a Cas12i polypeptide, which can be one of the following: (a) a Cas12i2 polypeptide comprising a sequence that is at least 90% identical to the sequence of SEQ ID NO: 1166, SEQ ID NO: 1167, SEQ ID NO: 1168, SEQ ID NO: 1169, SEQ ID NO: 1170, or SEQ ID NO: 1171; (b) a Cas12i4 polypeptide comprising a sequence that is at least 90% identical to the sequence of SEQ ID NO: 1202, SEQ ID NO: 1203, or SEQ ID NO: 1204; (c) a Cas12i1 polypeptide comprising a sequence that is at least 90% identical to the sequence of SEQ ID NO: 1211; or (d) a Cas12i3 polypeptide comprising a sequence that is at least 90% identical to the sequence of SEQ ID NO: 1212.

In specific examples, the Cas12i polypeptide is: (a) a Cas12i2 polypeptide comprising a sequence of SEQ ID NO: 1166, SEQ ID NO: 1167, SEQ ID NO: 1168, SEQ ID NO: 1169, SEQ ID NO: 1170, or SEQ ID NO: 1171; (b) a Cas12i4 polypeptide comprising a sequence of SEQ ID NO: 1202, SEQ ID NO: 1203, or SEQ ID NO: 1204; (c) a Cas12i1 polypeptide comprising a sequence of SEQ ID NO: 1211; or (d) a Cas12i3 polypeptide comprising a sequence of SEQ ID NO: 1212.

In any of the compositions of Embodiment 2, the RNA guide and the Cas12i polypeptide may form a ribonucleoprotein complex. In some examples, the ribonucleoprotein complex binds a target nucleic acid. In some examples, the composition is present within a cell.

In any of the compositions of Embodiment 2, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 3: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. The vectors may be expression vectors.

Embodiment 4: A composition comprising an RNA guide and a Cas12i polypeptide, wherein the RNA guide comprises (i) a spacer sequence that is substantially complementary or completely complementary to a region on a non-PAM strand (the complementary sequence of a target sequence) within an LDHA gene, and (ii) a direct repeat sequence.

In some examples, the target sequence is within exon 1, exon 2, exon 3, exon 4, exon 5, exon 6, exon 7, exon 8, or exon 9 of the LDHA gene, which may comprise the sequence of SEQ ID NO: 1172, the reverse complement of SEQ ID NO: 1172, a variant of the sequence of SEQ ID NO: 1172, or the reverse complement of a variant of SEQ ID NO: 1172.

In some examples, the spacer sequence comprises: (a) nucleotide 1 through nucleotide 16 of a sequence that is at least 90% identical to a sequence of any one of SEQ ID NOs: 588-1164; (b) nucleotide 1 through nucleotide 17 of a sequence that is at least 90% identical to a sequence of any one of SEQ ID NOs: 588-1164; (c) nucleotide 1 through nucleotide 18 of a sequence that is at least 90% identical to a sequence of any one of SEQ ID NOs: 588-1164; (d) nucleotide 1 through nucleotide 19 of a sequence that is at least 90% identical to a sequence of any one of SEQ ID NOs: 588-1164; (e) nucleotide 1 through nucleotide 20 of a sequence that is at least 90% identical to a sequence of any one of SEQ ID NOs: 588-1164; (f) nucleotide 1 through nucleotide 21 of a sequence that is at least 90% identical to a sequence of any one of SEQ ID NOs: 588-1164; (g) nucleotide 1 through nucleotide 22 of a sequence that is at least 90% identical to a sequence of any one of SEQ ID NOs: 588-1164; (h) nucleotide 1 through nucleotide 23 of a sequence that is at least 90% identical to a sequence of any one of SEQ ID NOs: 588-1164; (i) nucleotide 1 through nucleotide 24 of a sequence that is at least 90% identical to a sequence of any one of SEQ ID NOs: 588-1164; (j) nucleotide 1 through nucleotide 25 of a sequence that is at least 90% identical to a sequence of any one of SEQ ID NOs: 588-1164; (k) nucleotide 1 through nucleotide 26 of a sequence that is at least 90% identical to a sequence of any one of SEQ ID NOs: 588-1164; (l) nucleotide 1 through nucleotide 27 of a sequence that is at least 90% identical to a sequence of any one of SEQ ID NOs: 588-1164; (m) nucleotide 1 through nucleotide 28 of a sequence that is at least 90% identical to a sequence of any one of SEQ ID NOs: 588-1164; (n) nucleotide 1 through nucleotide 29 of a sequence that is at least 90% identical to a sequence of any one of SEQ ID NOs: 588-1164; or (o) nucleotide 1 through nucleotide 30 of a sequence that is at least 90% identical to a sequence of any one of SEQ ID NOs: 588-1164.

In some examples, the spacer sequence comprises: (a) nucleotide 1 through nucleotide 16 of any one of SEQ ID NOs: 588-1164; (b) nucleotide 1 through nucleotide 17 of any one of SEQ ID NOs: 588-1164; (c) nucleotide 1 through nucleotide 18 of any one of SEQ ID NOs: 588-1164; (d) nucleotide 1 through nucleotide 19 of any one of SEQ ID NOs: 588-1164; (e) nucleotide 1 through nucleotide 20 of any one of SEQ ID NOs: 588-1164; (f) nucleotide 1 through nucleotide 21 of any one of SEQ ID NOs: 588-1164; (g) nucleotide 1 through nucleotide 22 of any one of SEQ ID NOs: 588-1164; (h) nucleotide 1 through nucleotide 23 of any one of SEQ ID NOs: 588-1164; (i) nucleotide 1 through nucleotide 24 of any one of SEQ ID NOs: 588-1164; (j) nucleotide 1 through nucleotide 25 of any one of SEQ ID NOs: 588-1164; (k) nucleotide 1 through nucleotide 26 of any one of SEQ ID NOs: 588-1164; (l) nucleotide 1 through nucleotide 27 of any one of SEQ ID NOs: 588-1164; (m) nucleotide 1 through nucleotide 28 of any one of SEQ ID NOs: 588-1164; (n) nucleotide 1 through nucleotide 29 of any one of SEQ ID NOs: 588-1164; or (o) nucleotide 1 through nucleotide 30 of any one of SEQ ID NOs: 588-1164.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 1182-1199; (b) nucleotide 2 through nucleotide 36 of a sequence that is at least 90% identical to a sequence of any one of SEQ ID NOs: 1182-1199; (c) nucleotide 3 through nucleotide 36 of a sequence that is at least 90% identical to a sequence of any one of SEQ ID NOs: 1182-1199; (d) nucleotide 4 through nucleotide 36 of a sequence that is at least 90% identical to a sequence of any one of SEQ ID NOs: 1182-1199; (e) nucleotide 5 through nucleotide 36 of a sequence that is at least 90% identical to a sequence of any one of SEQ ID NOs: 1182-1199; (f) nucleotide 6 through nucleotide 36 of a sequence that is at least 90% identical to a sequence of any one of SEQ ID NOs: 1182-1199; (g) nucleotide 7 through nucleotide 36 of a sequence that is at least 90% identical to a sequence of any one of SEQ ID NOs: 1182-1199; (h) nucleotide 8 through nucleotide 36 of a sequence that is at least 90% identical to a sequence of any one of SEQ ID NOs: 1182-1199; (i) nucleotide 9 through nucleotide 36 of a sequence that is at least 90% identical to a sequence of any one of SEQ ID NOs: 1182-1199; (j) nucleotide 10 through nucleotide 36 of a sequence that is at least 90% identical to a sequence of any one of SEQ ID NOs: 1182-1199; (k) nucleotide 11 through nucleotide 36 of a sequence that is at least 90% identical to a sequence of any one of SEQ ID NOs: 1182-1199; (l) nucleotide 12 through nucleotide 36 of a sequence that is at least 90% identical to a sequence of any one of SEQ ID NOs: 1182-1199; (m) nucleotide 13 through nucleotide 36 of a sequence that is at least 90% identical to a sequence of any one of SEQ ID NOs: 1182-1199; (n) nucleotide 14 through nucleotide 36 of a sequence that is at least 90% identical to a sequence of any one of SEQ ID NOs: 1182-1199; or (o) a sequence that is at least 90% identical to a sequence of SEQ ID NO: 1200 or a portion thereof.

In some examples, the direct repeat sequence comprises: (a) nucleotide 1 through nucleotide 36 of any one of SEQ ID NOs: 1182-1199; (b) nucleotide 2 through nucleotide 36 of any one of SEQ ID NOs: 1182-1199; (c) nucleotide 3 through nucleotide 36 of any one of SEQ ID NOs: 1182-1199; (d) nucleotide 4 through nucleotide 36 of any one of SEQ ID NOs: 1182-1199; (e) nucleotide 5 through nucleotide 36 of any one of SEQ ID NOs: 1182-1199; (f) nucleotide 6 through nucleotide 36 of any one of SEQ ID NOs: 1182-1199; (g) nucleotide 7 through nucleotide 36 of any one of SEQ ID NOs: 1182-1199; (h) nucleotide 8 through nucleotide 36 of any one of SEQ ID NOs: 1182-1199; (i) nucleotide 9 through nucleotide 36 of any one of SEQ ID NOs: 1182-1199; (j) nucleotide 10 through nucleotide 36 of any one of SEQ ID NOs: 1182-1199; (k) nucleotide 11 through nucleotide 36 of any one of SEQ ID NOs: 1182-1199; (l) nucleotide 12 through nucleotide 36 of any one of SEQ ID NOs: 1182-1199; (m) nucleotide 13 through nucleotide 36 of any one of SEQ ID NOs: 1182-1199; (n) nucleotide 14 through nucleotide 36 of any one of SEQ ID NOs: 1182-1199; or (o) SEQ ID NO: 1200 or a portion thereof.

In some examples, the direct repeat sequence comprises: (a) nucleotide 1 through nucleotide 36 of a sequence that is at least 90% identical to SEQ ID NO: 1205; (b) nucleotide 2 through nucleotide 36 of a sequence that is at least 90% identical to SEQ ID NO: 1205; (c) nucleotide 3 through nucleotide 36 of a sequence that is at least 90% identical to SEQ ID NO: 1205; (d) nucleotide 4 through nucleotide 36 of a sequence that is at least 90% identical to SEQ ID NO: 1205; (e) nucleotide 5 through nucleotide 36 of a sequence that is at least 90% identical to SEQ ID NO: 1205; (f) nucleotide 6 through nucleotide 36 of a sequence that is at least 90% identical to SEQ ID NO: 1205; (g) nucleotide 7 through nucleotide 36 of a sequence that is at least 90% identical to SEQ ID NO: 1205; (h) nucleotide 8 through nucleotide 36 of a sequence that is at least 90% identical to SEQ ID NO: 1205; (i) nucleotide 9 through nucleotide 36 of a sequence that is at least 90% identical to SEQ ID NO: 1205; (j) nucleotide 10 through nucleotide 36 of a sequence that is at least 90% identical to SEQ ID NO: 1205; (k) nucleotide 11 through nucleotide 36 of a sequence that is at least 90% identical to SEQ ID NO: 1205; (1) nucleotide 12 through nucleotide 36 of a sequence that is at least 90% identical to SEQ ID NO: 1205; (m) nucleotide 13 through nucleotide 36 of a sequence that is at least 90% identical to SEQ ID NO: 1205; (n) nucleotide 14 through nucleotide 36 of a sequence that is at least 90% identical to SEQ ID NO: 1205; or (o) a sequence that is at least 90% identical to a sequence of SEQ ID NO: 1206 or SEQ ID NO: 1207 or a portion thereof.

In some examples, the direct repeat sequence comprises: (a) nucleotide 1 through nucleotide 36 of SEQ ID NO: 1205; (b) nucleotide 2 through nucleotide 36 of SEQ ID NO: 1205; (c) nucleotide 3 through nucleotide 36 of SEQ ID NO: 1205; (d) nucleotide 4 through nucleotide 36 of SEQ ID NO: 1205; (e) nucleotide 5 through nucleotide 36 of SEQ ID NO: 1205; (f) nucleotide 6 through nucleotide 36 of SEQ ID NO: 1205; (g) nucleotide 7 through nucleotide 36 of SEQ ID NO: 1205; (h) nucleotide 8 through nucleotide 36 of SEQ ID NO: 1205; (i) nucleotide 9 through nucleotide 36 of SEQ ID NO: 1205; (j) nucleotide 10 through nucleotide 36 of SEQ ID NO: 1205; (k) nucleotide 11 through nucleotide 36 of SEQ ID NO: 1205; (1) nucleotide 12 through nucleotide 36 of SEQ ID NO: 1205; (m) nucleotide 13 through nucleotide 36 of SEQ ID NO: 1205; (n) nucleotide 14 through nucleotide 36 of SEQ ID NO: 1205; or (o) SEQ ID NO: 1206 or SEQ ID NO: 1207 or a portion thereof.

In some examples, the direct repeat sequence comprises: (a) nucleotide 1 through nucleotide 36 of a sequence that is at least 90% identical to a sequence of SEQ ID NO: 1208 or SEQ ID NO: 1209; (b) nucleotide 2 through nucleotide 36 of a sequence that is at least 90% identical to a sequence of SEQ ID NO: 1208 or SEQ ID NO: 1209; (c) nucleotide 3 through nucleotide 36 of a sequence that is at least 90% identical to a sequence of SEQ ID NO: 1208 or SEQ ID NO: 1209; (d) nucleotide 4 through nucleotide 36 of a sequence that is at least 90% identical to a sequence of SEQ ID NO: 1208 or SEQ ID NO: 1209; (e) nucleotide 5 through nucleotide 36 of a sequence that is at least 90% identical to a sequence of SEQ ID NO: 1208 or SEQ ID NO: 1209; (f) nucleotide 6 through nucleotide 36 of a sequence that is at least 90% identical to a sequence of SEQ ID NO: 1208 or SEQ ID NO: 1209; (g) nucleotide 7 through nucleotide 36 of a sequence that is at least 90% identical to a sequence of SEQ ID NO: 1208 or SEQ ID NO: 1209; (h) nucleotide 8 through nucleotide 36 of a sequence that is at least 90% identical to a sequence of SEQ ID NO: 1208 or SEQ ID NO: 1209; (i) nucleotide 9 through nucleotide 36 of a sequence that is at least 90% identical to a sequence of SEQ ID NO: 1208 or SEQ ID NO: 1209; (j) nucleotide 10 through nucleotide 36 of a sequence that is at least 90% identical to a sequence of SEQ ID NO: 1208 or SEQ ID NO: 1209; (k) nucleotide 11 through nucleotide 36 of a sequence that is at least 90% identical to a sequence of SEQ ID NO: 1208 or SEQ ID NO: 1209; (1) nucleotide 12 through nucleotide 36 of a sequence that is at least 90% identical to a sequence of SEQ ID NO: 1208 or SEQ ID NO: 1209; (m) nucleotide 13 through nucleotide 36 of a sequence that is at least 90% identical to a sequence of SEQ ID NO: 1208 or SEQ ID NO: 1209; (n) nucleotide 14 through nucleotide 36 of a sequence that is at least 90% identical to a sequence of SEQ ID NO: 1208 or SEQ ID NO: 1209; (o) nucleotide 15 through nucleotide 36 of a sequence that is at least 90% identical to a sequence of SEQ ID NO: 1208 or SEQ ID NO: 1209; or (p) a sequence that is at least 90% identical to a sequence of SEQ ID NO: 1210 or a portion thereof.

In some examples, the direct repeat sequence comprises: (a) nucleotide 1 through nucleotide 36 of SEQ ID NO: 1208 or SEQ ID NO: 1209; (b) nucleotide 2 through nucleotide 36 of SEQ ID NO: 1208 or SEQ ID NO: 1209; (c) nucleotide 3 through nucleotide 36 of SEQ ID NO: 1208 or SEQ ID NO: 1209; (d) nucleotide 4 through nucleotide 36 of SEQ ID NO: 1208 or SEQ ID NO: 1209; (e) nucleotide 5 through nucleotide 36 of SEQ ID NO: 1208 or SEQ ID NO: 1209; (f) nucleotide 6 through nucleotide 36 of SEQ ID NO: 1208 or SEQ ID NO: 1209; (g) nucleotide 7 through nucleotide 36 of SEQ ID NO: 1208 or SEQ ID NO: 1209; (h) nucleotide 8 through nucleotide 36 of SEQ ID NO: 1208 or SEQ ID NO: 1209; (i) nucleotide 9 through nucleotide 36 of SEQ ID NO: 1208 or SEQ ID NO: 1209; (j) nucleotide 10 through nucleotide 36 of SEQ ID NO: 1208 or SEQ ID NO: 1209; (k) nucleotide 11 through nucleotide 36 of SEQ ID NO: 1208 or SEQ ID NO: 1209; (1) nucleotide 12 through nucleotide 36 of SEQ ID NO: 1208 or SEQ ID NO: 1209; (m) nucleotide 13 through nucleotide 36 of SEQ ID NO: 1208 or SEQ ID NO: 1209; (n) nucleotide 14 through nucleotide 36 of SEQ ID NO: 1208 or SEQ ID NO: 1209; (o) nucleotide 15 through nucleotide 36 of SEQ ID NO: 1208 or SEQ ID NO: 1209; or (p) SEQ ID NO: 1210 or a portion thereof.

In any of the compositions of Embodiment 4, the spacer sequence may be substantially complementary to the complement of a sequence of any one of SEQ ID NOs: 11-587.

In some examples, the target sequence is adjacent to a protospacer adjacent motif (PAM) comprising the sequence 5'-NTTN-3'. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In some examples, the target sequence is within 1, 2, 3, 4, or 5 nucleotides of the PAM sequence.

In any of the compositions of Embodiment 4, the Cas12i polypeptide is: (a) a Cas12i2 polypeptide comprising a sequence that is at least 90% identical to the sequence of SEQ ID NO: 1166, SEQ ID NO: 1167, SEQ ID NO: 1168, SEQ ID NO: 1169, SEQ ID NO: 1170, or SEQ ID NO: 1171; (b) a Cas12i4 polypeptide comprising a sequence that is at least 90% identical to the sequence of SEQ ID NO: 1202, SEQ ID NO: 1203, or SEQ ID NO: 1204; (c) a Cas12i1 polypeptide comprising a sequence that is at least 90% identical to the sequence of SEQ ID NO: 1211; or (d) a Cas12i3 polypeptide comprising a sequence that is at least 90% identical to the sequence of SEQ ID NO: 1212.

In some examples, the Cas12i polypeptide is: (a) a Cas12i2 polypeptide comprising a sequence of SEQ ID NO:

1166, SEQ ID NO: 1167, SEQ ID NO: 1168, SEQ ID NO: 1169, SEQ ID NO: 1170, or SEQ ID NO: 1171; (b) a Cas12i4 polypeptide comprising a sequence of SEQ ID NO: 1202, SEQ ID NO: 1203, or SEQ ID NO: 1204; (c) a Cas12i1 polypeptide comprising a sequence of SEQ ID NO: 1211; or (d) a Cas12i3 polypeptide comprising a sequence of SEQ ID NO: 1212.

In any of the composition of Embodiment 4, the RNA guide and the Cas12i polypeptide may form a ribonucleoprotein complex. In some examples, the ribonucleoprotein complex binds a target nucleic acid.

In any of the composition of Embodiment 4, the composition may be present within a cell.

In any of the composition of Embodiment 4, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 5: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. In some examples, the vectors are expression vectors.

Embodiment 6: An RNA guide comprising (i) a spacer sequence that is substantially complementary or completely complementary to a region on a non-PAM strand (the complementary sequence of a target sequence) within an LDHA gene, and (ii) a direct repeat sequence.

In some examples, the target sequence is within exon 1, exon 2, exon 3, exon 4, exon 5, exon 6, exon 7, exon 8, or exon 9 of the LDHA gene, which may comprise the sequence of SEQ ID NO: 1172, the reverse complement of SEQ ID NO: 1172, a variant of the sequence of SEQ ID NO: 1172, or the reverse complement of a variant of SEQ ID NO: 1172.

In some examples, the spacer sequence comprises: (a) nucleotide 1 through nucleotide 16 of a sequence that is at least 90% identical to a sequence of any one of SEQ ID NOs: 588-1164; (b) nucleotide 1 through nucleotide 17 of a sequence that is at least 90% identical to a sequence of any one of SEQ ID NOs: 588-1164; (c) nucleotide 1 through nucleotide 18 of a sequence that is at least 90% identical to a sequence of any one of SEQ ID NOs: 588-1164; (d) nucleotide 1 through nucleotide 19 of a sequence that is at least 90% identical to a sequence of any one of SEQ ID NOs: 588-1164; (e) nucleotide 1 through nucleotide 20 of a sequence that is at least 90% identical to a sequence of any one of SEQ ID NOs: 588-1164; (f) nucleotide 1 through nucleotide 21 of a sequence that is at least 90% identical to a sequence of any one of SEQ ID NOs: 588-1164; (g) nucleotide 1 through nucleotide 22 of a sequence that is at least 90% identical to a sequence of any one of SEQ ID NOs: 588-1164; (h) nucleotide 1 through nucleotide 23 of a sequence that is at least 90% identical to a sequence of any one of SEQ ID NOs: 588-1164; (i) nucleotide 1 through nucleotide 24 of a sequence that is at least 90% identical to a sequence of any one of SEQ ID NOs: 588-1164; (j) nucleotide 1 through nucleotide 25 of a sequence that is at least 90% identical to a sequence of any one of SEQ ID NOs: 588-1164; (k) nucleotide 1 through nucleotide 26 of a sequence that is at least 90% identical to a sequence of any one of SEQ ID NOs: 588-1164; (l) nucleotide 1 through nucleotide 27 of a sequence that is at least 90% identical to a sequence of any one of SEQ ID NOs: 588-1164; (m) nucleotide 1 through nucleotide 28 of a sequence that is at least 90% identical to a sequence of any one of SEQ ID NOs: 588-1164; (n) nucleotide 1 through nucleotide 29 of a sequence that is at least 90% identical to a sequence of any one of SEQ ID NOs: 588-1164; or (o) nucleotide 1 through nucleotide 30 of a sequence that is at least 90% identical to a sequence of any one of SEQ ID NOs: 588-1164.

In some examples, the spacer sequence comprises: (a) nucleotide 1 through nucleotide 16 of any one of SEQ ID NOs: 588-1164; (b) nucleotide 1 through nucleotide 17 of any one of SEQ ID NOs: 588-1164; (c) nucleotide 1 through nucleotide 18 of any one of SEQ ID NOs: 588-1164; (d) nucleotide 1 through nucleotide 19 of any one of SEQ ID NOs: 588-1164; (e) nucleotide 1 through nucleotide 20 of any one of SEQ ID NOs: 588-1164; (f) nucleotide 1 through nucleotide 21 of any one of SEQ ID NOs: 588-1164; (g) nucleotide 1 through nucleotide 22 of any one of SEQ ID NOs: 588-1164; (h) nucleotide 1 through nucleotide 23 of any one of SEQ ID NOs: 588-1164; (i) nucleotide 1 through nucleotide 24 of any one of SEQ ID NOs: 588-1164; (j) nucleotide 1 through nucleotide 25 of any one of SEQ ID NOs: 588-1164; (k) nucleotide 1 through nucleotide 26 of any one of SEQ ID NOs: 588-1164; (l) nucleotide 1 through nucleotide 27 of any one of SEQ ID NOs: 588-1164; (m) nucleotide 1 through nucleotide 28 of any one of SEQ ID NOs: 588-1164; (n) nucleotide 1 through nucleotide 29 of any one of SEQ ID NOs: 588-1164; or (o) nucleotide 1 through nucleotide 30 of any one of SEQ ID NOs: 588-1164.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 1182-1199; (b) nucleotide 2 through nucleotide 36 of a sequence that is at least 90% identical to a sequence of any one of SEQ ID NOs: 1182-1199; (c) nucleotide 3 through nucleotide 36 of a sequence that is at least 90% identical to a sequence of any one of SEQ ID NOs: 1182-1199; (d) nucleotide 4 through nucleotide 36 of a sequence that is at least 90% identical to a sequence of any one of SEQ ID NOs: 1182-1199; (e) nucleotide 5 through nucleotide 36 of a sequence that is at least 90% identical to a sequence of any one of SEQ ID NOs: 1182-1199; (f) nucleotide 6 through nucleotide 36 of a sequence that is at least 90% identical to a sequence of any one of SEQ ID NOs: 1182-1199; (g) nucleotide 7 through nucleotide 36 of a sequence that is at least 90% identical to a sequence of any one of SEQ ID NOs: 1182-1199; (h) nucleotide 8 through nucleotide 36 of a sequence that is at least 90% identical to a sequence of any one of SEQ ID NOs: 1182-1199; (i) nucleotide 9 through nucleotide 36 of a sequence that is at least 90% identical to a sequence of any one of SEQ ID NOs: 1182-1199; (j) nucleotide 10 through nucleotide 36 of a sequence that is at least 90% identical to a sequence of any one of SEQ ID NOs: 1182-1199; (k) nucleotide 11 through nucleotide 36 of a sequence that is at least 90% identical to a sequence of any one of SEQ ID NOs: 1182-1199; (l) nucleotide 12 through nucleotide 36 of a sequence that is at least 90% identical to a sequence of any one of SEQ ID NOs: 1182-1199; (m) nucleotide 13 through nucleotide 36 of a sequence that is at least 90% identical to a sequence of any one of SEQ ID NOs: 1182-1199; (n) nucleotide 14 through nucleotide 36 of a sequence that is at least 90% identical to a sequence of any one of SEQ ID NOs: 1182-1199; or (o) a sequence that is at least 90% identical to a sequence of SEQ ID NO: 1200 or a portion thereof.

In some examples, the direct repeat sequence comprises: (a) nucleotide 1 through nucleotide 36 of any one of SEQ ID NOs: 1182-1199; (b) nucleotide 2 through nucleotide 36 of any one of SEQ ID NOs: 1182-1199; (c) nucleotide 3 through nucleotide 36 of any one of SEQ ID NOs: 1182-1199; (d) nucleotide 4 through nucleotide 36 of any one of SEQ ID NOs: 1182-1199; (e) nucleotide 5 through nucleotide 36 of any one of SEQ ID NOs: 1182-1199; (f) nucleotide 6 through nucleotide 36 of any one of SEQ ID NOs: 1182-1199; (g) nucleotide 7 through nucleotide 36 of any one of SEQ ID NOs: 1182-1199; (h) nucleotide 8 through nucleotide 36 of any one of SEQ ID NOs: 1182-1199; (i) nucleotide 9 through nucleotide 36 of any one of SEQ ID NOs: 1182-1199; (j) nucleotide 10 through nucleotide 36 of any one of SEQ ID NOs: 1182-1199; (k) nucleotide 11 through nucleotide 36 of any one of SEQ ID NOs: 1182-1199; (l) nucleotide 12 through nucleotide 36 of any one of SEQ ID NOs: 1182-1199; (m) nucleotide 13 through nucleotide 36 of any one of SEQ ID NOs: 1182-1199; (n) nucleotide 14 through nucleotide 36 of any one of SEQ ID NOs: 1182-1199; or (o) SEQ ID NO: 1200 or a portion thereof.

In some examples, the direct repeat sequence comprises: (a) nucleotide 1 through nucleotide 36 of a sequence that is at least 90% identical to SEQ ID NO: 1205; (b) nucleotide 2 through nucleotide 36 of a sequence that is at least 90% identical to SEQ ID NO: 1205; (c) nucleotide 3 through nucleotide 36 of a sequence that is at least 90% identical to SEQ ID NO: 1205; (d) nucleotide 4 through nucleotide 36 of a sequence that is at least 90% identical to SEQ ID NO: 1205; (e) nucleotide 5 through nucleotide 36 of a sequence that is at least 90% identical to SEQ ID NO: 1205; (f) nucleotide 6 through nucleotide 36 of a sequence that is at least 90% identical to SEQ ID NO: 1205; (g) nucleotide 7 through nucleotide 36 of a sequence that is at least 90% identical to SEQ ID NO: 1205; (h) nucleotide 8 through nucleotide 36 of a sequence that is at least 90% identical to SEQ ID NO: 1205; (i) nucleotide 9 through nucleotide 36 of a sequence that is at least 90% identical to SEQ ID NO: 1205; (j) nucleotide 10 through nucleotide 36 of a sequence that is at least 90% identical to SEQ ID NO: 1205; (k) nucleotide 11 through nucleotide 36 of a sequence that is at least 90% identical to SEQ ID NO: 1205; (l) nucleotide 12 through nucleotide 36 of a sequence that is at least 90% identical to SEQ ID NO: 1205; (m) nucleotide 13 through nucleotide 36 of a sequence that is at least 90% identical to SEQ ID NO: 1205; (n) nucleotide 14 through nucleotide 36 of a sequence that is at least 90% identical to SEQ ID NO:

1205; or (o) a sequence that is at least 90% identical to a sequence of SEQ ID NO: 1206 or SEQ ID NO: 1207 or a portion thereof.

In some examples, the direct repeat sequence comprises: (a) nucleotide 1 through nucleotide 36 of SEQ ID NO: 1205; (b) nucleotide 2 through nucleotide 36 of SEQ ID NO: 1205; (c) nucleotide 3 through nucleotide 36 of SEQ ID NO: 1205; (d) nucleotide 4 through nucleotide 36 of SEQ ID NO: 1205; (e) nucleotide 5 through nucleotide 36 of SEQ ID NO: 1205; (f) nucleotide 6 through nucleotide 36 of SEQ ID NO: 1205; (g) nucleotide 7 through nucleotide 36 of SEQ ID NO: 1205; (h) nucleotide 8 through nucleotide 36 of SEQ ID NO: 1205; (i) nucleotide 9 through nucleotide 36 of SEQ ID NO: 1205; (j) nucleotide 10 through nucleotide 36 of SEQ ID NO: 1205; (k) nucleotide 11 through nucleotide 36 of SEQ ID NO: 1205; (1) nucleotide 12 through nucleotide 36 of SEQ ID NO: 1205; (m) nucleotide 13 through nucleotide 36 of SEQ ID NO: 1205; (n) nucleotide 14 through nucleotide 36 of SEQ ID NO: 1205; (or o) SEQ ID NO: 1206 or SEQ ID NO: 1207 or a portion thereof.

In some examples, the direct repeat sequence comprises: (a) nucleotide 1 through nucleotide 36 of a sequence that is at least 90% identical to a sequence of SEQ ID NO: 1208 or SEQ ID NO: 1209; (b) nucleotide 2 through nucleotide 36 of a sequence that is at least 90% identical to a sequence of SEQ ID NO: 1208 or SEQ ID NO: 1209; (c) nucleotide 3 through nucleotide 36 of a sequence that is at least 90% identical to a sequence of SEQ ID NO: 1208 or SEQ ID NO: 1209; (d) nucleotide 4 through nucleotide 36 of a sequence that is at least 90% identical to a sequence of SEQ ID NO: 1208 or SEQ ID NO: 1209; (e) nucleotide 5 through nucleotide 36 of a sequence that is at least 90% identical to a sequence of SEQ ID NO: 1208 or SEQ ID NO: 1209; (f) nucleotide 6 through nucleotide 36 of a sequence that is at least 90% identical to a sequence of SEQ ID NO: 1208 or SEQ ID NO: 1209; (g) nucleotide 7 through nucleotide 36 of a sequence that is at least 90% identical to a sequence of SEQ ID NO: 1208 or SEQ ID NO: 1209; (h) nucleotide 8 through nucleotide 36 of a sequence that is at least 90% identical to a sequence of SEQ ID NO: 1208 or SEQ ID NO: 1209; (i) nucleotide 9 through nucleotide 36 of a sequence that is at least 90% identical to a sequence of SEQ ID NO: 1208 or SEQ ID NO: 1209; (j) nucleotide 10 through nucleotide 36 of a sequence that is at least 90% identical to a sequence of SEQ ID NO: 1208 or SEQ ID NO: 1209; (k) nucleotide 11 through nucleotide 36 of a sequence that is at least 90% identical to a sequence of SEQ ID NO: 1208 or SEQ ID NO: 1209; (1) nucleotide 12 through nucleotide 36 of a sequence that is at least 90% identical to a sequence of SEQ ID NO: 1208 or SEQ ID NO: 1209; (m) nucleotide 13 through nucleotide 36 of a sequence that is at least 90% identical to a sequence of SEQ ID NO: 1208 or SEQ ID NO: 1209; (n) nucleotide 14 through nucleotide 36 of a sequence that is at least 90% identical to a sequence of SEQ ID NO: 1208 or SEQ ID NO: 1209; (o) nucleotide 15 through nucleotide 36 of a sequence that is at least 90% identical to a sequence of SEQ ID NO: 1208 or SEQ ID NO: 1209; or (p) a sequence that is at least 90% identical to a sequence of SEQ ID NO: 1210 or a portion thereof.

In some examples, the direct repeat sequence comprises: (a) nucleotide 1 through nucleotide 36 of SEQ ID NO: 1208 or SEQ ID NO: 1209; (b) nucleotide 2 through nucleotide 36 of SEQ ID NO: 1208 or SEQ ID NO: 1209; (c) nucleotide 3 through nucleotide 36 of SEQ ID NO: 1208 or SEQ ID NO: 1209; (d) nucleotide 4 through nucleotide 36 of SEQ ID NO: 1208 or SEQ ID NO: 1209; (e) nucleotide 5 through nucleotide 36 of SEQ ID NO: 1208 or SEQ ID NO: 1209; (f) nucleotide 6 through nucleotide 36 of SEQ ID NO: 1208 or SEQ ID NO: 1209; (g) nucleotide 7 through nucleotide 36 of SEQ ID NO: 1208 or SEQ ID NO: 1209; (h) nucleotide 8 through nucleotide 36 of SEQ ID NO: 1208 or SEQ ID NO: 1209; (i) nucleotide 9 through nucleotide 36 of SEQ ID NO: 1208 or SEQ ID NO: 1209; (j) nucleotide 10 through nucleotide 36 of SEQ ID NO: 1208 or SEQ ID NO: 1209; (k) nucleotide 11 through nucleotide 36 of SEQ ID NO: 1208 or SEQ ID NO: 1209; (1) nucleotide 12 through nucleotide 36 of SEQ ID NO: 1208 or SEQ ID NO: 1209; (m) nucleotide 13 through nucleotide 36 of SEQ ID NO: 1208 or SEQ ID NO: 1209; (n) nucleotide 14 through nucleotide 36 of SEQ ID NO: 1208 or SEQ ID NO: 1209; (o) nucleotide 15 through nucleotide 36 of SEQ ID NO: 1208 or SEQ ID NO: 1209; or (p) SEQ ID NO: 1210 or a portion thereof.

In any of the RNA guide of Embodiment 6, the spacer sequence may be substantially complementary to the complement of a sequence of any one of SEQ ID NOs: 11-587.

In any of the RNA guide of Embodiment 6, the target sequence may be adjacent to a protospacer adjacent motif (PAM) comprising the sequence 5'-NTTN-3', wherein N is any nucleotide. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In other examples, the target sequence is within 1, 2, 3, 4, or 5 nucleotides of the PAM sequence.

In some examples, the RNA guide has a sequence that is at least 90% identical to a sequence of any one of SEQ ID NOs: 1213-1229. In specific examples, the RNA guide has the sequence of any one of SEQ ID NOs: 1213-1229.

Embodiment 7: A nucleic acid encoding an RNA guide as described herein.

Embodiment 8: A vector comprising such an RNA guide as described herein.

Embodiment 9: A cell comprising a composition, an RNA guide, a nucleic acid, or a vector as described herein. In some examples, the cell is a eukaryotic cell, an animal cell, a mammalian cell, a human cell, a primary cell, a cell line, a stem cell, or a T cell.

Embodiment 10: A kit comprising a composition, an RNA guide, a nucleic acid, or a vector as described herein.

Embodiment 11: A method of editing an LDHA sequence, the method comprising contacting an LDHA sequence with a composition or an RNA guide as described herein. In some examples, the method is carried out in vitro. In other examples, the method is carried out ex vivo.

In some examples, the LDHA sequence is in a cell.

In some examples, the composition or the RNA guide induces a deletion in the LDHA sequence. In some examples, the deletion is adjacent to a 5'-NTTN-3' sequence, wherein N is any nucleotide. In some specific examples, the deletion is downstream of the 5'-NTTN-3' sequence. In some specific examples, the deletion is up to about 40 nucleotides in length. In some instances, the deletion is from about 4 nucleotides to 40 nucleotides, about 4 nucleotides to 25 nucleotides, about 10 nucleotides to 25 nucleotides, or about 10 nucleotides to 15 nucleotides in length.

In some examples, the deletion starts within about 5 nucleotides to about 15 nucleotides, about 5 nucleotides to about 10 nucleotides, or about 10 nucleotides to about 15 nucleotides of the 5'-NTTN-3' sequence.

In some examples, the deletion starts within about 5 nucleotides to about 15 nucleotides, about 5 nucleotides to about 10 nucleotides, or about 10 nucleotides to about 15 nucleotides downstream of the 5'-NTTN-3' sequence.

In some examples, the deletion ends within about 20 nucleotides to about 30 nucleotides, about 20 nucleotides to about 25 nucleotides, or about 25 nucleotides to about 30 nucleotides of the 5'-NTTN-3' sequence.

In some examples, the deletion ends within about 20 nucleotides to about 30 nucleotides, about 20 nucleotides to about 25 nucleotides, about 25 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 15 nucleotides downstream of the 5'-NTTN-3' sequence and ends within about 25 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 10 nucleotides downstream of the 5'-NTTN-3' sequence and ends within about 25 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 10 nucleotides to about 15 nucleotides downstream of the 5'-NTTN-3' sequence and ends within about 25 nucleotides to about 30 nucleotides downstream of the 5'-NTTN-3' sequence.

In some examples, the 5'-NTTN-3' sequence is 5'-CTTT-3', 5'-CTTC-3', 5'-GTTT-3', 5'-GTTC-3', 5'-TTTC-3', 5'-GTTA-3', or 5'-GTTG-3'.

In some examples, the deletion overlaps with a mutation in the LDHA sequence. In some instances, the deletion overlaps with an insertion in the LDHA sequence. In some instances, the deletion removes a repeat expansion of the LDHA sequence or a portion thereof. In some instances, the deletion disrupts one or both alleles of the LDHA sequence.

In any of the composition, RNA guide, nucleic acid, vector, cell, kit, or method of Embodiments 1-11 described herein, the RNA guide may comprise the sequence of any one of SEQ ID NOs: 1213-1229.

Embodiment 12: A method of treating primary hyperoxaluria (PH), which optionally is PH1, PH2, or PH3, in a subject, the method comprising administering a composition, an RNA guide, or a cell described herein to the subject.

In any of the compositions, RNA guides, cells, kits, or methods described herein, the RNA guide and/or the polyribonucleotide encoding the Cas12i polypeptide are comprised within a lipid nanoparticle. In some examples, the RNA guide and the polyribonucleotide encoding the Cas12i polypeptide are comprised within the same lipid nanoparticle. In other examples, the RNA guide and the polyribonucleotide encoding the Cas12i polypeptide are comprised within separate lipid nanoparticles.

Embodiment 13: An RNA guide comprising (i) a spacer sequence that is complementary to a target site within an LDHA gene (the target site being on the non-PAM strand and complementary to a target sequence), and (ii) a direct repeat sequence, wherein the target sequence is any one of SEQ ID NOs: 1237, 1239, 1248, 1245, or 1249, or the reverse complement thereof.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 1182-1199; (b) nucleotide 2 through nucleotide 36 of a sequence that is at least 90% identical to a sequence of any one of SEQ ID NOs: 1182-1199; (c) nucleotide 3 through nucleotide 36 of a sequence that is at least 90% identical to a sequence of any one of SEQ ID NOs: 1182-1199; (d) nucleotide 4 through nucleotide 36 of a sequence that is at least 90% identical to a sequence of any one of SEQ ID NOs: 1182-1199; (e) nucleotide 5 through nucleotide 36 of a sequence that is at least 90% identical to a sequence of any one of SEQ ID NOs: 1182-1199; (f) nucleotide 6 through nucleotide 36 of a sequence that is at least 90% identical to a sequence of any one of SEQ ID NOs: 1182-1199; (g) nucleotide 7 through nucleotide 36 of a sequence that is at least 90% identical to a sequence of any one of SEQ ID NOs: 1182-1199; (h) nucleotide 8 through nucleotide 36 of a sequence that is at least 90% identical to a sequence of any one of SEQ ID NOs: 1182-1199; (i) nucleotide 9 through nucleotide 36 of a sequence that is at least 90% identical to a sequence of any one of SEQ ID NOs: 1182-1199; (j) nucleotide 10 through nucleotide 36 of a sequence that is at least 90% identical to a sequence of any one of SEQ ID NOs: 1182-1199; (k) nucleotide 11 through nucleotide 36 of a sequence that is at least 90% identical to a sequence of any one of SEQ ID NOs: 1182-1199; (l) nucleotide 12 through nucleotide 36 of a sequence that is at least 90% identical to a sequence of any one of SEQ ID NOs: 1182-1199; (m) nucleotide 13 through nucleotide 36 of a sequence that is at least 90% identical to a sequence of any one of SEQ ID NOs: 1182-1199; (n) nucleotide 14 through nucleotide 36 of a sequence that is at least 90% identical to a sequence of any one of SEQ ID NOs: 1182-1199; or (o) a sequence that is at least 90% identical to a sequence of SEQ ID NO: 1200 or a portion thereof.

In some examples, the direct repeat sequence comprises: (a) nucleotide 1 through nucleotide 36 of any one of SEQ ID NOs: 1182-1199; (b) nucleotide 2 through nucleotide 36 of any one of SEQ ID NOs: 1182-1199; (c) nucleotide 3 through nucleotide 36 of any one of SEQ ID NOs: 1182-1199; (d) nucleotide 4 through nucleotide 36 of any one of SEQ ID NOs: 1182-1199; (e) nucleotide 5 through nucleotide 36 of any one of SEQ ID NOs: 1182-1199; (f) nucleotide 6 through nucleotide 36 of any one of SEQ ID NOs: 1182-1199; (g) nucleotide 7 through nucleotide 36 of any one of SEQ ID NOs: 1182-1199; (h) nucleotide 8 through nucleotide 36 of any one of SEQ ID NOs: 1182-1199; (i) nucleotide 9 through nucleotide 36 of any one of SEQ ID NOs: 1182-1199; (j) nucleotide 10 through nucleotide 36 of any one of SEQ ID NOs: 1182-1199; (k) nucleotide 11 through nucleotide 36 of any one of SEQ ID NOs: 1182-1199; (l) nucleotide 12 through nucleotide 36 of any one of SEQ ID NOs: 1182-1199; (m) nucleotide 13 through nucleotide 36 of any one of SEQ ID NOs: 1182-1199; (n) nucleotide 14 through nucleotide 36 of any one of SEQ ID NOs: 1182-1199; or (o) SEQ ID NO: 1200 or a portion thereof.

In some examples, the direct repeat sequence comprises: (a) nucleotide 1 through nucleotide 36 of a sequence that is at least 90% identical to SEQ ID NO: 1205; (b) nucleotide 2 through nucleotide 36 of a sequence that is at least 90% identical to SEQ ID NO: 1205; (c) nucleotide 3 through nucleotide 36 of a sequence that is at least 90% identical to SEQ ID NO: 1205; (d) nucleotide 4 through nucleotide 36 of a sequence that is at least 90% identical to SEQ ID NO: 1205; (e) nucleotide 5 through nucleotide 36 of a sequence that is at least 90% identical to SEQ ID NO: 1205; (f) nucleotide 6 through nucleotide 36 of a sequence that is at least 90% identical to SEQ ID NO: 1205; (g) nucleotide 7 through nucleotide 36 of a sequence that is at least 90% identical to SEQ ID NO: 1205; (h) nucleotide 8 through nucleotide 36 of a sequence that is at least 90% identical to SEQ ID NO: 1205; (i) nucleotide 9 through nucleotide 36 of a sequence that is at least 90% identical to SEQ ID NO: 1205; (j) nucleotide 10 through nucleotide 36 of a sequence that is at least 90% identical to SEQ ID NO: 1205; (k) nucleotide 11 through nucleotide 36 of a sequence that is at least 90% identical to SEQ ID NO: 1205; (l) nucleotide 12 through nucleotide 36 of a sequence that is at least 90% identical to SEQ ID NO: 1205; (m) nucleotide 13 through nucleotide 36 of a sequence that is at least 90% identical to SEQ ID NO: 1205; (n) nucleotide 14 through nucleotide 36 of a sequence that is at least 90% identical to SEQ ID NO: 1205; or (o) a sequence that is at least 90% identical to a sequence of SEQ ID NO: 1206 or SEQ ID NO: 1207 or a portion thereof.

In some examples, the direct repeat sequence comprises: (a) nucleotide 1 through nucleotide 36 of SEQ ID NO: 1205;

(b) nucleotide 2 through nucleotide 36 of SEQ ID NO: 1205;
(c) nucleotide 3 through nucleotide 36 of SEQ ID NO: 1205;
(d) nucleotide 4 through nucleotide 36 of SEQ ID NO: 1205;
(e) nucleotide 5 through nucleotide 36 of SEQ ID NO: 1205;
(f) nucleotide 6 through nucleotide 36 of SEQ ID NO: 1205;
(g) nucleotide 7 through nucleotide 36 of SEQ ID NO: 1205;
(h) nucleotide 8 through nucleotide 36 of SEQ ID NO: 1205;
(i) nucleotide 9 through nucleotide 36 of SEQ ID NO: 1205;
(j) nucleotide 10 through nucleotide 36 of SEQ ID NO: 1205; (k) nucleotide 11 through nucleotide 36 of SEQ ID NO: 1205; (l) nucleotide 12 through nucleotide 36 of SEQ ID NO: 1205; (m) nucleotide 13 through nucleotide 36 of SEQ ID NO: 1205; (n) nucleotide 14 through nucleotide 36 of SEQ ID NO: 1205; or (o) SEQ ID NO: 1206 or SEQ ID NO: 1207 or a portion thereof.

In some examples, the direct repeat sequence comprises: (a) nucleotide 1 through nucleotide 36 of a sequence that is at least 90% identical to a sequence of SEQ ID NO: 1208 or SEQ ID NO: 1209; (b) nucleotide 2 through nucleotide 36 of a sequence that is at least 90% identical to a sequence of SEQ ID NO: 1208 or SEQ ID NO: 1209; (c) nucleotide 3 through nucleotide 36 of a sequence that is at least 90% identical to a sequence of SEQ ID NO: 1208 or SEQ ID NO: 1209; (d) nucleotide 4 through nucleotide 36 of a sequence that is at least 90% identical to a sequence of SEQ ID NO: 1208 or SEQ ID NO: 1209; (e) nucleotide 5 through nucleotide 36 of a sequence that is at least 90% identical to a sequence of SEQ ID NO: 1208 or SEQ ID NO: 1209; (f) nucleotide 6 through nucleotide 36 of a sequence that is at least 90% identical to a sequence of SEQ ID NO: 1208 or SEQ ID NO: 1209; (g) nucleotide 7 through nucleotide 36 of a sequence that is at least 90% identical to a sequence of SEQ ID NO: 1208 or SEQ ID NO: 1209; (h) nucleotide 8 through nucleotide 36 of a sequence that is at least 90% identical to a sequence of SEQ ID NO: 1208 or SEQ ID NO: 1209; (i) nucleotide 9 through nucleotide 36 of a sequence that is at least 90% identical to a sequence of SEQ ID NO: 1208 or SEQ ID NO: 1209; (j) nucleotide 10 through nucleotide 36 of a sequence that is at least 90% identical to a sequence of SEQ ID NO: 1208 or SEQ ID NO: 1209; (k) nucleotide 11 through nucleotide 36 of a sequence that is at least 90% identical to a sequence of SEQ ID NO: 1208 or SEQ ID NO: 1209; (l) nucleotide 12 through nucleotide 36 of a sequence that is at least 90% identical to a sequence of SEQ ID NO: 1208 or SEQ ID NO: 1209; (m) nucleotide 13 through nucleotide 36 of a sequence that is at least 90% identical to a sequence of SEQ ID NO: 1208 or SEQ ID NO: 1209; (n) nucleotide 14 through nucleotide 36 of a sequence that is at least 90% identical to a sequence of SEQ ID NO: 1208 or SEQ ID NO: 1209; (o) nucleotide 15 through nucleotide 36 of a sequence that is at least 90% identical to a sequence of SEQ ID NO: 1208 or SEQ ID NO: 1209; or (p) a sequence that is at least 90% identical to a sequence of SEQ ID NO: 1210 or a portion thereof.

In some examples, the direct repeat sequence comprises: (a) nucleotide 1 through nucleotide 36 of SEQ ID NO: 1208 or SEQ ID NO: 1209; (b) nucleotide 2 through nucleotide 36 of SEQ ID NO: 1208 or SEQ ID NO: 1209; (c) nucleotide 3 through nucleotide 36 of SEQ ID NO: 1208 or SEQ ID NO: 1209; (d) nucleotide 4 through nucleotide 36 of SEQ ID NO: 1208 or SEQ ID NO: 1209; (e) nucleotide 5 through nucleotide 36 of SEQ ID NO: 1208 or SEQ ID NO: 1209; (f) nucleotide 6 through nucleotide 36 of SEQ ID NO: 1208 or SEQ ID NO: 1209; (g) nucleotide 7 through nucleotide 36 of SEQ ID NO: 1208 or SEQ ID NO: 1209; (h) nucleotide 8 through nucleotide 36 of SEQ ID NO: 1208 or SEQ ID NO: 1209; (i) nucleotide 9 through nucleotide 36 of SEQ ID NO: 1208 or SEQ ID NO: 1209; (j) nucleotide 10 through nucleotide 36 of SEQ ID NO: 1208 or SEQ ID NO: 1209; (k) nucleotide 11 through nucleotide 36 of SEQ ID NO: 1208 or SEQ ID NO: 1209; (l) nucleotide 12 through nucleotide 36 of SEQ ID NO: 1208 or SEQ ID NO: 1209; (m) nucleotide 13 through nucleotide 36 of SEQ ID NO: 1208 or SEQ ID NO: 1209; (n) nucleotide 14 through nucleotide 36 of SEQ ID NO: 1208 or SEQ ID NO: 1209; (o) nucleotide 15 through nucleotide 36 of SEQ ID NO: 1208 or SEQ ID NO: 1209; or (p) SEQ ID NO: 1210 or a portion thereof.

In some examples, the RNA guide has a sequence that is at least 90% identical to a sequence of any one of SEQ ID NOs: 1214, 1235, 1224, 1221, or 1225. In specific examples, the RNA guide has the sequence of any one of SEQ ID NOs: 1214, 1235, 1224, 1221, or 1225.

In some examples, each of the first three nucleotides of the RNA guide comprises a 2'-O-methyl phosphorothioate modification.

In some examples, each of the last four nucleotides of the RNA guide comprises a 2'-O-methyl phosphorothioate modification.

In some examples, each of the first to last, second to last, and third to last nucleotides of the RNA guide comprises a 2'-O-methyl phosphorothioate modification, and wherein the last nucleotide of the RNA guide is unmodified.

In some examples, the RNA guide has a sequence that is at least 90% identical to a sequence of any one of SEQ ID NOs: 1254-1263. In specific examples, the RNA guide has the sequence of any one of SEQ ID NOs: 1254-1263.

In some embodiments, an LDHA-targeting RNA guide comprises at least 90% identity to any one of SEQ ID NOs: 1254-1263. In some embodiments, an LDHA-targeting RNA guide comprises any one of SEQ ID NOs: 1254-1263. In some embodiments, an LDHA-targeting RNA guide comprising at least 90% identity to SEQ ID NO: 1254 or SEQ ID NO: 1255 binds the complementary region of LDHA target sequence of SEQ ID NO: 1237. In some embodiments, the LDHA-targeting RNA guide of SEQ ID NO: 1254 or SEQ ID NO: 1255 binds the complementary region of LDHA target sequence of SEQ ID NO: 1237. In some embodiments, an LDHA-targeting RNA guide comprising at least 90% identity to SEQ ID NO: 1256 or SEQ ID NO: 1257 binds the complementary region of the LDHA target sequence of SEQ ID NO: 1239. In some embodiments, the LDHA-targeting RNA guide of SEQ ID NO: 1256 or SEQ ID NO: 1257 binds the complementary region of the LDHA target sequence of SEQ ID NO: 1239. In some embodiments, an LDHA-targeting RNA guide comprising at least 90% identity to SEQ ID NO: 1258 or SEQ ID NO: 1259 binds the complementary region of the LDHA target sequence of SEQ ID NO: 1248. In some embodiments, the LDHA-targeting RNA guide of SEQ ID NO: 1258 or SEQ ID NO: 1259 binds the complementary region of the LDHA target sequence of SEQ ID NO: 1248. In some embodiments, an LDHA-targeting RNA guide comprising at least 90% identity to SEQ ID NO: 1260 or SEQ ID NO: 1261 binds the complementary region of the LDHA target sequence of SEQ ID NO: 1245. In some embodiments, the LDHA-targeting RNA guide of SEQ ID NO: 1260 or SEQ ID NO: 1261 binds the complementary region of the LDHA target sequence of SEQ ID NO: 1245. In some embodiments, an LDHA-targeting RNA guide comprising at least 90% identity to SEQ ID NO: 1262 or SEQ ID NO: 1263 binds the complementary region of the LDHA target sequence of SEQ ID NO: 1249. In some embodiments, the LDHA-targeting RNA guide of SEQ ID NO: 1262 or SEQ ID NO: 1263 binds the complementary region of the LDHA target sequence of SEQ ID NO: 1249.

Embodiment 14: A nucleic acid encoding an RNA guide as described herein.

Embodiment 15: A vector comprising the nucleic acid as described herein.

Embodiment 16: A vector system comprising one or more vectors encoding (i) the RNA guide of Embodiment 13 as described herein and (ii) a Cas12i polypeptide. In some examples, the vector system comprises a first vector encoding the RNA guide and a second vector encoding the Cas12i polypeptide.

Embodiment 17: A cell comprising the RNA guide, the nucleic acid, the vector, or the vector system of Embodiments 13-16 as described herein. In some examples, the cell is a eukaryotic cell, an animal cell, a mammalian cell, a human cell, a primary cell, a cell line, a stem cell, or a T cell.

Embodiment 18: A kit comprising the RNA guide, the nucleic acid, the vector, or the vector system of Embodiments 13-16 as described herein.

Embodiment 19: A method of editing an LDHA sequence, the method comprising contacting an LDHA sequence with an RNA guide of Embodiment 13 as described herein. In some examples, the LDHA sequence is in a cell.

In some examples, the RNA guide induces an indel (e.g., an insertion or deletion) in the LDHA sequence.

Embodiment 20: A method of treating primary hyperoxaluria (PH), which optionally is PH1, PH2, or PH3, in a subject, the method comprising administering the RNA guide of Embodiment 13 as described herein to the subject.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (1RL Press, (1986»; and B. Perbal, *A practical Guide To Molecular Cloning* (1984); F. M. Ausubel et al. (eds.).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are provided to further illustrate some embodiments of the present disclosure but are not intended to limit the scope of the present disclosure; it will be understood by their exemplary nature that other procedures, methodologies, or techniques known to those skilled in the art may alternatively be used.

Example 1—Cas12i2-Mediated Editing of LDHA Target Sites in HEK293T Cells

This Example describes the genomic editing of the LDHA gene using Cas12i2 introduced into HEK293T cells.

Cas12i2 RNA guides (crRNAs) were designed and ordered from Integrated DNA Technologies (IDT). For initial guide screening in HEK293T cells, target sequences were designed by tiling the coding exons of LDHA for 5'-NTTN-3' PAM sequences, and then spacer sequences were designed for the 20-bp target sequences downstream of the PAM sequence. The LDHA-targeting RNA guide sequences are shown in Table 7. TS stands for "top strand" of the LDHA gene, and BS stands for "bottom strand" of the LDHA gene. In the figures, "E #T #" can also be represented as "exon #target #."

TABLE 7 crRNA sequences for LDHA

| guide name | PAM* | Target strand (non-PAM strand) | crRNA sequence | target sequence |
|---|---|---|---|---|
| LDHA_E2T23 | CTTA | TS | AGAAAUCCGUCUUUCAUUG ACGGCCUUCAUUAAGAUAC UGAUG (SEQ ID NO: 1213) | CCTTCATTAAGATA CTGATG (SEQ ID NO: 1236) |
| LDHA_E3T1 | CTTT | BS | AGAAAUCCGUCUUUCAUUG ACGGUAGGACUUGGCAGAU GAACU (SEQ ID NO: 1214) | TAGGACTTGGCAG ATGAACT (SEQ ID NO: 1237) |

TABLE 7-continued crRNA sequences for LDHA

| guide name | PAM* | Target strand (non-PAM strand) | crRNA sequence | target sequence |
|---|---|---|---|---|
| LDHA_E3T2 | GTTC | TS | AGAAAUCCGUCUUUCAUUG ACGGAUCUGCCAAGUCCUA AAAGA (SEQ ID NO: 1215) | ATCTGCCAAGTCCT AAAAGA (SEQ ID NO: 1238) |
| LDHA_E3T3 | CTTC | TS | AGAAAUCCGUCUUUCAUUG ACGGGAUGACAUCAACAAG AGCAA (SEQ ID NO: 1235) | GATGACATCAACA AGAGCAA (SEQ ID NO: 1239) |
| LDHA_E3T9 | ATTT | BS | AGAAAUCCGUCUUUCAUUG ACGGGAUGUCUUUUAGGAC UUGGC (SEQ ID NO: 1216) | GATGTCTTTTAGGA CTTGGC (SEQ ID NO: 1240) |
| LDHA_E3T10 | TTTG | BS | AGAAAUCCGUCUUUCAUUG ACGGAUGUCUUUUAGGACU UGGCA (SEQ ID NO: 1217) | ATGTCTTTTAGGAC TTGGCA (SEQ ID NO: 1241) |
| LDHA_E3T12 | TTTA | BS | AGAAAUCCGUCUUUCAUUG ACGGGGACUUGGCAGAUGA ACUUG (SEQ ID NO: 1218) | GGACTTGGCAGAT GAACTTG (SEQ ID NO: 1242) |
| LDHA_E3T26 | GTTG | TS | AGAAAUCCGUCUUUCAUUG ACGGAAAUCAACCUUUGCC AGAGA (SEQ ID NO: 1219) | AAATCAACCTTTGC CAGAGA (SEQ ID NO: 1243) |
| LDHA_E3T27 | CTTG | TS | AGAAAUCCGUCUUUCAUUG ACGGUUGAAAUCAACCUUU GCCAG (SEQ ID NO: 1220) | TTGAAATCAACCTT TGCCAG (SEQ ID NO: 1244) |
| LDHA_E5T1 | CTTT | BS | AGAAAUCCGUCUUUCAUUG ACGGUUCAUAGUGGAUAUC UUGAC (SEQ ID NO: 1221) | TTCATAGTGGATAT CTTGAC (SEQ ID NO: 1245) |
| LDHA_E5T7 | TTTT | BS | AGAAAUCCGUCUUUCAUUG ACGGCUCCUUUUUCAUAGU GGAUA (SEQ ID NO: 1222) | CTCCTTTTTCATAG TGGATA (SEQ ID NO: 1246) |
| LDHA_E5T8 | TTTC | BS | AGAAAUCCGUCUUUCAUUG ACGGUCCUUUUUCAUAGUG GAU AU (SEQ ID NO: 1223) | TCCTTTTTCATAGT GGATAT (SEQ ID NO: 1247) |
| LDHA_E5T9 | TTTT | BS | AGAAAUCCGUCUUUCAUUG ACGGUCAUAGUGGAUAUCU UGACC (SEQ ID NO: 1224) | TCATAGTGGATATC TTGACC (SEQ ID NO: 1248) |
| LDHA_E5T10 | TTTT | BS | AGAAAUCCGUCUUUCAUUG ACGGCAUAGUGGAUAUCUU GACCU (SEQ ID NO: 1225) | CATAGTGGATATCT TGACCT (SEQ ID NO: 1249) |
| LDHA_E5T11 | TTTC | BS | AGAAAUCCGUCUUUCAUUG ACGGAUAGUGGAUAUCUUG ACCUA (SEQ ID NO: 1226) | ATAGTGGATATCTT GACCTA (SEQ ID NO: 1250) |
| LDHA_E5T28 | ATTA | TS | AGAAAUCCGUCUUUCAUUG ACGGGGUAACGGAAUCGGG CUGAA (SEQ ID NO: 1227) | GGTAACGGAATCG GGCTGAA (SEQ ID NO: 1251) |
| LDHA_E5T32 | CTTA | TS | AGAAAUCCGUCUUUCAUUG ACGGCCACUGGAAUCUCCA UGUUC (SEQ ID NO: 1228) | CCACTGGAATCTCC ATGTTC (SEQ ID NO: 1252) |
| LDHA_E5T33 | CTTA | TS | AGAAAUCCGUCUUUCAUUG ACGGUGCUUACCACUGGAA UCUCC (SEQ ID NO: 1229) | TGCTTACCACTGGA ATCTCC (SEQ ID NO: 1253) |

*The 3' three nucleotides represent the 5'-TTN-3' motif.

Cas12i2 RNP complexation reactions were made by mixing purified Cas12i2 polypeptide (400 μM) with crRNA (1 mM in 250 mM NaCl) at a 1:1 (Cas12i2:crRNA) volume ratio (2.5:1 crRNA:Cas12i2 molar ratio). Complexations were incubated on ice for 30-60 min.

HEK293T cells were harvested using TRYPLE™ (recombinant cell-dissociation enzymes; Thermo Fisher) and counted. Cells were washed once with PBS and resuspended in SF buffer+supplement (SF CELL LINE 4D-NUCLEOFECTOR™ X KIT S; Lonza #V4XC-2032) at a concentration of 16,480 cells/μL. Resuspended cells were dispensed at 3e5 cells/reaction into Lonza 16-well NUCLEOCUVETTE® strips. Complexed Cas12i2 RNP was added to each reaction at a final concentration of 10 μM (Cas12i2), and transfection enhancer oligos were then added at a final concentration of 4 The final volume of each electroporated reaction was 20 μL. Non-targeting guides were used as negative controls.

The strips were electroporated using an electroporation device (program CM-130, Lonza 4D-NUCLEOFECTOR™). Immediately following electroporation, 80 μL of pre-warmed DMEM+10% FBS was added to each well and mixed gently by pipetting. For each technical replicate plate, plated 10 μL (30,000 cells) of diluted nucleofected cells into pre-warmed 96-well plate with wells containing 100 μL DMEM+10% FBS. Editing plates were incubated for 3 days at 37° C. with 5% $CO_2$.

After 3 days, wells were harvested using TRYPLE™ (recombinant cell-dissociation enzymes; Thermo Fisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C.

Samples for Next Generation Sequencing (NGS) were prepared by rounds of PCR. The first round (PCR I) was used to amplify the genomic regions flanking the target site and add NGS adapters. The second round (PCR II) was used to add NGS indexes. Reactions were then pooled, purified by column purification, and quantified on a fluorometer (Qubit). Sequencing runs were done using a 150 cycle NGS instrument (NEXTSEQ™ v2.5) mid or high output kit (Illumina) and run on an NGS instrument (NEXTSEQ™ 550; Illumina).

For NGS analysis, the indel mapping function used a sample's fastq file, the amplicon reference sequence, and the forward primer sequence. For each read, a kmer-scanning algorithm was used to calculate the edit operations (match, mismatch, insertion, deletion) between the read and the reference sequence. In order to remove small amounts of primer dimer present in some samples, the first 30 nt of each read was required to match the reference and reads where over half of the mapping nucleotides are mismatches were filtered out as well. Up to 50,000 reads passing those filters were used for analysis, and reads were counted as an indel read if they contained an insertion or deletion. The % indels was calculated as the number of indel-containing reads divided by the number of reads analyzed (reads passing filters up to 50,000). The QC standard for the minimum number of reads passing filters was 10,000.

FIG. 1 shows LDHA indels in HEK293T cells following RNP delivery. Error bars represent the average of three technical replicates across one biological replicate. Following delivery, indels were detected within and/or adjacent to each of the LDHA target sites with each of the RNA guides. Delivery of E3T1 (SEQ ID NO: 1214), E3T9 (SEQ ID NO: 1216), EST1 (SEQ ID NO: 1221), E5T9 (SEQ ID NO: 1224), and E5T10 (SEQ ID NO: 1225) resulted in indels in over 70% of the NGS reads. Therefore, LDHA-targeting RNA guides induced indels in exon 2, exon 3, and exon 5 in HEK293T cells.

This Example thus shows that LDHA can be individually targeted by Cas12i2 RNPs in mammalian cells such as HEK293T cells.

Example 2—Cas12i2-Mediated Editing of LDHA Target Sites in Hepg2 Cells

This Example describes the genomic editing of the LDHA gene using Cas12i2 introduced into HepG2 cells by RNP.

RNP complexation reactions were performed as described in Example 1 with various RNA guides of Table 7. HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032) at a concentration of 13,889 cells/μL. Resuspended cells were dispensed at 2.5e5 cells/reaction into Lonza 16-well NUCLEOCUVETTE® strips. Complexed Cas12i2 RNP was added to each reaction at a final concentration of 20 μM (Cas12i2), with no transfection enhancer oligo. The final volume of each electroporated reaction was 20 Non-targeting guides were used as negative controls.

The strips were electroporated using an electroporation device (program DJ-100, Lonza 4D-NUCLEOFECTOR™). Immediately following electroporation, 80 μL of pre-warmed EMEM+10% FBS was added to each well and mixed gently by pipetting. For each technical replicate plate, plated 10 μL (25,000 cells) of diluted nucleofected cells into pre-warmed 96-well plate with wells containing 100 μL EMEM+10% FBS. Editing plates were incubated for 3 days at 37° C. with 5% $CO_2$.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. Samples were analyzed by NGS as described in Example 1.

Figure 2:
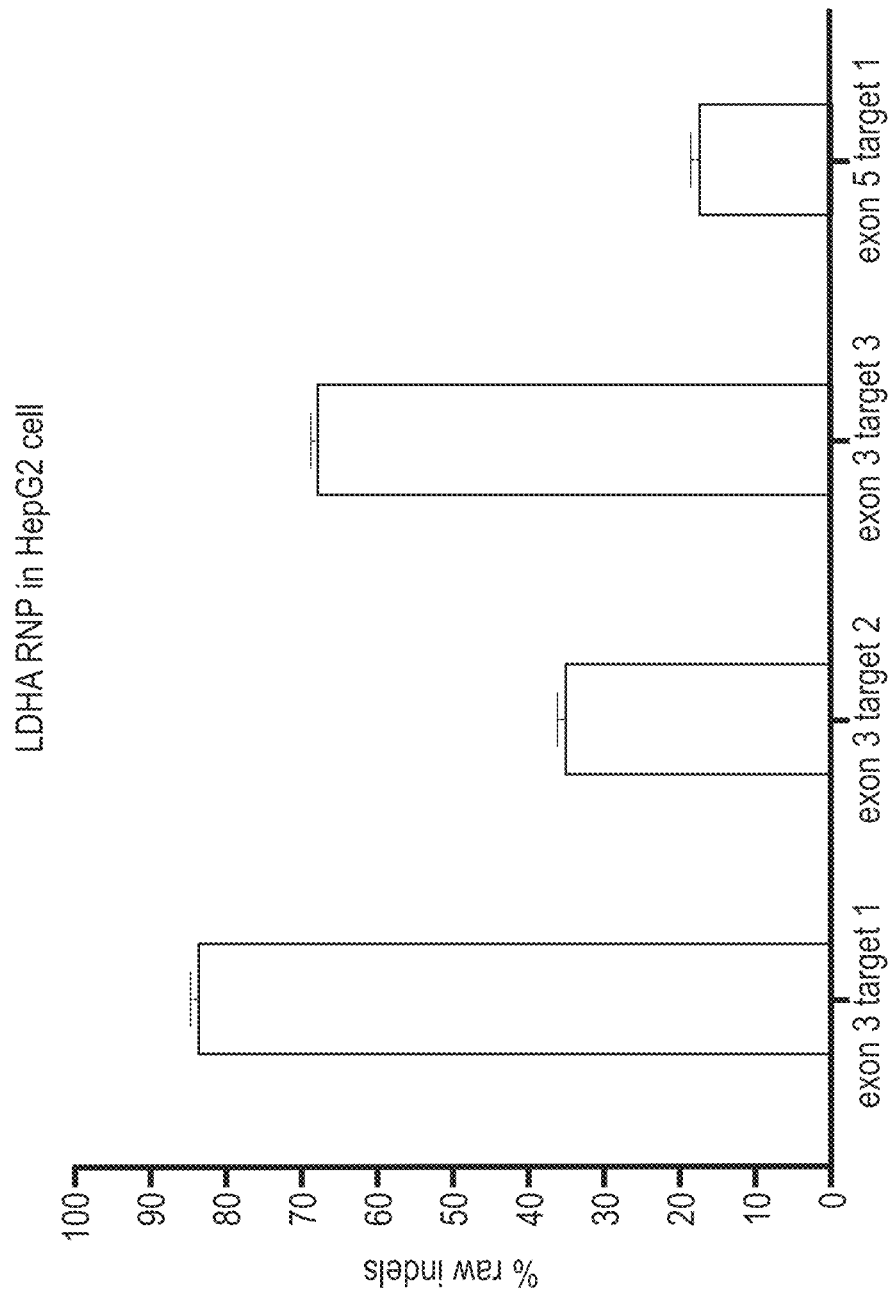
FIG. 2 is a graph showing the ability of RNPs prepared with a Cas12i2 polypeptide and a crRNA to edit LDHA target sequences in HepG2 cells.

FIG. 2 shows LDHA indels in HepG2 cells following RNP delivery. Error bars represent the average of three technical replicates across one biological replicate. Following delivery, indels were detected within and/or adjacent to each of the LDHA target sites with each of the RNA guides. Therefore, LDHA-targeting RNA guides induced indels in exon 3 and exon 5 in HepG2 cells.

Example 3—Cas12i2-Mediated Editing of LDHA Target Sites in Primary Hepatocytes

This Example describes the genomic editing of the LDHA using Cas12i2 introduced into primary hepatocytes cells by RNP.

RNP complexation reactions were performed as described in Example 1 with RNA guides of Table 7. Primary hepatocyte cells from human donors were thawed from liquid nitrogen very quickly in a 37° C. water bath. The cells were added to pre-warmed hepatocyte recovery media (Thermofisher, CM7000) and centrifuged at 100 g for 10 minutes. The cell pellet was resuspended in appropriate volume of hepatocyte plating Medium (Williams' Medium E, Thermofisher A1217601 supplemented with Hepatocyte Plating Supplement Pack (serum-containing), Thermofisher CM3000). The cells were subjected to trypan blue viability count with an INCUCYTE® disposable hemocytometer (Fisher scientific, 22-600-100). The cells were then washed in PBS and resuspended in P3 buffer+supplement (P3 PRIMARY CELL 4D-NUCLEOFECTOR™ X Kit; Lonza, VXP-3032) at a concentration of ~7,500 cells/μL. Resuspended cells were dispensed at 150,000 cells/reaction into the 16 well Lonza NUCLEOCUVETTE strips or 500,000 cells/reaction into the single Lonza NUCLEOCUVETTES® for the mRNA readout. Complexed Cas12i2 RNP was added to each reaction at a final concentration of 20 μM (Cas12i2), and transfection enhancer oligos were then added at a final concentration of 4 The final volume of each electroporated reaction was either 20 μL in the 16 well nucleocuvette strip format or 100 μL in the single nucleocuvette format. Non-targeting guides were used as negative controls.

The strips were electroporated using DS-150 program, while the single nucleocuvettes were electroporated using CA137 program (Lonza 4D-NUCLEOFECTOR™). Immediately following electroporation, pre-warmed Hepatocyte plating medium was added to each well and mixed very gently by pipetting. For each technical replicate plate, plated all the cell suspension of diluted nucleofected cells into a pre-warmed collagen-coated 96-well plate or 24-well plate (Thermofisher) with wells containing Hepatocyte plating medium. The cells were then incubated in a 37° C. incubator. The media was changed to hepatocyte maintenance media (Williams' Medium E, Thermofisher A1217601 supplemented with William's E medium Cell Maintenance Cocktail, Thermofisher CM 4000) after the cells attached after 4 hours. Fresh hepatocyte maintenance media was replaced after 2 days.

After 4-5 days post RNP electroporation, media was aspirated and the cells were harvested by shaking (500 rpm) in a 37° C. incubator with 2 mg/ml collagenase IV (Thermofisher, 17104019) dissolved in PBS containing Ca/Mg (Thermofisher). After cells were dissociated from the plate, they were transferred to 96-well TWIN.TEC® PCR plates (Eppendorf) and centrifuged. Media was flicked off and cell pellets for the NGS readout were resuspended in 20 μL QUICKEXTRACT™ (DNA extraction buffer; Lucigen). Samples were then cycled in a PCR machine at 65° C. for 15 min, 68° C. for 15 min, 98° C. for 10 min and analyzed by NGS as described in Example 1.

For the mRNA readout, cell pellets were frozen at −80° C. and subsequently resuspended in lysis buffer and DNA/RNA extracted with the RNeasy kit (Qiagen) following manufacturer's instructions. The DNA extracted from the samples were analyzed by NGS. The RNA isolated was checked for quantity and purity using nanodrop, and subsequently used for cDNA synthesis using 5× iScript reverse transcription reaction mix (Bio-Rad laboratories), following manufacturer's recommendations. cDNA templated was appropriately diluted to be in linear range of the subsequent analysis. Diluted cDNA was used to set up a 20 μL Digital Droplet PCR (ddPCR-BioRad laboratories) reaction using target-specific primer and probe for LDHA, TTTTCCT-TAGAACACCAAAGATTGTCTCTGGCAAAGAC-TATAATGTAACTGCAAAC TCCAAGCTGGTCATTAT-CACGGCTGGGGCACGTCAGCAAGAGG-GAGAAAGCCGTC TTAATTTGGTCSEQ ID NO: 1264), and 2× ddPCR Supermix for Probes No dUTP (BioRad laboratories) following manufacturer's instructions. The reaction was used to generate droplets using Automated Droplet Generator (BioRad Laboratories), following manufacture's recommendations. The plate was sealed using PX1 PCR Plate Sealer (BioRad Laboratories) generated droplets were subjected to PCR amplification using C1000 Touch Thermal Cycler (BioRad Laboratories) using conditions recommended by the manufacturer. The PCR amplified droplets were read on QX200 Droplet Reader (BioRad Laboratories) and the acquired data was analyzed using QX Manager version 1.2 (BioRad Laboratories) to determine presence of absolute copy number of mRNA present in each reaction for the appropriate targets.

Figure 3:
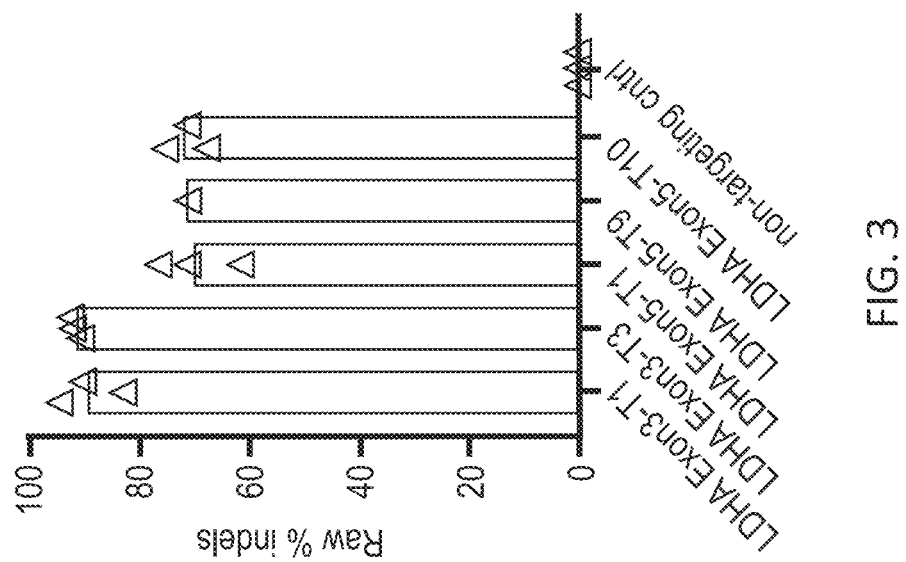
FIG. 3 is a graph showing the ability of RNPs prepared with a Cas12i2 polypeptide and a crRNA to edit LDHA target sequences in primary hepatocytes.
Figure 4:
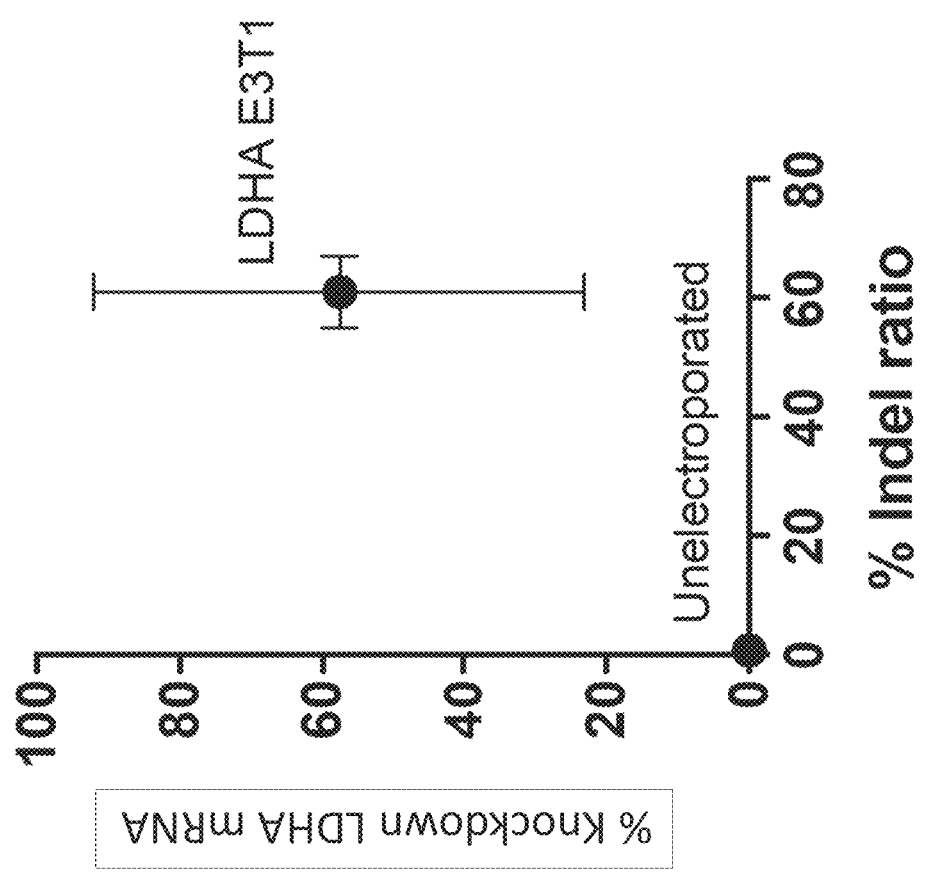
FIG. 4 is a graph showing knockdown of LDHA mRNA in primary human hepatocytes with a Cas12i2 polypeptide and an LDHA-targeting crRNA, E3T1 (SEQ ID NO: 1214).

As shown in FIG. 3, each RNA guide tested induced indels within and/or adjacent to the LDHA target sites. Indels were not induced with the non-targeting control. Therefore, LDHA-targeting RNA guides induced indels in primary hepatocytes. Indels for RNA guide E3T1 were then correlated with mRNA levels to determine whether indels led to mRNA knockdown and subsequent protein knockdown. FIG. 4 shows % mRNA knockdown of LDHA in edited cells compared to unedited control cells. RNA guide E3T1 resulted in knockdown of LDHA mRNA.

This Example thus shows that LDHA can be targeted by Cas12i2 RNPs in mammalian cells such as primary human hepatocytes.

Example 4—Editing of LDHA Target Sites in HepG2 Cells with Cas12i2 Variants

This Example describes indel assessment on LDHA target sites using variants introduced into HepG2 cells by transient transfection.

The Cas12i2 variants of SEQ ID NO: 1168 and SEQ ID NO: 1171 were individually cloned into a pcda3.1 backbone (Invitrogen). Nucleic acids encoding RNA guides E3T1, E3T3, E5T1, E5T9, and E5T10 (Table 7) were cloned into a pUC19 backbone (New England Biolabs). The plasmids were then maxi-prepped and diluted.

HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFEC-TOR™ X KIT S; Lonza #V4XC-2032).

Approximately 16 hours prior to transfection, 25,000 HepG2 cells in EMEM/10% FBS were plated into each well of a 96-well plate. On the day of transfection, the cells were 70-90% confluent. For each well to be transfected, a mixture of Lipofectamine™ 3000 and Opti-MEM® was prepared and then incubated at room temperature for 5 minutes (Solution 1). After incubation, the Lipofectamine™:Op-tiMEM® mixture was added to a separate mixture containing nuclease plasmid and RNA guide plasmid and P3000 reagent (Solution 2). In the case of negative controls, the crRNA was not included in Solution 2. The Solution 1 and Solution 2 were mixed by pipetting up and down and then incubated at room temperature for 15 minutes. Following incubation, the Solution 1 and Solution 2 mixture was added dropwise to each well of a 96 well plate containing the cells.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. and analyzed by NGS as described in Example 1.

Figure 5A:
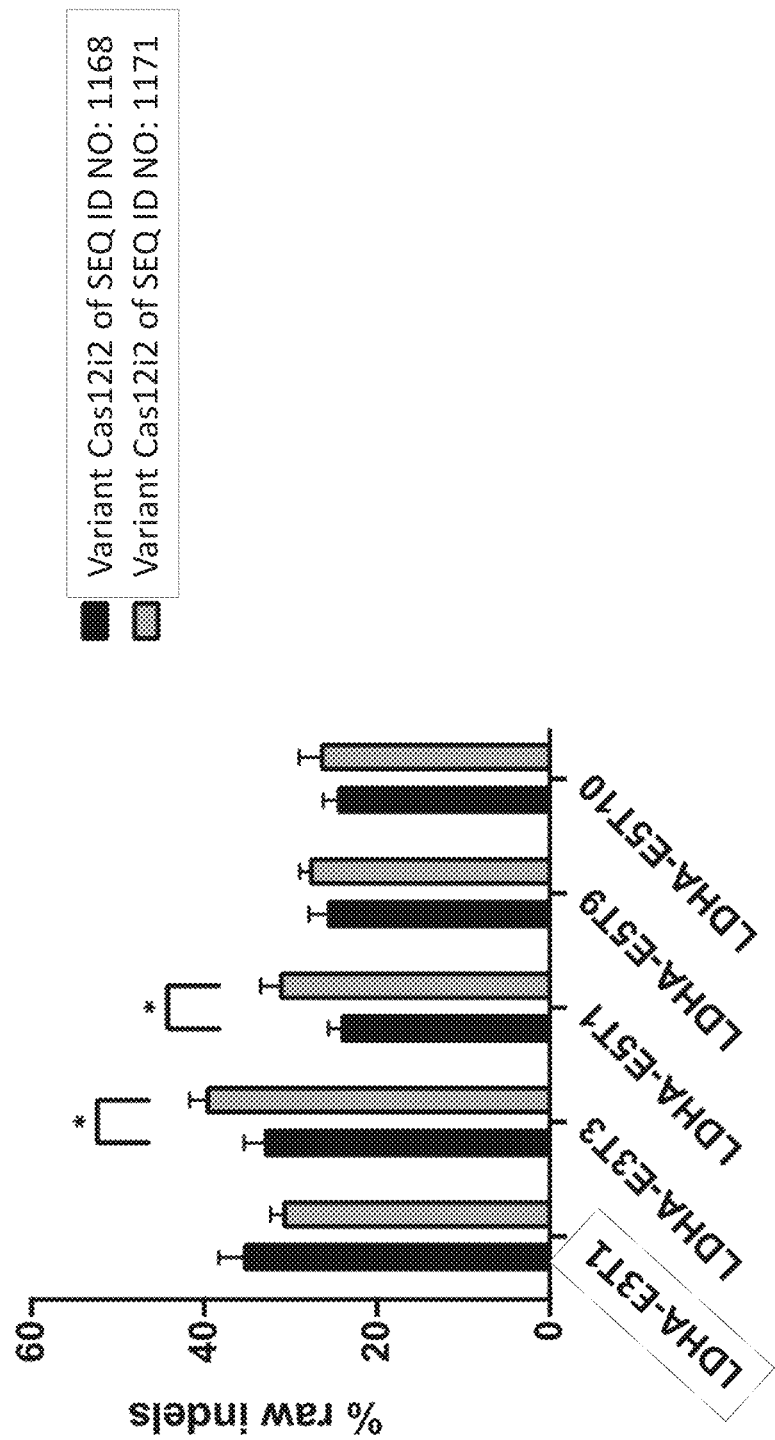
FIG. 5A is a graph showing % indels induced by LDHA-targeting crRNAs and the variant Cas12i2 polypeptide of SEQ ID NO: 1168 or SEQ ID NO: 1171 in HepG2 cells.
Figure 5B:
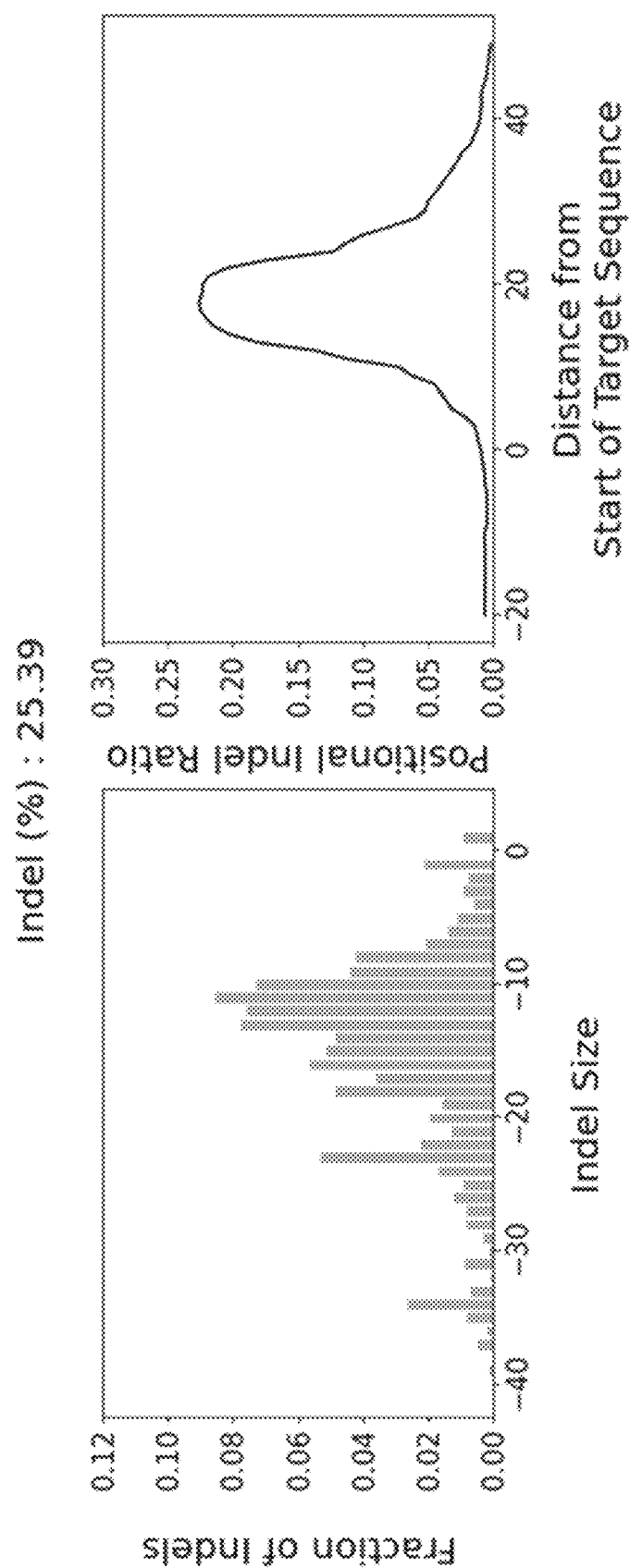
FIG. 5B shows the size (left) and start position (right) of indels induced in HepG2 cells by the variant Cas12i2 of SEQ ID NO: 1168 and the LDHA-targeting RNA guide of E5T9 (SEQ ID NO: 1224).

As shown in FIG. 5A, two guides, E3T3 and E5T1, demonstrated significantly higher activity with variant Cas12i2 of SEQ ID NO: 1171 compared to variant Cas12i2 of SEQ ID NO: 1168. Comparable indel activity with the two Cas12i2 variants was observed for E3T1, E5T9, and E5T10. FIG. 5B shows the indel size frequency (left) and indel start position relative to the PAM for E5T9 and the variant Cas12i2 of SEQ ID NO: 1168 in HepG2 cells. As shown on the left, deletions ranged in size from 1 nucleotide to about 40 nucleotides. The majority of the deletions were about 8 nucleotides to about 23 nucleotides in length. As shown on the right, the target sequence is represented as starting at position 0 and ending at position 20. Indels started within about 5 nucleotides and about 35 nucleotides downstream of the PAM sequence. The majority of indels started about 10 nucleotides to about 30 nucleotides downstream of the PAM sequence.

Thus, this Example shows that LDHA is capable of being targeted by multiple Cas12i2 polypeptides.

Example 5—Editing of LDHA in Primary Human Hepatocytes Using Cas12i2 mRNA Constructs This Example describes indel assessment on LDHA target sites via delivery of Cas12i2 mRNA and chemically modified LDHA-targeting RNA guides.

mRNA sequences corresponding to the variant Cas12i2 sequence of SEQ ID NO: 1168 and the variant Cas12i2 sequence of SEQ ID NO: 1171 were synthesized by Aldeveron with 1-pseudo-U modified nucleotides and using CleanCap® Reagent AG (TriLink Biotechnologies). The Cas12i2 mRNA sequences, shown in Table 8, further comprised a C-terminal NLS.

TABLE 8

Cas12i2 mRNA Sequences

| Description | mRNA sequence |
| --- | --- |
| mRNA corresponding to variant Cas12i2 of SEQ ID NO: 1168 | AUGAGCUCCGCCAUCAAGUCCUACAAGUCUGUGCUGCGGCCAAACGAGAGAAAGAAUCAGC UGCUGAAGUCCACCAUCCAGUGCCUGGAGGACGGCUCCGCCUUCUUUUUCAAGAUGCUGCA GGGCCUGUUUGGCGGCAUCACCCCCGAGAUCGUGAGAUUCAGCACAGAGCAGGAGAAGCAG CAGCAGGAUAUCGCCCUGUGGUGUGCCGUGAAUUGGUUCAGGCCUGUGAGCCAGGACUCCC UGACCCACACAAUCGCCUCCGAUAACCUGGUGGAGAAGUUUGAGGAGUACUAUGGCGGCAC AGCCAGCGACGCCAUCAAGCAGUACUUCAGCGCCUCCAUCGGCGAGUCCUACUAUUGGAAU GACUGCCGCCAGCAGUACUAUGAUCUGUGUCGGGAGCUGGGCGUGGAGGUGUCUGACCUGA CCCACGAUCUGGAGAUCCUGUGCCGGGAGAAGUGUCUGGCCGUGGCCACAGAGAGCAACCA GAACAAUUCUAUCAUCAGCGUGCUGUUUGGCACCGGCGAGAAGGAGGAUAGGUCUGUGAAG CUGCGCAUCACAAAGAAGAUCCUGGAGGCCAUCAGCAACCUGAAGGAGAUCCCAAAGAAUG UGGCCCCCAUCCAGGAGAUCAUCCUGAAUGUGGCCAAGGCCACCAAGGAGACAUUCAGACA GGUGUACGCAGGAAACCUGGGAGCACCAUCCACCCUGGAGAAGUUUAUCGCCAAGGACGGC CAGAAGGAGUUCGAUCUGAAGAAGCUGCAGACAGACCUGAAGAAAGUGAUCCGGGGCAAGU CUAAGGAGAGAUUGGUGCUGUCAGGAGGAGCUGAGGAGCUACGUGGAGCAGAAUACCAU CCAGUAUGACCUGUGGGCCUGGGGCGAGAUGUUCAACAAGGCCCACACCGCCCUGAAGAUC AAGUCCACAAGAAACUACAAUUUUGCCAAGCAGAGGCUGGAGCAGUUCAAGGAGAUCCAGU CUCUGAACAAUCUGCUGGUGGUGAAGAAGCUGAACGACUUUUUCGAUAGCGAGUUUUUCUC CGGCGAGGAGACCUACACAAUCUGCGUGCACCACCUGGGCGGCAAGGACCUGUCCAAGCUG UAUAAGGCCUGGGAGGACGAUCCCGCCGAUCCUGAGAAUGCCAUCGUGGUGCUGUGCGACG AUCUGAAGAACAAUUUUAAGAAGGAGCUAUCAGGAACAUCCUGCGCUACAUCUUCACCAU CCGCCAGGAGUGUAGCGCACAGGACAUCCUGGCAGCAGCAAAGUACAAUCAGCAGCUGGAU CGGUAUAAGAGCCAGAAGGCCAACCCAUCCGUGCUGGGCAAUCAGGGCUUUACCUGGACAA ACGCCGUGAUCCUGCCAGAGAAGGCCCAGCGGAACGACAGACCCAAUUCUCUGGAUCUGCG CAUCUGGCUGUACCUGAAGCUGCGGCACCCUGACGGCAGAUGGAAGAAGCACCACAUCCCA UUCUACGAUACCCGGUUUUUCCAGGAGAUCUAUGCCGCCGGCAAUAGCCCUGUGGACACCU GUCAGUUUAGGACACCCCGCUUCGGCUAUCACCUGCCUAAGCUGACCGAUCAGACAGCCAU CCGCGUGAACAAGAAGCACGUGAAGGCAGCAAAGACCGAGGCACGGAUCAGACUGGCCAUC CAGCAGGGCACACUGCCAGUGUCCAAUCUGAAGAUCACCGAGAUCUCCGCCACAAUCAACU CUAAGGGCCAGGUGCGCAUCCCCGUGAAGUUUCGGGUGGGAAGGCAGAAGGGAACCCUGCA GAUCGGCGACCGGUUCUGCGGCUACGAUCAGAACCAGACAGCCUCUCACGCCUAUAGCCUG UGGGAGGUGGUGAAGGAGGGCCAGUACCACAAGGAGCUGGGCUGUUUUGUGCGCUUCAUCU CUAGCGGCGACAUCGUGUCCAUCACCGAGAACCGGGGCAAUCAGUUUGAUCAGCUGUCUUA UGAGGGCCUGGCCUACCCCCAGUAUGCCGACUGGAGAAAGAAGGCCUCCAAGUUCGUGUCU CUGUGGCAGAUCACCAAGAAGAACAAGAAGAAGGAGAUCGUGACAGUGGAGGCCAAGGAGA AGUUUGACGCCAUCUGCAAGUACCAGCCUAGGCUGUAUAAGUUCAACAAGGAGUACGCCUA UCUGCUGCGGGAUAUCGUGAGAGGCAAGAGCCUGGUGGAGCUGCAGCAGAUCAGGCAGGAG AUCUUUCGCUUCAUCGAGCAGGACUGUGGAGUGACCCGCCUGGGAUCUCUGAGCCUGUCCA CCCUGGAGACAGUGAAGGCCGUGAAGGGCAUCAUCUACUCCUAUUUUUCUACAGCCCUGAA UGCCUCUAAGAACAAUCCCAUCAGCGACGAGCACGGAAGGAGUUUGAUCCUGAGCUGUUC GCCCUGCUGGAGAAGCUGGAGCUGAUCAGGACUCGGAAGAAGAAGCAGAAGGUGGAGAGAA UCGCCAAUAGCCUGAUCCAGACAUGCCUGGAGACAAAUAUCAAGUUCAUCAGGGGCGAGGG CGACCUGUCCACCACAAACAAUGCCACCAAGAAGAAGGCCAACUCUAGGAGCAUGGAUUGG CUGGCCAGAGGCGUGUUUAAUAAGAUCCGGCAGCUGGCCCCAAUGCACAACAUCACCCUGU UCGGCUGCGGCAGCCUGUACACAUCCCACCAGGACCCUCUGGGUGCACAGAAACCCAGAUAA GGCCAUGAAGUGUAGAUGGGCAGCAAUCCCAGUGAAGGACAUCGGCGAUUGGGUGCUGAGA AAGCUGUCCCAGAACCUGAGGGCCAAGAAUCGGGGCACCGGCGAGUACUAUCACCAGGGCG UGAAGGAGUUCCUGUCUCACUAUGAGCUGCAGGACCUGGAGGAGGAGCUGCUGAAGUGGCG GUCUGAUAGAAAGAGCAACAUCCCUUGCUGGGGUGCUGCAGAAUAGACUGGCCGAGAAGCUG GGCAACAAGGAGGCCGUGGUGUACAUCCCAGUGAGGGGCGGCCGCAUCUAUUUUGCAACCC ACAAGGUGGCAACAGGAGCCGUGAGCAUCGUGUUCGACCAGAAGCAAGUGUGGGUGUGUAA UGCAGAUCACGUGGCAGCAGCAAACAUCGCACUGACCGGCAAGGGCAUCGGCGAGCAGUCC UCUGACGAGGAGAACCCCGAUGGCUCCAGGAUCAAGCUGCAGCUGACAUCUAAAAGGCCGG CGGCCACGAAAAAGGCCGGCCAGGCAAAAAAGAAAAAGUAA (SEQ ID NO: 1265) |

TABLE 8-continued

Cas12i2 mRNA Sequences

| Description | mRNA sequence |
|---|---|
| mRNA corresponding to variant Cas12i2 of SEQ ID NO: 1171 | AUGAGCUCCGCCAUCAAGUCCUACAAGUCUGUGCUGCGGCCAAACGAGAGAAAGAAUCAGC UGCUGAAGUCCACCAUCCAGUGCCUGGAGGACGGCUCCGCCUUCUUUUUCAAGAUGCUGCA GGGCCUGUUUGGCGGCAUCACCCCCGAGAUCGUGAGAUUCAGCACAGAGCAGGAGAAGCAG CAGCAGGAUAUCGCCCUGUGGUGUGCCGUGAAUUGGUUCAGGCCUGUGAGCCAGGACUCCC UGACCCACACAAUCGCCUCCGAUAACCUGGUGGAGAAGUUUGAGGGAGUACUAUGGCGGCAC AGCCAGCGACGCCAUCAAGCAGUACUUCAGCGCCUCCAUCGGCGAGUCCUACUAUUGGAAU GACUGCCGCCAGCAGUACUAUGAUCUGUGUCGGGAGCUGGGCGUGGAGGUGUCUGACCUGA CCCACGAUCUGGAGAUCCUGUGCCGGGAGAAGUGUCUGGCCGUGGCCACAGAGAGCAACCA GAACAAUUCUAUCAUCAGCGUGCUGUUUGGCACCGGCGAGAAGGAGGAUAGGUCUGUGAAG CUGCGCAUCACAAAGAAGAUCCUGGAGGCCAUCAGCAACCUGAAGGAGAUCCCAAAGAAUG UGGCCCCCAUCCAGGAGAUCAUCCUGAAUGUGGCCAAGGCCACCAAGGAGACAUUCAGACA GGUGUACGCAGGAAACCUGGGAGCACCAUCCACCCUGGAGAAGUUUAUCGCCAAGGACGGC CAGAAGGAGUUCGAUCUGAAGAAGCUGCAGACAGACCUGAAGAAAGUGAUCCGGGGCAAGU CUAAGGAGAGAGAUUGGUGCUGUCAGGAGGAGCUGAGGAGCUACGUGGAGCAGAAUACCAU CCAGUAUGACCUGUGGGCCUGGGGCGAGAUGUUCAACAAGGCCCACACCGCCCUGAAGAUC AAGUCCACAAGAAACUACAAUUUUGCCAAGCAGAGGCUGGAGCAGUUCAAGGAGAUCCAGU CUCUGAACAAUCUGCUGGUGGUGAAGAAGCUGAACGACUUUUUCGAUAGCGAGUUUUUCUC CGGCGAGGAGACCUACACAAUCUGCGUGCACCACCUGGGCGGCAAGGACCUGUCCAAGCUG UAUAAGGCCUGGGAGGACGAUCCCGCCGAUCCUGAGAAUGCCAUCGUGGUGCUGUGCGACG AUCUGAAGAACAAUUUUAAGAAGGAGCCUAUCAGGAACAUCCUGCGCUACAUCUUCACCAU CCGCCAGGAGUGUAGCGCACAGGACAUCCUGGCAGCAGCAAAGUACAAUCAGCAGCUGGAU CGGUAUAAGAGCCAGAAGGCCAACCCAUCCGUGCUGGGCAAUCAGGGCUUUACCUGGACAA ACGCCGUGAUCCUGCCAGAGAAGGCCCAGCGGAACGACAGACCCAAUUCUCUGGAUCUGCG CAUCUGGCUGUACCUGAAGCUGCGGCACCCUGACGGCAGAUGGAAGAAGCACCACAUCCCA UUCUACGAUACCCGGUUUUUCCAGGAGAUCUAUGCCGCCGGCAAUAGCCCUGUGGACACCU GUCAGUUUAGGACACCCCGCUUCGGCUAUCACCUGCCUAAGCUGACCGAUCAGACAGCCAU CCGCGUGAACAAGAAGCACGUGAAGGCAGCAAAGACCGAGGCACGGAUCAGACUGGCCAUC CAGCAGGGCACACUGCCAGUGUCCAAUCUGAAGAUCACCGAGAUCUCCGCCACAAUCAACU CUAAGGGCCAGGUGCGCAUCCCCGUGAAGUUUCGGGUGGGAAGGCAGAAGGGAACCCUGCA GAUCGGCGACCGGUUCUGCGGCUACGAUCAGAACCAGACAGCCUCUCACGCCUAUAGCCUG UGGGAGGUGGUGAAGGAGGGCCAGUACCACAAGGAGCUGCGGUGUCGGGUGCGCUUCAUCU CUAGCGGCGACAUCGUGUCCAUCACCGAGAACCGGGGCAAUCAGUUUGAUCAGCUGUCUUA UGAGGGCCUGGCCUACCCCCAGUAUGCCGACUGGAGAAAGAAGGCCUCCAAGUUCGUGUCU CUGUGGCAGAUCACCAAGAAGAACAAGAAGAAGGAGAUCGUGACAGUGGAGGCCAAGGAGA AGUUUGACGCCAUCUGCAAGUACCAGCCUAGGCUGUAUAAGUUCAACAAGGAGUACGCCUA UCUGCUGCGGGAUAUCGUGAGAGGCAAGAGCCUGGUGGAGCUGCAGCAGAUCAGGCAGGAG AUCUUUCGCUUCAUCGAGCAGGACUGUGGAGUGACCCGCCUGGGAUCUCUGAGCCUGUCCA CCCUGGAGACAGUGAAGGCCGUGAAGGGCAUCAUCUACUCCUAUUUUUCUACAGCCCUGAA UGCCUCUAAGAACAAUCCCAUCAGCGACGAGCAGCGGAAGGAGUUUGAUCCUGAGCUGUUC GCCCUGCUGGAGAAGCUGGAGCUGAUCAGGACUCGGAAGAAGAAGCAGAAGGUGGAGAGAA UCGCCAAUAGCCUGAUCCAGACAUGCCUGGAGAACAAUAUCAAGUUCAUCAGGGGCGAGGG CGACCUGUCCACCACAAACAAUGCCACCAAGAAGAAGGCCAACUCUAGGAGCAUGGAUUGG CUGGCCAGAGGCGUGUUUAAUAAGAUCCGGCAGCUGGCCACCAUGCACAACAUCACCCUGU UCGGCUGCGGCAGCCUGUACACAUCCCACCAGGACCCUCUGGGUGCACAGAAACCCAGAUAA GGCCAUGAAGUGUAGAUGGGCAGCAAUCCCAGUGAAGGACAUCGGCGAUUGGGUGCUGAGA AAGCUGUCCCAGAACCUGAGGGCCAAGAAUCGGGGCACCGGCGAGUACUAUCACCAGGCG UGAAGGAGUUCCUGUCUCACUAUGAGCUGCAGGACCUGGAGGAGGAGCUGCUGAAGUGGCG GUCUGAUAGAAAGAGCAACAUCCCUUGCUGGGUGCUGCAGAAUAGACUGGCCGAGAAGCUG GGCAACAAGGAGGCCGUGGUGUACAUCCCAGUGAGGGGCGGCCGCAUCUAUUUUGCAACCC ACAAGGUGGCAACAGGAGCCGUGAGCAUCGUGUUCGACCAGAAGCAAGUGUGGGGUGUGUAA UGCAGAUCACGUGGCAGCAGCAAACAUCGCACUGACCGGCAAGGGCAUCGGCCGGCAGUCC UCUGACGAGGAGAACCCCGAUGGCGGCAGGAUCAAGCUGCAGCUGACAUCUAAAAGGCCGG CGGCCACGAAAAAGGCCGGCCAGGCAAAAAAGAAAAAGUAA (SEQ ID NO: 1266) |

Cas12i2 RNA guides were designed and ordered from Integrated DNA Technologies (IDT) as having 3' end modified phosphorothioated 2' O-methyl bases or 5' end and 3' end modified phosphorothioated 2' O-methyl bases guides, as specified in Table 9. Each variant Cas12i2 mRNA was mixed with a crRNA at a 1:1 (Cas12i2:crRNA) volume ratio (1050:1 crRNA:Cas12i2 molar ratio). The mRNA and crRNA were mixed immediately before electroporation. The primary human hepatocyte cells were cultured and electroporated as described in Example 3.

TABLE 9

Chemically Modified RNA Guide Sequences

| RNA Guide | Sequence |
|---|---|
| 3' end modified E3T1 | AGAAAUCCGUCUUUCAUUGACGGUAGGACUUGGCAGAUGA*mA*mC*mU (SEQ ID NO: 1267) |
| 5' and 3' end modified E3T1 | mA*mG*mA*AAUCCGUCUUUCAUUGACGGUAGGACUUGGCAGAUGA*mA*mC*mU (SEQ ID NO: 1268) |

Figure 6:
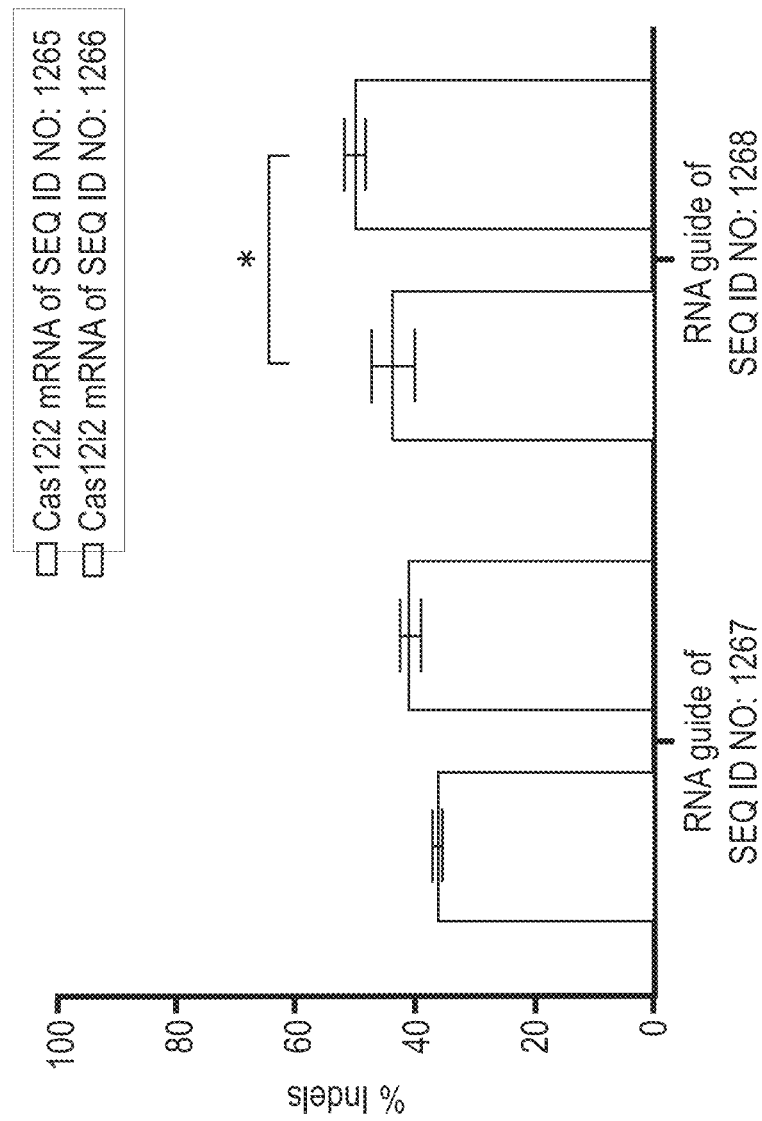
FIG. 6 is a graph showing % indels induced by chemically modified LDHA-targeting crRNAs of SEQ ID NO: 1267 and SEQ ID NO: 1268 and the variant Cas12i2 mRNA of SEQ ID NO: 1265 or SEQ ID NO: 1266.

FIG. 6 shows editing of an LDHA target site by a variant Cas12i2 mRNA and 3' end modified E3T1 (SEQ ID NO: 1267) or 5' and 3' end modified E3T1 (SEQ ID NO: 1268) RNA guide. Indels in the LDHA target site were introduced following electroporation of the Cas12i2 mRNA of SEQ ID NO: 1265 or SEQ ID NO: 1266 and either the RNA guide of SEQ ID NO: 1267 or SEQ ID NO: 1268. A higher percentage of NGS reads exhibited indels for RNA guide E3T1 with 5' and 3' end modifications (SEQ ID NO: 1268) compared to NGS reads for RNA guide with 3' end modifications only (SEQ ID NO: 1267). Approximately 50% of NGS reads comprised indels following electroporation of the Cas12i2 mRNA of SEQ ID NO: 1266 and the RNA guide of SEQ ID NO: 1268.

This Example thus shows that LDHA can be targeted by Cas12i2 mRNA constructs and chemically modified RNA guides in mammalian cells.

Example 6—Off-Target Analysis of Cas12i2 and LDHA-Targeting RNA Guides

This Example describes on-target versus off-target assessment of a Cas12i2 variant and an LDHA-targeting RNA guide.

HEK293T cells were transfected with a plasmid encoding the variant Cas12i2 of SEQ ID NO: 1168 or the variant Cas12i2 of SEQ ID NO: 1171 and a plasmid encoding E3T1 (SEQ ID NO: 1214), E5T1 (SEQ ID NO: 1221), E5T9 (SEQ ID NO: 1224), or E5T10 (SEQ ID NO: 1225) according the method described in Example 16 of PCT/US21/25257. The tagmentation-based tag integration site sequencing (TTISS) method described in Example 16 of PCT/US21/25257 was then carried out.

Figure 7A:
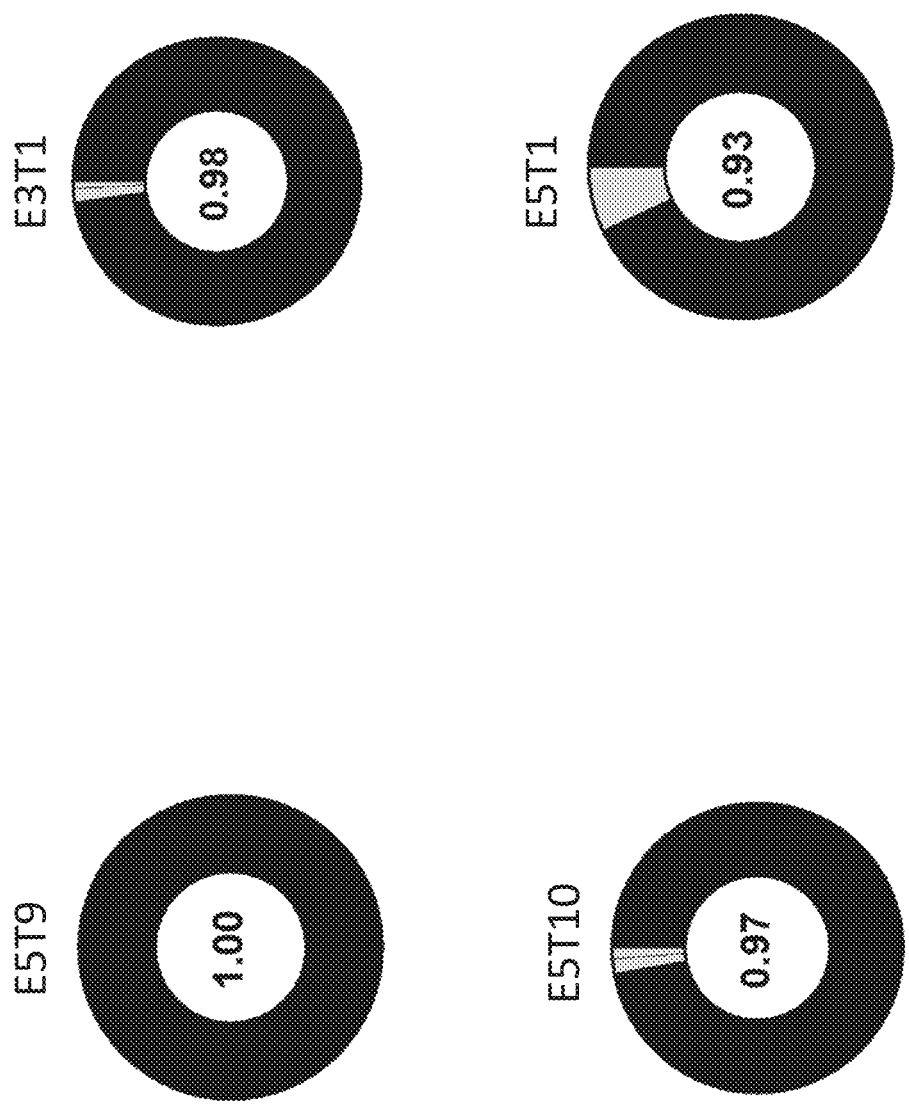
FIG. 7A shows plots depicting tagmentation-based tag integration site sequencing (TTISS) reads for variant Cas12i2 of SEQ ID NO: 1168 and LDHA-targeting RNA guides E5T9 (SEQ ID NO: 1224), E3T1 (SEQ ID NO: 1214), E5T10 (SEQ ID NO: 1225), and E5T1 (SEQ ID NO: 1221). The black wedge and centered number represent the fraction of on-target TTISS reads. Each gray wedge represents a unique off-target site identified by TTISS. The size of each gray wedge represents the fraction of TTISS reads mapping to a given off-target.
Figure 7B:
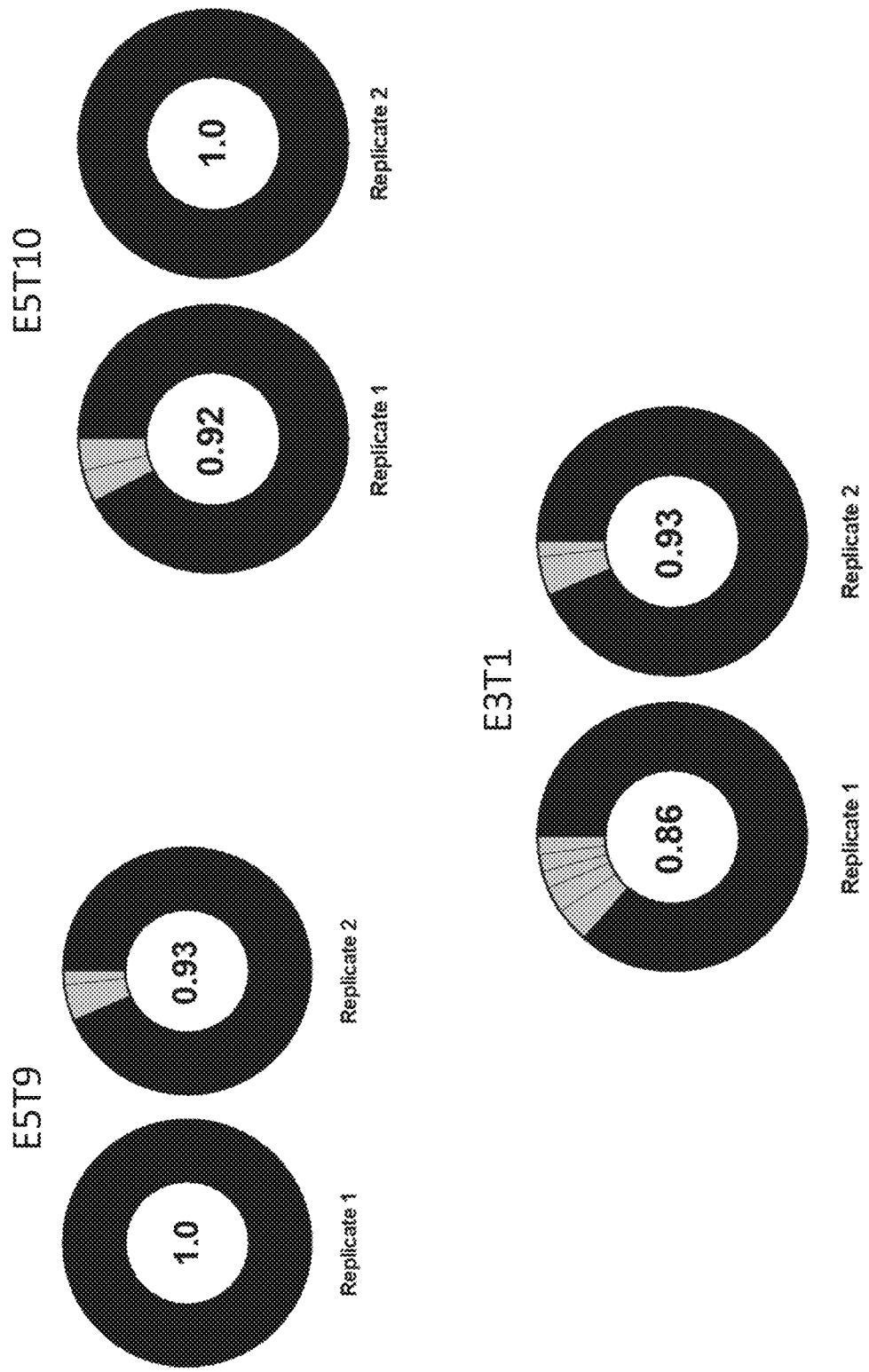
FIG. 7B shows plots depicting two replicates of TTISS reads for variant Cas12i2 of SEQ ID NO: 1171 and LDHA-targeting RNA guides E5T9 (SEQ ID NO: 1224), E5T10 (SEQ ID NO: 1225), and E3T1 (SEQ ID NO: 1214). The black wedge and centered number represent the fraction of on-target TTISS reads. Each gray wedge represents a unique off-target site identified by TTISS. The size of each gray wedge represents the fraction of TTISS reads mapping to a given off-target.

FIG. 7A and FIG. 7B show plots depicting on-target and off-target TTISS reads. The black wedge and centered number represent the fraction of on-target TTISS reads. Each grey wedge represents a unique off-target site identified by TTISS. The size of each grey wedge represents the fraction of TTISS reads mapping to a given off-target site. FIG. 7A shows TTISS reads for variant Cas12i2 of SEQ ID NO: 1168, and FIG. 7B shows TTISS reads for variant Cas12i2 of SEQ ID NO: 1171.

As shown in FIG. 7A, variant Cas12i2 of SEQ ID NO: 1168 paired with E5T9 demonstrated a low likelihood of off-target editing, as 100% of TTISS reads mapped to the on-target. No TTISS reads mapped to potential off-target sites. E3T1 and E5T10 also showed a low likelihood of off-target editing. For E3T1, 98% of TTISS reads mapped to the on-target, and two potential off-target sites represented a combined 2% of TTISS reads. For E5T10, 97% of TTISS reads mapped to the on-target, and two potential off-target sites represented a combined 3% of TTISS reads. E5T1 demonstrated a higher likelihood of off-target editing using the TTISS method.

As shown in FIG. 7B, variant Cas12i2 of SEQ ID NO: 1171 paired with the E5T9 demonstrated a low likelihood of off-target editing, as 100% of TTISS reads in replicate 1 and 93% of TTISS reads in replicate 2 mapped to the on-target, and two potential off-target sites represented the remaining 7% of TTISS reads in replicate 2. E5T10 also showed a low likelihood of off-target editing; 92% of TTISS reads in replicate 1 and 100% of TTISS reads in replicate 2 mapped to the on-target, and two potential off-target sites represented the remaining 8% of TTISS reads in replicate 1. Variant Cas12i2 of SEQ ID NO: 1171 paired with the E3T1 demonstrated a higher likelihood of off-target editing. 86% and 93% of TTISS reads mapping to the on-target in replicate 1 and replicate 2, respectively. 5 potential off-target sites represented the remaining 14% of TTISS reads in replicate 1, and 2 potential off-target sites represented the remaining 7% off TTISS reads in replicate 2 for E3T1.

Therefore, this Example shows that compositions comprising Cas12i2 and LDHA-targeting RNA guides comprise different off-target activity profiles.

Example 7—LDHA Protein Knockdown with Cas12i2 and LDHA-Targeting RNA Guides

This Example describes use of a Western Blot to identify knockdown of LDHA protein using variant Cas12i2 of SEQ ID NO: 1168 and LDHA-targeting RNA guides.

Primary hepatocyte cells from human donors were thawed from liquid nitrogen very quickly in a 37° C. water bath. The cells were added to pre-warmed hepatocyte recovery media (Thermo Fisher, CM7000) and centrifuged at 100 g for 10 minutes. The cell pellet was resuspended in appropriate volume of hepatocyte plating Medium (Williams' Medium E, Thermo Fisher A1217601 supplemented with Hepatocyte Plating Supplement Pack (serum-containing), Thermo Fisher CM3000). The cells were subjected to trypan blue viability count with an Inucyte disposable hemocytometer (Fisher scientific, 22-600-100). The cells were then washed in PBS and resuspended in P3 buffer+supplement (Lonza, VXP-3032) at a concentration of ~5000 cells/µL. Resuspended cells were dispensed at 500,000 cells/reaction into Lonza electroporation cuvettes For the RNP reactions, E3T1 (SEQ ID NO: 1214), E5T9 (SEQ ID NO: 1224), E5T1 (SEQ ID NO: 1221), and E5T10 (SEQ ID NO: 1225) were used as the LDHA-targeting RNA guides. RNPs were added to each reaction at a final concentration of 20 µM (Cas12i2), and transfection enhancer oligos were then added at a final concentration of 4 Unelectroporated cells and cells electroporated without cargo were used as negative controls.

The strips were electroporated using an electroporation device (program CA137, Lonza 4D-nucleofector). Immediately following electroporation, pre-warmed Hepatocyte plating medium was added to each well and mixed very gently by pipetting. For each technical replicate plate, 500,000 cells of diluted nucleofected cells were plated into a pre-warmed collagen-coated 24-well plate (Thermo Fisher) with wells containing Hepatocyte plating medium. The cells were then incubated at 37° C. The media was changed to hepatocyte maintenance media (Williams' Medium E, Thermo Fisher A1217601 supplemented with William's E medium Cell Maintenance Cocktail, Thermo Fisher CM 4000) after the cells attached after 24 hours. Fresh hepatocyte maintenance media was replaced every 48 hours.

7 days post RNP electroporation, the media was aspirated, and the cells were washed gently with PBS. Cells were then lysed with RIPA Lysis and Extraction buffer (Thermo Fisher 89901)+1× protease inhibitors (Thermo Fisher 78440) for 30 minutes on ice, mixing the samples every 5 minutes. Cell lysate was quantified via Pierce BCA Protein Assay Kit (Thermo Fisher 23227). 15 µg of total protein per sample was prepared for SDS-PAGE in 1× Laemmlli Sample buffer (BioRad 1610747) and 100 mM DTT, then heated at 95° C. for 10 minutes. Samples were run on a 4-15% TGX gel (BioRad 5671084) at 200V for 45 minutes. Samples were transferred to a 0.2 um nitrocellulose membrane (BioRad 1704159) using the Trans Blot Turbo System. The membrane was blocked in Intercept TBS Blocking Buffer (Li-cor 927-60001) for 30 minutes at room temperature. The blot was then incubated in a 1:1000 dilution of primary anti- LDHA antibody (Abcam ab52488) and 1:2500 dilution of primary anti-vinculin antibody (Sigma V9131) in blocking buffer at 4 C overnight. The blot was washed three times with TBST (Thermo Fisher 28360) for 5 minutes each, then incubated with a 1:12500 dilution of IR680 anti-mouse (Thermo Fisher PI35518) and IR800 anti-rabbit secondary antibodies (Thermo Fisher PISA535571) in TBST for 1 hour at room temperature. The blot was then washed three times with TBST for 5 minutes each and visualized on the Li-cor Odyssey CLX.

Figure 8:
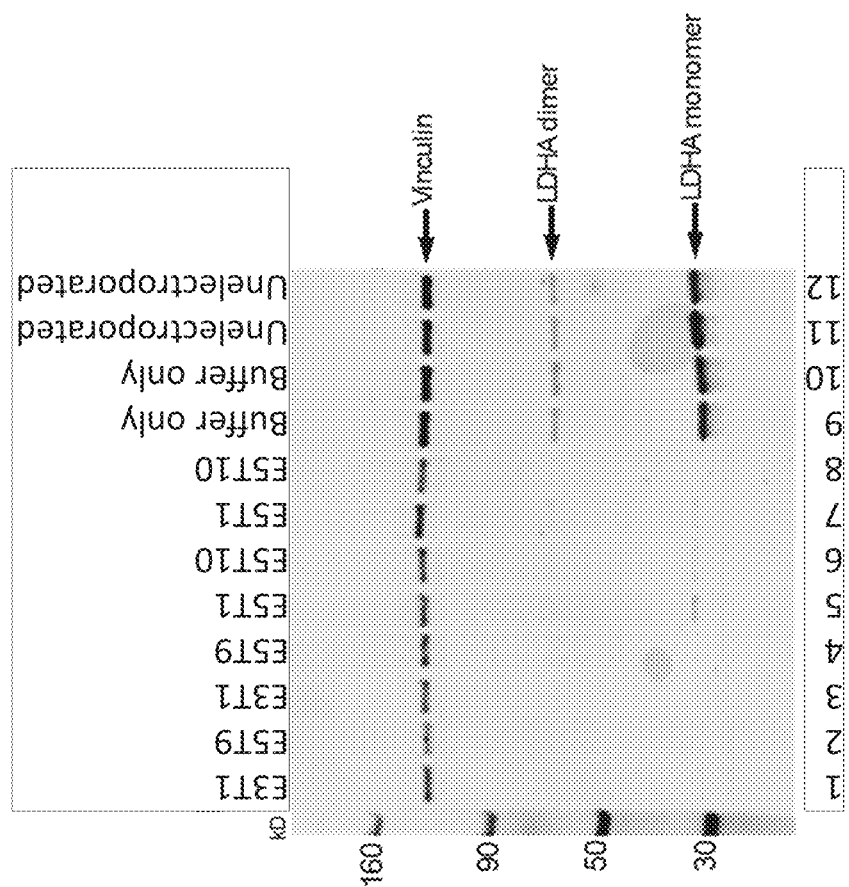
FIG. 8 is a Western Blot showing knockdown of LDHA protein following electroporation of primary human hepatocytes with variant Cas12i2 of SEQ ID NO: 1168 and RNA guides E3T1 (SEQ ID NO: 1214), E5T9 (SEQ ID NO: 1224), E5T1 (SEQ ID NO: 1221), or E5T10 (SEQ ID NO: 1225).

Knockdown of LDHA protein (monomer and dimer) was observed in primary human hepatocytes at Day 7 post editing by Cas12i2 RNPs targeting the LDHA gene (FIG. 8). This knockdown was seen across each of the four RNA guides, E3T1, E5T9, E5T1, and E5T10 (lanes 1-8). LDHA knockdown was not observed for the buffer only (lanes 9 and 10) or unelectroporated controls (lanes 11 and 12).

This Example thus shows that LDHA protein levels were decreased following editing with Cas12i2 and LDHA-targeting RNA guides.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A gene editing system for genetic editing of a lactate dehydrogenase A (LDHA) gene, comprising
   (i) a Cas12i2 polypeptide or a first nucleic acid encoding the Cas12i2 polypeptide, wherein the Cas12i2 polypeptide is a variant of SEQ ID NO:1166, and wherein, relative to SEQ ID NO: 1166, the Cas12i2 polypeptide comprises mutations at positions comprising D581, I926, and V1030; and wherein the mutations are amino acid substitutions of D581R, I926R, and V1030G, respectively;
   (ii) an RNA guide or a second nucleic acid encoding the RNA guide, wherein the RNA guide comprises a spacer sequence specific to a target sequence within an LDHA gene, the target sequence being adjacent to a protospacer adjacent motif (PAM) comprising the motif of 5'-TTN-3', which is located 5' to the target sequence.

2. The gene editing system of claim 1, wherein the mutations are at positions that further comprise G624, F626, P868, E1035, and S1046 in SEQ ID NO: 1166; and wherein the mutations at G624, F626, P868, E1035, and 51046 in SEQ ID NO: 1166 are amino acid substitutions G624R, F626R, P868T, E1035R, and S1046G, respectively.

3. The gene editing system of claim 1, wherein the Cas12i2 polypeptide comprises the amino acid sequence of SEQ ID NO: 1168 or SEQ ID NO: 1171.

4. The gene editing system of claim 1, which comprises the first nucleic acid encoding the Cas12i2 polypeptide.

5. The gene editing system of claim 4, wherein the first nucleic acid is a messenger RNA (mRNA).

6. The gene editing system of claim 1, wherein the target sequence is within exon 3 or exon 5 of the LDHA gene.

7. The gene editing system of claim 1, wherein the RNA guide comprises the spacer sequence and a direct repeat sequence.

8. The gene editing system of claim 7, wherein the direct repeat sequence comprises the nucleotide sequence of any one of SEQ ID NOs: 1-10, or a fragment thereof that is at least 23 nucleotides in length.

9. The gene editing system of claim 8, wherein the direct repeat sequence is 5'-AGAAAUCCGUCUUUCAUUGACGG-3' (SEQ ID NO: 10).

10. The gene editing system of claim 1, which comprises the second nucleic acid encoding the RNA guide.

11. The gene editing system of claim 1, wherein the system comprises the first nucleic acid encoding the Cas12i2 polypeptide, which is an mRNA, and wherein the system comprises the RNA guide.

12. The gene editing system of claim 11, wherein the RNA guide is chemically modified.

13. The gene editing system of claim 1, wherein the system further comprises lipid nanoparticles (LNPs).

14. The gene editing system of claim 13, wherein at least a portion of the LNPs encompasses the first nucleic acid encoding the Cas12i2 polypeptide, the RNA guide, or both.

15. The gene editing system of claim 14, wherein the first nucleic acid is an mRNA.

16. The gene editing system of claim 14, wherein the RNA guide is chemically modified.

17. A pharmaceutical composition comprising the gene editing system of claim 1.

18. The pharmaceutical composition of claim 17, which further comprises lipid nanoparticles (LNPs).

19. A kit comprising the elements (i) and (ii) set forth in claim 1.

20. A method for editing a lactate dehydrogenase A (LDHA) gene in a cell, the method comprising contacting a host cell with the gene editing system for editing the LDHA gene set forth in claim 1 to genetically edit the LDHA gene in the host cell.

21. A method for treating primary hyperoxaluria (PH) in a subject, comprising administering to a subject in need thereof a gene editing system for editing a lactate dehydrogenase A (LDHA) gene set forth in claim 1.

* * * * *